US006037135A

United States Patent [19]
Kubo et al.

[11] Patent Number: 6,037,135
[45] Date of Patent: Mar. 14, 2000

[54] METHODS FOR MAKING HLA BINDING PEPTIDES AND THEIR USES

[75] Inventors: Ralph T. Kubo, San Diego; Howard M. Grey; Alessandro Sette, both of La Jolla; Esteban Celis, San Diego, all of Calif.

[73] Assignee: Epimmune Inc., San Diego, Calif.

[21] Appl. No.: 08/159,339

[22] Filed: Nov. 29, 1993

Related U.S. Application Data

[63] Continuation-in-part of application No. 08/103,396, Aug. 6, 1993, abandoned, which is a continuation-in-part of application No. 08/027,746, Mar. 5, 1993, abandoned, which is a continuation-in-part of application No. 07/926,666, Aug. 7, 1992, abandoned.

[51] Int. Cl.$^7$ .............................. C12Q 1/00; C12Q 21/00
[52] U.S. Cl. .......................... 435/7.24; 435/7.1; 435/7.2; 530/328; 424/185.1
[58] Field of Search .................................... 424/88, 184.1, 424/185.1; 514/2, 14–16; 530/300, 326–329, 868, 338; 435/7.1, 7.2, 7.24

[56] References Cited

PUBLICATIONS

Parham, P. et al., Immunological Reviews 143:141–180, The origins of HLA–A, B, C polymorphism, 1995.
Van Eden et al., Vaccines 89, pp. 33–337, A modified PEPSCAN method for the rapid identication and characterization of T–cell epitopes in protein antigens, 1989.
Van der Zee et al., Eur. J. Immunology 19:43–47, Efficient mapping and characterization of a T cell epitope by the simultaneous synthesis of multiple peptides, 1989.
Paul, W.F. et al., Fundamental Immunology, 4th edition, pp. 274–285, 1999.
Bruss, V. A short linear sequence in the pre–S domain of the large hepatitis B virus envelope protein required from virion formation. J. Virology. Dec. 1997, vol. 71, No. 12, pp. 9350–9357.
Preisler–Adams, S. et al. Complete nucleotide sequence of a hepatitis B virus, subtype adw2, and identification of three types of C open reading frame. Nucleic Acids Res. 1993, vol. 21, No. 9, p. 2258.
Rammensee, H. et al. Peptides naturally presented by MHC Class I molecules. Annu. Rev. Immunol. 1993, vol. 11, pp. 213–244.
Engelhard, V. et al. Structure of peptides associated with MHC Class I molecules. Curr. Opin. Immunol. 1994, vol. 6, pp. 13–23.
Urban, J.L., et al., "Autoimmune T Cells: Immune Recognition of Normal and Variant Peptide Epitopes and Peptide––Based Therapy," Cell 59:257–271 (Oct. 20, 1989).
Wraith, D.C., et al., "Antigen Recognition in Autoimmune Encephalomyelitis and the Potential for Peptide–Mediated Immunotherapy," Cell 59:247–255 (Oct. 20, 1989).
Parker, K.C., et al., Peptide Binding to HLA–A2 and HLA–B27 Isolated from Escherichia coli, J. Biol. Chem. 267(8):5451–5459 Mar. 15, 1992.

Morrison, J., et al., "Identification of the nonamer peptide from influenza A matrix protein and the role of pockets of HLA–A2 in its recognition by cytotoxic T lymphocytes," Eur. J. Immunol., 22:903–907 (1992).
Shimojo, N., et al., Specificity of Peptide Binding by the HLA–A2.1 Molecule, J. of Immunol. 143(9):2939–2947 (Nov. 1, 1989).
Carreno, B.M., et al, "HLA–B37 and HLA–A2.1 molecules bind largely nonoverlapping sets of peptides," Proc. Natl. Acad. Sci. USA, 87:3420–3424 (May 1990).
Henderson, R.A., et al., "HLA–A2.1–Associated Peptides from a Mutant Cell Line: A Second Pathway of Antigen Presentation," Science 255:1264–1266 (Feb. 10, 1992).
Kannagi, M., et al., "Target Epitope in the Tax Protein of Human T–Cell Leukemia Virus Type I Recognized by Class I Major Histocompatibility Complex–Restricted Cytotoxic T Cells," J. of Virol. 66(5):2928–2933 (May 1992).
Falk, K., et al., "Allele–specific motifs revealed by sequenceing of self–peptide eluted from MHC molecules," Nature 351:290–296 May 23, 1991).
Jardetzky, T.S., et al., Identification of self peptides bound to purified HLA–B27, Nature 353:326–329 (Sep. 26, 1991).
Rotzschke, O., et al., "Naturally occurring peptide antigens derived from the MHC class–I–restricted processing pathway," Immunology Today 12(12):447–455 (1991).
De Bruijn, M.L.H., et al., Peptide loading of empty major histocompatibility complex molecules on RMA–S cells allows the induction of primary cytotoxic T lymphocyte responses, Eur. J. Immunol. 21:2963–2970 (1991).
Pamer, E.G., et al., "Precise prediction of a dominant class I MHC–restricted epitope of Listeria monocytogenes," Nature 353:852–855 (Oct. 31, 1991).
Cordingley, et al., J.B.C. 265:9062–65, 1990.
Maryanski, J. L. et al., J. Exp. Med. 167:1391–1405, "Synthetic peptides as antigens and competitors in recognition by H2–restricted cytolytic T cell specific for HLA", Apr. 1988.
Hunt, D.F., et al., "Characterization of Peptides Bound to the Class I MHC Molecule HLA–A2.1 by Mass Spectrometry," Science, 255:1261–1263 (Mar. 6, 1992).
Maryanski, J. L. et al., Cell 60:63–72, "Competitor analogs for defined T cell antigens: peptides incorporating a putative binding motif and polyproline or polyglycine spacers", Jan. 12, 1990.
Patarroyo, M. E. et al., Nature 328:629–632, "Induction of protective immunity against experimental infection with malaria using synthetic peptides", Aug. 1987.
Parker, K. C. et al., J. Immunol. 149:3580–3587, "Sequence motifs important for peptide binding to human MHC Class I molecule, HLA–A2", Dec. 1992.

(List continued on next page.)

Primary Examiner—Thomas M. Cunningham
Attorney, Agent, or Firm—Townsend and Townsend and Crew LLP

[57] ABSTRACT

Methods for making peptides comprising an HLA-A24.1-, HLA-A1-, HLA-A11-, and HLA-A3.2-restricted T cell epitope consisting of about 8–11 amino acid residues, and methods of making a peptide that binds to an HLA-A24.1, HLA-A1, HLA-A11, and HLA-A3.2 molecule at a dissociation constant of less than 500 nM.

68 Claims, 18 Drawing Sheets

OTHER PUBLICATIONS

Kumar, V. et al., PNAS 87:1337–1341, "Amino acid variations at a single residue in an autoimmune peptide profoundly affect its properties", Feb. 1990.

Engelhard, V. H., Annu. Rev. Immunol. 1994, 12:181–207, "Structure of peptides associated with Class I and Class II MHC molecules", 1994.

W. F. Paul (ed.), Fundamental Immunology, 3rd edition (1993), pp. 617–619, Raven Press, New York.

W. F. Paul, Fundamental Immunology, 2nd Edition (1989), pp. 473–487.

Maryanski, J. L., et al. Cell 60:63–72 (Jan. 12, 1990).

| | |
|---|---|
| CELLULAR SOURCE: HLA-ANTIGENS (5-10×10⁹ CELL EQUIVALENTS) | a) EBV TRANSFORMED B CELL LINES - HOMOZYGOUS<br>b) HLA-A TRANSFECTANTS - e.g. .221-HLA-AI<br>c) P815 TRANSFECTANTS (MOUSE MASTOCYTOMA) |
| DETERGENT LYSIS (10⁸ CELLS/ml) | 1% NP-40 OR 1% RENEX 30 PLUS PROTEASE INHIBITORS - 1 HR, 4°C |
| DETERGENT LYSATE | CENTRIFUGATION AT 15,000×g, 30 MIN. |
| AFFINITY CHROMATOGRAPHY | mAb-SEPHAROSE 5 mg/ml 5-10 ml COLUMN |
| PURIFIED HLA-A ANTIGEN | ANTICIPATED YIELDS 450-900 μg |
| ACID TREATMENT | 10% ACETIC ACID, 5 MIN, 100°C |
| PEPTIDES | YM3 FILTRATION, 3kD CUT-OFF |
| SEQUENCE/MOTIF | D. HUNT - HPLC/EI-TMS<br>CYTEL - HPLC/ABI 477A |

FIG. 1.

SEQUENCE LISTING (1) GENERAL INFORMATION:

(iii) NUMBER OF SEQUENCES: 1254

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified Base
      (B) LOCATION: 2...2
      (D) OTHER INFORMATION: Xaa = Leu, Met, Ile, Val, Ser, Ala, Thr,
         Phe, Cys, Gly, Asp or Glu
      (A) NAME/KEY: Modified Base
      (B) LOCATION: 9...9
      (D) OTHER INFORMATION: Xaa = Lys, Arg, Tyr, His or Phe (xi) SEQUENCE DESCRIPTION: SEQ ID NO:1:

Xaa Xaa Xaa Xaa Xaa Xaa Xaa Xaa Xaa
 1              5

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified Base
      (B) LOCATION: 2...2

(D) OTHER INFORMATION: Xaa = Leu, Met, Ile, Val, Ser, Ala,
                    Thr, Phe, Cys, Gly, Asp or Glu
                (A) NAME/KEY: Modified Base
                (B) LOCATION: 10...10
                (D) OTHER INFORMATION: Xaa = Lys, Arg, Tyr, His or Phe (xi) SEQUENCE DESCRIPTION: SEQ ID NO:2:

Xaa Xaa Xaa Xaa Xaa Xaa Xaa Xaa Xaa Xaa
 1               5                   10

(2) INFORMATION FOR SEQ ID NO:3:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Thr, Ser or Met
            (A) NAME/KEY: Modified Base
            (B) LOCATION: 2...2
            (D) OTHER INFORMATION: Xaa = Asp, Glu, Ala, Ser or Thr (xi) SEQUENCE DESCRIPTION: SEQ ID NO:3:

Xaa Xaa Xaa Xaa Xaa Xaa Xaa Xaa Tyr
 1               5

(2) INFORMATION FOR SEQ ID NO:4:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Thr, Ser or Met
            (A) NAME/KEY: Modified Base
            (B) LOCATION: 2...2
            (D) OTHER INFORMATION: Xaa = Asp, Glu, Ala, Ser or Thr (xi) SEQUENCE DESCRIPTION: SEQ ID NO:4:

Xaa Xaa Xaa Xaa Xaa Xaa Xaa Tyr Xaa
 1               5

(2) INFORMATION FOR SEQ ID NO:5:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Thr, Ser or Met
            (A) NAME/KEY: Modified Base
            (B) LOCATION: 2...2
            (D) OTHER INFORMATION: Xaa = Asp, Glu, Ala, Ser or Thr (xi) SEQUENCE DESCRIPTION: SEQ ID NO:5:

```
Xaa Xaa Xaa Xaa Xaa Xaa Xaa Xaa Xaa Tyr
1               5                   10

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Thr, Ser or Met
        (A) NAME/KEY: Modified Base
        (B) LOCATION: 3...3
        (D) OTHER INFORMATION: Xaa = Asp, Glu, Ala, Ser or Thr (xi) SEQUENCE DESCRIPTION: SEQ ID NO:6:

Xaa Xaa Xaa Xaa Xaa Xaa Xaa Xaa Xaa Tyr
1               5                   10

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 1...1
        (D) OTHER INFORMATION: Xaa = Thr, Ser or Met
        (A) NAME/KEY: Modified Base
        (B) LOCATION: 2...2
        (D) OTHER INFORMATION: Xaa = Asp, Glu, Ala, Ser or Thr (xi) SEQUENCE DESCRIPTION: SEQ ID NO:7:

Xaa Xaa Xaa Xaa Xaa Xaa Xaa Tyr Xaa Xaa
1               5                   10

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 1...1
        (D) OTHER INFORMATION: Xaa = Thr, Ser or Met
        (A) NAME/KEY: Modified Base
        (B) LOCATION: 2...2
        (D) OTHER INFORMATION: Xaa = Asp, Glu, Ala, Ser or Thr (xi) SEQUENCE DESCRIPTION: SEQ ID NO:8:

Xaa Xaa Xaa Xaa Xaa Xaa Xaa Xaa Tyr Xaa
1               5                   10

(2) INFORMATION FOR SEQ ID NO:9:

(i) SEQUENCE CHARACTERISTICS:
        (A) LENGTH: 11 amino acids
```

```
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Thr, Ser or Met
            (A) NAME/KEY: Modified Base
            (B) LOCATION: 3...3
            (D) OTHER INFORMATION: Xaa = Asp, Glu, Ala, Ser or Thr (xi) SEQUENCE DESCRIPTION: SEQ ID NO:9:

Xaa Xaa Xaa Xaa Xaa Xaa Xaa Xaa Xaa Tyr Xaa
 1               5                  10

(2) INFORMATION FOR SEQ ID NO:10:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Thr, Ser or Met
            (A) NAME/KEY: Modified Base
            (B) LOCATION: 3...3
            (D) OTHER INFORMATION: Xaa = Asp, Glu, Ala, Ser or Thr (xi) SEQUENCE DESCRIPTION: SEQ ID NO:10:

Xaa Xaa Xaa Xaa Xaa Xaa Xaa Xaa Xaa Xaa Tyr
 1               5                  10

(2) INFORMATION FOR SEQ ID NO:11:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa =Glu or Asp (xi) SEQUENCE DESCRIPTION: SEQ ID NO:11:

Xaa Xaa Xaa Xaa Xaa Xaa Tyr Xaa
 1               5

(2) INFORMATION FOR SEQ ID NO:12:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Glu or Asp
```

(xi) SEQUENCE DESCRIPTION: SEQ ID NO:12:

Xaa Xaa Xaa Xaa Xaa Xaa Xaa Tyr
1               5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Glu or Asp (xi) SEQUENCE DESCRIPTION: SEQ ID NO:13:

Xaa Xaa Xaa Xaa Xaa Xaa Xaa Tyr
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 1...1
        (D) OTHER INFORMATION: Xaa = Glu or Asp (xi) SEQUENCE DESCRIPTION: SEQ ID NO:14:

Xaa Xaa Xaa Xaa Xaa Xaa Tyr Xaa Xaa
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 1...1
        (D) OTHER INFORMATION: Xaa = Glu or Asp (xi) SEQUENCE DESCRIPTION: SEQ ID NO:15:

Xaa Xaa Xaa Xaa Xaa Xaa Xaa Tyr Xaa
1               5

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:

```
            (A) NAME/KEY: Modified Base
            (B) LOCATION: 2...2
            (D) OTHER INFORMATION: Xaa = Glu or Asp (xi) SEQUENCE DESCRIPTION: SEQ ID NO:16:

Xaa Xaa Xaa Xaa Xaa Xaa Xaa Tyr Xaa
  1               5

(2) INFORMATION FOR SEQ ID NO:17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Glu or Asp (xi) SEQUENCE DESCRIPTION: SEQ ID NO:17:

Xaa Xaa Xaa Xaa Xaa Xaa Xaa Xaa Tyr
  1               5

(2) INFORMATION FOR SEQ ID NO:18:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Glu or Asp (xi) SEQUENCE DESCRIPTION: SEQ ID NO:18:

Xaa Xaa Xaa Xaa Xaa Xaa Tyr Xaa Xaa Xaa
  1               5                  10

(2) INFORMATION FOR SEQ ID NO:19:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Glu or Asp (xi) SEQUENCE DESCRIPTION: SEQ ID NO:19:

Xaa Xaa Xaa Xaa Xaa Xaa Xaa Tyr Xaa Xaa
  1               5                  10

(2) INFORMATION FOR SEQ ID NO:20:

(i) SEQUENCE CHARACTERISTICS:
            (A) LENGTH: 10 amino acids
            (B) TYPE: amino acid
            (C) STRANDEDNESS: single
            (D) TOPOLOGY: linear
```

(ii) MOLECULE TYPE: peptide (ix) FEATURE:
            (A) NAME/KEY: Modified Base
            (B) LOCATION: 2...2
            (D) OTHER INFORMATION: Xaa = Glu or Asp (xi) SEQUENCE DESCRIPTION: SEQ ID NO:20:

Xaa Xaa Xaa Xaa Xaa Xaa Xaa Tyr Xaa Xaa
1               5                   10

(2) INFORMATION FOR SEQ ID NO:21:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Glu or Asp (xi) SEQUENCE DESCRIPTION: SEQ ID NO:21:

Xaa Xaa Xaa Xaa Xaa Xaa Xaa Xaa Tyr Xaa
1               5                   10

(2) INFORMATION FOR SEQ ID NO:22:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 3...3
            (D) OTHER INFORMATION: Xaa = Glu or Asp (xi) SEQUENCE DESCRIPTION: SEQ ID NO:22:

Xaa Xaa Xaa Xaa Xaa Xaa Xaa Xaa Tyr Xaa
1               5                   10

(2) INFORMATION FOR SEQ ID NO:23:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 3...3
            (D) OTHER INFORMATION: Xaa = Glu or Asp (xi) SEQUENCE DESCRIPTION: SEQ ID NO:23:

Xaa Xaa Xaa Xaa Xaa Xaa Xaa Xaa Xaa Tyr
1               5                   10

(2) INFORMATION FOR SEQ ID NO:24:

(i) SEQUENCE CHARACTERISTICS:

```
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 4...4
            (D) OTHER INFORMATION: Xaa = Glu or Asp (xi) SEQUENCE DESCRIPTION: SEQ ID NO:24:

Xaa Xaa Xaa Xaa Xaa Xaa Xaa Xaa Xaa Tyr
1               5                   10

(2) INFORMATION FOR SEQ ID NO:25:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Glu or Asp (xi) SEQUENCE DESCRIPTION: SEQ ID NO:25:

Xaa Xaa Xaa Xaa Xaa Xaa Tyr Xaa Xaa Xaa Xaa
1               5                   10

(2) INFORMATION FOR SEQ ID NO:26:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 1...1
            (D) OTHER INFORMATION: Xaa = Glu or Asp (xi) SEQUENCE DESCRIPTION: SEQ ID NO:26:

Xaa Xaa Xaa Xaa Xaa Xaa Xaa Tyr Xaa Xaa Xaa
1               5                   10

(2) INFORMATION FOR SEQ ID NO:27:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Glu or Asp (xi) SEQUENCE DESCRIPTION: SEQ ID NO:27:

Xaa Xaa Xaa Xaa Xaa Xaa Xaa Tyr Xaa Xaa Xaa
1               5                   10
```

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Glu or Asp (xi) SEQUENCE DESCRIPTION: SEQ ID NO:28:

```
Xaa Xaa Xaa Xaa Xaa Xaa Xaa Xaa Tyr Xaa Xaa
 1               5                  10
```

(2) INFORMATION FOR SEQ ID NO:29:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 3...3
        (D) OTHER INFORMATION: Xaa = Glu or Asp (xi) SEQUENCE DESCRIPTION: SEQ ID NO:29:

```
Xaa Xaa Xaa Xaa Xaa Xaa Xaa Xaa Tyr Xaa Xaa
 1               5                  10
```

(2) INFORMATION FOR SEQ ID NO:30:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 3...3
        (D) OTHER INFORMATION: Xaa = Glu or Asp (xi) SEQUENCE DESCRIPTION: SEQ ID NO:30:

```
Xaa Xaa Xaa Xaa Xaa Xaa Xaa Xaa Xaa Tyr Xaa
 1               5                  10
```

(2) INFORMATION FOR SEQ ID NO:31:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 4...4
        (D) OTHER INFORMATION: Xaa = Glu or Asp (xi) SEQUENCE DESCRIPTION: SEQ ID NO:31:

```
Xaa Xaa Xaa Xaa Xaa Xaa Xaa Xaa Xaa Tyr Xaa
 1               5                   10
```

(2) INFORMATION FOR SEQ ID NO:32:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 4...4
        (D) OTHER INFORMATION: Xaa = Glu or Asp (xi) SEQUENCE DESCRIPTION: SEQ ID NO:32:

```
Xaa Xaa Xaa Xaa Xaa Xaa Xaa Xaa Xaa Xaa Tyr
 1               5                   10
```

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Thr or Val (xi) SEQUENCE DESCRIPTION: SEQ ID NO:33:

```
Xaa Xaa Xaa Xaa Xaa Xaa Xaa Xaa Lys
 1               5
```

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Thr or Val (xi) SEQUENCE DESCRIPTION: SEQ ID NO:34:

```
Xaa Xaa Xaa Xaa Xaa Xaa Xaa Xaa Xaa Lys
 1               5                   10
```

(2) INFORMATION FOR SEQ ID NO:35:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base (B) LOCATION: 2...2
            (D) OTHER INFORMATION: Xaa = Tyr, Phe or Trp
            (A) NAME/KEY: Modified Base
            (B) LOCATION: 9...9
            (D) OTHER INFORMATION: Xaa = Phe, Ile, Trp, Met or Leu (xi) SEQUENCE DESCRIPTION: SEQ ID NO:35:

Xaa Xaa Xaa Xaa Xaa Xaa Xaa Xaa Xaa
1               5

(2) INFORMATION FOR SEQ ID NO:36:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified Base
         (B) LOCATION: 2...2
         (D) OTHER INFORMATION: Xaa = Tyr, Phe or Trp
         (A) NAME/KEY: Modified Base
         (B) LOCATION: 10...10
         (D) OTHER INFORMATION: Xaa = Phe, Ile, Trp, Met or Leu (xi) SEQUENCE DESCRIPTION: SEQ ID NO:36:

Xaa Xaa Xaa Xaa Xaa Xaa Xaa Xaa Xaa Xaa
1               5                   10

(2) INFORMATION FOR SEQ ID NO:37:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified Base
         (B) LOCATION: 2...2
         (D) OTHER INFORMATION: Xaa = Val, Leu or Met (xi) SEQUENCE DESCRIPTION: SEQ ID NO:37:

Xaa Xaa Xaa Xaa Xaa Xaa Xaa Xaa Lys
1               5

(2) INFORMATION FOR SEQ ID NO:38:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified Base
         (B) LOCATION: 2...2
         (D) OTHER INFORMATION: Xaa = Val, Leu or Met (xi) SEQUENCE DESCRIPTION: SEQ ID NO:38:

Xaa Xaa Xaa Xaa Xaa Xaa Xaa Xaa Xaa Lys
1               5                   10

(2) INFORMATION FOR SEQ ID NO:39:

```
        (i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Val, Leu or Met
            (A) NAME/KEY: Modified Base
            (B) LOCATION: 3...3
            (D) OTHER INFORMATION: Xaa = Tyr or Asp
            (A) NAME/KEY: Modified Base
            (B) LOCATION: 8...8
            (D) OTHER INFORMATION: Xaa = Gln or Asn (xi) SEQUENCE DESCRIPTION: SEQ ID NO:39:

Xaa Xaa Xaa Xaa Xaa Xaa Ile Xaa Lys Lys
  1               5                  10

(2) INFORMATION FOR SEQ ID NO:40:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Ser or Thr (xi) SEQUENCE DESCRIPTION: SEQ ID NO:40:

Xaa Xaa Xaa Xaa Xaa Xaa Xaa Xaa Tyr
  1               5

(2) INFORMATION FOR SEQ ID NO:41:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Ser or Thr (xi) SEQUENCE DESCRIPTION: SEQ ID NO:41:

Xaa Xaa Xaa Xaa Xaa Xaa Xaa Xaa Xaa Tyr
  1               5                  10

(2) INFORMATION FOR SEQ ID NO:42:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 3...3
```

(D) OTHER INFORMATION: Xaa = Asp or Glu (xi) SEQUENCE DESCRIPTION: SEQ ID NO:42:

Xaa Xaa Xaa Xaa Xaa Xaa Xaa Xaa Tyr
 1               5

(2) INFORMATION FOR SEQ ID NO:43:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 3...3
        (D) OTHER INFORMATION: Xaa = Asp or Glu (xi) SEQUENCE DESCRIPTION: SEQ ID NO:43:

Xaa Xaa Xaa Xaa Xaa Xaa Xaa Xaa Xaa Tyr
 1               5                  10

(2) INFORMATION FOR SEQ ID NO:44:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Ser or Thr
        (A) NAME/KEY: Modified Base
        (B) LOCATION: 3...3
        (D) OTHER INFORMATION: Xaa = Asp or Glu (xi) SEQUENCE DESCRIPTION: SEQ ID NO:44:

Xaa Xaa Xaa Pro Xaa Xaa Leu Xaa Tyr
 1               5

(2) INFORMATION FOR SEQ ID NO:45:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Thr or Val
        (A) NAME/KEY: Modified Base
        (B) LOCATION: 3...3
        (D) OTHER INFORMATION: Xaa = Met or Phe (xi) SEQUENCE DESCRIPTION: SEQ ID NO:45:

Xaa Xaa Xaa Xaa Xaa Xaa Xaa Gln Lys
 1               5

(2) INFORMATION FOR SEQ ID NO:46:

(i) SEQUENCE CHARACTERISTICS:

```
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified Base
         (B) LOCATION: 2...2
         (D) OTHER INFORMATION: Xaa = Thr or Val
         (A) NAME/KEY: Modified Base
         (B) LOCATION: 3...3
         (D) OTHER INFORMATION: Xaa = Met or Phe (xi) SEQUENCE DESCRIPTION: SEQ ID NO:46:

Xaa Xaa Xaa Xaa Xaa Xaa Xaa Gln Xaa Lys
 1               5                  10

(2) INFORMATION FOR SEQ ID NO:47:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified Base
         (B) LOCATION: 2...2
         (D) OTHER INFORMATION: Xaa = Thr or Val
         (A) NAME/KEY: Modified Base
         (B) LOCATION: 3...3
         (D) OTHER INFORMATION: Xaa = Met or Phe (xi) SEQUENCE DESCRIPTION: SEQ ID NO:47:

Xaa Xaa Xaa Xaa Xaa Xaa Xaa Gln Lys Lys
 1               5                  10

(2) INFORMATION FOR SEQ ID NO:48:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified Base
         (B) LOCATION: 3...3
         (D) OTHER INFORMATION: Xaa = Ile or Met
         (A) NAME/KEY: Modified Base
         (B) LOCATION: 4...4
         (D) OTHER INFORMATION: Xaa = Asp, Glu, Gly, Lys or Pro
         (A) NAME/KEY: Modified Base
         (B) LOCATION: 5...5
         (D) OTHER INFORMATION: Xaa = Lys, Met or Asn
         (A) NAME/KEY: Modified Base
         (B) LOCATION: 7...7
         (D) OTHER INFORMATION: Xaa = Asn or Val
         (A) NAME/KEY: Modified Base
         (B) LOCATION: 8...8
         (D) OTHER INFORMATION: Xaa = Ala, Glu, Lys, Gln or Ser
         (A) NAME/KEY: Modified Base
         (B) LOCATION: 9...9
         (D) OTHER INFORMATION: Xaa = Phe or Leu (xi) SEQUENCE DESCRIPTION: SEQ ID NO:48:

Xaa Tyr Xaa Xaa Xaa Val Xaa Xaa Xaa
 1               5
```

(2) INFORMATION FOR SEQ ID NO:49:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 3...3
        (D) OTHER INFORMATION: Xaa = Ile or Met
        (A) NAME/KEY: Modified Base
        (B) LOCATION: 4...4
        (D) OTHER INFORMATION: Xaa = Asp, Glu, Gly, Lys or Pro
        (A) NAME/KEY: Modified Base
        (B) LOCATION: 5...5
        (D) OTHER INFORMATION: Xaa = Lys, Met or Asn
        (A) NAME/KEY: Modified Base
        (B) LOCATION: 7...7
        (D) OTHER INFORMATION: Xaa = Asn or Val
        (A) NAME/KEY: Modified Base
        (B) LOCATION: 8...8
        (D) OTHER INFORMATION: Xaa = Ala, Glu, Lys, Gln or Ser
        (A) NAME/KEY: Modified Base
        (B) LOCATION: 10...10
        (D) OTHER INFORMATION: Xaa = Phe or Leu (xi) SEQUENCE DESCRIPTION: SEQ ID NO:49:

Xaa Tyr Xaa Xaa Xaa Val Xaa Xaa Xaa Xaa
 1            5               10

(2) INFORMATION FOR SEQ ID NO:50:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 3...3
        (D) OTHER INFORMATION: Xaa = Ile or Met
        (A) NAME/KEY: Modified Base
        (B) LOCATION: 4...4
        (D) OTHER INFORMATION: Xaa = Asp, Glu, Gly, Lys or Pro
        (A) NAME/KEY: Modified Base
        (B) LOCATION: 5...5
        (D) OTHER INFORMATION: Xaa = Leu, Met or Asn
        (A) NAME/KEY: Modified Base
        (B) LOCATION: 7...7
        (D) OTHER INFORMATION: Xaa = Asn or Val
        (A) NAME/KEY: Modified Base
        (B) LOCATION: 8...8
        (D) OTHER INFORMATION: Xaa = Ala, Glu, Lys, Gln or Ser
        (A) NAME/KEY: Modified Base
        (B) LOCATION: 9...9
        (D) OTHER INFORMATION: Xaa = Phe or Leu
        (A) NAME/KEY: Modified Base
        (B) LOCATION: 10...10
        (D) OTHER INFORMATION: Xaa = Phe or Leu (xi) SEQUENCE DESCRIPTION: SEQ ID NO:50:

Xaa Tyr Xaa Xaa Xaa Val Xaa Xaa Xaa Xaa
 1            5               10

(2) INFORMATION FOR SEQ ID NO:51:

(i) SEQUENCE CHARACTERISTICS:
        (A) LENGTH: 9 amino acids

-continued

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:51:

Xaa Ser Xaa Xaa Xaa Xaa Xaa Xaa Tyr
1               5

(2) INFORMATION FOR SEQ ID NO:52:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:52:

Xaa Ser Xaa Xaa Xaa Xaa Xaa Xaa Xaa Tyr
1               5                  10

(2) INFORMATION FOR SEQ ID NO:53:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:53:

Xaa Thr Xaa Xaa Xaa Xaa Xaa Xaa Tyr
1               5

(2) INFORMATION FOR SEQ ID NO:54:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:54:

Xaa Thr Xaa Xaa Xaa Xaa Xaa Xaa Xaa Tyr
1               5                  10

(2) INFORMATION FOR SEQ ID NO:55:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:55:

Xaa Xaa Asp Xaa Xaa Xaa Xaa Xaa Tyr
1               5

(2) INFORMATION FOR SEQ ID NO:56:

(i) SEQUENCE CHARACTERISTICS:
            (A) LENGTH: 10 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:56:

Xaa Xaa Asp Xaa Xaa Xaa Xaa Xaa Xaa Tyr
1               5                   10

(2) INFORMATION FOR SEQ ID NO:57:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Xaa Xaa Glu Xaa Xaa Xaa Xaa Xaa Tyr
1               5

(2) INFORMATION FOR SEQ ID NO:58:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

Xaa Xaa Glu Xaa Xaa Xaa Xaa Xaa Xaa Tyr
1               5                   10

(2) INFORMATION FOR SEQ ID NO:59:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

Xaa Val Xaa Xaa Xaa Xaa Xaa Xaa Lys
1               5

(2) INFORMATION FOR SEQ ID NO:60:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

Xaa Val Xaa Xaa Xaa Xaa Xaa Xaa Xaa Lys
1               5                   10

(2) INFORMATION FOR SEQ ID NO:61:

(i) SEQUENCE CHARACTERISTICS:
        (A) LENGTH: 9 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:61:

Xaa Leu Xaa Xaa Xaa Xaa Xaa Xaa Lys
 1               5

(2) INFORMATION FOR SEQ ID NO:62:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:62:

Xaa Leu Xaa Xaa Xaa Xaa Xaa Xaa Xaa Lys
 1               5                  10

(2) INFORMATION FOR SEQ ID NO:63:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:63:

Xaa Met Xaa Xaa Xaa Xaa Xaa Xaa Lys
 1               5

(2) INFORMATION FOR SEQ ID NO:64:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:64:

Xaa Met Xaa Xaa Xaa Xaa Xaa Xaa Xaa Lys
 1               5                  10

(2) INFORMATION FOR SEQ ID NO:65:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:65:

Xaa Thr Xaa Xaa Xaa Xaa Xaa Xaa Lys
 1               5

(2) INFORMATION FOR SEQ ID NO:66:

(i) SEQUENCE CHARACTERISTICS:
            (A) LENGTH: 10 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:66:

Xaa Thr Xaa Xaa Xaa Xaa Xaa Xaa Xaa Lys
1               5                   10

(2) INFORMATION FOR SEQ ID NO:67:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:67:

Xaa Val Xaa Xaa Xaa Xaa Xaa Xaa Lys
1               5

(2) INFORMATION FOR SEQ ID NO:68:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:68:

Xaa Val Xaa Xaa Xaa Xaa Xaa Xaa Xaa Lys
1               5                   10

(2) INFORMATION FOR SEQ ID NO:69:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:69:

Xaa Tyr Xaa Xaa Xaa Xaa Xaa Xaa Phe
1               5

(2) INFORMATION FOR SEQ ID NO:70:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:70:

Xaa Tyr Xaa Xaa Xaa Xaa Xaa Xaa Xaa Phe
1               5                   10

(2) INFORMATION FOR SEQ ID NO:71:

(i) SEQUENCE CHARACTERISTICS:
            (A) LENGTH: 9 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

Xaa Tyr Xaa Xaa Xaa Xaa Xaa Xaa Leu
1               5

(2) INFORMATION FOR SEQ ID NO:72:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

Xaa Tyr Xaa Xaa Xaa Xaa Xaa Xaa Xaa Leu
1               5                   10

(2) INFORMATION FOR SEQ ID NO:73:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

Ile His Asp Ile Ile Leu Glu Cys Val Tyr
1               5                   10

(2) INFORMATION FOR SEQ ID NO:74:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

Val Cys Asp Lys Cys Leu Lys Phe Tyr
1               5

(2) INFORMATION FOR SEQ ID NO:75:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Tyr Ser Lys Ile Ser Glu Tyr Arg His Tyr
1               5                   10

(2) INFORMATION FOR SEQ ID NO:76:

(i) SEQUENCE CHARACTERISTICS:
        (A) LENGTH: 9 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:76:

Ile Ser Glu Tyr Arg His Tyr Cys Tyr
 1               5

(2) INFORMATION FOR SEQ ID NO:77:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:77:

Gly Thr Thr Leu Glu Gln Gln Tyr Asn Lys
 1               5                  10

(2) INFORMATION FOR SEQ ID NO:78:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:78:

Thr Thr Leu Glu Gln Gln Tyr Asn Lys
 1               5

(2) INFORMATION FOR SEQ ID NO:79:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:79:

Leu Leu Ile Arg Cys Ile Asn Cys Gln Lys
 1               5                  10

(2) INFORMATION FOR SEQ ID NO:80:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:80:

His Gly Asp Thr Pro Thr Leu His Glu Tyr
 1               5                  10

(2) INFORMATION FOR SEQ ID NO:81:

(i) SEQUENCE CHARACTERISTICS:
            (A) LENGTH: 10 amino acids
```

```
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:81:

Gln Pro Glu Thr Thr Asp Leu Tyr Cys Tyr
 1               5                  10

(2) INFORMATION FOR SEQ ID NO:82:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:82:

Gln Ala Glu Pro Asp Arg Ala His Tyr
 1               5

(2) INFORMATION FOR SEQ ID NO:83:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:83:

Ile Val Cys Pro Ile Cys Ser Gln Lys
 1               5

(2) INFORMATION FOR SEQ ID NO:84:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:84:

Arg Phe Glu Asp Pro Thr Arg Arg Pro Tyr
 1               5                  10

(2) INFORMATION FOR SEQ ID NO:85:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:85:

Phe Glu Asp Pro Thr Arg Arg Pro Tyr
 1               5

(2) INFORMATION FOR SEQ ID NO:86:

(i) SEQUENCE CHARACTERISTICS:
          (A) LENGTH: 10 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:86:

Leu Gln Asp Ile Glu Ile Thr Cys Val Tyr
1               5                   10

(2) INFORMATION FOR SEQ ID NO:87:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:87:

Leu Thr Glu Val Phe Glu Phe Ala Phe Lys
1               5                   10

(2) INFORMATION FOR SEQ ID NO:88:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:88:

Tyr Ser Arg Ile Arg Glu Leu Arg His Tyr
1               5                   10

(2) INFORMATION FOR SEQ ID NO:89:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:89:

Ser Val Tyr Gly Asp Thr Leu Glu Lys
1               5

(2) INFORMATION FOR SEQ ID NO:90:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:90:

Leu Leu Ile Arg Cys Leu Arg Cys Gln Lys
1               5                   10

(2) INFORMATION FOR SEQ ID NO:91:

(i) SEQUENCE CHARACTERISTICS:
            (A) LENGTH: 9 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:91:

His Thr Met Leu Cys Met Cys Cys Lys
 1               5

(2) INFORMATION FOR SEQ ID NO:92:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:92:

Ser Leu Glu Gln Arg Ser Leu His Cys Lys
 1               5                  10

(2) INFORMATION FOR SEQ ID NO:93:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:93:

Ser Leu Phe Arg Ala Val Ile Thr Lys
 1               5

(2) INFORMATION FOR SEQ ID NO:94:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:94:

Ser Leu Phe Arg Ala Val Ile Thr Lys Lys
 1               5                  10

(2) INFORMATION FOR SEQ ID NO:95:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:95:

Asp Leu Val Gly Phe Leu Leu Leu Lys
 1               5

(2) INFORMATION FOR SEQ ID NO:96:

(i) SEQUENCE CHARACTERISTICS:
            (A) LENGTH: 10 amino acids
```

(B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:96:

Met Leu Glu Ser Val Ile Lys Asn Tyr Lys
 1               5                  10

(2) INFORMATION FOR SEQ ID NO:97:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:97:

Met Leu Glu Ser Val Ile Lys Asn Tyr
 1               5

(2) INFORMATION FOR SEQ ID NO:98:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:98:

Gln Leu Val Phe Gly Ile Asp Val Lys
 1               5

(2) INFORMATION FOR SEQ ID NO:99:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:99:

Glu Ala Asp Pro Thr Gly His Ser Tyr
 1               5

(2) INFORMATION FOR SEQ ID NO:100:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:100:

Leu Leu Gly Asp Asn Gln Ile Met Pro Lys
 1               5                  10

(2) INFORMATION FOR SEQ ID NO:101:

(i) SEQUENCE CHARACTERISTICS:
          (A) LENGTH: 10 amino acids

```
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:101:

Trp Glu Glu Leu Ser Val Met Glu Val Tyr
 1               5                  10

(2) INFORMATION FOR SEQ ID NO:102:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:102:

Val Tyr Asp Gly Arg Glu His Ser Ala Tyr
 1               5                  10

(2) INFORMATION FOR SEQ ID NO:103:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:103:

Leu Leu Thr Gln Asp Leu Val Gln Glu Lys
 1               5                  10

(2) INFORMATION FOR SEQ ID NO:104:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:104:

Leu Thr Gln Asp Leu Val Gln Glu Lys
 1               5

(2) INFORMATION FOR SEQ ID NO:105:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:105:

Leu Thr Gln Asp Leu Val Gln Glu Lys Tyr
 1               5                  10

(2) INFORMATION FOR SEQ ID NO:106:

(i) SEQUENCE CHARACTERISTICS:
          (A) LENGTH: 9 amino acids
```

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

Thr Gln Asp Leu Val Gln Glu Lys Tyr
1               5

(2) INFORMATION FOR SEQ ID NO:107:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Ile Val Gly Gly Trp Glu Cys Glu Lys
1               5

(2) INFORMATION FOR SEQ ID NO:108:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:

Leu Thr Ala Ala His Cys Ile Arg Asn Lys
1               5                   10

(2) INFORMATION FOR SEQ ID NO:109:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

Val Ser His Ser Phe Pro His Pro Leu Tyr
1               5                   10

(2) INFORMATION FOR SEQ ID NO:110:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

Pro Leu Tyr Asp Met Ser Leu Leu Lys
1               5

(2) INFORMATION FOR SEQ ID NO:111:

(i) SEQUENCE CHARACTERISTICS:
        (A) LENGTH: 10 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:111:

Asp Val Cys Ala Gln Val His Pro Gln Lys
 1               5                  10

(2) INFORMATION FOR SEQ ID NO:112:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:112:

Gln Val His Pro Gln Lys Val Thr Lys
 1               5

(2) INFORMATION FOR SEQ ID NO:113:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:113:

Pro Ser Leu Tyr Thr Lys Val Val His Tyr
 1               5                  10

(2) INFORMATION FOR SEQ ID NO:114:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:114:

Tyr Thr Lys Val Val His Tyr Arg Lys
 1               5

(2) INFORMATION FOR SEQ ID NO:115:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:115:

Lys Val Val His Tyr Arg Lys Trp Ile Lys
 1               5                  10

(2) INFORMATION FOR SEQ ID NO:116:

(i) SEQUENCE CHARACTERISTICS:
            (A) LENGTH: 9 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:116:

Val Val His Tyr Arg Lys Trp Ile Lys
1               5

(2) INFORMATION FOR SEQ ID NO:117:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:117:

Ser Thr Asn Pro Lys Pro Gln Arg Lys
1               5

(2) INFORMATION FOR SEQ ID NO:118:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:118:

Asn Thr Asn Arg Arg Pro Gln Asp Val Lys
1               5                   10

(2) INFORMATION FOR SEQ ID NO:119:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:119:

Arg Leu Gly Val Arg Ala Thr Arg Lys
1               5

(2) INFORMATION FOR SEQ ID NO:120:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:120:

Val Gln Asp Cys Asn Cys Ser Ile Tyr
1               5

(2) INFORMATION FOR SEQ ID NO:121:

(i) SEQUENCE CHARACTERISTICS:
            (A) LENGTH: 9 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:121:

Trp Met Asn Ser Thr Gly Phe Thr Lys
1               5

(2) INFORMATION FOR SEQ ID NO:122:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

Leu Thr Pro Arg Cys Met Val Asp Tyr
1               5

(2) INFORMATION FOR SEQ ID NO:123:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:123:

Phe Thr Ile Phe Lys Ile Arg Met Tyr
1               5

(2) INFORMATION FOR SEQ ID NO:124:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:124:

Lys Val Phe Pro Tyr Ala Leu Ile Asn Lys
1               5                   10

(2) INFORMATION FOR SEQ ID NO:125:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:125:

Ala Val Asp Leu Tyr His Phe Leu Lys
1               5

(2) INFORMATION FOR SEQ ID NO:126:

(i) SEQUENCE CHARACTERISTICS:
        (A) LENGTH: 9 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:126:

Tyr Leu Glu Pro Ala Ile Ala Lys Tyr
 1               5

(2) INFORMATION FOR SEQ ID NO:127:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:127:

Ala Tyr Ile Asp Asn Val Tyr Lys Phe
 1               5

(2) INFORMATION FOR SEQ ID NO:128:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:128:

Ala Tyr Ile Asp Asn Tyr Asn Lys Phe
 1               5

(2) INFORMATION FOR SEQ ID NO:129:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:129:

Ala Met Ala Ala Ala Ala Ala Ala Lys
 1               5

(2) INFORMATION FOR SEQ ID NO:130:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Leu, Met, Ile, Val, Ala, Ser, Thr,
                Gly, Asn, Gln, Cys, Phe, Asp or Glu
            (A) NAME/KEY: Modified Base
            (B) LOCATION: 9...9
            (D) OTHER INFORMATION: Xaa = Lys, Arg or His (xi) SEQUENCE DESCRIPTION: SEQ ID NO:130:
```

```
Xaa Xaa Xaa Xaa Xaa Xaa Xaa Xaa Xaa
1               5
```

(2) INFORMATION FOR SEQ ID NO:131:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Tyr, Phe or Trp
        (A) NAME/KEY: Modified Base
        (B) LOCATION: 9...9
        (D) OTHER INFORMATION: Xaa = Phe, Ile, Leu, Trp or Met (xi) SEQUENCE DESCRIPTION: SEQ ID NO:131:

```
Xaa Xaa Xaa Xaa Xaa Xaa Xaa Xaa Xaa
1               5
```

(2) INFORMATION FOR SEQ ID NO:132:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Thr, Ser or Met
        (A) NAME/KEY: Modified Base
        (B) LOCATION: 3...3
        (D) OTHER INFORMATION: Xaa = Asp, Glu, Ala, Ser or Met (xi) SEQUENCE DESCRIPTION: SEQ ID NO:132:

```
Xaa Xaa Xaa Xaa Xaa Xaa Xaa Xaa Tyr
1               5
```

(2) INFORMATION FOR SEQ ID NO:133:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:133:

```
Ile Val Tyr Arg Asp Gly Asn Pro Tyr
1               5
```

(2) INFORMATION FOR SEQ ID NO:134:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:134:

Ile Ser Glu Tyr Arg His Tyr Ala Tyr
1               5

(2) INFORMATION FOR SEQ ID NO:135:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:135:

Gln Gln Leu Leu Arg Arg Glu Val Tyr
1               5

(2) INFORMATION FOR SEQ ID NO:136:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:136:

Val Ala Asp Lys Ala Leu Lys Phe Tyr
1               5

(2) INFORMATION FOR SEQ ID NO:137:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:137:

Lys Ala Leu Lys Phe Tyr Ser Lys Ile
1               5

(2) INFORMATION FOR SEQ ID NO:138:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:138:

Arg Ala His Tyr Asn Ile Val Thr Phe
1               5

(2) INFORMATION FOR SEQ ID NO:139:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:139:

Ala Ala Asp Lys Ala Ala Ala Ala Tyr
1               5

(2) INFORMATION FOR SEQ ID NO:140:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:140:

Ala Thr Ala Lys Ala Ala Ala Ala Tyr
1               5

(2) INFORMATION FOR SEQ ID NO:141:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:141:

Ala Thr Asp Lys Ala Ala Ala Ala Tyr
1               5

(2) INFORMATION FOR SEQ ID NO:142:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:142:

Ala Leu Ala Lys Ala Ala Ala Ala Val
1               5

(2) INFORMATION FOR SEQ ID NO:143:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:143:

Ala Thr Ala Ala Ala Ala Ala Ala Lys
1               5

(2) INFORMATION FOR SEQ ID NO:144:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:144:

Ala Tyr Ala Lys Ala Ala Ala Ala Phe
1               5

(2) INFORMATION FOR SEQ ID NO:145:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:145:

Ala Ala Asp Lys Ala Ala Ala Ala Ala Tyr
1               5                   10

(2) INFORMATION FOR SEQ ID NO:146:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:146:

Ala Thr Ala Lys Ala Ala Ala Ala Ala Tyr
1               5                   10

(2) INFORMATION FOR SEQ ID NO:147:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:147:

Ala Thr Asp Lys Ala Ala Ala Ala Ala Tyr
1               5                   10

(2) INFORMATION FOR SEQ ID NO:148:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:148:

Ala Leu Ala Lys Ala Ala Ala Ala Ala Val
1               5                   10

(2) INFORMATION FOR SEQ ID NO:149:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:149:

```
Ala Met Ala Ala Ala Ala Ala Ala Ala Lys
 1               5                  10
```

(2) INFORMATION FOR SEQ ID NO:150:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:150:

```
Ala Thr Ala Ala Ala Ala Ala Ala Ala Lys
 1               5                  10
```

(2) INFORMATION FOR SEQ ID NO:151:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:151:

```
Ala Leu Ala Ala Ala Ala Ala Ala Lys
 1               5
```

(2) INFORMATION FOR SEQ ID NO:152:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:152:

```
Ala Val Ala Ala Ala Ala Ala Ala Lys
 1               5
```

(2) INFORMATION FOR SEQ ID NO:153:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:153:

```
Ala Ser Ala Ala Ala Ala Ala Ala Lys
 1               5
```

(2) INFORMATION FOR SEQ ID NO:154:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:154:

```
Ala Ile Ala Ala Ala Ala Ala Ala Lys
  1               5
```

(2) INFORMATION FOR SEQ ID NO:155:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:155:

```
Ala Ala Ala Ala Ala Ala Ala Ala Lys
  1               5
```

(2) INFORMATION FOR SEQ ID NO:156:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:156:

```
Ala Phe Ala Ala Ala Ala Ala Ala Lys
  1               5
```

(2) INFORMATION FOR SEQ ID NO:157:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:157:

```
Ala Gly Ala Ala Ala Ala Ala Ala Lys
  1               5
```

(2) INFORMATION FOR SEQ ID NO:158:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:158:

```
Ala Cys Ala Ala Ala Ala Ala Ala Lys
  1               5
```

(2) INFORMATION FOR SEQ ID NO:159:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:159:

Ala Asp Ala Ala Ala Ala Ala Ala Lys
1               5

(2) INFORMATION FOR SEQ ID NO:160:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:160:

Ala Asn Ala Ala Ala Ala Ala Ala Lys
1               5

(2) INFORMATION FOR SEQ ID NO:161:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:161:

Ala Lys Ala Ala Ala Ala Ala Ala Lys
1               5

(2) INFORMATION FOR SEQ ID NO:162:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:162:

Ala Tyr Ala Ala Ala Ala Ala Ala Lys
1               5

(2) INFORMATION FOR SEQ ID NO:163:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:163:

Ala Pro Ala Ala Ala Ala Ala Ala Lys
1               5

(2) INFORMATION FOR SEQ ID NO:164:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:164:

```
Ala Leu Ala Ala Ala Ala Ala Ala Arg
  1               5
```

(2) INFORMATION FOR SEQ ID NO:165:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:165:

```
Ala Leu Ala Ala Ala Ala Ala Ala Tyr
  1               5
```

(2) INFORMATION FOR SEQ ID NO:166:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:166:

```
Ala Leu Ala Ala Ala Ala Ala Ala Ala
  1               5
```

(2) INFORMATION FOR SEQ ID NO:167:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:167:

```
Ala Leu Ala Ala Ala Ala Ala Ala Gln
  1               5
```

(2) INFORMATION FOR SEQ ID NO:168:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:168:

```
Ala Leu Ala Ala Ala Ala Ala Ala Ser
  1               5
```

(2) INFORMATION FOR SEQ ID NO:169:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:169:

Ala Leu Ala Ala Ala Ala Ala Ala Thr
1               5

(2) INFORMATION FOR SEQ ID NO:170:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:170:

Ala Leu Ala Ala Ala Ala Ala Ala Asn
1               5

(2) INFORMATION FOR SEQ ID NO:171:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:171:

Ala Leu Ala Ala Ala Ala Ala Ala Glu
1               5

(2) INFORMATION FOR SEQ ID NO:172:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:172:

Ala Phe Ala Lys Ala Ala Ala Ala Phe
1               5

(2) INFORMATION FOR SEQ ID NO:173:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:173:

Ala Pro Ala Lys Ala Ala Ala Ala Phe
1               5

(2) INFORMATION FOR SEQ ID NO:174:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:174:

Ala Ala Ala Lys Ala Ala Ala Ala Phe
1               5

(2) INFORMATION FOR SEQ ID NO:175:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:175:

Ala Lys Ala Lys Ala Ala Ala Ala Phe
1               5

(2) INFORMATION FOR SEQ ID NO:176:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:176:

Ala Tyr Ala Lys Ala Ala Ala Ala Ile
1               5

(2) INFORMATION FOR SEQ ID NO:177:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:177:

Ala Tyr Ala Lys Ala Ala Ala Ala Leu
1               5

(2) INFORMATION FOR SEQ ID NO:178:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:178:

Ala Tyr Ala Lys Ala Ala Ala Ala Val
1               5

(2) INFORMATION FOR SEQ ID NO:179:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:179:

Ala Tyr Ala Lys Ala Ala Ala Ala Ala
1               5

(2) INFORMATION FOR SEQ ID NO:180:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:180:

Ala Tyr Ala Lys Ala Ala Ala Ala Tyr
1               5

(2) INFORMATION FOR SEQ ID NO:181:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:181:

Ala Tyr Ala Lys Ala Ala Ala Ala Lys
1               5

(2) INFORMATION FOR SEQ ID NO:182:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:182:

Ala Ser Ala Lys Ala Ala Ala Ala Tyr
1               5

(2) INFORMATION FOR SEQ ID NO:183:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:183:

Ala Met Ala Lys Ala Ala Ala Ala Tyr
1               5

(2) INFORMATION FOR SEQ ID NO:184:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:184:

Ala Ala Ala Lys Ala Ala Ala Ala Tyr
1               5

(2) INFORMATION FOR SEQ ID NO:185:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:185:

Ala Leu Ala Lys Ala Ala Ala Ala Tyr
1               5

(2) INFORMATION FOR SEQ ID NO:186:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:186:

Ala Ile Ala Lys Ala Ala Ala Ala Tyr
1               5

(2) INFORMATION FOR SEQ ID NO:187:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:187:

Ala Val Ala Lys Ala Ala Ala Ala Tyr
1               5

(2) INFORMATION FOR SEQ ID NO:188:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:188:

Ala Lys Ala Lys Ala Ala Ala Ala Tyr
1               5

(2) INFORMATION FOR SEQ ID NO:189:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:189:

Ala Asn Ala Lys Ala Ala Ala Ala Tyr
1               5

(2) INFORMATION FOR SEQ ID NO:190:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:190:

Ala Asp Ala Lys Ala Ala Ala Ala Tyr
1               5

(2) INFORMATION FOR SEQ ID NO:191:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:191:

Ala Gly Ala Lys Ala Ala Ala Ala Tyr
1               5

(2) INFORMATION FOR SEQ ID NO:192:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:192:

Ala Pro Ala Lys Ala Ala Ala Ala Tyr
1               5

(2) INFORMATION FOR SEQ ID NO:193:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:193:

Ala His Ala Lys Ala Ala Ala Ala Tyr
1               5

(2) INFORMATION FOR SEQ ID NO:194:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:194:

Ala Thr Ala Lys Ala Ala Ala Ala Ala
1               5

(2) INFORMATION FOR SEQ ID NO:195:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:195:

Ala Thr Ala Lys Ala Ala Ala Ala Phe
1               5

(2) INFORMATION FOR SEQ ID NO:196:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:196:

Ala Thr Ala Lys Ala Ala Ala Ala His
1               5

(2) INFORMATION FOR SEQ ID NO:197:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:197:

Ala Thr Ala Lys Ala Ala Ala Ala Val
1               5

(2) INFORMATION FOR SEQ ID NO:198:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:198:

Ala Thr Ala Lys Ala Ala Ala Ala Asn
1               5

(2) INFORMATION FOR SEQ ID NO:199:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:199:

```
Ala Thr Ala Lys Ala Ala Ala Ala Asp
  1               5
```

(2) INFORMATION FOR SEQ ID NO:200:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:200:

```
Ala Thr Ala Lys Ala Ala Ala Ala Trp
  1               5
```

(2) INFORMATION FOR SEQ ID NO:201:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:201:

```
Ala Thr Ala Lys Ala Ala Ala Ala Lys
  1               5
```

(2) INFORMATION FOR SEQ ID NO:202:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:202:

```
Ala Thr Ala Lys Ala Ala Ala Ala Ile
  1               5
```

(2) INFORMATION FOR SEQ ID NO:203:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:203:

```
Ala Thr Ala Lys Ala Ala Ala Ala Pro
  1               5
```

(2) INFORMATION FOR SEQ ID NO:204:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:204:

Ala Ala Glu Lys Ala Ala Ala Ala Tyr
1               5

(2) INFORMATION FOR SEQ ID NO:205:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:205:

Ala Ala Ala Lys Ala Ala Ala Ala Tyr
1               5

(2) INFORMATION FOR SEQ ID NO:206:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:206:

Ala Ala Ser Lys Ala Ala Ala Ala Tyr
1               5

(2) INFORMATION FOR SEQ ID NO:207:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:207:

Ala Ala Asn Lys Ala Ala Ala Ala Tyr
1               5

(2) INFORMATION FOR SEQ ID NO:208:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:208:

Ala Ala Gln Lys Ala Ala Ala Ala Tyr
1               5

(2) INFORMATION FOR SEQ ID NO:209:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:209:

Ala Ala Lys Lys Ala Ala Ala Ala Tyr
1               5

(2) INFORMATION FOR SEQ ID NO:210:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:210:

Ala Ala Asp Lys Ala Ala Ala Ala Ala
1               5

(2) INFORMATION FOR SEQ ID NO:211:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:211:

Ala Ala Asp Lys Ala Ala Ala Ala Trp
1               5

(2) INFORMATION FOR SEQ ID NO:212:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:212:

Ala Ala Asp Lys Ala Ala Ala Ala Phe
1               5

(2) INFORMATION FOR SEQ ID NO:213:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:213:

Ala Ala Asp Lys Ala Ala Ala Ala Lys
1               5

(2) INFORMATION FOR SEQ ID NO:214:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:214:

Glu Ile Asp Gly Pro Ala Gly Gln Ala
1               5

(2) INFORMATION FOR SEQ ID NO:215:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:215:

Thr Thr Asp Leu Tyr Ala Tyr Glu Gln
1               5

(2) INFORMATION FOR SEQ ID NO:216:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:216:

Met Ser Ala Ala Arg Ser Ser Arg Thr
1               5

(2) INFORMATION FOR SEQ ID NO:217:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:217:

His Val Asp Ile Arg Thr Leu Glu Asp
1               5

(2) INFORMATION FOR SEQ ID NO:218:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:218:

Trp Thr Gly Arg Ala Met Ser Ala Ala
1               5

(2) INFORMATION FOR SEQ ID NO:219:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:219:

Tyr Arg Asp Gly Asn Pro Tyr Ala Val
1               5

(2) INFORMATION FOR SEQ ID NO:220:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:220:

Leu Ile Arg Ala Ile Asn Ala Gln Lys
1               5

(2) INFORMATION FOR SEQ ID NO:221:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:221:

Ile Val Ala Pro Ile Ala Ser Gln Lys
1               5

(2) INFORMATION FOR SEQ ID NO:222:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:222:

Ile Ile Leu Glu Ala Val Tyr Ala Lys
1               5

(2) INFORMATION FOR SEQ ID NO:223:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:223:

His Leu Asp Lys Lys Gln Arg Phe His
1               5

(2) INFORMATION FOR SEQ ID NO:224:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:224:

```
Ala Met Ser Ala Ala Arg Ser Ser Arg
1               5
```

(2) INFORMATION FOR SEQ ID NO:225:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:225:

```
Ala Met Phe Gln Asp Pro Gln Glu Arg
1               5
```

(2) INFORMATION FOR SEQ ID NO:226:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:226:

```
Ala Val Tyr Ala Lys Gln Gln Leu Leu
1               5
```

(2) INFORMATION FOR SEQ ID NO:227:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:227:

```
His Tyr Asn Ile Val Thr Phe Ala Ala
1               5
```

(2) INFORMATION FOR SEQ ID NO:228:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:228:

```
Ser Ala Ala Arg Ser Ser Arg Thr Arg
1               5
```

(2) INFORMATION FOR SEQ ID NO:229:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:229:

```
Lys Phe Tyr Ser Lys Ile Ser Glu Tyr
 1               5
```

(2) INFORMATION FOR SEQ ID NO:230:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:230:

```
Ser Leu Tyr Gly Thr Thr Leu Glu Gln
 1               5
```

(2) INFORMATION FOR SEQ ID NO:231:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:231:

```
Tyr Asn Ile Val Thr Phe Ala Ala Lys
 1               5
```

(2) INFORMATION FOR SEQ ID NO:232:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:232:

```
Ala Val Ala Asp Lys Ala Leu Lys Phe
 1               5
```

(2) INFORMATION FOR SEQ ID NO:233:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:233:

```
Gln Gln Tyr Asn Lys Pro Leu Ala Asp
 1               5
```

(2) INFORMATION FOR SEQ ID NO:234:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:234:

Lys Ile Ser Glu Tyr Arg His Tyr Ala
1               5

(2) INFORMATION FOR SEQ ID NO:235:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:235:

Arg His Tyr Ala Tyr Ser Leu Tyr Gly
1               5

(2) INFORMATION FOR SEQ ID NO:236:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:236:

Ala Ala Arg Ser Ser Arg Thr Arg Arg
1               5

(2) INFORMATION FOR SEQ ID NO:237:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:237:

Ala Ala Lys Ala Asp Ser Thr Leu Arg
1               5

(2) INFORMATION FOR SEQ ID NO:238:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:238:

Val Tyr Ala Lys Gln Gln Leu Leu Arg
1               5

(2) INFORMATION FOR SEQ ID NO:239:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:239:

Tyr Ala Val Ala Asp Lys Ala Leu Lys
1               5

(2) INFORMATION FOR SEQ ID NO:240:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:240:

Lys Ala Asp Ser Thr Leu Arg Leu Ala
1               5

(2) INFORMATION FOR SEQ ID NO:241:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:241:

Ile Val Ala Pro Ile Ala Ser Gln Lys
1               5

(2) INFORMATION FOR SEQ ID NO:242:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:242:

Thr Gly Arg Ala Met Ser Ala Ala Arg
1               5

(2) INFORMATION FOR SEQ ID NO:243:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:243:

Val Ala Pro Ile Ala Ser Gln Lys Pro
1               5

(2) INFORMATION FOR SEQ ID NO:244:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:244:

Ala Tyr Ser Leu Tyr Gly Thr Thr Leu
1               5

(2) INFORMATION FOR SEQ ID NO:245:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:245:

Arg Phe His Asn Ile Arg Gly Arg Trp
1               5

(2) INFORMATION FOR SEQ ID NO:246:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:246:

Val Tyr Asp Phe Ala Phe Arg Asp Leu
1               5

(2) INFORMATION FOR SEQ ID NO:247:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:247:

Glu Tyr Arg His Tyr Ala Tyr Ser Leu
1               5

(2) INFORMATION FOR SEQ ID NO:248:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:248:

Leu Gln Thr Thr Ile His Asp Ile Ile
1               5

(2) INFORMATION FOR SEQ ID NO:249:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:249:

Pro Tyr Ala Val Ala Asp Lys Ala Leu
1               5

(2) INFORMATION FOR SEQ ID NO:250:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:250:

Met His Gln Lys Arg Thr Ala Met Phe
1               5

(2) INFORMATION FOR SEQ ID NO:251:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:251:

His Tyr Ala Tyr Ser Leu Tyr Gly Thr
1               5

(2) INFORMATION FOR SEQ ID NO:252:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:252:

Leu Leu Arg Arg Glu Val Tyr Asp Phe
1               5

(2) INFORMATION FOR SEQ ID NO:253:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:253:

Val Tyr Ala Lys Gln Gln Leu Leu Arg
1               5

(2) INFORMATION FOR SEQ ID NO:254:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:254:

His Leu Asp Met Leu Arg His Leu Tyr
1               5

(2) INFORMATION FOR SEQ ID NO:255:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:255:

Leu Leu Asp Ile Asp Glu Thr Glu Tyr
1               5

(2) INFORMATION FOR SEQ ID NO:256:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:256:

Gly Thr Gln Leu Phe Glu Asp Asn Tyr
1               5

(2) INFORMATION FOR SEQ ID NO:257:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:257:

Leu Thr Cys Ser Pro Gln Pro Glu Tyr
1               5

(2) INFORMATION FOR SEQ ID NO:258:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:258:

Glu Thr Leu Glu Glu Ile Thr Gly Tyr
1               5

(2) INFORMATION FOR SEQ ID NO:259:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:259:

```
Gln Leu Val Thr Gln Leu Met Pro Tyr
 1               5
```

(2) INFORMATION FOR SEQ ID NO:260:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:260:

```
Phe Thr His Gln Ser Asp Val Trp Ser Tyr
 1               5                  10
```

(2) INFORMATION FOR SEQ ID NO:261:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:261:

```
Arg Leu Leu Asp Ile Asp Glu Thr Glu Tyr
 1               5                  10
```

(2) INFORMATION FOR SEQ ID NO:262:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:262:

```
Thr Leu Glu Glu Ile Thr Gly Tyr Leu Tyr
 1               5                  10
```

(2) INFORMATION FOR SEQ ID NO:263:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:263:

```
Tyr Val Met Ala Gly Val Gly Ser Pro Tyr
 1               5                  10
```

(2) INFORMATION FOR SEQ ID NO:264:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:264:

Gly Thr Pro Thr Ala Glu Asn Pro Glu Tyr
1               5                   10

(2) INFORMATION FOR SEQ ID NO:265:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:265:

Arg Val Leu Gln Gly Leu Pro Arg Glu Tyr
1               5                   10

(2) INFORMATION FOR SEQ ID NO:266:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:266:

Leu Ile Gln Arg Asn Pro Gln Leu Cys Tyr
1               5                   10

(2) INFORMATION FOR SEQ ID NO:267:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:267:

Val Val Gln Gly Asn Leu Glu Leu Thr Tyr
1               5                   10

(2) INFORMATION FOR SEQ ID NO:268:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:268:

Met Gly Asp Leu Val Asp Ala Glu Glu Tyr
1               5                   10

(2) INFORMATION FOR SEQ ID NO:269:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:269:

Lys Ile Arg Lys Tyr Thr Met Arg Arg
1               5

(2) INFORMATION FOR SEQ ID NO:270:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:270:

Val Val Phe Gly Ile Leu Ile Lys Arg
1               5

(2) INFORMATION FOR SEQ ID NO:271:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:271:

Leu Val Lys Ser Pro Asn His Val Lys
1               5

(2) INFORMATION FOR SEQ ID NO:272:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:272:

Val Leu Arg Glu Asn Thr Ser Pro Lys
1               5

(2) INFORMATION FOR SEQ ID NO:273:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:273:

Ile Leu Ile Lys Arg Arg Gln Gln Lys
1               5

(2) INFORMATION FOR SEQ ID NO:274:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:274:

Ile Leu Trp Lys Asp Ile Phe His Lys
1               5

(2) INFORMATION FOR SEQ ID NO:275:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:275:

Lys Ile Thr Asp Phe Gly Leu Ala Arg
1               5

(2) INFORMATION FOR SEQ ID NO:276:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:276:

Gly Val Val Phe Gly Ile Leu Ile Lys
1               5

(2) INFORMATION FOR SEQ ID NO:277:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:277:

Gln Val Cys Thr Gly Thr Asp Met Lys
1               5

(2) INFORMATION FOR SEQ ID NO:278:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:278:

Leu Leu Asp His Val Arg Glu Asn Arg
1               5

(2) INFORMATION FOR SEQ ID NO:279:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:279:

Cys Val Asn Cys Ser Gln Phe Leu Arg
1               5

(2) INFORMATION FOR SEQ ID NO:280:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:280:

Thr Val Cys Ala Gly Gly Cys Ala Arg
1               5

(2) INFORMATION FOR SEQ ID NO:281:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:281:

Ile Leu Lys Glu Thr Glu Leu Arg Lys
1               5

(2) INFORMATION FOR SEQ ID NO:282:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:282:

Val Thr Ala Glu Asp Gly Thr Gln Arg
1               5

(2) INFORMATION FOR SEQ ID NO:283:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:283:

Asp Leu Ser Tyr Met Pro Ile Trp Lys
1               5

(2) INFORMATION FOR SEQ ID NO:284:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:284:

```
Thr Ile Leu Trp Lys Asp Ile Phe His Lys
 1               5                  10
```

(2) INFORMATION FOR SEQ ID NO:285:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:285:

```
Gly Thr Gln Arg Cys Glu Lys Cys Ser Lys
 1               5                  10
```

(2) INFORMATION FOR SEQ ID NO:286:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:286:

```
Lys Val Leu Arg Glu Asn Thr Ser Pro Lys
 1               5                  10
```

(2) INFORMATION FOR SEQ ID NO:287:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:287:

```
Gln Leu Arg Ser Leu Thr Glu Ile Leu Lys
 1               5                  10
```

(2) INFORMATION FOR SEQ ID NO:288:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:288:

```
Arg Leu Val His Arg Asp Leu Ala Ala Arg
 1               5                  10
```

(2) INFORMATION FOR SEQ ID NO:289:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:289:

```
Leu Leu Asn Trp Cys Met Gln Ile Ala Lys
1               5                   10
```

(2) INFORMATION FOR SEQ ID NO:290:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:290:

```
Thr Ile Asp Val Tyr Met Ile Met Val Lys
1               5                   10
```

(2) INFORMATION FOR SEQ ID NO:291:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:291:

```
Arg Ile Leu Lys Glu Thr Glu Leu Arg Lys
1               5                   10
```

(2) INFORMATION FOR SEQ ID NO:292:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:292:

```
Val Leu Val Lys Ser Pro Asn His Val Lys
1               5                   10
```

(2) INFORMATION FOR SEQ ID NO:293:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:293:

```
Ser Val Phe Gln Asn Leu Gln Val Ile Arg
1               5                   10
```

(2) INFORMATION FOR SEQ ID NO:294:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:294:

His Thr Val Pro Trp Asp Gln Leu Phe Arg
1               5                   10

(2) INFORMATION FOR SEQ ID NO:295:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:295:

Ile Leu Lys Gly Gly Val Leu Ile Gln Arg
1               5                   10

(2) INFORMATION FOR SEQ ID NO:296:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:296:

Leu Val Ser Glu Phe Ser Arg Met Ala Arg
1               5                   10

(2) INFORMATION FOR SEQ ID NO:297:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:297:

Gly Val Val Phe Gly Ile Leu Ile Lys Arg
1               5                   10

(2) INFORMATION FOR SEQ ID NO:298:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:298:

Cys Val Ala Arg Cys Pro Ser Gly Val Lys
1               5                   10

(2) INFORMATION FOR SEQ ID NO:299:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:299:

```
Val Val Phe Gly Ile Leu Ile Lys Arg Arg
1               5                   10
```

(2) INFORMATION FOR SEQ ID NO:300:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:300:

```
Gly Ile Leu Ile Lys Arg Arg Gln Gln Lys
1               5                   10
```

(2) INFORMATION FOR SEQ ID NO:301:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:301:

```
Arg Thr Val Cys Ala Gly Gly Cys Ala Arg
1               5                   10
```

(2) INFORMATION FOR SEQ ID NO:302:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:302:

```
Gly Leu Ala Cys His Gln Leu Cys Ala Arg
1               5                   10
```

(2) INFORMATION FOR SEQ ID NO:303:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:303:

```
Lys Ile Pro Val Ala Ile Lys Val Leu Arg
1               5                   10
```

(2) INFORMATION FOR SEQ ID NO:304:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:304:

Val Gly Glu Ala Asp Tyr Phe Glu Tyr
1               5

(2) INFORMATION FOR SEQ ID NO:305:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:305:

Pro Leu Arg Glu Ser Ile Val Cys Tyr
1               5

(2) INFORMATION FOR SEQ ID NO:306:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:306:

Pro Val Gly Glu Ala Asp Tyr Phe Glu Tyr
1               5                   10

(2) INFORMATION FOR SEQ ID NO:307:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:307:

Gly Thr Trp Val Ala Gly Val Phe Val Tyr
1               5                   10

(2) INFORMATION FOR SEQ ID NO:308:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:308:

Gly Val Phe Val Tyr Gly Gly Ser Lys
1               5

(2) INFORMATION FOR SEQ ID NO:309:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:309:

Lys Thr Ser Leu Tyr Asn Leu Arg Arg
 1               5

(2) INFORMATION FOR SEQ ID NO:310:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:310:

Ala Ile Lys Asp Leu Val Met Thr Lys
 1               5

(2) INFORMATION FOR SEQ ID NO:311:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:311:

Gln Thr His Ile Phe Ala Glu Val Leu Lys
 1               5                  10

(2) INFORMATION FOR SEQ ID NO:312:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:312:

Gly Thr Ala Leu Ala Ile Pro Gln Cys Arg
 1               5                  10

(2) INFORMATION FOR SEQ ID NO:313:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:313:

Cys Thr Glu Leu Lys Leu Ser Asp Tyr
 1               5

(2) INFORMATION FOR SEQ ID NO:314:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:314:

```
Ser Thr Leu Glu Leu Arg Ser Arg Tyr
1               5
```

(2) INFORMATION FOR SEQ ID NO:315:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:315:

```
Ile Leu Arg Gly Ser Val Ala His Lys
1               5
```

(2) INFORMATION FOR SEQ ID NO:316:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:316:

```
Arg Met Cys Asn Ile Leu Lys Gly Lys
1               5
```

(2) INFORMATION FOR SEQ ID NO:317:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:317:

```
Leu Met Gln Gly Ser Thr Leu Pro Arg
1               5
```

(2) INFORMATION FOR SEQ ID NO:318:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:318:

```
Met Ile Asp Gly Ile Gly Arg Phe Tyr
1               5
```

(2) INFORMATION FOR SEQ ID NO:319:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:319:

Met Val Leu Ser Ala Phe Asp Glu Arg
 1               5

(2) INFORMATION FOR SEQ ID NO:320:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:320:

Tyr Ile Gln Met Cys Thr Glu Leu Lys
 1               5

(2) INFORMATION FOR SEQ ID NO:321:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:321:

Gly Ile Asn Asp Arg Asn Phe Trp Arg
 1               5

(2) INFORMATION FOR SEQ ID NO:322:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:322:

Ser Leu Met Gln Gly Ser Thr Leu Pro Arg
 1               5                  10

(2) INFORMATION FOR SEQ ID NO:323:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:323:

Lys Met Ile Asp Gly Ile Gly Arg Phe Tyr
 1               5                  10

(2) INFORMATION FOR SEQ ID NO:324:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:324:

```
Leu Ile Leu Arg Gly Ser Val Ala His Lys
 1               5                  10
```

(2) INFORMATION FOR SEQ ID NO:325:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:325:

```
Arg Ser Gly Ala Ala Gly Ala Ala Val Lys
 1               5                  10
```

(2) INFORMATION FOR SEQ ID NO:326:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:326:

```
Ser Ser Thr Leu Glu Leu Arg Ser Arg Tyr
 1               5                  10
```

(2) INFORMATION FOR SEQ ID NO:327:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:327:

```
Arg Ser Arg Tyr Trp Ala Ile Arg Thr Arg
 1               5                  10
```

(2) INFORMATION FOR SEQ ID NO:328:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:328:

```
Arg Met Val Leu Ser Ala Phe Asp Glu Arg
 1               5                  10
```

(2) INFORMATION FOR SEQ ID NO:329:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:329:

Phe Tyr Ile Gln Met Cys Thr Glu Leu
1               5

(2) INFORMATION FOR SEQ ID NO:330:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:330:

Ala Tyr Glu Arg Met Cys Asn Ile Leu
1               5

(2) INFORMATION FOR SEQ ID NO:331:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:331:

Arg Phe Tyr Ile Gln Met Cys Thr Glu Leu
1               5                   10

(2) INFORMATION FOR SEQ ID NO:332:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:332:

Leu Leu Asp Thr Ala Ser Ala Leu Tyr
1               5

(2) INFORMATION FOR SEQ ID NO:333:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:333:

Ser Leu Asp Val Ser Ala Ala Phe Tyr
1               5

(2) INFORMATION FOR SEQ ID NO:334:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:334:

```
Pro Thr Thr Gly Arg Thr Ser Leu Tyr
1               5
```

(2) INFORMATION FOR SEQ ID NO:335:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:335:

```
Met Ser Thr Thr Asp Leu Glu Ala Tyr
1               5
```

(2) INFORMATION FOR SEQ ID NO:336:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:336:

```
Leu Thr Lys Gln Tyr Leu Asn Leu Tyr
1               5
```

(2) INFORMATION FOR SEQ ID NO:337:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:337:

```
Lys Val Gly Asn Phe Thr Gly Leu Tyr
1               5
```

(2) INFORMATION FOR SEQ ID NO:338:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:338:

```
Met Ser Pro Thr Asp Leu Glu Ala Tyr
1               5
```

(2) INFORMATION FOR SEQ ID NO:339:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:339:

Phe Ser Gln Phe Ser Arg Gly Asn Tyr
1               5

(2) INFORMATION FOR SEQ ID NO:340:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:340:

Pro Ser Ser Trp Ala Phe Ala Lys Tyr
1               5

(2) INFORMATION FOR SEQ ID NO:341:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:341:

Gln Ser Ala Val Arg Lys Glu Ala Tyr
1               5

(2) INFORMATION FOR SEQ ID NO:342:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:342:

Pro Leu Asp Lys Gly Ile Lys Pro Tyr
1               5

(2) INFORMATION FOR SEQ ID NO:343:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:343:

Ser Leu Met Leu Leu Tyr Lys Thr Tyr
1               5

(2) INFORMATION FOR SEQ ID NO:344:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:344:

```
Ala Ser Arg Asp Leu Val Val Ser Tyr
1               5
```

(2) INFORMATION FOR SEQ ID NO:345:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:345:

```
Pro Ser Arg Gly Arg Leu Gly Leu Tyr
1               5
```

(2) INFORMATION FOR SEQ ID NO:346:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:346:

```
Ser Ser Thr Ser Arg Asn Ile Asn Tyr
1               5
```

(2) INFORMATION FOR SEQ ID NO:347:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:347:

```
Asp Leu Leu Asp Thr Ala Ser Ala Leu Tyr
1               5                   10
```

(2) INFORMATION FOR SEQ ID NO:348:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:348:

```
Leu Leu Asp Pro Arg Val Arg Gly Leu Tyr
1               5                   10
```

(2) INFORMATION FOR SEQ ID NO:349:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:349:

```
Leu Ser Leu Asp Val Ser Ala Ala Phe Tyr
  1               5                  10
```

(2) INFORMATION FOR SEQ ID NO:350:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:350:

```
Phe Leu Cys Gln Gln Tyr Leu His Leu Tyr
  1               5                  10
```

(2) INFORMATION FOR SEQ ID NO:351:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:351:

```
Gln Thr Phe Gly Arg Lys Leu His Leu Tyr
  1               5                  10
```

(2) INFORMATION FOR SEQ ID NO:352:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:352:

```
Lys Thr Tyr Gly Arg Lys Leu His Leu Tyr
  1               5                  10
```

(2) INFORMATION FOR SEQ ID NO:353:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:353:

```
Lys Thr Phe Gly Arg Lys Leu His Leu Tyr
  1               5                  10
```

(2) INFORMATION FOR SEQ ID NO:354:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:354:

Leu Gln Asp Pro Arg Val Arg Ala Leu Tyr
 1               5                  10

(2) INFORMATION FOR SEQ ID NO:355:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:355:

Thr Thr Pro Ala Gln Gly Thr Ser Met Tyr
 1               5                  10

(2) INFORMATION FOR SEQ ID NO:356:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:356:

Leu Ser Ser Thr Ser Arg Asn Ile Asn Tyr
 1               5                  10

(2) INFORMATION FOR SEQ ID NO:357:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:357:

Pro Leu Asp Lys Gly Ile Lys Pro Tyr Tyr
 1               5                  10

(2) INFORMATION FOR SEQ ID NO:358:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:358:

His Ser Ala Ser Phe Cys Gly Ser Pro Tyr
 1               5                  10

(2) INFORMATION FOR SEQ ID NO:359:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:359:

Phe Leu Thr Lys Gln Tyr Leu Asn Leu Tyr
 1               5                  10

(2) INFORMATION FOR SEQ ID NO:360:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:360:

Arg Ser Ala Ser Phe Cys Gly Ser Pro Tyr
 1               5                  10

(2) INFORMATION FOR SEQ ID NO:361:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:361:

Trp Leu Trp Gly Met Asp Ile Asp Pro Tyr
 1               5                  10

(2) INFORMATION FOR SEQ ID NO:362:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:362:

His Thr Leu Trp Lys Ala Gly Ile Leu Tyr
 1               5                  10

(2) INFORMATION FOR SEQ ID NO:363:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:363:

Thr Ser Cys Pro Pro Ile Cys Pro Gly Tyr
 1               5                  10

(2) INFORMATION FOR SEQ ID NO:364:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:364:

```
Lys Ser Val Gln His Leu Glu Ser Leu Tyr
1               5                   10
```

(2) INFORMATION FOR SEQ ID NO:365:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:365:

```
Asn Leu Tyr Val Ser Leu Leu Leu Leu Tyr
1               5                   10
```

(2) INFORMATION FOR SEQ ID NO:366:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:366:

```
Leu Leu Tyr Gln Thr Phe Gly Arg Lys
1               5
```

(2) INFORMATION FOR SEQ ID NO:367:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:367:

```
Ile Met Pro Ala Arg Phe Tyr Pro Lys
1               5
```

(2) INFORMATION FOR SEQ ID NO:368:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:368:

```
Cys Leu His Gln Ser Pro Val Arg Lys
1               5
```

(2) INFORMATION FOR SEQ ID NO:369:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:369:

Ser Ala Ile Cys Ser Val Val Arg Arg
1               5

(2) INFORMATION FOR SEQ ID NO:370:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:370:

His Leu His Gln Asp Ile Ile Lys Lys
1               5

(2) INFORMATION FOR SEQ ID NO:371:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:371:

Ser Leu Pro Gln Glu His Ile Ile Gln Lys
1               5                   10

(2) INFORMATION FOR SEQ ID NO:372:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:372:

Ser Met Phe Pro Ser Cys Cys Cys Thr Lys
1               5                   10

(2) INFORMATION FOR SEQ ID NO:373:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:373:

Ser Met Tyr Pro Ser Cys Cys Cys Thr Lys
1               5                   10

(2) INFORMATION FOR SEQ ID NO:374:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:374:

```
Gln Ala Phe Thr Phe Ser Pro Thr Tyr Lys
  1               5                  10
```

(2) INFORMATION FOR SEQ ID NO:375:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:375:

```
Leu Leu Leu Tyr Gln Thr Phe Gly Arg Lys
  1               5                  10
```

(2) INFORMATION FOR SEQ ID NO:376:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:376:

```
Tyr Met Asp Asp Val Val Leu Gly Ala Lys
  1               5                  10
```

(2) INFORMATION FOR SEQ ID NO:377:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:377:

```
Thr Ser Ala Ile Cys Ser Val Val Arg Arg
  1               5                  10
```

(2) INFORMATION FOR SEQ ID NO:378:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:378:

```
Pro Thr Tyr Lys Ala Phe Leu Cys Lys
  1               5
```

(2) INFORMATION FOR SEQ ID NO:379:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:379:

Pro Thr Asp Leu Glu Ala Tyr Phe Lys
1               5

(2) INFORMATION FOR SEQ ID NO:380:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:380:

Lys Tyr Thr Ser Phe Pro Trp Leu Leu
1               5

(2) INFORMATION FOR SEQ ID NO:381:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:381:

Leu Tyr Ala Ala Val Thr Asn Phe Leu
1               5

(2) INFORMATION FOR SEQ ID NO:382:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:382:

Phe Tyr Pro Asn Leu Thr Lys Tyr Leu
1               5

(2) INFORMATION FOR SEQ ID NO:383:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:383:

Leu Tyr Ser Ser Thr Val Pro Ser Phe
1               5

(2) INFORMATION FOR SEQ ID NO:384:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:384:

Phe Tyr Pro Lys Val Thr Lys Tyr Leu
1               5

(2) INFORMATION FOR SEQ ID NO:385:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:385:

Phe Tyr Pro Asn Val Thr Lys Tyr Leu
1               5

(2) INFORMATION FOR SEQ ID NO:386:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:386:

Leu Tyr Ser Ile Leu Ser Pro Phe Leu
1               5

(2) INFORMATION FOR SEQ ID NO:387:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:387:

Leu Tyr Ser Ser Thr Val Pro Val Leu
1               5

(2) INFORMATION FOR SEQ ID NO:388:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:388:

Leu Tyr Asn Ile Leu Ser Pro Phe Leu
1               5

(2) INFORMATION FOR SEQ ID NO:389:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:389:

Asn Tyr Arg Val Ser Trp Pro Lys Phe
1               5

(2) INFORMATION FOR SEQ ID NO:390:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:390:

His Tyr Phe Gln Thr Arg His Tyr Leu
1               5

(2) INFORMATION FOR SEQ ID NO:391:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:391:

His Tyr Phe Lys Thr Arg His Tyr Leu
1               5

(2) INFORMATION FOR SEQ ID NO:392:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:392:

Gly Tyr Pro Ala Leu Met Pro Leu Tyr
1               5

(2) INFORMATION FOR SEQ ID NO:393:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:393:

Ala Tyr Arg Pro Pro Asn Ala Pro Ile
1               5

(2) INFORMATION FOR SEQ ID NO:394:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:394:

Leu Tyr Gln Thr Phe Gly Arg Lys Leu
1               5

(2) INFORMATION FOR SEQ ID NO:395:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:395:

Ser Tyr Gln His Phe Arg Arg Leu Leu
1               5

(2) INFORMATION FOR SEQ ID NO:396:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:396:

Leu Tyr Ser His Pro Ile Ile Leu Gly Phe
1               5                   10

(2) INFORMATION FOR SEQ ID NO:397:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:397:

Leu Tyr Ala Ala Val Thr Asn Phe Leu Leu
1               5                   10

(2) INFORMATION FOR SEQ ID NO:398:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:398:

Leu Tyr Arg Pro Leu Leu Ser Leu Pro Phe
1               5                   10

(2) INFORMATION FOR SEQ ID NO:399:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:399:

```
Ser Tyr Gln His Phe Arg Arg Leu Leu Leu
1               5                   10
```

(2) INFORMATION FOR SEQ ID NO:400:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:400:

```
Ser Tyr Gln His Phe Arg Lys Leu Leu Leu
1               5                   10
```

(2) INFORMATION FOR SEQ ID NO:401:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:401:

```
Tyr Tyr Pro Glu His Leu Val Asn His Tyr
1               5                   10
```

(2) INFORMATION FOR SEQ ID NO:402:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:402:

```
Ala Tyr Arg Pro Pro Asn Ala Pro Ile Leu
1               5                   10
```

(2) INFORMATION FOR SEQ ID NO:403:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:403:

```
Gly Tyr Arg Trp Met Cys Leu Arg Arg Phe
1               5                   10
```

(2) INFORMATION FOR SEQ ID NO:404:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:404:

```
Asn Phe Leu Leu Ser Leu Gly Ile His Leu
 1               5                  10
```

(2) INFORMATION FOR SEQ ID NO:405:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:405:

```
Tyr Val Ser Leu Met Leu Leu Tyr Lys
 1               5
```

(2) INFORMATION FOR SEQ ID NO:406:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:406:

```
Leu Leu Tyr Lys Thr Phe Gly Arg Lys
 1               5
```

(2) INFORMATION FOR SEQ ID NO:407:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:407:

```
Leu Leu Tyr Lys Thr Tyr Gly Arg Lys
 1               5
```

(2) INFORMATION FOR SEQ ID NO:408:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:408:

```
Val Thr Lys Tyr Leu Pro Leu Asp Lys
 1               5
```

(2) INFORMATION FOR SEQ ID NO:409:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:409:

Arg His Tyr Leu His Thr Leu Trp Lys
1               5

(2) INFORMATION FOR SEQ ID NO:410:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:410:

Ser Thr Val Pro Ser Phe Asn Pro Lys
1               5

(2) INFORMATION FOR SEQ ID NO:411:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:411:

Thr Thr Asp Leu Glu Ala Tyr Phe Lys
1               5

(2) INFORMATION FOR SEQ ID NO:412:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:412:

Tyr Val Ser Leu Leu Leu Leu Tyr Lys
1               5

(2) INFORMATION FOR SEQ ID NO:413:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:413:

Pro Thr Tyr Lys Ala Phe Leu Thr Lys
1               5

(2) INFORMATION FOR SEQ ID NO:414:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:414:

His Leu Tyr Pro Val Ala Arg Gln Arg
1               5

(2) INFORMATION FOR SEQ ID NO:415:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:415:

Ser Thr Asn Arg Gln Leu Gly Arg Lys
1               5

(2) INFORMATION FOR SEQ ID NO:416:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:416:

Ala Leu Arg Phe Thr Ser Ala Arg Arg
1               5

(2) INFORMATION FOR SEQ ID NO:417:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:417:

Pro Val Asn Arg Pro Ile Asp Trp Lys
1               5

(2) INFORMATION FOR SEQ ID NO:418:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:418:

Thr Val Asn Glu Asn Arg Arg Leu Lys
1               5

(2) INFORMATION FOR SEQ ID NO:419:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:419:

```
Val Val Asn His Tyr Phe Gln Thr Arg
1               5
```

(2) INFORMATION FOR SEQ ID NO:420:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:420:

```
Ser Thr Thr Ser Thr Gly Pro Cys Lys
1               5
```

(2) INFORMATION FOR SEQ ID NO:421:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:421:

```
Gln Val Leu Pro Lys Leu Leu His Lys
1               5
```

(2) INFORMATION FOR SEQ ID NO:422:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:422:

```
Leu Thr Lys Tyr Leu Pro Leu Asp Lys
1               5
```

(2) INFORMATION FOR SEQ ID NO:423:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:423:

```
Cys Leu His Gln Ser Ala Val Arg Lys
1               5
```

(2) INFORMATION FOR SEQ ID NO:424:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:424:

Val Val Asp Phe Ser Gln Phe Ser Arg
1               5

(2) INFORMATION FOR SEQ ID NO:425:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:425:

Pro Leu Tyr Ala Cys Ile Gln Ala Lys
1               5

(2) INFORMATION FOR SEQ ID NO:426:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:426:

Tyr Val Asn Thr Asn Met Gly Leu Lys
1               5

(2) INFORMATION FOR SEQ ID NO:427:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:427:

Pro Leu Tyr Ala Cys Ile Gln Ser Lys
1               5

(2) INFORMATION FOR SEQ ID NO:428:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:428:

Arg Leu Ala Asp Glu Gly Leu Asn Arg
1               5

(2) INFORMATION FOR SEQ ID NO:429:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:429:

```
Ala Val Asn His Tyr Phe Lys Thr Arg
1               5
```

(2) INFORMATION FOR SEQ ID NO:430:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:430:

```
Arg Leu Lys Leu Ile Met Pro Ala Arg
1               5
```

(2) INFORMATION FOR SEQ ID NO:431:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:431:

```
Ile Leu Tyr Lys Arg Glu Thr Thr Arg
1               5
```

(2) INFORMATION FOR SEQ ID NO:432:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:432:

```
Lys Val Phe Val Leu Gly Gly Cys Arg
1               5
```

(2) INFORMATION FOR SEQ ID NO:433:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:433:

```
Asn Val Ser Ile Pro Trp Thr His Lys
1               5
```

(2) INFORMATION FOR SEQ ID NO:434:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:434:

Leu Leu Leu Tyr Lys Thr Phe Gly Arg
1               5

(2) INFORMATION FOR SEQ ID NO:435:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:435:

Arg Leu Val Phe Gln Thr Ser Thr Arg
1               5

(2) INFORMATION FOR SEQ ID NO:436:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:436:

Phe Val Leu Gly Gly Cys Arg His Lys
1               5

(2) INFORMATION FOR SEQ ID NO:437:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:437:

Arg Leu Val Leu Gln Thr Ser Thr Arg
1               5

(2) INFORMATION FOR SEQ ID NO:438:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:438:

Met Leu Leu Tyr Lys Thr Tyr Gly Arg
1               5

(2) INFORMATION FOR SEQ ID NO:439:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:439:

Thr Val Asn Glu Lys Arg Arg Leu Lys
1               5

(2) INFORMATION FOR SEQ ID NO:440:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:440:

Asn Leu Tyr Pro Val Ala Arg Gln Arg
1               5

(2) INFORMATION FOR SEQ ID NO:441:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:441:

Leu Pro Tyr Arg Pro Thr Thr Gly Arg
1               5

(2) INFORMATION FOR SEQ ID NO:442:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:442:

Leu Val Ser Phe Gly Val Trp Ile Arg
1               5

(2) INFORMATION FOR SEQ ID NO:443:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:443:

Leu Val Gly Ser Ser Gly Leu Pro Arg
1               5

(2) INFORMATION FOR SEQ ID NO:444:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:444:

His Ile Ser Cys Leu Thr Phe Gly Arg
1               5

(2) INFORMATION FOR SEQ ID NO:445:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:445:

Ser Val Pro Ser Arg Leu Pro Asp Arg
1               5

(2) INFORMATION FOR SEQ ID NO:446:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:446:

Ser Val Pro Ser His Leu Pro Asp Arg
1               5

(2) INFORMATION FOR SEQ ID NO:447:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:447:

Thr Leu Pro Gln Glu His Ile Val Leu Lys
1               5                   10

(2) INFORMATION FOR SEQ ID NO:448:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:448:

Thr Val Pro Val Phe Asn Pro His Trp Lys
1               5                   10

(2) INFORMATION FOR SEQ ID NO:449:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:449:

Thr Leu Trp Lys Ala Gly Ile Leu Tyr Lys
 1               5                  10

(2) INFORMATION FOR SEQ ID NO:450:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:450:

Arg Leu Pro Tyr Arg Pro Thr Thr Gly Arg
 1               5                  10

(2) INFORMATION FOR SEQ ID NO:451:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:451:

Ser Thr Thr Asp Leu Glu Ala Tyr Phe Lys
 1               5                  10

(2) INFORMATION FOR SEQ ID NO:452:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:452:

Leu Leu Leu Tyr Lys Thr Phe Gly Arg Lys
 1               5                  10

(2) INFORMATION FOR SEQ ID NO:453:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:453:

Thr Val Asn Ala His Arg Asn Leu Pro Lys
 1               5                  10

(2) INFORMATION FOR SEQ ID NO:454:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:454:

```
Glu Ala Tyr Phe Lys Asp Cys Leu Phe Lys
 1               5                  10
```

(2) INFORMATION FOR SEQ ID NO:455:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:455:

```
Leu Val Val Asp Phe Ser Gln Phe Ser Arg
 1               5                  10
```

(2) INFORMATION FOR SEQ ID NO:456:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:456:

```
Met Leu Leu Tyr Lys Thr Tyr Gly Arg Lys
 1               5                  10
```

(2) INFORMATION FOR SEQ ID NO:457:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:457:

```
Thr Ala Tyr Ser His Leu Ser Thr Ser Lys
 1               5                  10
```

(2) INFORMATION FOR SEQ ID NO:458:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:458:

```
Ser Leu Gly Ile His Leu Asn Pro Asn Lys
 1               5                  10
```

(2) INFORMATION FOR SEQ ID NO:459:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:459:

```
Arg Leu Gly Leu Tyr Arg Pro Leu Leu Arg
  1               5                  10
```

(2) INFORMATION FOR SEQ ID NO:460:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:460:

```
Val Thr Gly Gly Val Phe Leu Val Asp Lys
  1               5                  10
```

(2) INFORMATION FOR SEQ ID NO:461:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:461:

```
Arg Ile Arg Thr Pro Arg Thr Pro Ala Arg
  1               5                  10
```

(2) INFORMATION FOR SEQ ID NO:462:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:462:

```
Thr Val Asn Gly His Gln Val Leu Pro Lys
  1               5                  10
```

(2) INFORMATION FOR SEQ ID NO:463:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:463:

```
Ser Leu Pro Phe Gln Pro Thr Thr Gly Arg
  1               5                  10
```

(2) INFORMATION FOR SEQ ID NO:464:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:464:

```
Thr Leu Pro Glu Thr Thr Val Val Arg Arg
1               5                   10
```

(2) INFORMATION FOR SEQ ID NO:465:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:465:

```
Gly Thr Asp Asn Ser Val Val Leu Ser Arg
1               5                   10
```

(2) INFORMATION FOR SEQ ID NO:466:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:466:

```
Ser Thr Leu Pro Glu Thr Thr Val Val Arg
1               5                   10
```

(2) INFORMATION FOR SEQ ID NO:467:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:467:

```
Lys Val Thr Lys Tyr Leu Pro Leu Asp Lys
1               5                   10
```

(2) INFORMATION FOR SEQ ID NO:468:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:468:

```
Ser Thr Arg His Gly Asp Lys Ser Phe Arg
1               5                   10
```

(2) INFORMATION FOR SEQ ID NO:469:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:469:

```
Val Leu Ser Cys Trp Trp Leu Gln Phe Arg
1               5                   10
```

(2) INFORMATION FOR SEQ ID NO:470:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:470:

```
Asn Val Thr Lys Tyr Leu Pro Leu Asp Lys
1               5                   10
```

(2) INFORMATION FOR SEQ ID NO:471:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:471:

```
Arg Val Cys Cys Gln Leu Asp Pro Ala Arg
1               5                   10
```

(2) INFORMATION FOR SEQ ID NO:472:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:472:

```
Ser Leu Gly Ile His Leu Asn Pro Gln Lys
1               5                   10
```

(2) INFORMATION FOR SEQ ID NO:473:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:473:

```
Tyr Leu Val Ser Phe Gly Val Trp Ile Arg
1               5                   10
```

(2) INFORMATION FOR SEQ ID NO:474:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:474:

```
Phe Val Gly Pro Leu Thr Val Asn Glu Lys
 1               5                  10
```

(2) INFORMATION FOR SEQ ID NO:475:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:475:

```
Tyr Val Gly Pro Leu Thr Val Asn Glu Lys
 1               5                  10
```

(2) INFORMATION FOR SEQ ID NO:476:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:476:

```
Arg Leu Ala Asp Glu Gly Leu Asn Arg Arg
 1               5                  10
```

(2) INFORMATION FOR SEQ ID NO:477:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:477:

```
Ile Val Leu Lys Leu Lys Gln Cys Phe Arg
 1               5                  10
```

(2) INFORMATION FOR SEQ ID NO:478:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:478:

```
Pro Ile Pro Ser Ser Trp Ala Phe Ala Lys
 1               5                  10
```

(2) INFORMATION FOR SEQ ID NO:479:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:479:

Leu Thr Val Asn Glu Asn Arg Arg Leu Lys
1               5                   10

(2) INFORMATION FOR SEQ ID NO:480:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:480:

Cys Thr Cys Gly Ser Ser Asp Leu Tyr
1               5

(2) INFORMATION FOR SEQ ID NO:481:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:481:

Asn Ile Val Asp Val Gln Tyr Leu Tyr
1               5

(2) INFORMATION FOR SEQ ID NO:482:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:482:

Arg Val Cys Glu Lys Met Ala Leu Tyr
1               5

(2) INFORMATION FOR SEQ ID NO:483:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:483:

Asp Val Val Cys Cys Ser Met Ser Tyr
1               5

(2) INFORMATION FOR SEQ ID NO:484:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:484:

```
Gly Leu Ser Ala Phe Ser Leu His Ser Tyr
 1               5                  10
```

(2) INFORMATION FOR SEQ ID NO:485:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:485:

```
Thr Leu His Gly Pro Thr Pro Leu Leu Tyr
 1               5                  10
```

(2) INFORMATION FOR SEQ ID NO:486:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:486:

```
Glu Tyr Val Leu Leu Leu Phe Leu Leu
 1               5
```

(2) INFORMATION FOR SEQ ID NO:487:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:487:

```
Met Tyr Val Gly Gly Val Glu His Arg Leu
 1               5                  10
```

(2) INFORMATION FOR SEQ ID NO:488:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:488:

```
Glu Tyr Val Leu Leu Leu Phe Leu Leu Leu
 1               5                  10
```

(2) INFORMATION FOR SEQ ID NO:489:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:489:

Ser Val Pro Ala Glu Ile Leu Arg Lys
1               5

(2) INFORMATION FOR SEQ ID NO:490:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:490:

Gln Leu Phe Thr Phe Ser Pro Arg Arg
1               5

(2) INFORMATION FOR SEQ ID NO:491:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:491:

Leu Ile Phe Cys His Ser Lys Lys Lys
1               5

(2) INFORMATION FOR SEQ ID NO:492:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:492:

His Leu Ile Phe Cys His Ser Lys Lys
1               5

(2) INFORMATION FOR SEQ ID NO:493:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:493:

Lys Thr Ser Glu Arg Ser Gln Pro Arg
1               5

(2) INFORMATION FOR SEQ ID NO:494:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:494:

Ala Val Cys Thr Arg Gly Val Ala Lys
 1               5

(2) INFORMATION FOR SEQ ID NO:495:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:495:

Glu Val Phe Cys Val Gln Pro Glu Lys
 1               5

(2) INFORMATION FOR SEQ ID NO:496:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:496:

Ile Thr Arg Val Glu Ser Glu Asn Lys
 1               5

(2) INFORMATION FOR SEQ ID NO:497:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:497:

Cys Ile Ile Thr Ser Leu Thr Gly Arg
 1               5

(2) INFORMATION FOR SEQ ID NO:498:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:498:

Gly Val Ala Gly Ala Leu Val Ala Phe Lys
 1               5                   10

(2) INFORMATION FOR SEQ ID NO:499:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:499:

His Leu His Ala Pro Thr Gly Ser Gly Lys
1               5                   10

(2) INFORMATION FOR SEQ ID NO:500:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:500:

Arg Met Tyr Val Gly Gly Val Glu His Arg
1               5                   10

(2) INFORMATION FOR SEQ ID NO:501:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:501:

His Leu Ile Phe Cys His Ser Lys Lys Lys
1               5                   10

(2) INFORMATION FOR SEQ ID NO:502:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:502:

Thr Leu Gly Phe Gly Ala Tyr Met Ser Lys
1               5                   10

(2) INFORMATION FOR SEQ ID NO:503:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:503:

Gly Val Gly Ile Tyr Leu Leu Pro Asn Arg
1               5                   10

(2) INFORMATION FOR SEQ ID NO:504:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:504:

Leu Leu Phe Leu Leu Leu Ala Asp Ala Arg
1               5                   10

(2) INFORMATION FOR SEQ ID NO:505:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:505:

Phe Arg Asp Tyr Val Asp Arg Phe Tyr
1               5

(2) INFORMATION FOR SEQ ID NO:506:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:506:

Ile Tyr Gln Tyr Met Asp Asp Leu Tyr
1               5

(2) INFORMATION FOR SEQ ID NO:507:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:507:

Thr Val Leu Asp Val Gly Asp Ala Tyr
1               5

(2) INFORMATION FOR SEQ ID NO:508:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:508:

Val Thr Val Leu Asp Val Gly Asp Ala Tyr
1               5                   10

(2) INFORMATION FOR SEQ ID NO:509:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:509:

```
Val Ile Tyr Gln Tyr Met Asp Asp Leu Tyr
 1               5                  10
```

(2) INFORMATION FOR SEQ ID NO:510:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:510:

```
Glu Val Asn Ile Val Thr Asp Ser Gln Tyr
 1               5                  10
```

(2) INFORMATION FOR SEQ ID NO:511:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:511:

```
Leu Val Ala Val His Val Ala Ser Gly Tyr
 1               5                  10
```

(2) INFORMATION FOR SEQ ID NO:512:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:512:

```
Pro Ala Glu Thr Gly Gln Glu Thr Ala Tyr
 1               5                  10
```

(2) INFORMATION FOR SEQ ID NO:513:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:513:

```
Ile Ser Lys Ile Gly Pro Glu Asn Pro Tyr
 1               5                  10
```

(2) INFORMATION FOR SEQ ID NO:514:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:514:

Gln Met Ala Val Phe Ile His Asn Phe Lys
1               5                   10

(2) INFORMATION FOR SEQ ID NO:515:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:515:

Arg Tyr Leu Lys Asp Gln Gln Leu Leu
1               5

(2) INFORMATION FOR SEQ ID NO:516:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:516:

Thr Tyr Gln Ile Tyr Gln Glu Pro Phe
1               5

(2) INFORMATION FOR SEQ ID NO:517:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:517:

Ile Tyr Gln Glu Pro Phe Lys Asn Leu
1               5

(2) INFORMATION FOR SEQ ID NO:518:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:518:

Ile Tyr Gln Tyr Met Asp Asp Leu Tyr
1               5

(2) INFORMATION FOR SEQ ID NO:519:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:519:

Ile Tyr Lys Arg Trp Ile Ile Leu Gly Leu
1               5                   10

(2) INFORMATION FOR SEQ ID NO:520:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:520:

Leu Tyr Pro Leu Ala Ser Leu Arg Ser Leu
1               5                   10

(2) INFORMATION FOR SEQ ID NO:521:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:521:

Lys Leu Ala Gly Arg Trp Pro Val Lys
1               5

(2) INFORMATION FOR SEQ ID NO:522:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:522:

Ala Val Phe Ile His Asn Phe Lys Arg
1               5

(2) INFORMATION FOR SEQ ID NO:523:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:523:

Ala Ile Phe Gln Ser Ser Met Thr Lys
1               5

(2) INFORMATION FOR SEQ ID NO:524:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:524:

Ile Val Ile Trp Gly Lys Thr Pro Lys
1               5

(2) INFORMATION FOR SEQ ID NO:525:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:525:

Lys Leu Thr Glu Asp Arg Trp Asn Lys
1               5

(2) INFORMATION FOR SEQ ID NO:526:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:526:

Gly Ile Pro His Pro Ala Gly Leu Lys
1               5

(2) INFORMATION FOR SEQ ID NO:527:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:527:

Gln Ile Ile Glu Gln Leu Ile Lys Lys
1               5

(2) INFORMATION FOR SEQ ID NO:528:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:528:

Lys Ile Trp Pro Ser Tyr Lys Gly Arg
1               5

(2) INFORMATION FOR SEQ ID NO:529:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:529:

Ile Ile Ala Thr Asp Ile Gln Thr Lys
1               5

(2) INFORMATION FOR SEQ ID NO:530:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:530:

Met Gly Tyr Glu Leu His Pro Asp Lys
1               5

(2) INFORMATION FOR SEQ ID NO:531:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:531:

Tyr Leu Ala Trp Val Pro Ala His Lys
1               5

(2) INFORMATION FOR SEQ ID NO:532:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:532:

Lys Ile Trp Pro Ser His Lys Gly Arg
1               5

(2) INFORMATION FOR SEQ ID NO:533:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:533:

Phe Val Asn Thr Pro Pro Leu Val Lys
1               5

(2) INFORMATION FOR SEQ ID NO:534:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:534:

Asn Thr Pro Val Phe Ala Ile Lys Lys
1               5

(2) INFORMATION FOR SEQ ID NO:535:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:535:

Thr Val Gln Cys Thr His Gly Ile Lys
1               5

(2) INFORMATION FOR SEQ ID NO:536:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:536:

Ile Leu Asp Ile Arg Gln Gly Pro Lys
1               5

(2) INFORMATION FOR SEQ ID NO:537:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:537:

Arg Asp Tyr Val Asp Arg Phe Tyr Lys
1               5

(2) INFORMATION FOR SEQ ID NO:538:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:538:

Gly Ile Ile Gln Ala Gln Pro Asp Lys
1               5

(2) INFORMATION FOR SEQ ID NO:539:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:539:

Val Leu Phe Leu Asp Gly Ile Asp Lys
1               5

(2) INFORMATION FOR SEQ ID NO:540:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:540:

Leu Val Asp Phe Arg Glu Leu Asn Lys
1               5

(2) INFORMATION FOR SEQ ID NO:541:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:541:

Lys Val Val Pro Arg Arg Lys Ala Lys
1               5

(2) INFORMATION FOR SEQ ID NO:542:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:542:

Met Thr Lys Ile Leu Glu Pro Phe Arg
1               5

(2) INFORMATION FOR SEQ ID NO:543:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:543:

Thr Val Tyr Tyr Gly Val Pro Val Trp Lys
1               5                   10

(2) INFORMATION FOR SEQ ID NO:544:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:544:

Thr Val Gln Pro Ile Val Leu Pro Glu Lys
 1               5                  10

(2) INFORMATION FOR SEQ ID NO:545:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:545:

Ala Val Phe Ile His Asn Phe Lys Arg Lys
 1               5                  10

(2) INFORMATION FOR SEQ ID NO:546:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:546:

Lys Val Leu Phe Leu Asp Gly Ile Asp Lys
 1               5                  10

(2) INFORMATION FOR SEQ ID NO:547:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:547:

Lys Leu Val Asp Phe Arg Glu Leu Asn Lys
 1               5                  10

(2) INFORMATION FOR SEQ ID NO:548:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:548:

Lys Leu Lys Pro Gly Met Asp Gly Pro Lys
 1               5                  10

(2) INFORMATION FOR SEQ ID NO:549:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:549:

```
Phe Leu Gly Lys Ile Trp Pro Ser Tyr Lys
 1               5                  10

(2) INFORMATION FOR SEQ ID NO:550:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:550:

Lys Ile Gln Asn Phe Arg Val Tyr Tyr Arg
 1               5                  10

(2) INFORMATION FOR SEQ ID NO:551:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:551:

Gly Ile Pro His Pro Ala Gly Leu Lys Lys
 1               5                  10

(2) INFORMATION FOR SEQ ID NO:552:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:552:

Leu Val Lys Leu Trp Tyr Gln Leu Glu Lys
 1               5                  10

(2) INFORMATION FOR SEQ ID NO:553:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:553:

Met Ile Gly Gly Ile Gly Gly Phe Ile Lys
 1               5                  10

(2) INFORMATION FOR SEQ ID NO:554:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:554:
```

```
Met Thr Lys Ile Leu Glu Pro Phe Arg Lys
  1               5                  10
```

(2) INFORMATION FOR SEQ ID NO:555:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:555:

```
Val Val Ile Gln Asp Asn Ser Asp Ile Lys
  1               5                  10
```

(2) INFORMATION FOR SEQ ID NO:556:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:556:

```
Phe Leu Gly Lys Ile Trp Pro Ser His Lys
  1               5                  10
```

(2) INFORMATION FOR SEQ ID NO:557:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:557:

```
Ile Val Gln Gln Gln Asn Asn Leu Leu Arg
  1               5                  10
```

(2) INFORMATION FOR SEQ ID NO:558:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:558:

```
Phe Thr Thr Pro Asp Lys Lys His Gln Lys
  1               5                  10
```

(2) INFORMATION FOR SEQ ID NO:559:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:559:

```
Leu Val Glu Ile Cys Thr Glu Met Glu Lys
 1               5                  10
```

(2) INFORMATION FOR SEQ ID NO:560:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:560:

```
Leu Val Gln Asn Ala Asn Pro Asp Cys Lys
 1               5                  10
```

(2) INFORMATION FOR SEQ ID NO:561:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:561:

```
Ala Val Cys Asp Lys Cys Leu Lys Phe Tyr
 1               5                  10
```

(2) INFORMATION FOR SEQ ID NO:562:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:562:

```
Val Tyr Cys Lys Thr Val Leu Glu Leu
 1               5
```

(2) INFORMATION FOR SEQ ID NO:563:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:563:

```
Cys Tyr Ser Leu Tyr Gly Thr Thr Leu
 1               5
```

(2) INFORMATION FOR SEQ ID NO:564:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:564:

Val Tyr Asp Phe Ala Phe Arg Asp Leu
1               5

(2) INFORMATION FOR SEQ ID NO:565:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:565:

Leu Tyr Asn Leu Leu Ile Arg Cys Leu
1               5

(2) INFORMATION FOR SEQ ID NO:566:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:566:

Val Tyr Gly Asp Thr Leu Glu Lys Leu
1               5

(2) INFORMATION FOR SEQ ID NO:567:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:567:

Ser Ile Pro His Ala Ala Cys His Lys
1               5

(2) INFORMATION FOR SEQ ID NO:568:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:568:

Lys Leu Arg His Leu Asn Glu Lys Arg
1               5

(2) INFORMATION FOR SEQ ID NO:569:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:569:

Leu Ile Arg Cys Leu Arg Cys Gln Lys
1               5

(2) INFORMATION FOR SEQ ID NO:570:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:570:

Ile Ile Leu Glu Cys Val Tyr Cys Lys
1               5

(2) INFORMATION FOR SEQ ID NO:571:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:571:

Cys Ile Asp Phe Tyr Ser Arg Ile Arg
1               5

(2) INFORMATION FOR SEQ ID NO:572:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:572:

Gly Ile Val Cys Pro Ile Cys Ser Gln Lys
1               5                   10

(2) INFORMATION FOR SEQ ID NO:573:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:573:

Asp Ile Ile Leu Glu Cys Val Tyr Cys Lys
1               5                   10

(2) INFORMATION FOR SEQ ID NO:574:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:574:

```
Lys Leu Arg His Leu Asn Glu Lys Arg Arg
 1               5                  10
```

(2) INFORMATION FOR SEQ ID NO:575:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:575:

```
Cys Val Tyr Cys Lys Gln Gln Leu Leu Arg
 1               5                  10
```

(2) INFORMATION FOR SEQ ID NO:576:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:576:

```
Glu Val Asp Pro Ile Gly His Leu Tyr
 1               5
```

(2) INFORMATION FOR SEQ ID NO:577:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:577:

```
Glu Ala Asp Pro Thr Ser Asn Thr Tyr
 1               5
```

(2) INFORMATION FOR SEQ ID NO:578:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:578:

```
Glu Val Asp Pro Ile Gly His Val Tyr
 1               5
```

(2) INFORMATION FOR SEQ ID NO:579:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:579:

Leu Val Gln Glu Lys Tyr Leu Glu Tyr
1               5

(2) INFORMATION FOR SEQ ID NO:580:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:580:

Thr Ser Tyr Val Lys Val Leu Glu Tyr
1               5

(2) INFORMATION FOR SEQ ID NO:581:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:581:

Ser Ser Leu Pro Thr Thr Met Asn Tyr
1               5

(2) INFORMATION FOR SEQ ID NO:582:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:582:

Gly Ser Val Val Gly Asn Trp Gln Tyr
1               5

(2) INFORMATION FOR SEQ ID NO:583:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:583:

Ser Ser Phe Ser Thr Thr Ile Asn Tyr
1               5

(2) INFORMATION FOR SEQ ID NO:584:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:584:

```
Ala Ser Ser Leu Pro Thr Thr Met Asn Tyr
 1               5                  10
```

(2) INFORMATION FOR SEQ ID NO:585:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:585:

```
Glu Thr Ser Tyr Val Lys Val Leu Glu Tyr
 1               5                  10
```

(2) INFORMATION FOR SEQ ID NO:586:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:586:

```
Ala Ser Ser Phe Ser Thr Thr Ile Asn Tyr
 1               5                  10
```

(2) INFORMATION FOR SEQ ID NO:587:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:587:

```
Asp Leu Val Gln Glu Lys Tyr Leu Glu Tyr
 1               5                  10
```

(2) INFORMATION FOR SEQ ID NO:588:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:588:

```
Thr Thr Ile Asn Phe Thr Arg Gln Arg
 1               5
```

(2) INFORMATION FOR SEQ ID NO:589:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:589:

Ala Leu Ala Glu Thr Ser Tyr Val Lys
1               5

(2) INFORMATION FOR SEQ ID NO:590:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:590:

His Ser Ala Tyr Gly Glu Pro Arg Lys
1               5

(2) INFORMATION FOR SEQ ID NO:591:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:591:

Leu Phe Arg Ala Val Ile Thr Lys Lys
1               5

(2) INFORMATION FOR SEQ ID NO:592:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:592:

Arg Val Arg Phe Phe Phe Pro Ser Leu Arg
1               5                   10

(2) INFORMATION FOR SEQ ID NO:593:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:593:

Ala Asp Leu Val Gly Phe Leu Leu Leu Lys
1               5                   10

(2) INFORMATION FOR SEQ ID NO:594:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:594:

Glu Ser Leu Phe Arg Ala Val Ile Thr Lys
1               5                   10

(2) INFORMATION FOR SEQ ID NO:595:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:595:

Tyr Val Ile Lys Val Ser Ala Arg Val Arg
1               5                   10

(2) INFORMATION FOR SEQ ID NO:596:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:596:

Leu Ser Val Met Glu Val Tyr Asp Gly Arg
1               5                   10

(2) INFORMATION FOR SEQ ID NO:597:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:597:

Lys Ala Glu Met Leu Glu Ser Val Ile Lys
1               5                   10

(2) INFORMATION FOR SEQ ID NO:598:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:598:

Arg Ala Leu Ala Glu Thr Ser Tyr Val Lys
1               5                   10

(2) INFORMATION FOR SEQ ID NO:599:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:599:

Asn Tyr Pro Leu Trp Ser Gln Ser Tyr
1               5

(2) INFORMATION FOR SEQ ID NO:600:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:600:

Asn Tyr Lys His Cys Phe Pro Glu Ile Phe
1               5                   10

(2) INFORMATION FOR SEQ ID NO:601:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:601:

Leu Tyr Ile Phe Ala Thr Cys Leu Gly Leu
1               5                   10

(2) INFORMATION FOR SEQ ID NO:602:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:602:

Ser Tyr Val Lys Val Leu Glu Tyr Val Ile
1               5                   10

(2) INFORMATION FOR SEQ ID NO:603:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:603:

Ser Val Met Glu Val Tyr Asp Gly Arg
1               5

(2) INFORMATION FOR SEQ ID NO:604:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:604:

```
Gly Ser Asp Cys Thr Thr Ile His Tyr
 1               5
```

(2) INFORMATION FOR SEQ ID NO:605:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:605:

```
Gly Thr Ala Lys Ser Val Thr Cys Thr Tyr
 1               5                   10
```

(2) INFORMATION FOR SEQ ID NO:606:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:606:

```
Arg Val Glu Gly Asn Leu Arg Val Glu Tyr
 1               5                   10
```

(2) INFORMATION FOR SEQ ID NO:607:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:607:

```
Arg Val Arg Ala Met Ala Ile Tyr Lys
 1               5
```

(2) INFORMATION FOR SEQ ID NO:608:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:608:

```
Cys Thr Tyr Ser Pro Ala Leu Asn Lys
 1               5
```

(2) INFORMATION FOR SEQ ID NO:609:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:609:

Asn Thr Ser Ser Ser Pro Gln Pro Lys
 1               5

(2) INFORMATION FOR SEQ ID NO:610:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:610:

Arg Thr Glu Glu Glu Asn Leu Arg Lys
 1               5

(2) INFORMATION FOR SEQ ID NO:611:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:611:

Glu Leu Asn Glu Ala Leu Glu Leu Lys
 1               5

(2) INFORMATION FOR SEQ ID NO:612:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:612:

Arg Thr Glu Glu Glu Asn Leu Arg Lys Lys
 1               5                  10

(2) INFORMATION FOR SEQ ID NO:613:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:613:

Lys Thr Tyr Gln Gly Ser Tyr Gly Phe Arg
 1               5                  10

(2) INFORMATION FOR SEQ ID NO:614:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:614:

```
Val Val Arg Arg Cys Pro His His Glu Arg
1               5                   10
```

(2) INFORMATION FOR SEQ ID NO:615:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:615:

```
Asn Thr Ser Ser Ser Pro Gln Pro Lys Lys
1               5                   10
```

(2) INFORMATION FOR SEQ ID NO:616:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:616:

```
Arg Val Cys Ala Cys Pro Gly Arg Asp Arg
1               5                   10
```

(2) INFORMATION FOR SEQ ID NO:617:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:617:

```
Gly Leu Ala Pro Pro Gln His Leu Ile Arg
1               5                   10
```

(2) INFORMATION FOR SEQ ID NO:618:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:618:

```
Lys Gly Glu Tyr Phe Val Glu Met Tyr
1               5
```

(2) INFORMATION FOR SEQ ID NO:619:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:619:

Leu Gly Glu Tyr Ile Arg Lys Arg Tyr
1               5

(2) INFORMATION FOR SEQ ID NO:620:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:620:

Ala Ser Cys His Leu Thr Glu Leu Tyr
1               5

(2) INFORMATION FOR SEQ ID NO:621:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:621:

Glu Ser Tyr Lys His Glu Gln Val Tyr
1               5

(2) INFORMATION FOR SEQ ID NO:622:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:622:

Leu Ser Glu Leu Ser Leu Leu Ser Leu Tyr
1               5                   10

(2) INFORMATION FOR SEQ ID NO:623:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:623:

Leu Thr Gln Leu Gly Met Glu Gln His Tyr
1               5                   10

(2) INFORMATION FOR SEQ ID NO:624:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:624:

Lys Gly Glu Tyr Phe Val Glu Met Tyr Tyr
 1               5                  10

(2) INFORMATION FOR SEQ ID NO:625:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:625:

Leu Val Asn Glu Ile Leu Asn His Met Lys
 1               5                  10

(2) INFORMATION FOR SEQ ID NO:626:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:626:

Ala Thr Gln Ile Pro Ser Tyr Lys Lys
 1               5

(2) INFORMATION FOR SEQ ID NO:627:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:627:

Glu Thr Leu Lys Ser Glu Glu Phe Gln Lys
 1               5                  10

(2) INFORMATION FOR SEQ ID NO:628:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:628:

Leu Tyr Phe Glu Lys Gly Glu Tyr Phe
 1               5

(2) INFORMATION FOR SEQ ID NO:629:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:629:

Leu Tyr Cys Glu Ser Val His Asn Phe
1               5

(2) INFORMATION FOR SEQ ID NO:630:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:630:

Pro Tyr Lys Asp Phe Ile Ala Thr Leu
1               5

(2) INFORMATION FOR SEQ ID NO:631:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:631:

Val Tyr Asn Gly Leu Leu Pro Pro Tyr
1               5

(2) INFORMATION FOR SEQ ID NO:632:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:632:

Pro Tyr Ala Ser Cys His Leu Thr Glu Leu
1               5                   10

(2) INFORMATION FOR SEQ ID NO:633:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:633:

Ala Leu Pro Glu Arg Pro Ser Leu Tyr
1               5

(2) INFORMATION FOR SEQ ID NO:634:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:634:

Ser Leu Leu Lys Asn Arg Phe Leu Arg
1               5

(2) INFORMATION FOR SEQ ID NO:635:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:635:

Ser Leu Tyr Thr Lys Val Val His Tyr Arg
1               5                   10

(2) INFORMATION FOR SEQ ID NO:636:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:636:

Arg Ile Val Gly Gly Trp Glu Cys Glu Lys
1               5                   10

(2) INFORMATION FOR SEQ ID NO:637:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:637:

Val Thr Lys Phe Met Leu Cys Ala Gly Arg
1               5                   10

(2) INFORMATION FOR SEQ ID NO:638:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:638:

Met Leu Leu Arg Leu Ser Glu Pro Ala
1               5

(2) INFORMATION FOR SEQ ID NO:639:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:639:

```
Lys Val Tyr Leu Ala Trp Val Pro Ala His Lys
 1               5                  10
```

(2) INFORMATION FOR SEQ ID NO:640:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:640:

```
Lys Met Ile Gly Gly Ile Gly Gly Phe Ile Lys
 1               5                  10
```

(2) INFORMATION FOR SEQ ID NO:641:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:641:

```
Trp Thr Tyr Gln Ile Tyr Gln Glu Pro Phe Lys
 1               5                  10
```

(2) INFORMATION FOR SEQ ID NO:642:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:642:

```
Val Thr Val Tyr Tyr Gly Val Pro Val Trp Lys
 1               5                  10
```

(2) INFORMATION FOR SEQ ID NO:643:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:643:

```
Phe Leu Leu Thr Arg Ile Leu Thr Ile
 1               5
```

(2) INFORMATION FOR SEQ ID NO:644:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:644:

Phe Leu Pro Ser Asp Phe Phe Pro Ser Val
1               5                   10

(2) INFORMATION FOR SEQ ID NO:645:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:645:

Gly Leu Tyr Ser Ser Thr Val Pro Val
1               5

(2) INFORMATION FOR SEQ ID NO:646:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:646:

Val Leu Val His Pro Gln Trp Val Leu
1               5

(2) INFORMATION FOR SEQ ID NO:647:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:647:

Phe Leu Pro Ser Asp Tyr Phe Pro Ser Val
1               5                   10

(2) INFORMATION FOR SEQ ID NO:648:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:648:

Ile Leu Leu Trp Asp Pro Ile Pro Val
1               5

(2) INFORMATION FOR SEQ ID NO:649:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:649:

```
Lys Leu Gln Cys Val Asp Leu Val His Ile
  1               5                  10
```

(2) INFORMATION FOR SEQ ID NO:650:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:650:

```
Met Leu Leu Arg Leu Ser Glu Pro Ala Glu Leu
  1               5                  10
```

(2) INFORMATION FOR SEQ ID NO:651:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:651:

```
Gly Thr Glu Lys Leu Ile Glu Thr Tyr
  1               5
```

(2) INFORMATION FOR SEQ ID NO:652:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:652:

```
Gly Thr Ala Ser Phe Phe Phe Leu Tyr
  1               5
```

(2) INFORMATION FOR SEQ ID NO:653:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:653:

```
Cys Ser Ala Val Pro Val Tyr Ile Tyr
  1               5
```

(2) INFORMATION FOR SEQ ID NO:654:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:654:

```
Leu Thr Phe Met Ile Ala Ala Thr Tyr
 1               5
```

(2) INFORMATION FOR SEQ ID NO:655:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:655:

```
Gly Thr Glu Lys Leu Ile Glu Thr Tyr Phe
 1               5                  10
```

(2) INFORMATION FOR SEQ ID NO:656:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:656:

```
Leu Ile Glu Thr Tyr Phe Ser Lys Asn Tyr
 1               5                  10
```

(2) INFORMATION FOR SEQ ID NO:657:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:657:

```
Phe Ser Lys Asn Tyr Gln Asp Tyr Glu Tyr
 1               5                  10
```

(2) INFORMATION FOR SEQ ID NO:658:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:658:

```
His Pro Asp Lys Phe Val Gly Ile Thr Tyr
 1               5                  10
```

(2) INFORMATION FOR SEQ ID NO:659:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:659:

Gly Ser Leu Cys Ala Asp Ala Arg Met Tyr
 1               5                  10

(2) INFORMATION FOR SEQ ID NO:660:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:660:

Val Phe Ala Cys Ser Ala Val Pro Val Tyr
 1               5                  10

(2) INFORMATION FOR SEQ ID NO:661:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:661:

Ala Cys Ser Ala Val Pro Val Tyr Ile Tyr
 1               5                  10

(2) INFORMATION FOR SEQ ID NO:662:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:662:

Lys Leu Ile Glu Thr Tyr Phe Ser Lys
 1               5

(2) INFORMATION FOR SEQ ID NO:663:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:663:

Thr Val Thr Gly Gly Gln Lys Gly Arg
 1               5

(2) INFORMATION FOR SEQ ID NO:664:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:664:

```
Ala Thr Tyr Asn Phe Ala Val Leu Lys
  1               5
```

(2) INFORMATION FOR SEQ ID NO:665:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:665:

```
Ala Val Arg Gln Ile Phe Gly Asp Tyr Lys
  1               5                  10
```

(2) INFORMATION FOR SEQ ID NO:666:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:666:

```
Ala Thr Val Thr Gly Gly Gln Lys Gly Arg
  1               5                  10
```

(2) INFORMATION FOR SEQ ID NO:667:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:667:

```
Ser Ile Gly Ser Leu Cys Ala Asp Ala Arg
  1               5                  10
```

(2) INFORMATION FOR SEQ ID NO:668:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:668:

```
Val Leu Pro Trp Ile Ala Phe Pro Gly Lys
  1               5                  10
```

(2) INFORMATION FOR SEQ ID NO:669:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:669:

Val Leu Lys Leu Met Gly Arg Gly Thr Lys
1               5                  10

(2) INFORMATION FOR SEQ ID NO:670:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:670:

Val Ile Tyr Gly Thr Ala Ser Phe Phe
1               5

(2) INFORMATION FOR SEQ ID NO:671:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:671:

Ser Ala Thr Val Thr Gly Gly Gln Lys
1               5

(2) INFORMATION FOR SEQ ID NO:672:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:672:

Cys Asp Ser Ile Ala Phe Pro Ser Lys
1               5

(2) INFORMATION FOR SEQ ID NO:673:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:673:

Ile Gly Ser Leu Cys Ala Asp Ala Arg
1               5

(2) INFORMATION FOR SEQ ID NO:674:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:674:

Gly Ser Asn Leu Leu Ser Ile Cys Lys
1               5

(2) INFORMATION FOR SEQ ID NO:675:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:675:

Lys Thr Ala Glu Phe Gln Met Thr Phe
1               5

(2) INFORMATION FOR SEQ ID NO:676:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:676:

Met Thr Phe His Leu Phe Ile Ala Ala
1               5

(2) INFORMATION FOR SEQ ID NO:677:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:677:

Ser Leu Val Ala Thr Gly Leu Cys Phe Phe
1               5                   10

(2) INFORMATION FOR SEQ ID NO:678:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:678:

Ala Leu Phe Cys Gly Cys Gly His Glu Ala
1               5                   10

(2) INFORMATION FOR SEQ ID NO:679:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:679:

Val Ile His Ala Phe Gln Tyr Val Ile Tyr
1               5                   10

(2) INFORMATION FOR SEQ ID NO:680:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:680:

Gly Asp Tyr Lys Thr Thr Ile Cys Gly Lys
1               5                   10

(2) INFORMATION FOR SEQ ID NO:681:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:681:

Thr Gly Gly Gln Lys Gly Arg Gly Ser Arg
1               5                   10

(2) INFORMATION FOR SEQ ID NO:682:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:682:

Leu Gly Lys Trp Leu Gly His Pro Asp Lys
1               5                   10

(2) INFORMATION FOR SEQ ID NO:683:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:683:

Thr Cys Asp Ser Ile Ala Phe Pro Ser Lys
1               5                   10

(2) INFORMATION FOR SEQ ID NO:684:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:684:

```
Cys Gly Ser Asn Leu Leu Ser Ile Cys Lys
1               5                   10
```

(2) INFORMATION FOR SEQ ID NO:685:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:685:

```
Lys Thr Ala Glu Phe Gln Met Thr Phe His
1               5                   10
```

(2) INFORMATION FOR SEQ ID NO:686:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:686:

```
Met Thr Phe His Leu Phe Ile Ala Ala Phe
1               5                   10
```

(2) INFORMATION FOR SEQ ID NO:687:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:687:

```
Phe Met Ile Ala Ala Thr Tyr Asn Phe Ala
1               5                   10
```

(2) INFORMATION FOR SEQ ID NO:688:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:688:

```
Ala Ala Thr Tyr Asn Phe Ala Val Leu Lys
1               5                   10
```

(2) INFORMATION FOR SEQ ID NO:689:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:689:

```
Phe Ala Ser Leu Val Ala Thr Gly Leu
  1               5
```

(2) INFORMATION FOR SEQ ID NO:690:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:690:

```
Glu Ala Leu Thr Gly Thr Glu Lys Leu
  1               5
```

(2) INFORMATION FOR SEQ ID NO:691:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:691:

```
Asn Tyr Gln Asp Tyr Glu Tyr Leu Ile
  1               5
```

(2) INFORMATION FOR SEQ ID NO:692:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:692:

```
Asp Tyr Glu Tyr Leu Ile Asn Val Ile
  1               5
```

(2) INFORMATION FOR SEQ ID NO:693:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:693:

```
Ile Tyr Gly Thr Ala Ser Phe Phe Phe
  1               5
```

(2) INFORMATION FOR SEQ ID NO:694:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:694:

```
Ser Phe Phe Phe Leu Tyr Gly Ala Leu
1               5
```

(2) INFORMATION FOR SEQ ID NO:695:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:695:

```
Phe Phe Phe Leu Tyr Gly Ala Leu Leu
1               5
```

(2) INFORMATION FOR SEQ ID NO:696:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:696:

```
Phe Phe Leu Tyr Gly Ala Leu Leu Leu
1               5
```

(2) INFORMATION FOR SEQ ID NO:697:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:697:

```
Gly Ala Leu Leu Leu Ala Glu Gly Phe
1               5
```

(2) INFORMATION FOR SEQ ID NO:698:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:698:

```
Ile Phe Gly Asp Tyr Lys Thr Thr Ile
1               5
```

(2) INFORMATION FOR SEQ ID NO:699:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:699:

Lys Trp Leu Gly His Pro Asp Lys Phe
1               5

(2) INFORMATION FOR SEQ ID NO:700:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:700:

Lys Phe Val Gly Ile Thr Tyr Ala Leu
1               5

(2) INFORMATION FOR SEQ ID NO:701:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:701:

Thr Tyr Ala Leu Thr Val Val Trp Leu
1               5

(2) INFORMATION FOR SEQ ID NO:702:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:702:

Tyr Ala Leu Thr Val Val Trp Leu Leu
1               5

(2) INFORMATION FOR SEQ ID NO:703:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:703:

Ser Ala Val Pro Val Tyr Ile Tyr Phe
1               5

(2) INFORMATION FOR SEQ ID NO:704:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:704:

```
Glu Phe Gln Met Thr Phe His Leu Phe
  1               5
```

(2) INFORMATION FOR SEQ ID NO:705:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:705:

```
Thr Phe His Leu Phe Ile Ala Ala Phe
  1               5
```

(2) INFORMATION FOR SEQ ID NO:706:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:706:

```
Ala Phe Val Gly Ala Ala Ala Thr Leu
  1               5
```

(2) INFORMATION FOR SEQ ID NO:707:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:707:

```
Gly Ala Ala Ala Thr Leu Val Ser Leu
  1               5
```

(2) INFORMATION FOR SEQ ID NO:708:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:708:

```
Ala Ala Ala Thr Leu Val Ser Leu Leu
  1               5
```

(2) INFORMATION FOR SEQ ID NO:709:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:709:

```
Ala Ala Thr Tyr Asn Phe Ala Val Leu
1               5
```

(2) INFORMATION FOR SEQ ID NO:710:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:710:

```
Thr Tyr Asn Phe Ala Val Leu Lys Leu
1               5
```

(2) INFORMATION FOR SEQ ID NO:711:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:711:

```
Cys Ala Arg Cys Leu Val Gly Ala Pro Phe
1               5                   10
```

(2) INFORMATION FOR SEQ ID NO:712:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:712:

```
Pro Phe Ala Ser Leu Val Ala Thr Gly Leu
1               5                   10
```

(2) INFORMATION FOR SEQ ID NO:713:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:713:

```
Leu Phe Cys Gly Cys Gly His Glu Ala Leu
1               5                   10
```

(2) INFORMATION FOR SEQ ID NO:714:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:714:

```
Glu Ala Leu Thr Gly Thr Glu Lys Leu Ile
 1               5                  10
```

(2) INFORMATION FOR SEQ ID NO:715:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:715:

```
Glu Tyr Leu Ile Asn Val Ile His Ala Phe
 1               5                  10
```

(2) INFORMATION FOR SEQ ID NO:716:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:716:

```
Gln Tyr Val Ile Tyr Gly Thr Ala Ser Phe
 1               5                  10
```

(2) INFORMATION FOR SEQ ID NO:717:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:717:

```
Ile Tyr Gly Thr Ala Ser Phe Phe Phe Leu
 1               5                  10
```

(2) INFORMATION FOR SEQ ID NO:718:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:718:

```
Ser Phe Phe Phe Leu Tyr Gly Ala Leu Leu
 1               5                  10
```

(2) INFORMATION FOR SEQ ID NO:719:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:719:

```
Phe Phe Phe Leu Tyr Gly Ala Leu Leu Leu
  1               5                  10
```

(2) INFORMATION FOR SEQ ID NO:720:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:720:

```
Phe Tyr Thr Thr Gly Ala Val Arg Gln Ile
  1               5                  10
```

(2) INFORMATION FOR SEQ ID NO:721:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:721:

```
Thr Tyr Ala Leu Thr Val Val Trp Leu Leu
  1               5                  10
```

(2) INFORMATION FOR SEQ ID NO:722:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:722:

```
Phe Ala Cys Ser Ala Val Pro Val Tyr Ile
  1               5                  10
```

(2) INFORMATION FOR SEQ ID NO:723:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:723:

```
Thr Trp Thr Thr Cys Asp Ser Ile Ala Phe
  1               5                  10
```

(2) INFORMATION FOR SEQ ID NO:724:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:724:

```
Ala Phe Pro Ser Lys Thr Ser Ala Ser Ile
 1               5                  10
```

(2) INFORMATION FOR SEQ ID NO:725:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:725:

```
Cys Ala Asp Ala Arg Met Tyr Gly Val Leu
 1               5                  10
```

(2) INFORMATION FOR SEQ ID NO:726:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:726:

```
Asp Ala Arg Met Tyr Gly Val Leu Pro Trp
 1               5                  10
```

(2) INFORMATION FOR SEQ ID NO:727:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:727:

```
Met Tyr Gly Val Leu Pro Trp Ile Ala Phe
 1               5                  10
```

(2) INFORMATION FOR SEQ ID NO:728:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:728:

```
Thr Ala Glu Phe Gln Met Thr Phe His Leu
 1               5                  10
```

(2) INFORMATION FOR SEQ ID NO:729:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:729:

```
Glu Phe Gln Met Thr Phe His Leu Phe Ile
1               5                   10
```

(2) INFORMATION FOR SEQ ID NO:730:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:730:

```
Ala Ala Phe Val Gly Ala Ala Ala Thr Leu
1               5                   10
```

(2) INFORMATION FOR SEQ ID NO:731:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:731:

```
Gly Ala Ala Ala Thr Leu Val Ser Leu Leu
1               5                   10
```

(2) INFORMATION FOR SEQ ID NO:732:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:732:

```
Ala Ala Thr Leu Val Ser Leu Leu Thr Phe
1               5                   10
```

(2) INFORMATION FOR SEQ ID NO:733:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:733:

```
Thr Phe Met Ile Ala Ala Thr Tyr Asn Phe
1               5                   10
```

(2) INFORMATION FOR SEQ ID NO:734:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:734:

Ile Ala Ala Thr Tyr Asn Phe Ala Val Leu
 1               5                  10

(2) INFORMATION FOR SEQ ID NO:735:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:735:

Thr Tyr Asn Phe Ala Val Leu Lys Leu Met
 1               5                  10

(2) INFORMATION FOR SEQ ID NO:736:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:736:

His Pro Asp Lys Phe Val Gly Ile
 1               5

(2) INFORMATION FOR SEQ ID NO:737:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:737:

Phe Pro Ser Lys Thr Ser Ala Ser Ile
 1               5

(2) INFORMATION FOR SEQ ID NO:738:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:738:

Val Pro Val Tyr Ile Tyr Phe Asn Thr Trp
 1               5                  10

(2) INFORMATION FOR SEQ ID NO:739:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:739:

```
Leu Pro Trp Ile Ala Phe Pro Gly Lys Val
 1               5                  10
```

(2) INFORMATION FOR SEQ ID NO:740:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:740:

```
Phe Pro Gly Lys Val Cys Gly Ser Asn Leu
 1               5                  10
```

(2) INFORMATION FOR SEQ ID NO:741:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:741:

```
Gly Leu Gln Gly Val Pro Gly Pro Lys
 1               5
```

(2) INFORMATION FOR SEQ ID NO:742:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:742:

```
Gly Leu Asp Gly Ala Lys Gly Glu Lys
 1               5
```

(2) INFORMATION FOR SEQ ID NO:743:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:743:

```
Gly Val Pro Gly Pro Ala Gly Pro Lys
 1               5
```

(2) INFORMATION FOR SEQ ID NO:744:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:744:

```
Gly Leu His Gly Pro Pro Gly Asp Lys
  1               5
```

(2) INFORMATION FOR SEQ ID NO:745:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:745:

```
Leu Leu Gly Pro Leu Gly His Asp Gly Lys
  1               5                   10
```

(2) INFORMATION FOR SEQ ID NO:746:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:746:

```
Pro Leu Gly His Asp Gly Lys Gly Pro Arg
  1               5                   10
```

(2) INFORMATION FOR SEQ ID NO:747:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:747:

```
Pro Leu Gly Pro Gln Gly Pro Leu Gly Lys
  1               5                   10
```

(2) INFORMATION FOR SEQ ID NO:748:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:748:

```
Gly Leu Pro Val Gln Gly Cys Trp Asn Lys
  1               5                   10
```

(2) INFORMATION FOR SEQ ID NO:749:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:749:

Gly Ala Leu Gly Met Leu Gly Gln Lys
 1               5

(2) INFORMATION FOR SEQ ID NO:750:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:750:

Leu Gly Pro Leu Gly His Asp Gly Lys
 1               5

(2) INFORMATION FOR SEQ ID NO:751:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:751:

Leu Gly Pro Gln Gly Pro Leu Gly Lys
 1               5

(2) INFORMATION FOR SEQ ID NO:752:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:752:

Gly Ser Pro Gly Glu Lys Gly Glu Lys
 1               5

(2) INFORMATION FOR SEQ ID NO:753:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:753:

Gly Ser Arg Gly Pro Lys Gly Asp Lys
 1               5

(2) INFORMATION FOR SEQ ID NO:754:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:754:

```
Leu Gly Ala Leu Gly Met Leu Gly Gln Lys
  1               5                  10
```

(2) INFORMATION FOR SEQ ID NO:755:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:755:

```
Leu Gly Lys Asp Gly Pro Pro Gly Val Lys
  1               5                  10
```

(2) INFORMATION FOR SEQ ID NO:756:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:756:

```
Asn Gly His Pro Gly Ser Pro Gly Glu Lys
  1               5                  10
```

(2) INFORMATION FOR SEQ ID NO:757:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:757:

```
Pro Gly Ser Pro Gly Glu Lys Gly Glu Lys
  1               5                  10
```

(2) INFORMATION FOR SEQ ID NO:758:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:758:

```
Pro Gly Leu Gln Gly Val Pro Gly Pro Lys
  1               5                  10
```

(2) INFORMATION FOR SEQ ID NO:759:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:759:

Lys Gly Glu Ala Gly Leu Asp Gly Ala Lys
 1               5                  10

(2) INFORMATION FOR SEQ ID NO:760:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:760:

Ala Gly Leu Asp Gly Ala Lys Gly Glu Lys
 1               5                  10

(2) INFORMATION FOR SEQ ID NO:761:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:761:

Lys Gly Glu Lys Gly Phe Gln Gly Glu Lys
 1               5                  10

(2) INFORMATION FOR SEQ ID NO:762:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:762:

Lys Gly Phe Gln Gly Glu Lys Gly Asp Arg
 1               5                  10

(2) INFORMATION FOR SEQ ID NO:763:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:763:

Ile Gly Val Pro Gly Pro Ala Gly Pro Lys
 1               5                  10

(2) INFORMATION FOR SEQ ID NO:764:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:764:

Ala Gly Pro Lys Gly Glu Arg Gly Ser Lys
1               5                  10

(2) INFORMATION FOR SEQ ID NO:765:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:765:

His Gly Pro Pro Gly Asp Lys Gly Asn Arg
1               5                  10

(2) INFORMATION FOR SEQ ID NO:766:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:766:

Lys Gly Asn Arg Gly Glu Arg Gly Lys Lys
1               5                  10

(2) INFORMATION FOR SEQ ID NO:767:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:767:

Arg Gly Lys Lys Gly Ser Arg Gly Pro Lys
1               5                  10

(2) INFORMATION FOR SEQ ID NO:768:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:768:

Lys Gly Ser Arg Gly Pro Lys Gly Asp Lys
1               5                  10

(2) INFORMATION FOR SEQ ID NO:769:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:769:

Leu Ala Leu Met Gly Pro Leu Gly Leu
1               5

(2) INFORMATION FOR SEQ ID NO:770:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:770:

Gln Ala Gly Ser Pro Val Pro Gly Leu
1               5

(2) INFORMATION FOR SEQ ID NO:771:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:771:

Leu Ala Leu Met Gly Pro Leu Gly Leu Leu
1               5                   10

(2) INFORMATION FOR SEQ ID NO:772:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:772:

Gln Ala Gly Ser Pro Val Pro Gly Leu Leu
1               5                   10

(2) INFORMATION FOR SEQ ID NO:773:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:773:

Gly Pro Leu Gly Ala Leu Gly Met
1               5

(2) INFORMATION FOR SEQ ID NO:774:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:774:

```
Gly Pro Pro Gly Pro Pro Gly Leu
1               5
```

(2) INFORMATION FOR SEQ ID NO:775:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:775:

```
Gly Pro Pro Gly Leu Gln Gly Val
1               5
```

(2) INFORMATION FOR SEQ ID NO:776:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:776:

```
Gly Pro Lys Gly Glu Ala Gly Leu
1               5
```

(2) INFORMATION FOR SEQ ID NO:777:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:777:

```
Pro Pro Gly Thr Pro Gly Pro Ile
1               5
```

(2) INFORMATION FOR SEQ ID NO:778:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:778:

```
Gly Pro Thr Gly Ala Ala Gly Leu
1               5
```

(2) INFORMATION FOR SEQ ID NO:779:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:779:

Cys Pro Leu Gly Gln Asp Gly Leu
1               5

(2) INFORMATION FOR SEQ ID NO:780:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:780:

Gly Pro Leu Gly Leu Leu Gly Gln Ile
1               5

(2) INFORMATION FOR SEQ ID NO:781:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:781:

Gly Pro Leu Gly Ala Leu Gly Met Leu
1               5

(2) INFORMATION FOR SEQ ID NO:782:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:782:

Gly Pro Arg Gly Lys Leu Gly Asp Met
1               5

(2) INFORMATION FOR SEQ ID NO:783:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:783:

Gly Pro Leu Gly Pro Gln Gly Pro Leu
1               5

(2) INFORMATION FOR SEQ ID NO:784:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:784:

```
Gly Pro Pro Gly Thr Pro Gly Pro Ile
 1               5
```

(2) INFORMATION FOR SEQ ID NO:785:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:785:

```
Pro Pro Gly Pro Pro Gly Leu Gln Gly Val
 1               5                   10
```

(2) INFORMATION FOR SEQ ID NO:786:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:786:

```
Val Pro Gly Pro Lys Gly Glu Ala Gly Leu
 1               5                   10
```

(2) INFORMATION FOR SEQ ID NO:787:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:787:

```
Pro Pro Gly Thr Pro Gly Pro Ile Gly Val
 1               5                   10
```

(2) INFORMATION FOR SEQ ID NO:788:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:788:

```
Ala Pro Gly Leu Asp Ala Pro Cys Pro Leu
 1               5                   10
```

(2) INFORMATION FOR SEQ ID NO:789:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:789:

```
Ala Pro Cys Pro Leu Gly Gln Asp Gly Leu
  1               5                  10
```

(2) INFORMATION FOR SEQ ID NO:790:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:790:

```
Cys Pro Leu Gly Gln Asp Gly Leu Pro Val
  1               5                  10
```

(2) INFORMATION FOR SEQ ID NO:791:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:791:

```
Gly Thr Asp Gly Ile Pro Gly Ala Lys
  1               5
```

(2) INFORMATION FOR SEQ ID NO:792:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:792:

```
Gly Thr Asp Gly Pro Lys Gly Ala Ser
  1               5
```

(2) INFORMATION FOR SEQ ID NO:793:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:793:

```
Gly Thr Asp Gly Ile Pro Gly Ala Lys Gly
  1               5                  10
```

(2) INFORMATION FOR SEQ ID NO:794:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:794:

```
Gly Thr Asp Gly Pro Lys Gly Ala Ser Gly
  1               5                  10
```

(2) INFORMATION FOR SEQ ID NO:795:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:795:

```
Gln Met Ala Gly Gly Phe Asp Glu Lys
  1               5
```

(2) INFORMATION FOR SEQ ID NO:796:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:796:

```
Gly Val Ser Gly Pro Met Gly Pro Arg
  1               5
```

(2) INFORMATION FOR SEQ ID NO:797:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:797:

```
Gly Thr Pro Gly Leu Pro Gly Val Lys
  1               5
```

(2) INFORMATION FOR SEQ ID NO:798:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:798:

```
Gly Thr Asp Gly Ile Pro Gly Ala Lys
  1               5
```

(2) INFORMATION FOR SEQ ID NO:799:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:799:

Gly Val Met Gly Phe Pro Gly Pro Lys
 1               5

(2) INFORMATION FOR SEQ ID NO:800:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:800:

Gly Leu Pro Gly Ala Pro Gly Leu Arg
 1               5

(2) INFORMATION FOR SEQ ID NO:801:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:801:

Gly Leu Val Gly Pro Arg Gly Glu Arg
 1               5

(2) INFORMATION FOR SEQ ID NO:802:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:802:

Gly Thr Pro Gly Thr Asp Gly Pro Lys
 1               5

(2) INFORMATION FOR SEQ ID NO:803:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:803:

Gly Leu Gln Gly Met Pro Gly Glu Arg
 1               5

(2) INFORMATION FOR SEQ ID NO:804:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:804:

Gly Ile Ala Gly Pro Lys Gly Asp Arg
1               5

(2) INFORMATION FOR SEQ ID NO:805:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:805:

Gly Val Thr Gly Pro Lys Gly Ala Arg
1               5

(2) INFORMATION FOR SEQ ID NO:806:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:806:

Gly Ile Val Gly Leu Pro Gly Gln Arg
1               5

(2) INFORMATION FOR SEQ ID NO:807:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:807:

Gly Leu Pro Gly Gln Arg Gly Glu Arg
1               5

(2) INFORMATION FOR SEQ ID NO:808:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:808:

Gly Ile Gln Gly Pro Gln Gly Pro Arg
1               5

(2) INFORMATION FOR SEQ ID NO:809:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:809:

```
Pro Leu Gly Pro Lys Gly Gln Thr Gly Lys
1               5                   10
```

(2) INFORMATION FOR SEQ ID NO:810:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:810:

```
Ala Thr Gly Phe Pro Gly Ala Ala Gly Arg
1               5                   10
```

(2) INFORMATION FOR SEQ ID NO:811:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:811:

```
Leu Thr Gly Pro Ala Gly Glu Pro Gly Arg
1               5                   10
```

(2) INFORMATION FOR SEQ ID NO:812:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:812:

```
Pro Ile Gly Pro Pro Gly Pro Arg Gly Arg
1               5                   10
```

(2) INFORMATION FOR SEQ ID NO:813:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:813:

```
Gly Ala Pro Gly Phe Pro Gly Pro Arg
1               5
```

(2) INFORMATION FOR SEQ ID NO:814:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:814:

Gly Ala Thr Gly Pro Leu Gly Pro Lys
1               5

(2) INFORMATION FOR SEQ ID NO:815:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:815:

Leu Gly Pro Lys Gly Gln Thr Gly Lys
1               5

(2) INFORMATION FOR SEQ ID NO:816:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:816:

Gly Phe Lys Gly Glu Gln Gly Pro Lys
1               5

(2) INFORMATION FOR SEQ ID NO:817:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:817:

Lys Gly Ala Asn Gly Glu Pro Gly Lys
1               5

(2) INFORMATION FOR SEQ ID NO:818:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:818:

Gly Ala Pro Gly Leu Val Gly Pro Arg
1               5

(2) INFORMATION FOR SEQ ID NO:819:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:819:

Gly Ala Gln Gly Leu Gln Gly Pro Arg
1               5

(2) INFORMATION FOR SEQ ID NO:820:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:820:

Gly Ala Ala Gly Ile Ala Gly Pro Lys
1               5

(2) INFORMATION FOR SEQ ID NO:821:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:821:

Lys Gly Pro Glu Gly Ala Pro Gly Lys
1               5

(2) INFORMATION FOR SEQ ID NO:822:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:822:

Gly Ala Asp Gly Gln Pro Gly Ala Lys
1               5

(2) INFORMATION FOR SEQ ID NO:823:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:823:

Gly Ala Pro Gly Ala Ser Gly Asp Arg
1               5

(2) INFORMATION FOR SEQ ID NO:824:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:824:

```
Ser Ala Phe Ala Gly Leu Gly Pro Arg
1               5
```

(2) INFORMATION FOR SEQ ID NO:825:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:825:

```
Pro Gly Thr Pro Gly Leu Pro Gly Val Lys
1               5                  10
```

(2) INFORMATION FOR SEQ ID NO:826:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:826:

```
Arg Gly Tyr Pro Gly Leu Asp Gly Ala Lys
1               5                  10
```

(2) INFORMATION FOR SEQ ID NO:827:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:827:

```
Lys Gly Glu Ala Gly Ala Pro Gly Val Lys
1               5                  10
```

(2) INFORMATION FOR SEQ ID NO:828:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:828:

```
Met Gly Pro Arg Gly Leu Pro Gly Glu Arg
1               5                  10
```

(2) INFORMATION FOR SEQ ID NO:829:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:829:

Pro Gly Phe Pro Gly Ala Pro Gly Ala Lys
1               5                  10

(2) INFORMATION FOR SEQ ID NO:830:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:830:

Arg Gly Pro Glu Gly Ala Gln Gly Pro Arg
1               5                  10

(2) INFORMATION FOR SEQ ID NO:831:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:831:

Gln Gly Ala Thr Gly Pro Leu Gly Pro Lys
1               5                  10

(2) INFORMATION FOR SEQ ID NO:832:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:832:

Thr Gly Lys Pro Gly Ile Ala Gly Phe Lys
1               5                  10

(2) INFORMATION FOR SEQ ID NO:833:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:833:

Ala Gly Phe Lys Gly Glu Gln Gly Pro Lys
1               5                  10

(2) INFORMATION FOR SEQ ID NO:834:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:834:

Pro Gly Gln Asp Gly Leu Ala Gly Pro Lys
1               5                   10

(2) INFORMATION FOR SEQ ID NO:835:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:835:

Ala Gly Pro Lys Gly Ala Pro Gly Glu Arg
1               5                   10

(2) INFORMATION FOR SEQ ID NO:836:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:836:

Arg Gly Pro Ser Gly Leu Ala Gly Pro Lys
1               5                   10

(2) INFORMATION FOR SEQ ID NO:837:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:837:

Pro Gly Val Met Gly Phe Pro Gly Pro Lys
1               5                   10

(2) INFORMATION FOR SEQ ID NO:838:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:838:

Ala Gly Ala Pro Gly Leu Val Gly Pro Arg
1               5                   10

(2) INFORMATION FOR SEQ ID NO:839:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:839:

```
Pro Gly Thr Pro Gly Thr Asp Gly Pro Lys
1               5                   10
```

(2) INFORMATION FOR SEQ ID NO:840:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:840:

```
Pro Gly Leu Gln Gly Met Pro Gly Glu Arg
1               5                   10
```

(2) INFORMATION FOR SEQ ID NO:841:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:841:

```
Arg Gly Ala Ala Gly Ile Ala Gly Pro Lys
1               5                   10
```

(2) INFORMATION FOR SEQ ID NO:842:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:842:

```
Lys Gly Asp Arg Gly Asp Val Gly Glu Lys
1               5                   10
```

(2) INFORMATION FOR SEQ ID NO:843:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:843:

```
Pro Gly Pro Ala Gly Ala Asn Gly Glu Lys
1               5                   10
```

(2) INFORMATION FOR SEQ ID NO:844:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:844:

```
Lys Gly Glu Gln Gly Glu Ala Gly Gln Lys
  1               5                  10
```

(2) INFORMATION FOR SEQ ID NO:845:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:845:

```
Gln Gly Pro Thr Gly Val Thr Gly Pro Lys
  1               5                  10
```

(2) INFORMATION FOR SEQ ID NO:846:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:846:

```
Ser Gly Lys Asp Gly Pro Lys Gly Ala Arg
  1               5                  10
```

(2) INFORMATION FOR SEQ ID NO:847:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:847:

```
Gln Gly Pro Ala Gly Pro Pro Gly Glu Lys
  1               5                  10
```

(2) INFORMATION FOR SEQ ID NO:848:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:848:

```
Arg Gly Ile Val Gly Leu Pro Gly Gln Arg
  1               5                  10
```

(2) INFORMATION FOR SEQ ID NO:849:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:849:

Arg Gly Ile Gln Gly Pro Gln Gly Pro Arg
1               5                   10

(2) INFORMATION FOR SEQ ID NO:850:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:850:

Gln Gly Pro Gln Gly Pro Arg Gly Asp Lys
1               5                   10

(2) INFORMATION FOR SEQ ID NO:851:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:851:

Lys Gly Glu Ala Gly Glu Pro Gly Glu Arg
1               5                   10

(2) INFORMATION FOR SEQ ID NO:852:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:852:

Ala Gly Glu Pro Gly Glu Arg Gly Leu Lys
1               5                   10

(2) INFORMATION FOR SEQ ID NO:853:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:853:

Ser Gly Pro Ala Gly Pro Ser Gly Pro Arg
1               5                   10

(2) INFORMATION FOR SEQ ID NO:854:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:854:

```
Met Ser Ala Phe Ala Gly Leu Gly Pro Arg
1               5                   10
```

(2) INFORMATION FOR SEQ ID NO:855:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:855:

```
Gly Ala Arg Gly Gln Pro Gly Val Met
1               5
```

(2) INFORMATION FOR SEQ ID NO:856:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:856:

```
Gly Ala Asn Gly Ile Pro Gly Pro Ile
1               5
```

(2) INFORMATION FOR SEQ ID NO:857:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:857:

```
Lys Ala Gly Gly Ala Gln Leu Gly Val Met
1               5                   10
```

(2) INFORMATION FOR SEQ ID NO:858:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:858:

```
Pro Ala Gly Ala Pro Gly Pro Gln Gly Phe
1               5                   10
```

(2) INFORMATION FOR SEQ ID NO:859:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:859:

Leu Ala Gly Gln Arg Gly Ile Val Gly Leu
1               5                   10

(2) INFORMATION FOR SEQ ID NO:860:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:860:

Glu Ala Gly Glu Pro Gly Glu Arg Gly Leu
1               5                   10

(2) INFORMATION FOR SEQ ID NO:861:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:861:

Glu Pro Gly Val Ser Gly Pro Met
1               5

(2) INFORMATION FOR SEQ ID NO:862:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:862:

Gly Pro Gln Gly Ala Arg Gly Phe
1               5

(2) INFORMATION FOR SEQ ID NO:863:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:863:

Gly Pro Met Gly Pro Arg Gly Leu
1               5

(2) INFORMATION FOR SEQ ID NO:864:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:864:

Gly Pro Ala Gly Gly Pro Gly Phe
1               5

(2) INFORMATION FOR SEQ ID NO:865:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:865:

Glu Pro Gly Gly Val Gly Pro Ile
1               5

(2) INFORMATION FOR SEQ ID NO:866:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:866:

Gly Pro Ser Gly Phe Gln Gly Leu
1               5

(2) INFORMATION FOR SEQ ID NO:867:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:867:

Gly Pro Arg Gly Glu Arg Gly Phe
1               5

(2) INFORMATION FOR SEQ ID NO:868:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:868:

Gly Pro Pro Gly Leu Gln Gly Met
1               5

(2) INFORMATION FOR SEQ ID NO:869:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:869:

Gly Pro Pro Gly Thr Ser Gly Ile
1               5

(2) INFORMATION FOR SEQ ID NO:870:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:870:

Gly Pro Gln Gly Pro Thr Gly Val
1               5

(2) INFORMATION FOR SEQ ID NO:871:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:871:

Gly Pro Pro Gly Ala Thr Gly Phe
1               5

(2) INFORMATION FOR SEQ ID NO:872:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:872:

Phe Pro Gly Ala Ala Gly Arg Val
1               5

(2) INFORMATION FOR SEQ ID NO:873:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:873:

Gly Pro Pro Gly Pro Gln Gly Leu
1               5

(2) INFORMATION FOR SEQ ID NO:874:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:874:

```
Gly Pro Val Gly Pro Pro Gly Leu
  1               5
```

(2) INFORMATION FOR SEQ ID NO:875:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:875:

```
Gly Pro Ala Gly Ala Arg Gly Ile
  1               5
```

(2) INFORMATION FOR SEQ ID NO:876:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:876:

```
Pro Pro Gly Pro Gly Ile Asp Met
  1               5
```

(2) INFORMATION FOR SEQ ID NO:877:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:877:

```
Gly Pro Asp Pro Leu Gln Tyr Met
  1               5
```

(2) INFORMATION FOR SEQ ID NO:878:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:878:

```
Gly Pro Ala Gly Pro Pro Gly Pro Val
  1               5
```

(2) INFORMATION FOR SEQ ID NO:879:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:879:

Asp Pro Gln Gly Ala Thr Gly Pro Leu
1               5

(2) INFORMATION FOR SEQ ID NO:880:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:880:

Gly Pro Lys Gly Asp Arg Gly Asp Val
1               5

(2) INFORMATION FOR SEQ ID NO:881:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:881:

Gly Pro Arg Gly Pro Pro Gly Pro Val
1               5

(2) INFORMATION FOR SEQ ID NO:882:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:882:

Pro Pro Gly Pro Pro Gly Pro Gly Ile
1               5

(2) INFORMATION FOR SEQ ID NO:883:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:883:

Gly Pro Pro Gly Pro Gly Ile Asp Met
1               5

(2) INFORMATION FOR SEQ ID NO:884:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:884:

Gly Pro Gly Ile Asp Met Ser Ala Phe
1               5

(2) INFORMATION FOR SEQ ID NO:885:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:885:

Asn Pro Gly Glu Pro Gly Glu Pro Gly Val
1               5                   10

(2) INFORMATION FOR SEQ ID NO:886:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:886:

Pro Pro Gly Pro Gln Gly Ala Arg Gly Phe
1               5                   10

(2) INFORMATION FOR SEQ ID NO:887:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:887:

Phe Pro Gly Thr Pro Gly Leu Pro Gly Val
1               5                   10

(2) INFORMATION FOR SEQ ID NO:888:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:888:

Leu Pro Gly Val Lys Gly His Arg Gly Tyr
1               5                   10

(2) INFORMATION FOR SEQ ID NO:889:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:889:

```
Ser Pro Gly Pro Met Gly Pro Arg Gly Leu
 1               5                   10
```

(2) INFORMATION FOR SEQ ID NO:890:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:890:

```
Ala Pro Gly Ile Ala Gly Ala Pro Gly Phe
 1               5                   10
```

(2) INFORMATION FOR SEQ ID NO:891:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:891:

```
Ala Pro Gly Glu Arg Gly Pro Ser Gly Leu
 1               5                   10
```

(2) INFORMATION FOR SEQ ID NO:892:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:892:

```
Asp Pro Gly Arg Pro Gly Glu Pro Gly Leu
 1               5                   10
```

(2) INFORMATION FOR SEQ ID NO:893:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:893:

```
Glu Pro Gly Leu Pro Gly Ala Arg Gly Leu
 1               5                   10
```

(2) INFORMATION FOR SEQ ID NO:894:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:894:

```
Glu Pro Gly Lys Ala Gly Glu Lys Gly Leu
 1               5                  10
```

(2) INFORMATION FOR SEQ ID NO:895:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:895:

```
Leu Pro Gly Ala Pro Gly Leu Arg Gly Leu
 1               5                  10
```

(2) INFORMATION FOR SEQ ID NO:896:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:896:

```
Ala Pro Gly Pro Ser Gly Phe Gln Gly Leu
 1               5                  10
```

(2) INFORMATION FOR SEQ ID NO:897:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:897:

```
Val Pro Gly Glu Ala Gly Ala Pro Gly Leu
 1               5                  10
```

(2) INFORMATION FOR SEQ ID NO:898:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:898:

```
Pro Pro Gly Ala Gln Gly Pro Pro Gly Leu
 1               5                  10
```

(2) INFORMATION FOR SEQ ID NO:899:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:899:

```
Met Pro Gly Glu Arg Gly Ala Ala Gly Ile
  1               5                  10
```

(2) INFORMATION FOR SEQ ID NO:900:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:900:

```
Ala Pro Gly Lys Asp Gly Gly Arg Gly Leu
  1               5                  10
```

(2) INFORMATION FOR SEQ ID NO:901:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:901:

```
Ala Pro Gly Pro Gln Gly Pro Thr Gly Val
  1               5                  10
```

(2) INFORMATION FOR SEQ ID NO:902:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:902:

```
Pro Pro Gly Arg Ala Gly Glu Pro Gly Leu
  1               5                  10
```

(2) INFORMATION FOR SEQ ID NO:903:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:903:

```
Leu Pro Gly Gln Arg Gly Glu Arg Gly Phe
  1               5                  10
```

(2) INFORMATION FOR SEQ ID NO:904:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:904:

Pro Pro Gly Pro Val Gly Pro Pro Gly Leu
1               5                   10

(2) INFORMATION FOR SEQ ID NO:905:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:905:

Pro Pro Gly Arg Asp Gly Ala Ala Gly Val
1               5                   10

(2) INFORMATION FOR SEQ ID NO:906:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:906:

Gly Pro Pro Gly Pro Pro Gly Pro Gly Ile
1               5                   10

(2) INFORMATION FOR SEQ ID NO:907:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:907:

Gly Pro Arg Glu Lys Gly Pro Asp Pro Leu
1               5                   10

(2) INFORMATION FOR SEQ ID NO:908:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:908:

Thr Thr Asn Leu Arg Pro Thr Thr Tyr
1               5

(2) INFORMATION FOR SEQ ID NO:909:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:909:

Asn Ser Asp Arg Asp Ala Arg Phe Arg
1               5

(2) INFORMATION FOR SEQ ID NO:910:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:910:

Arg Thr Glu Thr Asp Phe Ser Asn Leu
1               5

(2) INFORMATION FOR SEQ ID NO:911:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:911:

Glu Thr Asp Phe Ser Asn Leu Phe Ala
1               5

(2) INFORMATION FOR SEQ ID NO:912:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:912:

Gly Met Glu Gly Phe Asn Leu Glu Leu
1               5

(2) INFORMATION FOR SEQ ID NO:913:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:913:

Leu Ser Asp His Pro Glu Ser Leu Glu
1               5

(2) INFORMATION FOR SEQ ID NO:914:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:914:

Leu Met Glu Gln Ile Thr Leu Lys Lys
 1               5

(2) INFORMATION FOR SEQ ID NO:915:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:915:

Thr Ser Glu Gln Ser His Tyr Ser Ile
 1               5

(2) INFORMATION FOR SEQ ID NO:916:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:916:

Gly Thr Asp Asn Val Ile Leu Ile Lys
 1               5

(2) INFORMATION FOR SEQ ID NO:917:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:917:

Ile Leu Glu Ala Lys Gln Lys Gly Tyr
 1               5

(2) INFORMATION FOR SEQ ID NO:918:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:918:

Cys Leu Glu Leu Ala Glu Tyr Leu Tyr
 1               5

(2) INFORMATION FOR SEQ ID NO:919:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:919:

Met Met Glu Ser Gly Thr Thr Met Val
1               5

(2) INFORMATION FOR SEQ ID NO:920:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:920:

Glu Ser Gly Thr Thr Met Val Gly Tyr
1               5

(2) INFORMATION FOR SEQ ID NO:921:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:921:

Gln Ser Asp Ile Asp Phe Leu Ile Glu
1               5

(2) INFORMATION FOR SEQ ID NO:922:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:922:

Asn Thr Thr Asn Leu Arg Pro Thr Thr Tyr
1               5                   10

(2) INFORMATION FOR SEQ ID NO:923:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:923:

Asn Ser Asp Arg Asp Ala Arg Phe Arg Arg
1               5                   10

(2) INFORMATION FOR SEQ ID NO:924:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:924:

```
Arg Thr Glu Thr Asp Phe Ser Asn Leu Phe
 1               5                  10
```

(2) INFORMATION FOR SEQ ID NO:925:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:925:

```
Glu Thr Asp Phe Ser Asn Leu Phe Ala Arg
 1               5                  10
```

(2) INFORMATION FOR SEQ ID NO:926:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:926:

```
Gly Met Glu Gly Phe Asn Leu Glu Leu Ser
 1               5                  10
```

(2) INFORMATION FOR SEQ ID NO:927:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:927:

```
Leu Ser Asp His Pro Glu Ser Leu Glu Gln
 1               5                  10
```

(2) INFORMATION FOR SEQ ID NO:928:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:928:

```
Leu Val Asp Cys Arg Asp Thr Leu Lys Tyr
 1               5                  10
```

(2) INFORMATION FOR SEQ ID NO:929:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:929:

```
Ser Thr Ala Asn Thr Asn Met Phe Thr Tyr
1               5                   10
```

(2) INFORMATION FOR SEQ ID NO:930:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:930:

```
Leu Met Glu Gln Ile Thr Leu Lys Lys Met
1               5                   10
```

(2) INFORMATION FOR SEQ ID NO:931:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:931:

```
Asn Met Tyr Ser Ile Met Ala Ala Arg Tyr
1               5                   10
```

(2) INFORMATION FOR SEQ ID NO:932:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:932:

```
Tyr Ser Ile Met Ala Ala Arg Tyr Lys Tyr
1               5                   10
```

(2) INFORMATION FOR SEQ ID NO:933:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:933:

```
Thr Ser Glu Gln Ser His Tyr Ser Ile Lys
1               5                   10
```

(2) INFORMATION FOR SEQ ID NO:934:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:934:

```
Gly Thr Asp Asn Val Ile Leu Ile Lys Cys
 1               5                  10
```

(2) INFORMATION FOR SEQ ID NO:935:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:935:

```
Gln Pro Asp Lys Gln Tyr Asp Val Ser Tyr
 1               5                  10
```

(2) INFORMATION FOR SEQ ID NO:936:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:936:

```
Met Met Glu Ser Gly Thr Thr Met Val Gly
 1               5                  10
```

(2) INFORMATION FOR SEQ ID NO:937:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:937:

```
Gln Ser Asp Ile Asp Phe Leu Ile Glu Glu
 1               5                  10
```

(2) INFORMATION FOR SEQ ID NO:938:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:938:

```
Met Tyr Ser Ile Met Ala Ala Arg Tyr
 1               5
```

(2) INFORMATION FOR SEQ ID NO:939:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:939:

```
Glu Ile Ala Asp Ile Cys Glu Lys Tyr
 1               5
```

(2) INFORMATION FOR SEQ ID NO:940:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:940:

```
Val Asn Ala Thr Ala Gly Thr Thr Val Tyr
 1               5                   10
```

(2) INFORMATION FOR SEQ ID NO:941:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:941:

```
Met Glu Ser Gly Thr Thr Met Val Gly Tyr
 1               5                   10
```

(2) INFORMATION FOR SEQ ID NO:942:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:942:

```
Leu Leu Ser Cys Glu Asn Ser Asp Arg
 1               5
```

(2) INFORMATION FOR SEQ ID NO:943:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:943:

```
Asp Ile Leu Leu Asn Tyr Val Arg Lys
 1               5
```

(2) INFORMATION FOR SEQ ID NO:944:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:944:

Leu Val Asp Cys Arg Asp Thr Leu Lys
 1               5

(2) INFORMATION FOR SEQ ID NO:945:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:945:

Val Leu Met Glu Gln Ile Thr Leu Lys
 1               5

(2) INFORMATION FOR SEQ ID NO:946:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:946:

Asn Met Tyr Ser Ile Met Ala Ala Arg
 1               5

(2) INFORMATION FOR SEQ ID NO:947:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:947:

Val Ile Leu Ile Lys Cys Asn Glu Arg
 1               5

(2) INFORMATION FOR SEQ ID NO:948:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:948:

Leu Ile Lys Cys Asn Glu Arg Gly Lys
 1               5

(2) INFORMATION FOR SEQ ID NO:949:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:949:

Ile Ile Pro Ala Asp Phe Glu Ala Lys
 1               5

(2) INFORMATION FOR SEQ ID NO:950:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:950:

Gly Leu Leu Met Ser Arg Lys His Arg
 1               5

(2) INFORMATION FOR SEQ ID NO:951:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:951:

Leu Met Ser Arg Lys His Arg His Lys
 1               5

(2) INFORMATION FOR SEQ ID NO:952:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:952:

Asp Val Ser Tyr Asp Thr Gly Asp Lys
 1               5

(2) INFORMATION FOR SEQ ID NO:953:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:953:

Glu Leu Ala Glu Tyr Leu Tyr Ala Lys
 1               5

(2) INFORMATION FOR SEQ ID NO:954:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:954:

```
Tyr Leu Tyr Ala Lys Ile Lys Asn Arg
 1               5
```

(2) INFORMATION FOR SEQ ID NO:955:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:955:

```
Gly Val Pro Asp Ser Pro Gln Arg Arg
 1               5
```

(2) INFORMATION FOR SEQ ID NO:956:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:956:

```
Asn Leu Leu Ser Cys Glu Asn Ser Asp Arg
 1               5                  10
```

(2) INFORMATION FOR SEQ ID NO:957:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:957:

```
Val Val Asp Ile Leu Leu Asn Tyr Val Arg
 1               5                  10
```

(2) INFORMATION FOR SEQ ID NO:958:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:958:

```
Ser Leu Glu Gln Ile Leu Val Asp Cys Arg
 1               5                  10
```

(2) INFORMATION FOR SEQ ID NO:959:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:959:

```
Ile Leu Val Asp Cys Arg Asp Thr Leu Lys
1               5                   10
```

(2) INFORMATION FOR SEQ ID NO:960:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:960:

```
Phe Val Leu Met Glu Gln Ile Thr Leu Lys
1               5                   10
```

(2) INFORMATION FOR SEQ ID NO:961:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:961:

```
Val Leu Met Glu Gln Ile Thr Leu Lys Lys
1               5                   10
```

(2) INFORMATION FOR SEQ ID NO:962:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:962:

```
Lys Thr Lys Gly Met Ala Ala Val Pro Lys
1               5                   10
```

(2) INFORMATION FOR SEQ ID NO:963:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:963:

```
Asn Val Ile Leu Ile Lys Cys Asn Glu Arg
1               5                   10
```

(2) INFORMATION FOR SEQ ID NO:964:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:964:

```
Ile Leu Ile Lys Cys Asn Glu Arg Gly Lys
 1               5                   10

(2) INFORMATION FOR SEQ ID NO:965:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:965:

Lys Ile Ile Pro Ala Asp Phe Glu Ala Lys
 1               5                   10

(2) INFORMATION FOR SEQ ID NO:966:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:966:

Leu Leu Met Ser Arg Lys His Arg His Lys
 1               5                   10

(2) INFORMATION FOR SEQ ID NO:967:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:967:

Leu Leu Gln Cys Ser Ala Ile Leu Val Lys
 1               5                   10

(2) INFORMATION FOR SEQ ID NO:968:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:968:

Asp Ile Phe Lys Phe Trp Leu Met Trp Lys
 1               5                   10

(2) INFORMATION FOR SEQ ID NO:969:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:969:
```

Thr Val Gly Phe Glu Asn Gln Ile Asn Lys
1               5                   10

(2) INFORMATION FOR SEQ ID NO:970:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:970:

Lys Leu His Lys Val Ala Pro Lys Ile Lys
1               5                   10

(2) INFORMATION FOR SEQ ID NO:971:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:971:

Met Val Gly Tyr Gln Pro Gln Gly Asp Lys
1               5                   10

(2) INFORMATION FOR SEQ ID NO:972:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:972:

Cys Gly Val Ala His Gly Cys Thr Arg
1               5

(2) INFORMATION FOR SEQ ID NO:973:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:973:

Lys Ser Arg Leu Val Ser Ala Phe Lys
1               5

(2) INFORMATION FOR SEQ ID NO:974:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:974:

Phe Ala Arg Asp Leu Leu Pro Ala Lys
1               5

(2) INFORMATION FOR SEQ ID NO:975:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:975:

Ser Thr Lys Val Leu Asp Phe His His
1               5

(2) INFORMATION FOR SEQ ID NO:976:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:976:

Phe Thr Tyr Glu Ile Ala Pro Val Phe
1               5

(2) INFORMATION FOR SEQ ID NO:977:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:977:

Tyr Ser Ile Met Ala Ala Arg Tyr Lys
1               5

(2) INFORMATION FOR SEQ ID NO:978:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:978:

Val Leu Phe Thr Ser Glu Gln Ser His
1               5

(2) INFORMATION FOR SEQ ID NO:979:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:979:

```
Gly Gly Gly Leu Leu Met Ser Arg Lys
  1               5
```

(2) INFORMATION FOR SEQ ID NO:980:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:980:

```
Asn Ser Val Thr Trp Asn Pro His Lys
  1               5
```

(2) INFORMATION FOR SEQ ID NO:981:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:981:

```
Cys Ser Ala Ile Leu Val Lys Glu Lys
  1               5
```

(2) INFORMATION FOR SEQ ID NO:982:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:982:

```
Ala Gly Tyr Leu Leu Gln Pro Asp Lys
  1               5
```

(2) INFORMATION FOR SEQ ID NO:983:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:983:

```
Cys Gly Arg His Val Asp Ile Phe Lys
  1               5
```

(2) INFORMATION FOR SEQ ID NO:984:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:984:

Ile Phe Lys Phe Trp Leu Met Trp Lys
1               5

(2) INFORMATION FOR SEQ ID NO:985:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:985:

Lys Phe Trp Leu Met Trp Lys Ala Lys
1               5

(2) INFORMATION FOR SEQ ID NO:986:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:986:

Val Gly Phe Glu Asn Gln Ile Asn Lys
1               5

(2) INFORMATION FOR SEQ ID NO:987:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:987:

Gln Gly Asp Lys Ala Asn Phe Phe Arg
1               5

(2) INFORMATION FOR SEQ ID NO:988:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:988:

Cys Gly Val Ala His Gly Cys Thr Arg Lys
1               5                   10

(2) INFORMATION FOR SEQ ID NO:989:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:989:

```
Ser Ala Phe Lys Glu Arg Gln Ser Ser Lys
  1               5                  10
```

(2) INFORMATION FOR SEQ ID NO:990:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:990:

```
Val Asp Ile Leu Leu Asn Tyr Val Arg Lys
  1               5                  10
```

(2) INFORMATION FOR SEQ ID NO:991:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:991:

```
Thr Leu Lys Tyr Gly Val Arg Thr Gly His
  1               5                  10
```

(2) INFORMATION FOR SEQ ID NO:992:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:992:

```
Ser Ile Met Ala Ala Arg Tyr Lys Tyr Phe
  1               5                  10
```

(2) INFORMATION FOR SEQ ID NO:993:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:993:

```
Phe Gly Thr Asp Asn Val Ile Leu Ile Lys
  1               5                  10
```

(2) INFORMATION FOR SEQ ID NO:994:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:994:

```
Trp Gly Gly Gly Leu Leu Met Ser Arg Lys
 1               5                  10
```

(2) INFORMATION FOR SEQ ID NO:995:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:995:

```
Cys Ala Gly Tyr Leu Leu Gln Pro Asp Lys
 1               5                  10
```

(2) INFORMATION FOR SEQ ID NO:996:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:996:

```
Thr Gly Asp Lys Ala Ile Gln Cys Gly Arg
 1               5                  10
```

(2) INFORMATION FOR SEQ ID NO:997:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:997:

```
Gln Cys Gly Arg His Val Asp Ile Phe Lys
 1               5                  10
```

(2) INFORMATION FOR SEQ ID NO:998:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:998:

```
Cys Phe Trp Tyr Ile Pro Gln Ser Leu Arg
 1               5                  10
```

(2) INFORMATION FOR SEQ ID NO:999:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:999:

```
Gly Ala Asp Pro Asn Thr Thr Asn Leu
 1               5
```

(2) INFORMATION FOR SEQ ID NO:1000:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1000:

```
Val Ala His Gly Cys Thr Arg Lys Leu
 1               5
```

(2) INFORMATION FOR SEQ ID NO:1001:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1001:

```
Gly Phe Leu Gln Arg Thr Asn Ser Leu
 1               5
```

(2) INFORMATION FOR SEQ ID NO:1002:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1002:

```
Arg Phe Arg Arg Thr Glu Thr Asp Phe
 1               5
```

(2) INFORMATION FOR SEQ ID NO:1003:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1003:

```
Gln Phe Leu Leu Glu Val Val Asp Ile
 1               5
```

(2) INFORMATION FOR SEQ ID NO:1004:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1004:

Thr Phe Asp Arg Ser Thr Lys Val Leu
1               5

(2) INFORMATION FOR SEQ ID NO:1005:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1005:

Asp Phe His His Pro His Gln Leu Leu
1               5

(2) INFORMATION FOR SEQ ID NO:1006:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1006:

Phe Phe Asn Gln Leu Ser Thr Gly Leu
1               5

(2) INFORMATION FOR SEQ ID NO:1007:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1007:

Gly Ala Ile Ser Asn Met Tyr Ser Ile
1               5

(2) INFORMATION FOR SEQ ID NO:1008:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1008:

Met Ala Ala Val Pro Lys Leu Val Leu
1               5

(2) INFORMATION FOR SEQ ID NO:1009:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1009:

```
Ala Ala Val Pro Lys Leu Val Leu Phe
1               5
```

(2) INFORMATION FOR SEQ ID NO:1010:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1010:

```
Gly Phe Gly Thr Asp Asn Val Ile Leu
1               5
```

(2) INFORMATION FOR SEQ ID NO:1011:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1011:

```
Pro Ala Asp Phe Glu Ala Lys Ile Leu
1               5
```

(2) INFORMATION FOR SEQ ID NO:1012:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1012:

```
Gly Ala Phe Asp Pro Ile Gln Glu Ile
1               5
```

(2) INFORMATION FOR SEQ ID NO:1013:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1013:

```
Leu Trp Leu His Val Asp Ala Ala Trp
1               5
```

(2) INFORMATION FOR SEQ ID NO:1014:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1014:

Asp Ala Ala Trp Gly Gly Gly Leu Leu
1               5

(2) INFORMATION FOR SEQ ID NO:1015:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1015:

Ala Ala Trp Gly Gly Gly Leu Leu Met
1               5

(2) INFORMATION FOR SEQ ID NO:1016:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1016:

Ser Tyr Asp Thr Gly Asp Lys Ala Ile
1               5

(2) INFORMATION FOR SEQ ID NO:1017:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1017:

Leu Ala Glu Tyr Leu Tyr Ala Lys Ile
1               5

(2) INFORMATION FOR SEQ ID NO:1018:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1018:

Cys Phe Trp Tyr Ile Pro Gln Ser Leu
1               5

(2) INFORMATION FOR SEQ ID NO:1019:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1019:

```
Val Ala Pro Lys Ile Lys Ala Leu Met
 1               5
```

(2) INFORMATION FOR SEQ ID NO:1020:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1020:

```
Lys Ala Asn Phe Phe Arg Met Val Ile
 1               5
```

(2) INFORMATION FOR SEQ ID NO:1021:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1021:

```
Ala Ala Thr Gln Ser Asp Ile Asp Phe
 1               5
```

(2) INFORMATION FOR SEQ ID NO:1022:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1022:

```
Asp Phe Ser Asn Leu Phe Ala Arg Asp Leu
 1               5                   10
```

(2) INFORMATION FOR SEQ ID NO:1023:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1023:

```
Gln Phe Leu Leu Glu Val Val Asp Ile Leu
 1               5                   10
```

(2) INFORMATION FOR SEQ ID NO:1024:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1024:

Arg Phe Phe Asn Gln Leu Ser Thr Gly Leu
 1               5                  10

(2) INFORMATION FOR SEQ ID NO:1025:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1025:

Met Phe Thr Tyr Glu Ile Ala Pro Val Phe
 1               5                  10

(2) INFORMATION FOR SEQ ID NO:1026:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1026:

Thr Tyr Glu Ile Ala Pro Val Phe Val Leu
 1               5                  10

(2) INFORMATION FOR SEQ ID NO:1027:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1027:

Val Phe Val Leu Met Glu Gln Ile Thr Leu
 1               5                  10

(2) INFORMATION FOR SEQ ID NO:1028:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1028:

Gly Trp Ser Ser Lys Asp Gly Asp Gly Ile
 1               5                  10

(2) INFORMATION FOR SEQ ID NO:1029:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1029:

```
Gly Ala Ile Ser Asn Met Tyr Ser Ile Met
1               5                   10
```

(2) INFORMATION FOR SEQ ID NO:1030:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1030:

```
Tyr Phe Pro Glu Val Lys Thr Lys Gly Met
1               5                   10
```

(2) INFORMATION FOR SEQ ID NO:1031:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1031:

```
Met Ala Ala Val Pro Lys Leu Val Leu Phe
1               5                   10
```

(2) INFORMATION FOR SEQ ID NO:1032:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1032:

```
Gly Phe Gly Thr Asp Asn Val Ile Leu Ile
1               5                   10
```

(2) INFORMATION FOR SEQ ID NO:1033:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1033:

```
Glu Ala Lys Gln Lys Gly Tyr Val Pro Phe
1               5                   10
```

(2) INFORMATION FOR SEQ ID NO:1034:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1034:

Thr Ala Gly Thr Thr Val Tyr Gly Ala Phe
1               5                   10

(2) INFORMATION FOR SEQ ID NO:1035:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1035:

Ile Ala Asp Ile Cys Glu Lys Tyr Asn Leu
1               5                   10

(2) INFORMATION FOR SEQ ID NO:1036:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1036:

Asp Ala Ala Trp Gly Gly Gly Leu Leu Met
1               5                   10

(2) INFORMATION FOR SEQ ID NO:1037:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1037:

Ser Ala Ile Leu Val Lys Glu Lys Gly Ile
1               5                   10

(2) INFORMATION FOR SEQ ID NO:1038:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1038:

Met Trp Lys Ala Lys Gly Thr Val Gly Phe
1               5                   10

(2) INFORMATION FOR SEQ ID NO:1039:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1039:

```
Gly Phe Glu Asn Gln Ile Asn Lys Cys Leu
 1               5                  10
```

(2) INFORMATION FOR SEQ ID NO:1040:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1040:

```
Tyr Ala Lys Ile Lys Asn Arg Glu Glu Phe
 1               5                  10
```

(2) INFORMATION FOR SEQ ID NO:1041:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1041:

```
Val Ala Pro Lys Ile Lys Ala Leu Met Met
 1               5                  10
```

(2) INFORMATION FOR SEQ ID NO:1042:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1042:

```
Pro Ala Ala Thr Gln Ser Asp Ile Asp Phe
 1               5                  10
```

(2) INFORMATION FOR SEQ ID NO:1043:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1043:

```
Ala Ala Thr Gln Ser Asp Ile Asp Phe Leu
 1               5                  10
```

(2) INFORMATION FOR SEQ ID NO:1044:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1044:

Asp Phe Leu Ile Glu Glu Ile Glu Arg Leu
 1               5                  10

(2) INFORMATION FOR SEQ ID NO:1045:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1045:

Arg Pro Thr Thr Tyr Asp Thr Trp
 1               5

(2) INFORMATION FOR SEQ ID NO:1046:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1046:

His Pro Glu Ser Leu Glu Gln Ile
 1               5

(2) INFORMATION FOR SEQ ID NO:1047:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1047:

His Pro Arg Phe Phe Asn Gln Leu
 1               5

(2) INFORMATION FOR SEQ ID NO:1048:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1048:

Asn Pro His Lys Met Met Gly Val
 1               5

(2) INFORMATION FOR SEQ ID NO:1049:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1049:

Gln Pro Asp Lys Gln Tyr Asp Val
1               5

(2) INFORMATION FOR SEQ ID NO:1050:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1050:

Ile Pro Gln Ser Leu Arg Gly Val
1               5

(2) INFORMATION FOR SEQ ID NO:1051:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1051:

Ser Pro Gln Arg Arg Glu Lys Leu
1               5

(2) INFORMATION FOR SEQ ID NO:1052:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1052:

Ala Pro Lys Ile Lys Ala Leu Met
1               5

(2) INFORMATION FOR SEQ ID NO:1053:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1053:

His Pro His Gln Leu Leu Glu Gly Met
1               5

(2) INFORMATION FOR SEQ ID NO:1054:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1054:

His Pro Glu Ser Leu Glu Gln Ile Leu
1               5

(2) INFORMATION FOR SEQ ID NO:1055:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1055:

Ser Pro Gly Gly Ala Ile Ser Asn Met
1               5

(2) INFORMATION FOR SEQ ID NO:1056:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1056:

Phe Pro Glu Val Lys Thr Lys Gly Met
1               5

(2) INFORMATION FOR SEQ ID NO:1057:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1057:

Ile Pro Ala Asp Phe Glu Ala Lys Ile
1               5

(2) INFORMATION FOR SEQ ID NO:1058:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1058:

Asp Pro Ile Gln Glu Ile Ala Asp Ile
1               5

(2) INFORMATION FOR SEQ ID NO:1059:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1059:

Asn Pro His Lys Met Met Gly Val Leu
1               5

(2) INFORMATION FOR SEQ ID NO:1060:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1060:

Glu Pro Glu His Thr Ser Val Cys Phe
1               5

(2) INFORMATION FOR SEQ ID NO:1061:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1061:

Ala Pro Lys Ile Lys Ala Leu Met Met
1               5

(2) INFORMATION FOR SEQ ID NO:1062:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1062:

Gln Pro Gln Gly Asp Lys Ala Asn Phe
1               5

(2) INFORMATION FOR SEQ ID NO:1063:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1063:

Asn Pro Ala Ala Thr Gln Ser Asp Ile
1               5

(2) INFORMATION FOR SEQ ID NO:1064:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1064:

```
His Pro Glu Ser Leu Glu Gln Ile Leu Val
 1               5                  10
```

(2) INFORMATION FOR SEQ ID NO:1065:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1065:

```
Ala Pro Val Phe Val Leu Met Glu Gln Ile
 1               5                  10
```

(2) INFORMATION FOR SEQ ID NO:1066:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1066:

```
Ser Pro Gly Gly Ala Ile Ser Asn Met Tyr
 1               5                  10
```

(2) INFORMATION FOR SEQ ID NO:1067:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1067:

```
Ile Pro Ala Asp Phe Glu Ala Lys Ile Leu
 1               5                  10
```

(2) INFORMATION FOR SEQ ID NO:1068:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1068:

```
Asn Pro His Lys Met Met Gly Val Leu Leu
 1               5                  10
```

(2) INFORMATION FOR SEQ ID NO:1069:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1069:

```
Glu Pro Glu His Thr Ser Val Cys Phe Trp
1               5                   10
```

(2) INFORMATION FOR SEQ ID NO:1070:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1070:

```
Gln Pro Gln Gly Asp Lys Ala Asn Phe Phe
1               5                   10
```

(2) INFORMATION FOR SEQ ID NO:1071:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1071:

```
Pro Ser Gln Arg His Gly Ser Lys Tyr
1               5
```

(2) INFORMATION FOR SEQ ID NO:1072:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1072:

```
Thr Met Asp His Ala Arg His Gly Phe
1               5
```

(2) INFORMATION FOR SEQ ID NO:1073:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1073:

```
Ala Ser Asp Tyr Lys Ser Ala His Lys
1               5
```

(2) INFORMATION FOR SEQ ID NO:1074:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1074:

```
Thr Met Asp His Ala Arg His Gly Phe Leu
 1               5                  10
```

(2) INFORMATION FOR SEQ ID NO:1075:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1075:

```
Ala Ser Asp Tyr Lys Ser Ala His Lys Gly
 1               5                  10
```

(2) INFORMATION FOR SEQ ID NO:1076:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1076:

```
Arg Pro Ser Gln Arg His Gly Ser Lys Tyr
 1               5                  10
```

(2) INFORMATION FOR SEQ ID NO:1077:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1077:

```
Phe Leu Pro Arg His Arg Asp Thr Gly Ile
 1               5                  10
```

(2) INFORMATION FOR SEQ ID NO:1078:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1078:

```
Ser Leu Ser Arg Phe Ser Trp Gly Ala
 1               5
```

(2) INFORMATION FOR SEQ ID NO:1079:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1079:

```
Ser Leu Pro Gln Lys Ser His Gly Arg
1               5
```

(2) INFORMATION FOR SEQ ID NO:1080:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1080:

```
Arg Thr Pro Pro Ser Gln Gly Lys
1               5
```

(2) INFORMATION FOR SEQ ID NO:1081:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1081:

```
Ala Thr Ala Ser Thr Met Asp His Ala Arg
1               5                   10
```

(2) INFORMATION FOR SEQ ID NO:1082:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1082:

```
Asp Thr Gly Ile Leu Asp Ser Ile Gly Arg
1               5                   10
```

(2) INFORMATION FOR SEQ ID NO:1083:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1083:

```
Ser Ile Gly Arg Phe Phe Gly Gly Asp Arg
1               5                   10
```

(2) INFORMATION FOR SEQ ID NO:1084:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1084:

```
Gly Val Asp Ala Gln Gly Thr Leu Ser Lys
 1               5                  10
```

(2) INFORMATION FOR SEQ ID NO:1085:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1085:

```
Thr Ala Ser Thr Met Asp His Ala Arg
 1               5
```

(2) INFORMATION FOR SEQ ID NO:1086:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1086:

```
His Ala Arg His Gly Phe Leu Pro Arg
 1               5
```

(2) INFORMATION FOR SEQ ID NO:1087:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1087:

```
Thr Gly Ile Leu Asp Ser Ile Gly Arg
 1               5
```

(2) INFORMATION FOR SEQ ID NO:1088:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1088:

```
Ile Gly Arg Phe Phe Gly Gly Asp Arg
 1               5
```

(2) INFORMATION FOR SEQ ID NO:1089:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1089:

Gly Gly Asp Arg Gly Ala Pro Lys Arg
1               5

(2) INFORMATION FOR SEQ ID NO:1090:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1090:

Gly Ala Pro Lys Arg Gly Ser Gly Lys
1               5

(2) INFORMATION FOR SEQ ID NO:1091:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1091:

Lys Gly Arg Gly Leu Ser Leu Ser Arg
1               5

(2) INFORMATION FOR SEQ ID NO:1092:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1092:

Tyr Gly Gly Arg Ala Ser Asp Tyr Lys
1               5

(2) INFORMATION FOR SEQ ID NO:1093:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1093:

Val Asp Ala Gln Gly Thr Leu Ser Lys
1               5

(2) INFORMATION FOR SEQ ID NO:1094:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1094:

```
Gln Gly Thr Leu Ser Lys Ile Phe Lys
  1               5
```

(2) INFORMATION FOR SEQ ID NO:1095:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1095:

```
Arg Gly Ala Pro Lys Arg Gly Ser Gly Lys
  1               5                  10
```

(2) INFORMATION FOR SEQ ID NO:1096:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1096:

```
Thr Ala His Tyr Gly Ser Leu Pro Gln Lys
  1               5                  10
```

(2) INFORMATION FOR SEQ ID NO:1097:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1097:

```
His Phe Phe Lys Asn Ile Val Thr Pro Arg
  1               5                  10
```

(2) INFORMATION FOR SEQ ID NO:1098:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1098:

```
Arg Phe Ser Trp Gly Ala Glu Gly Gln Arg
  1               5                  10
```

(2) INFORMATION FOR SEQ ID NO:1099:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1099:

Arg Ala Ser Asp Tyr Lys Ser Ala His Lys
1               5                   10

(2) INFORMATION FOR SEQ ID NO:1100:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1100:

Lys Tyr Leu Ala Thr Ala Ser Thr Met
1               5

(2) INFORMATION FOR SEQ ID NO:1101:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1101:

Gly Ala Glu Gly Gln Arg Pro Gly Phe
1               5

(2) INFORMATION FOR SEQ ID NO:1102:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1102:

Asp Tyr Lys Ser Ala His Lys Gly Phe
1               5

(2) INFORMATION FOR SEQ ID NO:1103:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1103:

Asp Ala Gln Gly Thr Leu Ser Lys Ile
1               5

(2) INFORMATION FOR SEQ ID NO:1104:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1104:

```
Pro Ala Arg Thr Ala His Tyr Gly Ser Leu
 1               5                  10
```

(2) INFORMATION FOR SEQ ID NO:1105:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1105:

```
Asp Ala Gln Gly Thr Leu Ser Lys Ile Phe
 1               5                  10
```

(2) INFORMATION FOR SEQ ID NO:1106:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1106:

```
His Pro Ala Arg Thr Ala His Tyr
 1               5
```

(2) INFORMATION FOR SEQ ID NO:1107:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1107:

```
Leu Pro Arg His Arg Asp Thr Gly Ile
 1               5
```

(2) INFORMATION FOR SEQ ID NO:1108:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1108:

```
Leu Pro Arg His Arg Asp Thr Gly Ile Leu
 1               5                  10
```

(2) INFORMATION FOR SEQ ID NO:1109:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1109:

```
Asn Pro Val Val His Phe Phe Lys Asn Ile
 1               5                  10
```

(2) INFORMATION FOR SEQ ID NO:1110:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1110:

```
Pro Pro Ser Gln Gly Lys Gly Arg Gly Leu
 1               5                  10
```

(2) INFORMATION FOR SEQ ID NO:1111:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1111:

```
Phe Thr Phe Ser Pro Thr Tyr Lys Ala Phe Leu Ser Lys
 1               5                  10
```

(2) INFORMATION FOR SEQ ID NO:1112:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1112:

```
Gly Thr Leu Pro Gln Glu His Ile Val Leu Lys Leu Lys
 1               5                  10
```

(2) INFORMATION FOR SEQ ID NO:1113:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1113:

```
Phe Thr Phe Ser Pro Thr Tyr Lys Ala Phe Leu Cys Lys
 1               5                  10
```

(2) INFORMATION FOR SEQ ID NO:1114:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1114:

Gly Thr Leu Pro Gln Glu His Ile Val Leu Lys Ile Lys
1               5                   10

(2) INFORMATION FOR SEQ ID NO:1115:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1115:

Leu Val Val Ser Tyr Val Asn Thr Asn Met Gly Leu Lys
1               5                   10

(2) INFORMATION FOR SEQ ID NO:1116:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1116:

Ser Thr Thr Asp Leu Glu Ala Tyr Phe Lys Asp Cys Leu Phe Lys
1               5                   10                  15

(2) INFORMATION FOR SEQ ID NO:1117:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1117:

Leu Val Val Ser Tyr Val Asn Val Asn Met Gly Leu Lys
1               5                   10

(2) INFORMATION FOR SEQ ID NO:1118:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1118:

Gly Thr Leu Pro Gln Asp His Ile Val Gln Lys Ile Lys
1               5                   10

(2) INFORMATION FOR SEQ ID NO:1119:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1119:

```
Ser Thr Ser Ser Cys Leu His Gln Ser Ala Val Arg Lys
1               5                   10
```

(2) INFORMATION FOR SEQ ID NO:1120:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1120:

```
Thr Thr Val Asn Ala His Gln Ile Leu Pro Lys Val Leu His Lys
1               5                   10                  15
```

(2) INFORMATION FOR SEQ ID NO:1121:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1121:

```
Arg Thr Pro Ala Arg Val Thr Gly Gly Val Phe Leu Val Asp Lys
1               5                   10                  15
```

(2) INFORMATION FOR SEQ ID NO:1122:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1122:

```
His Thr Thr Asn Phe Ala Ser Lys
1               5
```

(2) INFORMATION FOR SEQ ID NO:1123:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1123:

```
Phe Thr Phe Ser Pro Thr Tyr Lys
1               5
```

(2) INFORMATION FOR SEQ ID NO:1124:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1124:

Pro Thr Tyr Lys Ala Phe Leu Cys Lys Gln Tyr
1               5                   10

(2) INFORMATION FOR SEQ ID NO:1125:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1125:

Cys Thr Thr Pro Ala Gln Gly Thr Ser Met Tyr
1               5                   10

(2) INFORMATION FOR SEQ ID NO:1126:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1126:

Pro Thr Ser Cys Pro Pro Thr Cys Pro Gly Tyr
1               5                   10

(2) INFORMATION FOR SEQ ID NO:1127:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1127:

Leu Met Pro Leu Tyr Ala Cys Ile Gln Ser Lys
1               5                   10

(2) INFORMATION FOR SEQ ID NO:1128:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1128:

Arg Val Thr Gly Gly Val Phe Leu Val Asp Lys
1               5                   10

(2) INFORMATION FOR SEQ ID NO:1129:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1129:

His Thr Leu Trp Lys Ala Gly Ile Leu Tyr Lys
 1               5                  10

(2) INFORMATION FOR SEQ ID NO:1130:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1130:

Gln Thr Arg His Tyr Leu His Thr Leu Trp Lys
 1               5                  10

(2) INFORMATION FOR SEQ ID NO:1131:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1131:

Gly Thr Asp Asn Ser Val Val Leu Ser Arg Lys
 1               5                  10

(2) INFORMATION FOR SEQ ID NO:1132:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1132:

Ser Tyr Val Asn Thr Asn Met Gly Leu Lys Phe
 1               5                  10

(2) INFORMATION FOR SEQ ID NO:1133:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1133:

Leu Tyr Ser Ile Leu Ser Pro Phe
 1               5

(2) INFORMATION FOR SEQ ID NO:1134:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1134:

Trp Tyr Trp Gly Pro Ser Leu Tyr Ser Ile Leu
1               5                   10

(2) INFORMATION FOR SEQ ID NO:1135:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1135:

Leu Tyr Ser Ile Leu Ser Pro Phe Leu Pro Leu
1               5                   10

(2) INFORMATION FOR SEQ ID NO:1136:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1136:

Pro Tyr Lys Glu Phe Gly Ala Thr Val Glu Leu
1               5                   10

(2) INFORMATION FOR SEQ ID NO:1137:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1137:

Cys Thr Trp Met Asn Ser Thr Gly Phe Thr Lys
1               5                   10

(2) INFORMATION FOR SEQ ID NO:1138:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1138:

Met Tyr Val Gly Asp Leu Cys Gly Ser Val Phe
1               5                   10

(2) INFORMATION FOR SEQ ID NO:1139:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1139:

Val Tyr Leu Leu Pro Arg Arg Gly Pro Arg Leu
1               5                   10

(2) INFORMATION FOR SEQ ID NO:1140:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1140:

Ile Thr Lys Ile Gln Asn Phe Arg Val Tyr Tyr
1               5                   10

(2) INFORMATION FOR SEQ ID NO:1141:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1141:

Ile Val Ala Ser Cys Asp Lys Cys Gln Leu Lys
1               5                   10

(2) INFORMATION FOR SEQ ID NO:1142:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1142:

Lys Val Lys Gln Trp Pro Leu Thr Glu Glu Lys
1               5                   10

(2) INFORMATION FOR SEQ ID NO:1143:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1143:

Thr Val Asn Asp Ile Gln Lys Leu Val Gly Lys
1               5                   10

(2) INFORMATION FOR SEQ ID NO:1144:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1144:

```
Asp Val Lys Gln Leu Thr Glu Ala Val Gln Lys
 1               5                  10
```

(2) INFORMATION FOR SEQ ID NO:1145:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1145:

```
Ala Val Val Ile Gln Asp Asn Ser Asp Ile Lys
 1               5                  10
```

(2) INFORMATION FOR SEQ ID NO:1146:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1146:

```
Leu Thr Glu Asp Arg Trp Asn Lys Pro Gln Lys
 1               5                  10
```

(2) INFORMATION FOR SEQ ID NO:1147:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1147:

```
Ala Thr Asp Ile Gln Thr Lys Glu Leu Gln Lys
 1               5                  10
```

(2) INFORMATION FOR SEQ ID NO:1148:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1148:

```
Gln Thr Lys Glu Leu Gln Lys Gln Ile Thr Lys
 1               5                  10
```

(2) INFORMATION FOR SEQ ID NO:1149:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1149:

```
Trp Thr Val Gln Pro Ile Val Leu Pro Glu Lys
 1               5                  10
```

(2) INFORMATION FOR SEQ ID NO:1150:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1150:

```
Gln Val Pro Leu Arg Pro Met Thr Tyr Lys
 1               5                  10
```

(2) INFORMATION FOR SEQ ID NO:1151:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1151:

```
Gln Val Pro Leu Tyr Pro Met Thr Phe Lys
 1               5                  10
```

(2) INFORMATION FOR SEQ ID NO:1152:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1152:

```
Val Pro Leu Arg Pro Met Thr Tyr Lys
 1               5
```

(2) INFORMATION FOR SEQ ID NO:1153:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1153:

```
Ala Val Asp Leu Ser His Phe Leu Lys
 1               5
```

(2) INFORMATION FOR SEQ ID NO:1154:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1154:

```
Ala Thr Leu Tyr Cys Val His Gln Arg
1               5
```

(2) INFORMATION FOR SEQ ID NO:1155:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1155:

```
Arg Leu Arg Asp Leu Leu Leu Ile Val
1               5
```

(2) INFORMATION FOR SEQ ID NO:1156:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1156:

```
Arg Leu Arg Asp Leu Leu Leu Ile Val Thr Arg
1               5                   10
```

(2) INFORMATION FOR SEQ ID NO:1157:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1157:

```
Arg Leu Arg Asp Tyr Leu Leu Ile Val Thr Arg
1               5                   10
```

(2) INFORMATION FOR SEQ ID NO:1158:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1158:

```
Leu Arg Asp Leu Leu Leu Ile Val Thr Arg
1               5                   10
```

(2) INFORMATION FOR SEQ ID NO:1159:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1159:

```
Gln Ile Tyr Gln Glu Pro Phe Lys Asn Leu Lys
 1               5                   10
```

(2) INFORMATION FOR SEQ ID NO:1160:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1160:

```
Ala Val Phe Ile His Asn Phe Lys
 1               5
```

(2) INFORMATION FOR SEQ ID NO:1161:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1161:

```
Arg Thr Leu Asn Ala Trp Val Lys
 1               5
```

(2) INFORMATION FOR SEQ ID NO:1162:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1162:

```
Glu Thr Ala Tyr Phe Leu Leu Lys
 1               5
```

(2) INFORMATION FOR SEQ ID NO:1163:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1163:

```
Arg Leu Arg Pro Gly Gly Lys Lys Lys
 1               5
```

(2) INFORMATION FOR SEQ ID NO:1164:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1164:

Lys Ile Arg Leu Arg Pro Gly Gly Lys Lys
 1               5                  10

(2) INFORMATION FOR SEQ ID NO:1165:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1165:

Lys Ile Arg Leu Arg Pro Gly Gly Lys
 1               5

(2) INFORMATION FOR SEQ ID NO:1166:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1166:

Glu Thr Thr Asp Leu Tyr Cys Tyr
 1               5

(2) INFORMATION FOR SEQ ID NO:1167:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1167:

Gly Thr Leu Gly Ile Val Cys Pro Ile Cys Ser Gln Lys
 1               5                  10

(2) INFORMATION FOR SEQ ID NO:1168:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1168:

Leu Met Gly Thr Leu Gly Ile Val Cys Pro Ile Cys Ser Gln Lys
 1               5                  10                  15

(2) INFORMATION FOR SEQ ID NO:1169:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1169:

```
Ala Val Cys Asp Lys Cys Leu Lys
1               5
```

(2) INFORMATION FOR SEQ ID NO:1170:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1170:

```
Pro Tyr Ala Val Cys Asp Lys Cys Leu Lys Phe
1               5                   10
```

(2) INFORMATION FOR SEQ ID NO:1171:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1171:

```
His Tyr Cys Tyr Ser Leu Tyr Gly Thr Thr Leu
1               5                   10
```

(2) INFORMATION FOR SEQ ID NO:1172:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1172:

```
Phe Tyr Ser Arg Ile Arg Glu Leu
1               5
```

(2) INFORMATION FOR SEQ ID NO:1173:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1173:

```
Thr Leu Glu Lys Leu Thr Asn Thr Gly Leu Tyr
1               5                   10
```

(2) INFORMATION FOR SEQ ID NO:1174:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1174:

```
Lys Thr Val Leu Glu Leu Thr Glu Val Phe Glu Phe Ala Phe Lys
1               5                   10                  15
```

(2) INFORMATION FOR SEQ ID NO:1175:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1175:

```
Thr Met Leu Cys Met Cys Cys Lys
1               5
```

(2) INFORMATION FOR SEQ ID NO:1176:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1176:

```
Asn Thr Ser Leu Gln Asp Ile Glu Ile Thr Cys Val Tyr Cys Lys
1               5                   10                  15
```

(2) INFORMATION FOR SEQ ID NO:1177:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1177:

```
Glu Val Phe Glu Phe Ala Phe Lys
1               5
```

(2) INFORMATION FOR SEQ ID NO:1178:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1178:

```
Lys Gln Ser Ser Lys Ala Leu Gln Arg
1               5
```

(2) INFORMATION FOR SEQ ID NO:1179:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1179:

```
Ala Thr Gly Phe Lys Gln Ser Ser Lys
 1               5
```

(2) INFORMATION FOR SEQ ID NO:1180:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1180:

```
His Ser Ala Thr Gly Phe Lys Gln Ser Ser Lys
 1               5                   10
```

(2) INFORMATION FOR SEQ ID NO:1181:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1181:

```
Phe Lys Gln Ser Ser Lys Ala Leu Gln Arg
 1               5                   10
```

(2) INFORMATION FOR SEQ ID NO:1182:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1182:

```
Val Thr Cys Leu Gly Leu Ser Tyr
 1               5
```

(2) INFORMATION FOR SEQ ID NO:1183:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1183:

```
Ile Thr Lys Lys Val Ala Asp Leu Val Gly Phe Leu Leu Leu Lys
 1               5                   10                  15
```

(2) INFORMATION FOR SEQ ID NO:1184:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1184:

```
Leu Val Gly Phe Leu Leu Leu Lys
  1               5
```

(2) INFORMATION FOR SEQ ID NO:1185:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1185:

```
Val Thr Lys Ala Glu Met Leu Glu Ser Val Ile Lys Asn Tyr Lys
  1               5                  10                  15
```

(2) INFORMATION FOR SEQ ID NO:1186:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1186:

```
Thr Ser Cys Ile Leu Glu Ser Leu Phe Arg
  1               5                  10
```

(2) INFORMATION FOR SEQ ID NO:1187:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1187:

```
Asn Tyr Lys His Cys Phe Pro Glu Ile
  1               5
```

(2) INFORMATION FOR SEQ ID NO:1188:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1188:

```
Ser Tyr Val Leu Val Thr Cys Leu
  1               5
```

(2) INFORMATION FOR SEQ ID NO:1189:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1189:

Glu Thr Asp Pro Ile Ser His Thr Tyr
1               5

(2) INFORMATION FOR SEQ ID NO:1190:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1190:

Glu Thr Asp Pro Thr Ser His Leu Tyr
1               5

(2) INFORMATION FOR SEQ ID NO:1191:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1191:

Glu Thr Asp Pro Thr Ser Asn Thr Tyr
1               5

(2) INFORMATION FOR SEQ ID NO:1192:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1192:

Glu Thr Asp Pro Thr Ser His Val Tyr
1               5

(2) INFORMATION FOR SEQ ID NO:1193:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1193:

Glu Thr Asp Pro Thr Ser His Ser Tyr
1               5

(2) INFORMATION FOR SEQ ID NO:1194:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1194:

```
Glu Thr Asp Pro Ala Ser His Thr Tyr
 1               5
```

(2) INFORMATION FOR SEQ ID NO:1195:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1195:

```
Glu Val Asp Pro Thr Ser His Thr Tyr
 1               5
```

(2) INFORMATION FOR SEQ ID NO:1196:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1196:

```
Glu Thr Asp Pro Thr Gly His Thr Tyr
 1               5
```

(2) INFORMATION FOR SEQ ID NO:1197:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1197:

```
Glu Thr Asp Arg Thr Ser His Thr Tyr
 1               5
```

(2) INFORMATION FOR SEQ ID NO:1198:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1198:

```
Glu Ala Asp Pro Thr Ser His Thr Tyr
 1               5
```

(2) INFORMATION FOR SEQ ID NO:1199:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1199:

Glu Thr Val Pro Thr Ser His Thr Tyr
1               5

(2) INFORMATION FOR SEQ ID NO:1200:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1200:

Glu Thr Asp Pro Thr Ser His Thr Tyr
1               5

(2) INFORMATION FOR SEQ ID NO:1201:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1201:

Glu Thr Asp Pro Thr Gly His Ser Tyr
1               5

(2) INFORMATION FOR SEQ ID NO:1202:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1202:

Met Phe Pro Asp Leu Glu Ser Glu Phe
1               5

(2) INFORMATION FOR SEQ ID NO:1203:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1203:

Thr Thr Ile Asn Tyr Thr Leu Trp Arg
1               5

(2) INFORMATION FOR SEQ ID NO:1204:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1204:

Val Ile Phe Ser Lys Ala Ser Glu Tyr
1               5

(2) INFORMATION FOR SEQ ID NO:1205:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1205:

Leu Val His Phe Leu Leu Leu Lys Tyr
1               5

(2) INFORMATION FOR SEQ ID NO:1206:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1206:

Leu Val His Phe Leu Leu Leu Lys Tyr Arg
1               5                   10

(2) INFORMATION FOR SEQ ID NO:1207:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1207:

Pro Val Ile Phe Ser Lys Ala Ser Glu Tyr
1               5                   10

(2) INFORMATION FOR SEQ ID NO:1208:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1208:

Ser Thr Thr Ile Asn Tyr Thr Leu Trp Arg
1               5                   10

(2) INFORMATION FOR SEQ ID NO:1209:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1209:

```
Val Val Glu Val Val Pro Ile Ser His
 1               5
```

(2) INFORMATION FOR SEQ ID NO:1210:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1210:

```
Glu Tyr Leu Gln Leu Val Phe Gly Ile
 1               5
```

(2) INFORMATION FOR SEQ ID NO:1211:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1211:

```
Ile Phe Ser Lys Ala Ser Glu Tyr Leu
 1               5
```

(2) INFORMATION FOR SEQ ID NO:1212:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1212:

```
Ser Phe Ser Thr Thr Ile Asn Tyr Thr Leu
 1               5                  10
```

(2) INFORMATION FOR SEQ ID NO:1213:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1213:

```
Leu Tyr Ile Leu Val Thr Cys Leu Gly Leu
 1               5                  10
```

(2) INFORMATION FOR SEQ ID NO:1214:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1214:

```
Phe Ala Thr Cys Leu Gly Leu Ser Tyr
 1               5
```

(2) INFORMATION FOR SEQ ID NO:1215:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1215:

```
Val Val Gly Asn Trp Gln Tyr Phe Phe Pro Val Ile Phe Ser Lys
 1               5                  10                  15
```

(2) INFORMATION FOR SEQ ID NO:1216:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1216:

```
Leu Ile Ile Val Leu Ala Ile Ile Ala Arg
 1               5                  10
```

(2) INFORMATION FOR SEQ ID NO:1217:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1217:

```
Tyr Phe Phe Pro Val Ile Phe Ser Lys
 1               5
```

(2) INFORMATION FOR SEQ ID NO:1218:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1218:

```
Asn Trp Gln Tyr Phe Phe Pro Val Ile
 1               5
```

(2) INFORMATION FOR SEQ ID NO:1219:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1219:

```
Asn Trp Gln Tyr Phe Phe Pro Val Ile Phe
 1               5                  10
```

(2) INFORMATION FOR SEQ ID NO:1220:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1220:

```
Ile Phe Ser Lys Ala Ser Ser Ser Leu
 1               5
```

(2) INFORMATION FOR SEQ ID NO:1221:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1221:

```
Glu Val Asp Pro Thr Ser Asn Thr Tyr
 1               5
```

(2) INFORMATION FOR SEQ ID NO:1222:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1222:

```
Arg Tyr Pro Leu Thr Phe Gly Trp Cys Tyr
 1               5                  10
```

(2) INFORMATION FOR SEQ ID NO:1223:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1223:

```
Arg Tyr Pro Leu Thr Phe Gly Trp Cys
 1               5
```

(2) INFORMATION FOR SEQ ID NO:1224:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1224:

```
Ala Thr Gln Ile Pro Ser Tyr Lys
 1               5
```

(2) INFORMATION FOR SEQ ID NO:1225:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1225:

```
Leu Thr Glu Leu Tyr Phe Glu Lys
 1               5
```

(2) INFORMATION FOR SEQ ID NO:1226:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1226:

```
His Ser Phe Pro His Pro Leu Tyr
 1               5
```

(2) INFORMATION FOR SEQ ID NO:1227:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1227:

```
Thr Gln Glu Pro Ala Leu Gly Thr Thr Cys Tyr
 1               5                  10
```

(2) INFORMATION FOR SEQ ID NO:1228:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1228:

```
Val Thr Lys Phe Met Leu Cys Ala Gly Arg Trp Thr Gly Gly Lys
 1               5                  10                  15
```

(2) INFORMATION FOR SEQ ID NO:1229:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1229:

His Val Ile Ser Asn Asp Val Cys Ala Gln Val His Pro Gln Lys
1               5                   10                  15

(2) INFORMATION FOR SEQ ID NO:1230:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1230:

Leu Tyr Asp Met Ser Leu Leu Lys Asn Arg Phe
1               5                   10

(2) INFORMATION FOR SEQ ID NO:1231:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Tyr, Phe or Trp
        (A) NAME/KEY: Modified Base
        (B) LOCATION: 8...8
        (D) OTHER INFORMATION: Xaa = Phe, Ile, Leu or Trp (xi) SEQUENCE DESCRIPTION: SEQ ID NO:1231:

Xaa Xaa Xaa Xaa Xaa Xaa Xaa Xaa
1               5

(2) INFORMATION FOR SEQ ID NO:1232:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Tyr, Phe or Trp
        (A) NAME/KEY: Modified Base
        (B) LOCATION: 9...9
        (D) OTHER INFORMATION: Xaa = Phe, Ile, Leu or Trp (xi) SEQUENCE DESCRIPTION: SEQ ID NO:1232:

Xaa Xaa Xaa Xaa Xaa Xaa Xaa Xaa Xaa
1               5

(2) INFORMATION FOR SEQ ID NO:1233:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:

```
            (A) NAME/KEY: Modified Base
            (B) LOCATION: 2...2
            (D) OTHER INFORMATION: Xaa = Tyr, Phe or Trp
            (A) NAME/KEY: Modified Base
            (B) LOCATION: 10...10
            (D) OTHER INFORMATION: Xaa = Phe, Ile, Leu or Trp (xi) SEQUENCE DESCRIPTION: SEQ ID NO:1233:

Xaa Xaa Xaa Xaa Xaa Xaa Xaa Xaa Xaa Xaa
  1               5                  10

(2) INFORMATION FOR SEQ ID NO:1234:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Tyr, Phe or Trp
            (A) NAME/KEY: Modified Base
            (B) LOCATION: 11...11
            (D) OTHER INFORMATION: Xaa = Phe, Ile, Leu or Trp (xi) SEQUENCE DESCRIPTION: SEQ ID NO:1234:

Xaa Xaa Xaa Xaa Xaa Xaa Xaa Xaa Xaa Xaa Xaa
  1               5                  10

(2) INFORMATION FOR SEQ ID NO:1235:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Thr, Ser or Met (xi) SEQUENCE DESCRIPTION: SEQ ID NO:1235:

Xaa Xaa Xaa Xaa Xaa Xaa Xaa Tyr
  1               5

(2) INFORMATION FOR SEQ ID NO:1236:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Thr, Ser or Met (xi) SEQUENCE DESCRIPTION: SEQ ID NO:1236:

Xaa Xaa Xaa Xaa Xaa Xaa Xaa Xaa Tyr
  1               5

(2) INFORMATION FOR SEQ ID NO:1237:
```

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Thr, Ser or Met (xi) SEQUENCE DESCRIPTION: SEQ ID NO:1237:

Xaa Xaa Xaa Xaa Xaa Xaa Xaa Xaa Xaa Tyr
 1               5                  10

(2) INFORMATION FOR SEQ ID NO:1238:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 2...2
            (D) OTHER INFORMATION: Xaa = Thr, Ser or Met (xi) SEQUENCE DESCRIPTION: SEQ ID NO:1238:

Xaa Xaa Xaa Xaa Xaa Xaa Xaa Xaa Xaa Xaa Tyr
 1               5                  10

(2) INFORMATION FOR SEQ ID NO:1239:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 3...3
            (D) OTHER INFORMATION: Xaa = Asp, Glu, Ala or Ser (xi) SEQUENCE DESCRIPTION: SEQ ID NO:1239:

Xaa Xaa Xaa Xaa Xaa Xaa Xaa Tyr
 1               5

(2) INFORMATION FOR SEQ ID NO:1240:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified Base
            (B) LOCATION: 3...3
            (D) OTHER INFORMATION: Xaa = Asp, Glu, Ala or Ser (xi) SEQUENCE DESCRIPTION: SEQ ID NO:1240:

Xaa Xaa Xaa Xaa Xaa Xaa Xaa Xaa Tyr 1          5

(2) INFORMATION FOR SEQ ID NO:1241:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 3...3
        (D) OTHER INFORMATION: Xaa = Asp, Glu, Ala or Ser (xi) SEQUENCE DESCRIPTION: SEQ ID NO:1241:

Xaa Xaa Xaa Xaa Xaa Xaa Xaa Xaa Xaa Tyr
1               5                   10

(2) INFORMATION FOR SEQ ID NO:1242:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 3...3
        (D) OTHER INFORMATION: Xaa = Asp, Glu, Ala or Ser (xi) SEQUENCE DESCRIPTION: SEQ ID NO:1242:

Xaa Xaa Xaa Xaa Xaa Xaa Xaa Xaa Xaa Xaa Tyr
1               5                   10

(2) INFORMATION FOR SEQ ID NO:1243:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Ala, Ser, Gly, Asn, Cys,
            Phe or Asp
        (A) NAME/KEY: Modified Base
        (B) LOCATION: 8...8
        (D) OTHER INFORMATION: Xaa = Lys, Arg or His (xi) SEQUENCE DESCRIPTION: SEQ ID NO:1243:

Xaa Xaa Xaa Xaa Xaa Xaa Xaa Xaa
1               5

(2) INFORMATION FOR SEQ ID NO:1244:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide

```
    (ix) FEATURE:
          (A) NAME/KEY: Modified Base
          (B) LOCATION: 2...2
          (D) OTHER INFORMATION: Xaa = Ala, Ser, Gly, Asn, Cys,
              Phe or Asp
          (A) NAME/KEY: Modified Base
          (B) LOCATION: 9...9
          (D) OTHER INFORMATION: Xaa = Lys, Arg or His (xi) SEQUENCE DESCRIPTION: SEQ ID NO:1244:

Xaa Xaa Xaa Xaa Xaa Xaa Xaa Xaa Xaa
 1               5

(2) INFORMATION FOR SEQ ID NO:1245:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified Base
          (B) LOCATION: 2...2
          (D) OTHER INFORMATION: Xaa = Ala, Ser, Gly, Asn, Cys,
              Phe or Asp
          (A) NAME/KEY: Modified Base
          (B) LOCATION: 10...10
          (D) OTHER INFORMATION: Xaa = Lys, Arg or His (xi) SEQUENCE DESCRIPTION: SEQ ID NO:1245:

Xaa Xaa Xaa Xaa Xaa Xaa Xaa Xaa Xaa Xaa
 1               5                  10

(2) INFORMATION FOR SEQ ID NO:1246:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified Base
          (B) LOCATION: 2...2
          (D) OTHER INFORMATION: Xaa = Ala, Ser, Gly, Asn, Cys,
              Phe or Asp
          (A) NAME/KEY: Modified Base
          (B) LOCATION: 11...11
          (D) OTHER INFORMATION: Xaa = Lys, Arg or His (xi) SEQUENCE DESCRIPTION: SEQ ID NO:1246:

Xaa Xaa Xaa Xaa Xaa Xaa Xaa Xaa Xaa Xaa Xaa
 1               5                  10

(2) INFORMATION FOR SEQ ID NO:1247:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified Base
          (B) LOCATION: 2...2
          (D) OTHER INFORMATION: Xaa = Leu, Met, Ile, Val, Ala, Ser,
              Thr, Gly, Asn, Cys, Phe or Asp
```

(A) NAME/KEY: Modified Base
            (B) LOCATION: 8...8
            (D) OTHER INFORMATION: Xaa = Lys, Arg or His (xi) SEQUENCE DESCRIPTION: SEQ ID NO:1247:

Xaa Xaa Xaa Xaa Xaa Xaa Xaa Xaa
 1               5

(2) INFORMATION FOR SEQ ID NO:1248:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Leu, Met, Ile, Val, Ala, Ser,
            Thr, Gly, Asn, Cys, Phe or Asp
        (A) NAME/KEY: Modified Base
        (B) LOCATION: 9...9
        (D) OTHER INFORMATION: Xaa = Lys, Arg or His (xi) SEQUENCE DESCRIPTION: SEQ ID NO:1248:

Xaa Xaa Xaa Xaa Xaa Xaa Xaa Xaa Xaa
 1               5

(2) INFORMATION FOR SEQ ID NO:1249:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Leu, Met, Ile, Val, Ala, Ser,
            Thr, Gly, Asn, Cys, Phe or Asp
        (A) NAME/KEY: Modified Base
        (B) LOCATION: 10...10
        (D) OTHER INFORMATION: Xaa = Lys, Arg or His (xi) SEQUENCE DESCRIPTION: SEQ ID NO:1249:

Xaa Xaa Xaa Xaa Xaa Xaa Xaa Xaa Xaa Xaa
 1               5                  10

(2) INFORMATION FOR SEQ ID NO:1250:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Leu, Met, Ile, Val, Ala, Ser,
            Thr, Gly, Asn, Cys, Phe or Asp
        (A) NAME/KEY: Modified Base
        (B) LOCATION: 11...11
        (D) OTHER INFORMATION: Xaa = Lys, Arg or His (xi) SEQUENCE DESCRIPTION: SEQ ID NO:1250:

Xaa Xaa Xaa Xaa Xaa Xaa Xaa Xaa Xaa Xaa Xaa
1               5                  10

(2) INFORMATION FOR SEQ ID NO:1251:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Leu, Met, Ile, Val, Ser, Ala,
            Thr, Phe, Cys, Gly or Asp
        (A) NAME/KEY: Modified Base
        (B) LOCATION: 8...8
        (D) OTHER INFORMATION: Xaa = Lys, Arg, Tyr, His or Phe (xi) SEQUENCE DESCRIPTION: SEQ ID NO:1251:

Xaa Xaa Xaa Xaa Xaa Xaa Xaa Xaa
1               5

(2) INFORMATION FOR SEQ ID NO:1252:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Leu, Met, Ile, Val, Ser, Ala,
            Thr, Phe, Cys, Gly or Asp
        (A) NAME/KEY: Modified Base
        (B) LOCATION: 9...9
        (D) OTHER INFORMATION: Xaa = Lys, Arg, Tyr, His or Phe (xi) SEQUENCE DESCRIPTION: SEQ ID NO:1252:

Xaa Xaa Xaa Xaa Xaa Xaa Xaa Xaa Xaa
1               5

(2) INFORMATION FOR SEQ ID NO:1253:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified Base
        (B) LOCATION: 2...2
        (D) OTHER INFORMATION: Xaa = Leu, Met, Ile, Val, Ser, Ala,
            Thr, Phe, Cys, Gly or Asp
        (A) NAME/KEY: Modified Base
        (B) LOCATION: 10...10
        (D) OTHER INFORMATION: Xaa = Lys, Arg, Tyr, His or Phe (xi) SEQUENCE DESCRIPTION: SEQ ID NO:1253:

Xaa Xaa Xaa Xaa Xaa Xaa Xaa Xaa Xaa Xaa
1               5                  10

```
(2) INFORMATION FOR SEQ ID NO:1254:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified Base
         (B) LOCATION: 2...2
         (D) OTHER INFORMATION: Xaa = Leu, Met, Ile, Val, Ser, Ala,
             Thr, Phe, Cys, Gly or Asp
         (A) NAME/KEY: Modified Base
         (B) LOCATION: 11...11
         (D) OTHER INFORMATION: Xaa = Lys, Arg, Tyr, His or Phe (xi) SEQUENCE DESCRIPTION: SEQ ID NO:1254:

Xaa Xaa Xaa Xaa Xaa Xaa Xaa Xaa Xaa Xaa Xaa
 1               5                  10
```

METHODS FOR MAKING HLA BINDING PEPTIDES AND THEIR USES

CROSS-REFERENCE TO RELATED APPLICATIONS

The present application is a continuation-in-part of U.S. Ser. No. 08/103,396, filed Aug. 6, 1993 and now abandoned, which is a continuation-in-part of U.S. Ser. No. 08/027,746, filed Mar. 5, 1993 and now abandoned, which is a continuation-in-part of U.S. Ser. No. 07/926,666, filed Aug. 7, 1992 and now abandoned, each of which is incorporated herein by reference.

FEDERALLY SPONSORED RESEARCH AND DEVELOPMENT

This invention was funded, in part, by the United States government under grants with the National Institutes of Health. The U.S. government has certain rights in this invention.

BACKGROUND OF THE INVENTION

The present invention relates to compositions and methods for preventing, treating or diagnosing a number of pathological states such as viral diseases and cancers. In particular, it provides novel peptides capable of binding selected major histocompatibility complex (MHC) molecules and inducing an immune response.

MHC molecules are classified as either Class I or Class II molecules. Class II MHC molecules are expressed primarily on cells involved in initiating and sustaining immune responses, such as T lymphocytes, B lymphocytes, macrophages, etc. Class II MHC molecules are recognized by helper T lymphocytes and induce proliferation of helper T lymphocytes and amplification of the immune response to the particular immunogenic peptide that is displayed. Class I MHC molecules are expressed on almost all nucleated cells and are recognized by cytotoxic T lymphocytes (CTLs), which then destroy the antigen-bearing cells. CTLs are particularly important in tumor rejection and in fighting viral infections. The CTL recognizes the antigen in the form of a peptide fragment bound to the MHC class I molecules rather than the intact foreign antigen itself. The antigen must normally be endogenously synthesized by the cell, and a portion of the protein antigen is degraded into small peptide fragments in the cytoplasm. Some of these small peptides translocate into a pre-Golgi compartment and interact with class I heavy chains to facilitate proper folding and association with the subunit β2 microglobulin. The peptide-MHC class I complex is then routed to the cell surface for expression and potential recognition by specific CTLs.

Investigations of the crystal structure of the human MHC class I molecule, HLA-A2.1, indicate that a peptide binding groove is created by the folding of the α1 and α2 domains of the class I heavy chain (Bjorkman et al., Nature 329:506 (1987). In these investigations, however, the identity of peptides bound to the groove was not determined.

Buus et al., Science 242:1065 (1988) first described a method for acid elution of bound peptides from MHC. Subsequently, Rammensee and his coworkers (Falk et al., Nature 351:290 (1991) have developed an approach to characterize naturally processed peptides bound to class I molecules. Other investigators have successfully achieved direct amino acid sequencing of the more abundant peptides in various HPLC fractions by conventional automated sequencing of peptides eluted from class I molecules of the B type (Jardetzky, et al., Nature 353:326 (1991) and of the A2.1 type by mass spectrometry (Hunt, et al., Science 225:1261 (1992). A review of the characterization of naturally processed peptides in MHC Class I has been presented by Rotzschke and Falk (Rötzschke and Falk, Immunol. Today 12:447 (1991).

Sette et al., Proc. Natl. Acad. Sci. USA 86:3296 (1989) showed that MHC allele specific motifs could be used to predict MHC binding capacity. Schaeffer et al., Proc. Natl. Acad. Sci. USA 86:4649 (1989) showed that MHC binding was related to immunogenicity. Several authors (De Bruijn et al., Eur. J. Immunol., 21:2963-2970 (1991); Pamer et al., 991 Nature 353:852–955 (1991)) have provided preliminary evidence that class I binding motifs can be applied to the identification of potential immunogenic peptides in animal models. Class I motifs specific for a number of human alleles of a given class I isotype have yet to be described. It is desirable that the combined frequencies of these different alleles should be high enough to cover a large fraction or perhaps the majority of the human outbred population.

Despite the developments in the art, the prior art has yet to provide a useful human peptide-based vaccine or therapeutic agent based on this work. The present invention provides these and other advantages.

SUMMARY OF THE INVENTION

The present invention provides compositions comprising immunogenic peptides having binding motifs for MHC Class I molecules. The immunogenic peptides are typically between about 8 and about 11 residues and comprise conserved residues involved in binding proteins encoded by the appropriate MHC allele. A number of allele specific motifs have been identified.

For instance, the motif for HLA-A3.2 comprises from the N-terminus to C-terminus a first conserved residue of L, M, I, V, S, A, T and F at position 2 and a second conserved residue of K, R or Y at the C-terminal end. Other first conserved residues are C, G or D and alternatively E. Other second conserved residues are H or F. The first and second conserved residues are preferably separated by 6 to 7 residues (SEQ ID NOS:1 and 2).

The motif for HLA-A1 comprises from the N-terminus to the C-terminus a first conserved residue of T, S or M, a second conserved residue of D or E, and a third conserved residue of Y. Other second conserved residues are A, S or T. The first and second conserved residues are adjacent and are preferably separated from the third conserved residue by 6 to 7 residues (SEQ ID NOS:3–10). A second motif consists of a first conserved residue of E or D and a second conserved residue of Y where the first and second conserved residues are separated by 5 to 6 residues (SEQ ID NOS:11–32).

The motif for HLA-A11 comprises from the N-terminus to the C-terminus a first conserved residue of T or V at position 2 and a C-terminal conserved residue of K. The first and second conserved residues are preferably separated by 6 or 7 residues (SEQ ID NOS:33 and 34).

The motif for HLA-A24.1 comprises from the N-terminus to the C-terminus a first conserved residue of Y, F or W at position 2 and a C terminal conserved residue of F, I, W, M or L. The first and second conserved residues are preferably separated by 6 to 7 residues (SEQ ID NOS:35 and 36).

Epitopes on a number of potential target proteins can be identified in this manner. Examples of suitable antigens include prostate specific antigen (PSA), hepatitis B core and surface antigens (HBVc, HBVs) hepatitis C antigens, malignant melanoma antigen (MAGE-1) Epstein-Barr virus antigens, human immunodeficiency type-1 virus (HIV1) and papilloma virus antigens. The peptides are thus useful in pharmaceutical compositions for both in vivo and ex vivo therapeutic and diagnostic applications.

Definitions

The term "peptide" is used interchangeably with "oligopeptide" in the present specification to designate a series of residues, typically L-amino acids, connected one to the other typically by peptide bonds between the alpha-amino and carbonyl groups of adjacent amino acids. The oligopeptides of the invention are less than about 15 residues in length and usually consist of between about 8 and about 11 residues, preferably 9 or 10 residues.

An "immunogenic peptide" is a peptide which comprises an allele-specific motif such that the peptide will bind the MHC allele and be capable of inducing a CTL response. Thus, immunogenic peptides are capable of binding to an appropriate class I MHC molecule and inducing a cytotoxic T cell response against the antigen from which the immunogenic peptide is derived.

A "conserved residue" is an amino acid which occurs in a significantly higher frequency than would be expected by random distribution at a particular position in a peptide motif. Typically a conserved residue is one at which the immunogenic peptide may provide a contact point with the MHC molecule. One to three, preferably two, conserved residues within a peptide of defined length defines a motif for an immunogenic peptide. These residues are typically in close contact with the peptide binding groove, with their side chains buried in specific pockets of the groove itself. Typically, an immunogenic peptide will comprise up to three conserved residues, more usually two conserved residues.

As used herein, "negative binding residues" are amino acids which if present at certain positions will result in a peptide being a nonbinder or poor binder and in turn fail to induce a CTL response despite the presence of the appropriate conserved residues within the peptide.

The term "motif" refers to the pattern of residues in a peptide of defined length, usually about 8 to about 11 amino acids, which is recognized by a particular MHC allele. The peptide motifs are typically different for each human MHC allele and differ in the pattern of the highly conserved residues.

The binding motif for an allele can be defined with increasing degrees of precision. In one case, all of the conserved residues are present in the correct positions in a peptide and there are no negative binding residues present.

The phrases "isolated" or "biologically pure" refer to material which is substantially or essentially free from components which normally accompany it as found in its native state. Thus, the peptides of this invention do not contain materials normally associated with their in situ environment, e.g., MHC I molecules on antigen presenting cells. Even where a protein has been isolated to a homogenous or dominant band, there are trace contaminants in the range of 5–10% of native protein which co-purify with the desired protein. Isolated peptides of this invention do not contain such endogenous co-purified protein.

The term "residue" refers to an amino acid or amino acid mimetic incorporated in a oligopeptide by an amide bond or amide bond mimetic.

BRIEF DESCRIPTION OF THE DRAWINGS

FIG. 1 is a flow diagram of an HLA-A purification scheme.

Lane 1—Molecular weight standards.
Lane 2—A3.2 acid eluate
Lane 3—A3.2 a second acid eluate
Lane 4—Base elution #1
Lane 5—Base elution #2
Lane 6—Concentrated base elution 1
Lane 7—Concentrated base elution 2
Lane 8—BSA—10 µg
Lane 9—BSA—3 µg
Lane 10—BSA—1 µg

DESCRIPTION OF THE PREFERRED EMBODIMENTS

Figure 2:
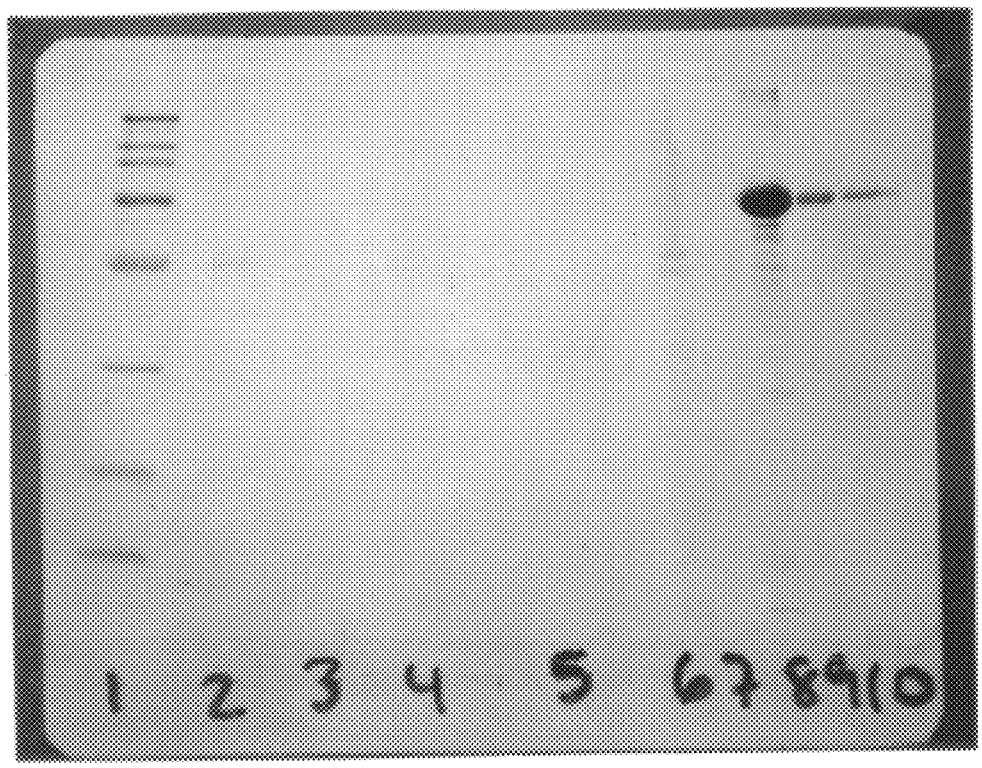
FIG. 2 is an SDS-PAGE analysis of affinity purified HLA-A3.2 from the cell line EHM using an affinity column prepared with the mAb GAP A3 coupled to protein A-Sepharose.

The present invention relates to the determination of allele-specific peptide motifs for human Class I MHC (sometimes referred to as HLA) allele subtypes. These motifs are then used to define T cell epitopes from any desired antigen, particularly those associated with human viral diseases, cancers or autoimmune diseases, for which the amino acid sequence of the potential antigen or autoantigen targets is known.

Epitopes on a number of potential target proteins can be identified in this manner. Examples of suitable antigens include prostate specific antigen (PSA), hepatitis B core and surface antigens (HBVc, HBVs) hepatitis C antigens, Epstein-Barr virus antigens, melanoma antigens (e.g., MAGE-1), human immunodeficiency virus (HIV) antigens and human papilloma virus (HPV) antigens.

Autoimmune associated disorders for which the peptides of the invention may be employed to relieve the symptoms of, treat or prevent the occurrence or reoccurrence of include, for example, multiple sclerosis (MS), rheumatoid arthritis (RA), Sjogren syndrome, scleroderma, polymyositis, dermatomyositis, systemic lupus erythematosus, juvenile rheumatoid arthritis, ankylosing spondylitis, myasthenia gravis (MG), bullous pemphigoid (antibodies to basement membrane at dermal-epidermal junction), pemphigus (antibodies to mucopolysaccharide protein complex or intracellular cement substance), glomerulonephritis (antibodies to glomerular basement membrane), Goodpasture's syndrome, autoimmune hemolytic anemia (antibodies to erythrocytes), Hashimoto's disease (antibodies to thyroid), pernicious anemia (antibodies to intrinsic factor), idiopathic thrombocytopenic purpura (antibodies to platelets), Grave's disease, and Addison's disease (antibodies to thyroglobulin), and the like.

The autoantigens associated with a number of these diseases have been identified. For example, in experimentally induced autoimmune diseases, antigens involved in pathogenesis have been characterized: in arthritis in rat and mouse, native type-II collagen is identified in collagen-induced arthritis, and mycobacterial heat shock protein in adjuvant arthritis; thyroglobulin has been identified in experimental allergic thyroiditis (EAT) in mouse; acetyl choline receptor (AChR) in experimental allergic myasthenia gravis (EAMG); and myelin basic protein (MBP) and proteolipid protein (PLP) in experimental allergic encephalomyelitis (EAE) in mouse and rat. In addition, target antigens have been identified in humans: type-II collagen in human rheumatoid arthritis; and acetyl choline receptor in myasthenia gravis.

Without wishing to be bound by theory, it is believed that the presentation of antigen by HLA Class I mediates suppression of autoreactive T cells by $CD8^+$ suppressor T cells (see, e.g., Jiang et al. *Science* 256:1213 (1992)). Such suppressor T cells release cytokines such as transforming growth factor-$\beta$ (TGF-$\beta$), which specifically inhibit the autoreactive T cells. Miller et al. *Proc. Natl. Acad. Sci. USA* 89:421–425 (1992).

Peptides comprising the epitopes from these antigens are synthesized and then tested for their ability to bind to the appropriate MHC molecules in assays using, for example, purified class I molecules and radioiodonated peptides and/or cells expressing empty class I molecules by, for instance, immunofluorescent staining and flow microfluorimetry, peptide-dependent class I assembly assays, and inhibition of CTL recognition by peptide competition. Those peptides that bind to the class I molecule are further evaluated for their ability to serve as targets for CTLs derived from infected or immunized individuals, as well as for their capacity to induce primary in vitro or in vivo CTL responses that can give rise to CTL populations capable of reacting with virally infected target cells or tumor cells as potential therapeutic agents.

The MHC class I antigens are encoded by the HLA-A, B, and C loci. HLA-A and B antigens are expressed at the cell surface at approximately equal densities, whereas the expression of HLA-C is significantly lower (perhaps as much as 10-fold lower). Each of these loci have a number of alleles. The peptide binding motifs of the invention are relatively specific for each allelic subtype.

For peptide-based vaccines, the peptides of the present invention preferably comprise a motif recognized by an MHC I molecule having a wide distribution in the human population. Since the MHC alleles occur at different frequencies within different ethnic groups and races, the choice of target MHC allele may depend upon the target population. Table 1 shows the frequency of various alleles at the HLA-A locus products among different races. For instance, the majority of the Caucasoid population can be covered by peptides which bind to four HLA-A allele subtypes, specifically HLA-A2.1, A1, A3.2, and A24.1. Similarly, the majority of the Asian population is encompassed with the addition of peptides binding to a fifth allele HLA-A11.2.

TABLE 1

| A Allele/Subtype | N(69)* | A(54) | C(502) |
| --- | --- | --- | --- |
| A1 | 10.1(7) | 1.8(1) | 27.4(138) |
| A2.1 | 11.5(8) | 37.0(20) | 39.8(199) |
| A2.2 | 10.1(7) | 0 | 3.3(17) |
| A2.3 | 1.4(1) | 5.5(3) | 0.8(4) |
| A2.4 | — | — | — |
| A2.5 | — | — | — |
| A3.1 | 1.4(1) | 0 | 0.2(0) |
| A3.2 | 5.7(4) | 5.5(3) | 21.5(108) |
| A11.1 | 0 | 5.5(3) | 0 |
| A11.2 | 5.7(4) | 31.4(17) | 8.7(44) |
| A11.3 | 0 | 3.7(2) | 0 |
| A23 | 4.3(3) | — | 3.9(20) |
| A24 | 2.9(2) | 27.7(15) | 15.3(77) |
| A24.2 | — | — | — |
| A24.3 | — | — | — |
| A25 | 1.4(1) | — | 6.9(35) |
| A26.1 | 4.3(3) | 9.2(5) | 5.9(30) |
| A26.2 | 7.2(5) | — | 1.0(5) |
| A26V | — | 3.7(2) | — |
| A28.1 | 10.1(7) | — | 1.6(8) |
| A28.2 | 1.4(1) | — | 7.5(38) |
| A29.1 | 1.4(1) | — | 1.4(7) |
| A29.2 | 10.1(7) | 1.8(1) | 5.3(27) |
| A30.1 | 8.6(6) | — | 4.9(25) |
| A30.2 | 1.4(1) | — | 0.2(1) |

TABLE 1-continued

| A Allele/Subtype | N(69)* | A(54) | C(502) |
|---|---|---|---|
| A30.3 | 7.2(5) | — | 3.9(20) |
| A31 | 4.3(3) | 7.4(4) | 6.9(35) |
| A32 | 2.8(2) | — | 7.1(36) |
| Aw33.1 | 8.6(6) | — | 2.5(13) |
| Aw33.2 | 2.8(2) | 16.6(9) | 1.2(6) |
| Aw34.1 | 1.4(1) | — | — |
| Aw34.2 | 14.5(10) | — | 0.8(4) |
| Aw36 | 5.9(4) | — | — |

Table compiled from B. DuPont, Immunobiology; of HLA, Vol. I, Histocompatibility Testing 1987, Springer-Veriag, New York 1989.
N - negroid; A = Asian; C = caucasoid. Numbers in parenthesis represent the number of individuals included in the analysis.

The nomenclature used to describe peptide compounds follows the conventional practice wherein the amino group is presented to the left (the N-terminus) and the carboxyl group to the right (the C-terminus) of each amino acid residue. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids is represented by a lower case single letter or a lower case three letter symbol. Glycine has no asymmetric carbon atom and is simply referred to as "Gly" or G.

The procedures used to identify peptides of the present invention generally follow the methods disclosed in Falk et al., *Nature* 351:290 (1991), which is incorporated herein by reference. Briefly, the methods involve large-scale isolation of MHC class I molecules, typically by immunoprecipitation or affinity chromatography, from the appropriate cell or cell line. Examples of other methods for isolation of the desired MHC molecule equally well known to the artisan include ion exchange chromatography, lectin chromatography, size exclusion, high performance ligand chromatography, and a combination of all of the above techniques.

A large number of cells with defined MHC molecules, particularly MHC Class I molecules, are known and readily available. For example, human EBV-transformed B cell lines have been shown to be excellent sources for the preparative isolation of class I and class II MHC molecules. Well-characterized cell lines are available from private and commercial sources, such as American Type Culture Collection ("Catalogue of Cell Lines and Hybridomas," 6th edition (1988) Rockville, Md., U.S.A.); National Institute of General Medical Sciences 1990/1991 Catalog of Cell Lines (NIGMS) Human Genetic Mutant Cell Repository, Camden, N.J.; and ASHI Repository, Bingham and Women's Hospital, 75 Francis Street, Boston, Mass. 02115. Table 2 lists some B cell lines suitable for use as sources for HLA-A alleles. All of these cell lines can be grown in large batches and are therefore useful for large scale production of MHC molecules. One of skill will recognize that these are merely exemplary cell lines and that many other cell sources can be employed. Similar EBV B cell lines homozygous for HLA-B and HLA-C could serve as sources for HLA-B and HLA-C alleles, respectively.

TABLE 2

HUMAN CELL LINES (HLA-A SOURCES)

| HLA-A allele | B cell line |
|---|---|
| A1 | MAT |
|  | COX (9022) |
|  | STEINLIN |
|  | (9087) |
| A2.1 | JY |
| A3.2 | EHM (9080) |
|  | HO301 (9055)GM3107 |
| A24.1 | KT3 (9107),TISI (9042) |
| A11 | BVR (GM6828A) |
|  | WT100 (GM8602)WT52 |
|  | (GM8603) |

In the typical case, immunoprecipitation is used to isolate the desired allele. A number of protocols can be used, depending upon the specificity of the antibodies used. For example, allele-specific mAb reagents can be used for the affinity purification of the HLA-A, HLA-B, and HLA-C molecules. Several mAb reagents for the isolation of HLA-A molecules are available (Table 3). Thus, for each of the targeted HLA-A alleles, reagents are available that may be used for the direct isolation of the HLA-A molecules. Affinity columns prepared with these mAbs using standard techniques are successfully used to purify the respective HLA-A allele products.

In addition to allele-specific mAbs, broadly reactive anti-HLA-A, B, C mAbs, such as W6/32 and B9.12.1, and one anti-HLA-B, C mAb, B1.23.2, could be used in alternative affinity purification protocols as described in the example section below.

TABLE 3

ANTIBODY REAGENTS

| anti-HLA | Name |
|---|---|
| HLA-A1 | 12/18 |
| HLA-A3 | GAPA3 (ATCC, HB122) |
| HLA-11,24.1 | A11.1M (ATCC, HB164) |
| HLA-A,B,C monomorphic | W6/32 (ATCC, HB95) B9.12.1 (INSERM-CNRS) |
| HLA-B,C monomorphic | B.1.23.2 (INSERM-CNRS) |

The peptides bound to the peptide binding groove of the isolated MHC molecules are eluted typically using acid treatment. Peptides can also be dissociated from class I molecules by a variety of standard denaturing means, such as heat, pH, detergents, salts, chaotropic agents, or a combination thereof.

Peptide fractions are further separated from the MHC molecules by reversed-phase high performance liquid chromatography (HPLC) and sequenced. Peptides can be separated by a variety of other standard means well known to the artisan, including filtration, ultrafiltration, electrophoresis, size chromatography, precipitation with specific antibodies, ion exchange chromatography, isoelectrofocusing, and the like.

Sequencing of the isolated peptides can be performed according to standard techniques such as Edman degradation (Hunkapiller, M. W., et al., *Methods Enzymol.* 91, 399 [1983]). Other methods suitable for sequencing include mass spectrometry sequencing of individual peptides as previously described (Hunt, et al., *Science* 225:1261 (1992), which is incorporated herein by reference). Amino acid sequencing of bulk heterogeneous peptides (e.g., pooled HPLC fractions) from different class I molecules typically reveals a characteristic sequence motif for each class I allele.

Definition of motifs specific for different class I alleles allows the identification of potential peptide epitopes from an antigenic protein whose amino acid sequence is known. Typically, identification of potential peptide epitopes is initially carried out using a computer to scan the amino acid sequence of a desired antigen for the presence of motifs. The epitopic sequences are then synthesized. The capacity to bind MHC Class molecules is measured in a variety of different ways. One means is a Class I molecular binding assay as described in Example 10, below. Other alternatives described in the literature include inhibition of antigen presentation (Sette, et al., *J. Immunol.* 141:3893 (1991), in vitro assembly assays (Townsend, et al., *Cell* 62:285 (1990), and FACS based assays using mutated cells, such as RMA.S (Melief, et al., *Eur. J. Immunol.* 21:2963 [1991]).

Next, peptides that test positive in the MHC class I binding assay are assayed for the ability of the peptides to induce specific CTL responses in vitro. For instance, antigen-presenting cells that have been incubated with a peptide can be assayed for the ability to induce CTL responses in responder cell populations. Antigen-presenting cells can be normal cells such as peripheral blood mononuclear cells or dendritic cells (Inaba, et al., *J. Exp. Med.* 166:182 (1987); Boog, *Eur. J. Immunol.* 18:219 [1988]).

Alternatively, mutant mammalian cell lines that are deficient in their ability to load class I molecules with internally processed peptides, such as the mouse cell lines RMA-S (Kärre, et al. *Nature*, 319:675 (1986); Ljunggren, et al., *Eur. J. Immunol.* 21:2963–2970 (1991)), and the human somatic T cell hybridoma, T-2 (Cerundolo, et al., *Nature* 345:449–452 (1990)) and which have been transfected with the appropriate human class I genes are conveniently used, when peptide is added to them, to test for the capacity of the peptide to induce in vitro primary CTL responses. Other eukaryotic cell lines which could be used include various insect cell lines such as mosquito larvae (ATCC cell lines CCL 125, 126, 1660, 1591, 6585, 6586), silkworm (ATTC CRL 8851), armyworm (ATCC CRL 1711), moth (ATCC CCL 80) and Drosophila cell lines such as a Schneider cell line (see Schneider *J. Embryol. Exp. Morphol.* 27:353–365 [1927]). That have been transfected with the appropriate human class I MHC allele encoding genes and the human $B_2$ microglobulin genes.

Peripheral blood lymphocytes are conveniently isolated following simple venipuncture or leukapheresis of normal donors or patients and used as the responder cell sources of CTL precursors. In one embodiment, the appropriate antigen-presenting cells are incubated with 10–100 μM of peptide in serum-free media for 4 hours under appropriate culture conditions. The peptide-loaded antigen-presenting cells are then incubated with the responder cell populations in vitro for 7 to 10 days under optimized culture conditions. Positive CTL activation can be determined by assaying the cultures for the presence of CTLs that kill radiolabeled target cells, both specific peptide-pulsed targets as well as target cells expressing endogenously processed form of the relevant virus or tumor antigen from which the peptide sequence was derived.

Specificity and MHC restriction of the CTL is determined by testing against different peptide target cells expressing appropriate or inappropriate human MHC class I. The peptides that test positive in the MHC binding assays and give rise to specific CTL responses are referred to herein as immunogenic peptides.

The immunogenic peptides can be prepared synthetically, or by recombinant DNA technology or isolated from natural sources such as whole viruses or tumors. Although the peptide will preferably be substantially free of other naturally occurring host cell proteins and fragments thereof, in some embodiments the peptides can be synthetically conjugated to native fragments or particles. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. When possible, it may be desirable to optimize peptides of the invention to a length of 9 or 10 amino acid residues, commensurate in size with endogenously processed viral peptides or tumor cell peptides that are bound to MHC class I molecules on the cell surface.

Peptides having the desired activity may be modified as necessary to provide certain desired attributes, e.g., improved pharmacological characteristics, while increasing or at least retaining substantially all of the biological activity of the unmodified peptide to bind the desired MHC molecule and activate the appropriate T cell. For instance, the peptides may be subject to various changes, such as substitutions, either conservative or nonconservative, where such changes might provide for certain advantages in their use, such as improved MHC binding. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures, as described in e.g., Merrifield, *Science* 232:341–347 (1986), Barany and Merrifield, *The Peptides,* Gross and Meienhofer, eds. (New York, Academic Press), pp. 1–284 (1979); and Stewart and Young, *Solid Phase Peptide Synthesis,* (Rockford, Ill., Pierce), 2d Ed. (1984), incorporated by reference herein.

The peptides can also be modified by extending or decreasing the compound's amino acid sequence, e.g., by the addition or deletion of amino acids. The peptides or analogs of the invention can also be modified by altering the order or composition of certain residues, it being readily appreciated that certain amino acid residues essential for biological activity, e.g., those at critical contact sites or conserved residues, may generally not be altered without an adverse effect on biological activity. The noncritical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Typically, a series of peptides with single amino acid substitutions is employed to determine the effect of electrostatic charge, hydrophobicity, etc. on binding. For instance, a series of positively charged (e.g., Lys or Arg) or negatively charged (e.g., Glu) amino acid substitutions are made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding.

Amino acid substitutions are typically of single residues. Substitutions, deletions, insertions or any combination thereof may be combined to arrive at a final peptide. Substitutional variants are those in which at least one residue of a peptide has been removed and a different residue inserted in its place. Such substitutions generally are made in accordance with the following Table 4 when it is desired to finely modulate the characteristics of the peptide.

TABLE 4

| Original Residue | Exemplary Substitution |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg |
| Met | leu; ile |
| Phe | met; leu; tyr |
| Ser | thr |
| Thr | ser |
| Trp | tyr |
| Tyr | trp; phe |
| Val | ile; leu |

Substantial changes in function (e.g., affinity for MHC molecules or T cell receptors) are made by selecting substitutions that are less conservative than those in Table 4, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in peptide properties will be those in which (a) hydrophilic residue, e.g. seryl, is substituted for (or by) a hydrophobic residue, e.g. leucyl, isoleucyl, phenylalanyl, valyl or alanyl; (b) a residue having an electropositive side chain, e.g., lysyl, arginyl, or histidyl, is substituted for (or by) an electronegative residue, e.g. glutamyl or aspartyl; or (c) a residue having a bulky side chain, e.g. phenylalanine, is substituted for (or by) one not having a side chain, e.g., glycine.

The peptides may also comprise isosteres of two or more residues in the immunogenic peptide. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, peptides and Proteins,* Vol. VII (Weinstein ed., 1983).

Modifications of peptides with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., *Eur. J. Drug Metab Pharmacokin.* 11:291–302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides of the present invention or analogs thereof which have CTL stimulating activity may be modified to provide desired attributes other than improved serum half life. For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated.

In some embodiments it may be desirable to include in the pharmaceutical compositions of the invention at least one component which assists in priming CTL. Lipids have been identified as agents capable of assisting the priming CTL in vivo against viral antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunogenic peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide. See, Deres et al., *Nature* 342:561–564 (1989), incorporated herein by reference. Peptides of the invention can be coupled to $P_3CSS$, for example, and the lipopeptide administered to an individual to specifically prime a CTL response to the target antigen. Further, as the induction of neutralizing antibodies can also be primed with $P_3CSS$ conjugated to a peptide which displays an appropriate epitope, the two compositions can be combined to more effectively elicit both humoral and cell-mediated responses to infection.

In addition, additional amino acids can be added to the termini of a peptide to provide for ease of linking peptides one to another, for coupling to a carrier support, or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. Modification at the C terminus in some cases may alter binding characteristics of the peptide. In addition, the peptide or oligopeptide sequences can differ from the natural sequence by being modified by terminal-$NH_2$ acylation, e.g., by alkanoyl ($C_1$–$C_{20}$) or thioglycolyl acetylation, terminal-carboxyl amidation, e.g., ammonia, methylamine, etc. In some instances these modifications may provide sites for linking to a support or other molecule.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984), supra.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982), which is incorporated herein by reference. Thus, fusion proteins which comprise one or more peptide sequences of the invention can be used to present the appropriate T cell epitope.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides of the present invention and pharmaceutical and vaccine compositions thereof are useful for administration to mammals, particularly humans, to treat and/or prevent viral infection and cancer. Examples of diseases which can be treated using the immunogenic peptides of the invention include prostate cancer, hepatitis B, hepatitis C, AIDS, renal carcinoma, cervical carcinoma, lymphoma, CMV and condlyloma acuminatum.

For pharmaceutical compositions, the immunogenic peptides of the invention are administered to an individual already suffering from cancer or infected with the virus of interest. Those in the incubation phase or the acute phase of infection can be treated with the immunogenic peptides separately or in conjunction with other treatments, as appropriate. In therapeutic applications, compositions are administered to a patient in an amount sufficient to elicit an effective CTL response to the virus or tumor antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg about 5000 μg of peptide for a 70 kg patient, followed by boosting dosages of from about 1.0 μg to about 1000 μg of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

For therapeutic use, administration should begin at the first sign of viral infection or the detection or surgical removal of tumors or shortly after diagnosis in the case of acute infection. This is followed by boosting doses until at least symptoms are substantially abated and for a period thereafter. In chronic infection, loading doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic infection and to stimulate the immune system to eliminate virus-infected cells in carriers. It is important to provide an amount of immuno-potentiating peptide in a formulation and mode of administration sufficient to effectively stimulate a cytotoxic T cell response. Thus, for treatment of chronic infection, a representative dose is in the range of about 1.0 µg to about 5000 µg, preferably about 5 µg to 1000 µg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides of the invention may also be administered via liposomes, which target the peptides to a particular cells tissue, such as lymphoid tissue. Liposomes are also useful in increasing the half-life of the peptides. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the immunogenic peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of an immunogenic peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of the virus or tumor cells. Useful carriers are well known in the art, and include, e.g., thyroglobulin, albumins such as bovine serum albumin, tetanus toxoid, polyamino acids such as poly(lysine:glutamic acid), hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, CTL responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

Vaccine compositions containing the peptides of the invention are administered to a patient susceptible to or otherwise at risk of viral infection or cancer to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 µg to about 5000 µg per 70 kilogram patient, more commonly from about 10 µg to about 500 µg mg per 70 kg of body weight.

In some instances it may be desirable to combine the peptide vaccines of the invention with vaccines which induce neutralizing antibody responses to the virus of interest, particularly to viral envelope antigens.

For therapeutic or immunization purposes, the peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

Antigenic peptides may be used to elicit CTL ex vivo, as well. The resulting CTL, can be used to treat chronic infections (viral or bacterial) or tumors in patients that do not respond to other conventional forms of therapy, or will not respond to a peptide vaccine approach of therapy. Ex vivo CTL responses to a particular pathogen (infectious agent or tumor antigen) are induced by incubating in tissue culture the patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will destroy their specific target cell (an infected cell or a tumor cell). In order to optimize the in vitro conditions for the generation of specific cytotoxic T cells, the culture of stimulator cells is maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that will allow about 200, and preferably 200 or more, human Class I MHC molecules loaded with peptide to be expressed on the surface of each stimulator cell. Preferably, the stimulator cells are incubated with >20 µg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+ (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses. Peptide loading of empty major histocompatability complex molecules on cells enables the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), non-infected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8–10 residues, 2) a transmembrane heavy polymorphic protein chain which bears the peptide-binding site in its α1 and α2 domains, and 3) a non-covalently associated non-polymorphic light chain, $\beta_2$microglobulin. Removing the bound peptides and/or dissociating the $\beta_2$microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destablize $\beta_2$microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6 - 5 \times 10^7$ cells used in mice.

Preferably, as discussed above, the activated CD8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells is not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The immunogenic peptides of this invention may also be used to make monoclonal antibodies. Such antibodies may be useful as potential diagnostic or therapeutic agents.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

The following examples are offered by way of illustration, not by way of limitation.

EXAMPLE 1

Class I Antigen Isolation

A flow diagram of an HLA-A antigen purification scheme is presented in FIG. 1. Briefly, the cells bearing the appropriate allele were grown in large batches (6–8 liters yielding $\sim 5 \times 10^9$ cells), harvested by centrifugation and washed. All cell lines were maintained in RPMI 1640 media (Sigma) supplemented with 10% fetal bovine serum (FBS) and antibiotics. For large-scale cultures, cells were grown in roller bottle culture in RPMI 1640 with 10% FBS or with 10% horse serum and antibiotics. Cells were harvested by centrifugation at 1500 RPM IEC-CRUSOOO centrifuge with 259 rotor and washed three times with phosphate-buffered saline (PBS)(0.01 M $PO_4$, 0.154 M NaCl, pH 7.2).

Cells were pelleted and stored at −70° C. or treated with detergent lysing solution to prepare detergent lysates. Cell lysates were prepared by the addition of stock detergent solution [1% NP-40 (Sigma) or Renex 30 (Accurate Chem. Sci. Corp., Westbury, N.Y. 11590), 150 mM NaCl, 50 mM Tris, pH 8.0] to the cell pellets (previously counted) at a ratio of $50-100 \times 10^6$ cells per ml detergent solution. A cocktail of protease inhibitors was added to the premeasured volume of stock detergent solution immediately prior to the addition to the cell pellet. Addition of the protease inhibitor cocktail produced final concentrations of the following: phenylmethylsulfonyl fluoride (PMSF), 2 mM; aprotinin, 5 µg/ml; leupeptin, 10 µg/ml; pepstatin, 10 µg/ml; iodoacetamide, 100 µM; and EDTA, 3 ng/ml. Cell lysis was allowed to proceed at 4° C. for 1 hour with periodic mixing. Routinely $5-10 \times 10^9$ cells were lysed in 50–100 ml of detergent solution. The lysate was clarified by centrifugation at 15,000×g for 30 minutes at 4° C. and subsequent passage of the supernatant fraction through a 0.2µ filter unit (Nalgene).

The HLA-A antigen purification was achieved using affinity columns prepared with mAb-conjugated Sepharose beads. For antibody production, cells were grown in RPMI with 10% FBS in large tissue culture flasks (Corning 25160-225). Antibodies were purified from clarified tissue culture medium by ammonium sulfate fractionation followed by affinity chromatography on protein-A-Sepharose (Sigma). Briefly, saturated ammonium sulfate was added slowly with stirring to the tissue culture supernatant to 45% (volume to volume) overnight at 4° C. to precipitate the immunoglobulins. The precipitated proteins were harvested by centrifugation at 10,000×g for 30 minutes. The precipitate was then dissolved in a minimum volume of PBS and transferred to dialysis tubing (Spectro/Por 2, Mol. wt. cutoff 12,000–14,000, Spectum Medical Ind.). Dialysis was against PBS ($\geq 20$ times the protein solution volume) with 4–6 changes of dialysis buffer over a 24–48 hour period at 4° C. The dialyzed protein solution was clarified by centrifugation (10,000×g for 30 minutes) and the pH of the solution adjusted to pH 8.0 with 1N NaOH. Protein-A-Sepharose (Sigma) was hydrated according to the manufacturer's instructions, and a protein-A-Sepharose column was prepared. A column of 10 ml bed volume typically binds 50–100 mg of mouse IgG.

The protein sample was loaded onto the protein-A-Sepharose column using a peristaltic pump for large loading volumes or by gravity for smaller volumes (<100 ml). The column was washed with several volumes of PBS, and the eluate was monitored at A280 in a spectrophotometer until base line was reached. The bound antibody was eluted using 0.1 M citric acid at suitable pH (adjusted to the appropriate pH with 1N NaOH). For mouse IgG-1 pH 6.5 was used; for IgG2a pH 4.5 was used; and for IgG2b and IgG3 pH 3.0 was used. 2 M Tris base was used to neutralize the eluate. Fractions containing the antibody (monitored by A280) were pooled, dialyzed against PBS and further concentrated using an Amicon Stirred Cell system (Amicon Model 8050 with YM30 membrane). The anti-A2 mAb, BB7.2, and the anti-A3 mAb, GAPA3, are particularly useful for affinity purification.

The HLA-A antigen was purified using affinity columns prepared with mAb-conjugated Sepharose beads. The affinity columns were prepared by incubating protein-A-Sepharose beads (Sigma) with affinity-purified mAb as described above. Five to 10 mg of mAb per ml of bead is the preferred ratio. The mAb bound beads were washed with borate buffer (borate buffer: 100 mM sodium tetraborate, 154 mM NaCl, pH 8.2) until the washes show A280 at base line. Dimethyl pimelimidate (20 mM) in 200 mM triethanolamine was added to covalently crosslink the bound mAb to the protein-A-Sepharose (Schneider et al., *J. Biol. Chem.* 257:10766 (1982). After incubation for 45 minutes at room temperature on a rotator, the excess crosslinking reagent was removed by washing the beads twice with 10–20 ml of 20 mM ethanolamine, pH 8.2. Between each wash the slurry was placed on a rotator for 5 minutes at room temperature. The beads were washed with borate buffer and with PBS plus 0.02% sodium azide.

The cell lysate ($5-10 \times 10^9$ cell equivalents) was then slowly passed over a 5–10 ml affinity column (flow rate of 0.1–0.25 ml per minute) to allow the binding of the antigen to the immobilized antibody. After the lysate was allowed to pass through the column, the column was washed sequentially with 20 column volumes of detergent stock solution plus 0.1% sodium dodecyl sulfate, 20 column volumes of 0.5 M NaCl, 20 mM Tris, pH 8.0, and 10 column volumes of 20 mM Tris, pH 8.0. The HLA-A antigen bound to the mAb was eluted with a basic buffer solution (50 mM diethylamine in water). As an alternative, acid solutions such as 0.15–0.25 M acetic acid were also used to elute the bound antigen. An aliquot of the eluate (1/50) was removed for protein quantification using either a calorimetric assay (BCA assay, Pierce) or by SDS-PAGE, or both. SDS-PAGE analysis was performed as described by Laemmli (Laemmli, U. K., *Nature* 227:680 (1970)) using known amounts of bovine serum albumin (Sigma) as a protein standard.

Allele specific antibodies were used to purify the specific MHC molecule. In the case of HLA-A2 and HLA-A3 mAbs BB7.2 and GAPA3 were used respectively. An example of SDS PAGE analysis of purified HLA-A3.2 molecules is shown in FIG. 2.

FIG. 2 shows SDS-PAGE (12.5%) analysis of affinity purified HLA-A3.2 from the cell line EHM. An affinity column (10 ml) was prepared with protein A-sepharose beads coupled to the monoclonal antibody GAPA3 which is specific for HLA-A3. A detergent lysate of $5 \times 10^9$ cells was passaged over the column and the column was washed extensively. The bound HLA-A3.2 molecules were eluted from the column with 0.15M acetic acid, 50 ml. One ml of the eluate was removed and lyophilized to concentrate the sample. The sample was taken up to 50 μl with Laemmli sample buffer and 20 μl were loaded in lane 2. Lane 1 contained molecular weight standards: Myosin, 230 kD; β-galactosidase, 116 kD; phosphorylase B, 97.4 kD; bovine serum albumin, 66.2 kD; ovalbumin, 45 kD; carbonic anhydrase, 31 kD; soybean trypsin inhibitor, 21.5 kD; and lysozyme, 14.4 kD. Standard concentrations of bovine serum albumin were run in lanes 8, 10 μg, 9, 3 μg, and 10, 1 μg to aid in the estimation of protein yield. For this particular HLA-A3.2 preparation, the estimated yield was approximately 112 μg.

For HLA-A11, A24.1 and A1, an alternative protocol was used whereby anti-HLA-B and C monoclonal antibodies were used to deplete HLA-B and C molecules. The remaining HLA-A molecules were subsequently purified using the W6/32 mAb as described below.

Based on the density of class I expression as indicated by the results of immunofluorescent staining analysis, it is anticipated that average yields of class I antigen isolated from the EBV B cell lines will range from 800–1200 μg per $10^{10}$ cell equivalents.

EXAMPLE 2

An Alternative Class I Purification Protocol

HLA-A2.1 molecules were isolated using the mAb B1.23.2 which detects an epitope expressed by HLA-B and C allele molecules, but not by HLA-A antigens. The mAb, W6/32, detects all human class I molecules, including HLA-A, B and C. As mentioned above, these mAbs react well with the B cell lines serving as sources of HLA-A antigens. The B1.23.2 mAb reacts with the various human B cell lines, but fails to react with a mouse cell line that expresses a transfected HLA-A2.1 protein or a chimeric A2.1 mouse $K^b$ molecule. It does react with the human cell line, CIR (Alexander, J., et al., *Immunogenetics*, 29, 380 [1989]), that lacks expression of HLA-A and B molecules, but expresses low levels of HLA-C molecules. This pattern of reactivity illustrates how the B1.23.2 mAb can be used to deplete the B cell lysates of HLA-B and C molecules.

Affinity columns were prepared using the affinity-purified B1.23.2 and W6/32 mAbs, respectively, as described above. The procedures for the preparation of the affinity columns are essentially identical to the procedures described for the preparation of the allele-specific mAb columns described above. The B1.23.2 mAb affinity column was used to deplete the detergent lysates of HLA-B and C molecules using the protocol as described above. The cell lysate depleted of HLA-B and C was then passed over a W6/32 mAb affinity column. The MHC molecule that was eluted from this second passage was the A allele product.

This alternative affinity purification is useful for the purification of any HLA-A allele product, and does not rely on the need for allele-specific mAbs. In addition, it could also be used to isolate any class I molecule type from transfected cell lines.

EXAMPLE 3

Isolation and Sequencing of Naturally Processed Peptides

For the HLA-A preparations derived from the base (50 mM diethylamine) elution protocol, the eluate was immediately neutralized with 1 N acetic acid to pH 7.0–7.5. The neutralized eluate was concentrated to a volume of 1–2 ml in an Amicon stirred cell [Model 8050, with YM3 membranes (Amicon)]. Ten ml of ammonium acetate (0.01 M, pH 8.0) was added to the concentrator to remove the nonvolatile salts, and the sample was concentrated to approximately 1 ml. A small sample (⅕₀) was removed for protein quantitation as described above. The remainder was recovered into a 15 ml polypropylene conical centrifuge tube (Falcon, 2097) (Becton Dickinson). Glacial acetic acid was added to obtain a final concentration of 10% acetic acid. The acidified sample was placed in a boiling water bath for 5 minutes to allow for the dissociation of the bound peptides. The sample was cooled on ice, returned to the concentrator and the filtrate was collected. Additional aliquots of 10% acetic acid (1–2 ml) were added to the concentrator, and this filtrate was pooled with the original filtrate. Finally, 1–2 ml of distilled water was added to the concentrator, and this filtrate was pooled as well.

The retentate contains the bulk of the HLA-A heavy chain and $\beta_2$-microglobulin, while the filtrate contains the naturally processed bound peptides and other components with molecular weights less than about 3000. The pooled filtrate material was lyophilized in order to concentrate the peptide fraction. The sample was then ready for further analysis.

For HPLC (high performance liquid chromatography) separation of the peptide fractions, the lyophilized sample was dissolved in 50 μl of distilled water, or into 0.1% trifluoracetic acid (TFA) (Applied Biosystems) in water and injected into a C18 reverse-phase narrow bore column (Beckman C18 Ultrasphere, 10×250 mm), using a gradient system described by Stone and Williams (Stone, K. L. and Williams K. R., in, Macromolecular Sequencing and Synthesis; Selected 15 Methods and Applications, A. R. Liss, New York, 1988, pp. 7–24). Buffer A was 0.06% TFA in water (Burdick-Jackson) and buffer B was 0.052% TFA in 80% acetonitrile (Burdick-Jackson). The flow rate was 0.250 ml/minute with the following gradient: 0–60 min., 2–37.5% B; 60–95 min., 37.5–75% B; 95–105 min., 75–98% B. The Gilson narrow bore HPLC configuration is particularly useful for this purpose, although other configurations work equally well.

Figure 3:
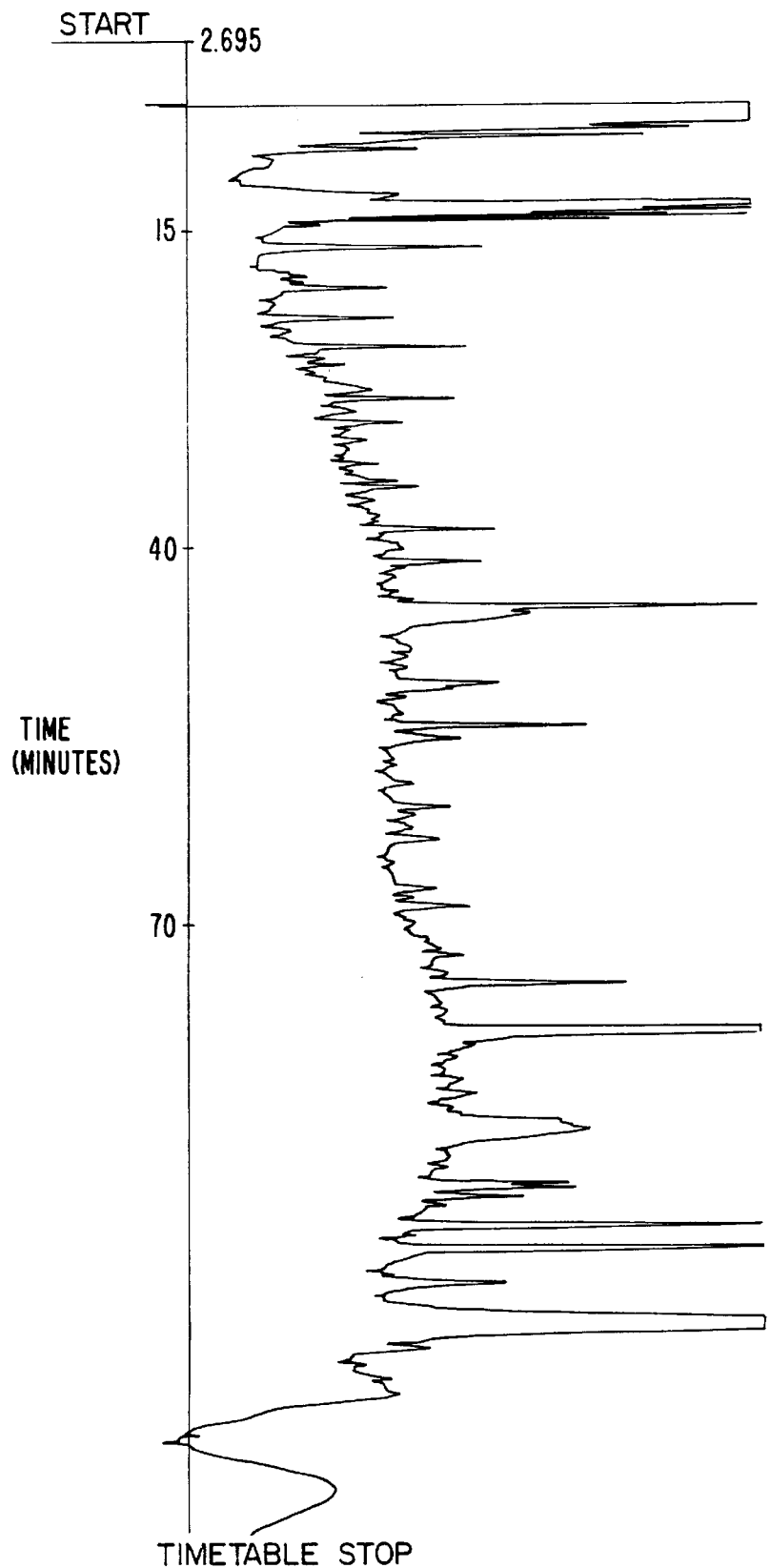
FIG. 3 shows reverse phase high performance liquid chromatography (RP-HPLC) separation of HLA-A3 acid eluted peptides.

A large number of peaks were detected by absorbance at 214 nm, many of which appear to be of low abundance (FIG. 3). Whether a given peak represents a single peptide or a peptide mixture was not determined. Pooled fractions were then sequenced to determine motifs specific for each allele as described below.

Pooled peptide fractions, prepared as described above were analyzed by automated Edman sequencing using the Applied Biosystems Model 477A automated sequencer. The sequencing method is based on the technique developed by Pehr Edman in the 1950s for the sequential degradation of proteins and peptides to determine the sequence of the constituent amino acids.

The protein or peptide to be sequenced was held by a 12-mm diameter porous glass fiber filter disk in a heated, argon-purged reaction chamber. The filter was generally pretreated treated with BioBrene Plus™ and then cycled through one or more repetitions of the Edman reaction to reduce contaminants and improve the efficiency of subsequent sample sequencing. Following the pretreatment of the filter, a solution of the sample protein or peptide (10 pmol–5 nmol range) was loaded onto the glass filter and dried. Thus, the sample was left embedded in the film of the pretreated disk. Covalent attachment of the sample to the filter was usually not necessary because the Edman chemistry utilized relatively apolar solvents, in which proteins and peptides are poorly soluble.

Briefly, the Edman degradation reaction has three steps: coupling, cleavage, and conversion. In coupling step, phenylisothiocyanate (PITC) is added. The PITC reacts quantitatively with the free amino-terminal amino acid of the protein to form the phenylthiocarbamyl-protein in a basic environment. After a period of time for the coupling step, the excess chemicals are extracted and the highly volatile organic acid, trifluoroacetic acid, TFA, is used to cleave the PITC-coupled amino acid residue from the amino terminus of the protein yielding the anilinothiazolinone (ATZ) derivative of the amino acid. The remaining protein/peptide is left with a new amino terminus and is ready for the next Edman cycle. The ATZ amino acid is extracted and transferred to a conversion flask, where upon addition of 25% TFA in water, the ATZ amino acid is converted to the more stable phenylthiohydantoin (PTH) amino acid that can be identified and quantified following automatic injection into the Model 120 PTH Analyzer which uses a microbore C-18 reverse-phase HPLC column for the analysis.

In the present procedures, peptide mixtures were loaded onto the glass filters. Thus, a single amino acid sequence usually does not result. Rather, mixtures of amino acids in different yield are found. When the particular residue is conserved among the peptides being sequenced, increased yield for that amino acid is observed.

EXAMPLE 4

Definition of an A3.2 Specific Motif

There is some ambiguity in the international nomenclature of A3 alleles. The A3.2 allele herein is expressed by cell lines EHM, H0301, and GM3107. This particular subtype is currently referred to as the 3.2 allele (Yang, in *Immunobiology of HLA,* Vol. 1, Dupont ed., Springer-Verlag, New York pp. 43–44 and 54–55, 1989), or the product of the A*0301 gene (its sequence corresponds to the one published by Strachan, et al., *EMBO J.,* 3:887 (1984), and has been verified by direct cloning and sequencing of the A3 gene found in EHM cell line. The HLA-A3.2 encoded by the A*0301 gene referred to in this document is the commonly expressed HLA-A3 allelic form.

In one case using MAT cells, pooled peptide fractions prepared as described in Example 3 above were obtained from HLA-A3.2 homozygous cell lines, for example, CM3107. The pooled fractions were HPLC fractions corresponding to 7% to 19% $CH_3CN$. For this class I molecule, this region of the chromatogram was most abundant in peptides. Data from independent experiments were averaged as described below.

The amino acid sequence analyses from four independent experiments were analyzed and the results are shown in Table 5. For each position except the first, the data were analyzed by modifying the method described by Falk et al. to allow for comparison of experiments from different HLA types. This modified procedure yielded quantitative yet standardized values while allowing the averaging of data from different experiments involving the same HLA type.

The raw sequenator data was converted to a simple matrix of 10 rows (each representing one Edman degradation cycle) and 16 columns (each representing one of the twenty amino acids; W, C, R and H were eliminated for technical reasons. The data corresponding to the first row (first cycle) was not considered further because, this cycle is usually heavily contaminated by free amino acids.). The values of each row were summed to yield a total pmoles value for that particular cycle. For each row, values for each amino acid were then divided by the corresponding total yield value, to determine what fraction of the total signal is attributable to each amino acid at each cycle. By doing so, an "Absolute Frequency"

table was generated. This absolute frequency table allows correction for the declining yields of each cycle.

Starting from the absolute frequency table, a "relative frequency" table was then generated to allow comparisons among different amino acids. To do so the data from each column was summed, and then averaged. Then, each value was divided next by the average column value to obtain relative frequency values. These values quantitate, in a standardized manner, increases and decreases per cycle, for each of the different sixteen amino acid types. Tables generated from data from different experiments can thus be added together to generate average relative frequency values (and their standard deviations). All standard deviations can then be averaged, to estimate a standard deviation value applicable to the samples from each table. Any particular value exceeding 1.00 by more than two standard deviations is considered to correspond to a significant increase.

The results of the foregoing analysis for HLA-A3.2 were as follows: at position 2, a 2.2-fold increase in valine (V) with lesser increases (1.5–1.7) for structurally similar residues leucine (L) and methionine (M). At position 3, tyrosine (Y) and aspartic acid (D) showed increases in frequency. At position 7 isoleucine (I) was increased, and at position 8 asparagine (N) and glutamine (Q) were increased. At positions 9 and 10, lysine (K) was increased more than 2-fold over the expected random yield.

Cysteine was not modified and thus not detected. PTH-tryptophan coeluted with diphenylurea, and in some experiments, PTH-arginine coeluted with the major derivative of PTH-threonine. Therefore, cysteine and tryptophan are not detectable and arginine is detected only in the absence of threonine.

Previously described MHC structures showed instances of critically conserved residues at position 2 (or 3) and at the C terminus (either position 9 or 10). These residues are referred to as "conserved" residues. The modified data analysis of this invention considered the conserved positions at the N and C terminals.

Thus, the HLA-A3.2 motif should have position two occupied by V, L or M, a length of 9 or 10 amino acids, and a C-terminal position occupied by K (SEQ ID NOS:37 and 38).

TABLE 5

Summary
HLA-A3.2 Allele-Specific Motif (SEQ ID NO:39)

| Position | Conserved Residues |
| --- | --- |
| 1 | — |
| 2 | V,L,M |
| 3 | Y,D |
| 4 | — |
| 5 | — |
| 6 | — |
| 7 | I |
| 8 | Q,N |
| 9 | K |
| 10 | K |

EXAMPLE 5

Definition of HLA-A1-specific Peptide Motifs

HLA-A1 molecules were isolated and their naturally processed peptides characterized, as described in Example 3 above. In one case using MAT cells, pooled fractions corresponding to 19% to 50% $CH_3CN$ were used. As in the preceding example, residues showing at any given position except the first position, at least a two standard deviation increase over the random expected yield were identified and shown in Table 6. On the basis of these data, only Serine (S) and Threonine (T) were increased at position two. At position 3, aspartic acid (D) and glutamic acid (E) were elevated and at position 9 and 10 tyrosine (Y) showed a marked increase. Other increases noted were proline (P) at position 4 and leucine (L) at position 7. Therefore, the motifs for HLA-A1 based on these data would have residues at position 2 occupied by S or T, a peptide length of 9 or 10 amino acids and a C-terminal residue of Y (SEQ ID NOS:40 and 41). Alternatively, another motif would comprise a D or E at position 3 together with a C terminal residue of Y (SEQ ID NOS:42 and 43).

TABLE 6

Summary
HLA-A1 Allele-Specific Motif (SEQ ID NO:44)

| Position | Conserved Residues |
| --- | --- |
| 1 | — |
| 2 | S, T |
| 3 | D,E |
| 4 | P |
| 5 | — |
| 6 | — |
| 7 | L |
| 8 | — |
| 9 | Y |

EXAMPLE 6

Definition of HLA-A11 Allele-specific Peptide Motifs

HLA-A11 motifs were defined by amino acid sequence analysis of pooled HPLC fractions, in one case corresponding to 7% to 45% $CH_3CN$ of fractionated peptides eluted from HLA-A11 molecules purified from the cell line BVR. On the basis of the data presented in Table 7, a motif for A11 consists of a conserved residue at position 2 of threonine (T) or valine (V), a peptide length of 9 or 10 amino acids, and a C-terminal conserved residue of lysine (K). At position 3 increases in methionine (M) and phenylalanine (F) were also seen and at position 8 glutamine (Q) was increased (SEQ ID NOS:45 and 46).

TABLE 7

Summary
HLA-A11 Allele-Specific Motif (SEQ ID NO:47)

| Position | Conserved Residues |
| --- | --- |
| 1 | — |
| 2 | T,V |
| 3 | M,F |
| 4 | — |
| 5 | — |
| 6 | — |
| 7 | — |
| 8 | Q |
| 9 | K |
| 10 | K |

EXAMPLE 7

Definition of HLA-A24.1 Specific Peptide Motifs

HLA-A24.1 allele-specific motifs were defined by amino acid sequence analysis of pooled fractions in one case corresponding to 7% to 19% CH$_3$CN of HPLC fractionated peptides eluted from HLA-A24.1 molecules purified from the cell line KT3. On the basis of the data presented in Table 8 a motif for HLA-A24.1 consists of a conserved residue at position 2 occupied by tyrosine (Y), a peptide length of 9 or 10 amino acids, and a C-terminal conserved residue of phenylalanine (F) or leucine (L). Increases were also observed at several other positions: isoleucine (I) and methionine (M) at position 3; aspartic acid (D), glutamic acid (E), glycine (G), lysine (K) and proline (P) at position 4; lysine (K), methionine (M) and asparagine (N) at position 5; valine (V) at position 6; asparagine (N) and valine (V) at position 7; and, alanine (A), glutamic acid (E), lysine (K), glutamine (Q) and serine (S) at position 8 (SEQ ID NOS:48 and 49).

TABLE 8

Summary
HLA-A24.1 Allele-Specific Motif (SEQ ID NO:50)

| Position | Conserved Residues |
|---|---|
| 1 | — |
| 2 | Y |
| 3 | I,M |
| 4 | D,E,G,K,P |
| 5 | L,M,N |
| 6 | V |
| 7 | N,V |
| 8 | A,E,K,Q,S |
| 9 | F,L |
| 10 | F,L |

EXAMPLE 8

Identification of Immunogenic Peptides

Using the motifs identified above for various MHC class I allele amino acid sequences from various viral and tumor-related proteins were analyzed for the presence of these motifs. Sequences for all of the target antigens were obtained from the GenBank data base (Release No. 71.0; 3/92). The identification of motifs was done using the "FINDPATTERNS" program (Devereux, Haeberli and Smithes (1984). Nucleic Acids Research 12(1); 387–395).

The amino acid sequence or the nucleotide sequence encoding products was obtained from the GenBank database. In the cases of Human Papilloma Virus (HPV), Prostate Specific Antigen (PSA), p53 oncogene, Epstein Barr Nuclear Antigen-1 (EBNA-1), and c-erb2 oncogene (also called HER-2/neu), and Melanoma Antigen-1 (MAGE-1), a single sequence exists.

In the cases of Hepatitis B Virus (HBV), Hepatitis C Virus (HCV), and Human Immunodeficiency Virus (HIV) several strains/isolates exist and many sequences have been placed in GenBank.

For HBV, binding motifs were identified for the adr, adw and ayw types. In order to avoid replication of identical sequences, all of the adr motifs and only those motifs from adw and ayw that are not present in adr were added to the list of peptides.

In the case of HCV, a consensus sequence from residue 1 to residue 782 was derived from 9 viral isolates. Motifs were identified on those regions that had no or very little (one residue) variation between the 9 isolates. The sequences of residues 783 to 3010 from 5 viral isolates were also analyzed. Motifs common to all the isolates were identified and added to the peptide list.

Finally, a consensus sequence for HIV type 1 for North American viral isolates (10–12 viruses) was obtained from the Los Alamos National Laboratory database (May 1991 release) and analyzed in order to identify motifs that are constant throughout most viral isolates. Motifs that bear a small degree of variation (one residue, in 2 forms) were also added to the peptide list.

Several motifs for each allele shown below were used to screen several antigens. Protein E6 of human papilloma virus (HPV) type 16 using motifs from all of the alleles disclosed above are shown (Table 9). Protein E7 of HPV type 18 was also searched for motifs from all alleles (Table 9) Melanoma antigens MAGE 1, 2 and 3 were searched for motifs from all alleles (Table 10). The antigen PSA was searched for motifs from all alleles (Table 11). Finally, core and envelope proteins from hepatitis C virus were also searched (Table 12). In the tables and the description of the motifs, the conventional symbol letter for each amino acid was used. The letter "X" represents a wild card character (any amino acid).

The following motifs were screened in the present search:

| For HLA-A1 (A*0101) [SEQ ID NO:]: | |
|---|---|
| 1 | XSXXXXXXY [51] |
| 2 | XSXXXXXXXY [52] |
| 3 | XTXXXXXXY [53] |
| 4 | XTXXXXXXXY [54] |
| 5 | XXDXXXXXY [55] |
| 6 | XXDXXXXXXY [56] |
| 7 | XXEXXXXXY [57] |
| 8 | XXEXXXXXXY [58] |

| For HLA-A3.2 (A*0301) [SEQ ID NO:] | |
|---|---|
| 1 | XVXXXXXXK [59] |
| 2 | XVXXXXXXXK [60] |
| 3 | XLXXXXXXK [61] |
| 4 | XLXXXXXXXK [62] |
| 5 | XMXXXXXXK [63] |
| 6 | XMXXXXXXXK [64] |

| For HLA-A11 (A*1101) [SEQ ID NO:]: | |
|---|---|
| 1 | XTXXXXXXK [65] |
| 2 | XTXXXXXXXK [66] |
| 3 | XVXXXXXXK [67] |
| 4 | XVXXXXXXXK [68] |

| For HLA-A24.1 (A*2401) [SEQ ID NO:]: | |
|---|---|
| 1 | XYXXXXXXF [69] |
| 2 | XYXXXXXXXF [70] |
| 3 | XYXXXXXXL [71] |
| 4 | XYXXXXXXXL [72] |

TABLE 9

Peptides with MHC Class I Binding Motifs

| AA Position | Sequence | Antigen | HLA molecule | SEQ ID NO: |
|---|---|---|---|---|
| 30 | IHDIILECVY | HPV16.E6 | A1 | 73 |
| 69 | VCDKCLKFY | HPV16.E6 | A1 | 74 |
| 77 | YSKISEYRHY | HPV16.E6 | A1 | 75 |
| 80 | ISEYRHYCY | HPV16.E6 | A1 | 76 |
| 92 | GTTLEQQYNK | HPV16.E6 | A11 | 77 |
| 93 | TTLEQQYNK | HPV16.E6 | A11 | 78 |
| 106 | LLIRCINCQK | HPV16.E6 | A3 | 79 |
| 2 | HGDTPTLHEY | HPV16.E7 | A1 | 80 |
| 16 | QPETTDLYCY | HPV16.E7 | A1 | 81 |
| 44 | QAEPDRAHY | HPV16.E7 | A1 | 82 |

TABLE 9-continued

Peptides with MHC Class I Binding Motifs

| AA Position | Sequence | Antigen | HLA molecule | SEQ ID NO: |
|---|---|---|---|---|
| 89 | IVCPICSQK | HPV16.E7 | A3, A11 | 83 |
| 3 | RFEDPTRRPY | HPV18.E6 | A1 | 84 |
| 4 | FEDPTRRPY | HPV18.E6 | A1 | 85 |
| 25 | LQDIEITCVY | HPV18.E6 | A1 | 86 |
| 41 | LTEVFEFAFK | HPV18.E6 | A11 | 87 |
| 72 | YSRIRELRHY | HPV18.E6 | A1 | 88 |
| 84 | SVYGDTLEK | HPV18.E6 | A3, A11 | 89 |
| 101 | LLIRCLRCQK | HPV18.E6 | A3 | 90 |
| 59 | HTMLCMCCK | HPV18.E7 | A11 | 91 |

Human Papilloma Virus 16 and 18 (E6 and E7 Proteins)

TABLE 10

Peptides with MHC Class I Binding Motifs

| AA Position | Sequence | Antigen | HLA molecule | SEQ ID NO: |
|---|---|---|---|---|
| 2 | SLEQRSLHCK | MAGE 1 | A3 | 92 |
| 96 | SLFHAVITK | MAGE 1 | A3 | 93 |
| 96 | SLFRAVITKK | MAGE 1 | A3 | 94 |
| 108 | DLVGFLLLK | MAGE 1 | A3 | 95 |
| 128 | MLESVIKNYK | MAGE 1 | A1 | 96 |
| 128 | MLESVIKNY | MAGE 1 | A3 | 97 |
| 152 | QLVFGIDVK | MAGE 1 | A1 | 98 |
| 161 | EADPTGHSY | MAGE 1 | A1 | 99 |
| 182 | LLGDNQIMPK | MAGE 1 | A3 | 100 |
| 215 | WEELSVMEVY | MAGE 1 | A1 | 101 |
| 223 | VYDGREHSAY | MAGE 1 | A1 | 102 |
| 238 | LLTQDLVQEK | MAGE 1 | A3 | 103 |
| 239 | LTQDLVQEK | MAGE 1 | A11 | 104 |
| 239 | LTQDLVQEKY | MAGE 1 | A1 | 105 |
| 240 | TQDLVQEKY | MAGE 1 | A1 | 106 |

Melanoma Antigen MAGE 1

TABLE 11

Peptides with MHC Class I Binding Motifs

| AA Position | Sequence | Antigen | HLA molecule | SEQ ID NO: |
|---|---|---|---|---|
| 21 | IVGGWECEK | PSA | A3, A11 | 107 |
| 57 | LTAAHCIRNK | PSA | A11 | 108 |
| 88 | VSHSFPHPLY | PSA | A1 | 109 |
| 95 | PLYDMSLLK | PSA | A3 | 110 |
| 178 | DVCAQVHPQK | PSA | A3, A11 | 111 |
| 182 | QVHPQKVTK | PSA | A3, A11 | 112 |
| 236 | PSLYTKVVHY | PSA | A1 | 113 |
| 239 | YTKVVHYRK | PSA | A11 | 114 |
| 241 | KVVHYRKWIK | PSA | A3, A11 | 115 |
| 242 | VVHYRKWIK | PSA | A3, A11 | 116 |

Prostate Specific Antigen (PSA)

TABLE 12

Peptides with MHC Class I Binding Motifs

| AA Position | Sequence | Antigen | HLA molecule | SEQ ID NO: |
|---|---|---|---|---|
| 2 | STNPKPQRK | HCV | A11 | 117 |
| 14 | NTNRRPQDVK | HCV | A11 | 118 |
| 43 | RLGVRATRK | HCV | A3 | 119 |
| 302 | VQDCNCSIY | HCV | A1 | 120 |
| 556 | WMNSTGFTK | HCV | A3 | 121 |

TABLE 12-continued

Peptides with MHC Class I Binding Motifs

| AA Position | Sequence | Antigen | HLA molecule | SEQ ID NO: |
|---|---|---|---|---|
| 605 | LTPRCMVDY | HCV | A1 | 122 |
| 626 | FTIFKIRMY | HCV | A1 | 123 |

Hepatitis C Virus (Consensus Sequence)

EXAMPLE 9

Identification of Immunogenic Peptides

Using the motifs disclosed here, amino acid sequences from various antigens were screened for further motifs. Screening was carried out as described in Example 8. Table 37 provides the results of searches of the following antigens HBV, HCV, HIV, HPV, MAGE, PSA, Leukemia β3A2 CMI, and PAP. Only peptides with binding affinity of at least 1% as compared to the standard peptide in assays described above are presented. Binding as compared to the standard peptide is shown for each peptide.

EXAMPLE 10

Quantitative HLA Class I Binding Assay

To verify that motif-containing peptide sequences are indeed capable of binding to the appropriate class I molecules, specific binding assays were established. HLA-A3.2 molecules were purified from GM3107 EBV cells by affinity chromatography using the GAPA3 mAb (anti-A3) to isolate A3.2. Prior to the step, the lysate was depleted of HLA B and C molecules by repeated passages over a B1.23.2 column (this antibody is B,C specific) generally as described in Example 2, above.

As a radiolabeled probe, the peptide 941.12 (KVFPYALINK (SEQ ID NO:124)), containing an A3.2 motif, was used. This peptide contains the anchor residues $V_2$ and $K_{10}$, associated with A3.2-specific binders, described above. A Y residue was inserted at position 5 to allow for radiolodination. Peptides were labeled by the use of the Chloramine T method Buus et al., Science 235:1352 (1987), which is incorporated herein by reference.

Figure 4:
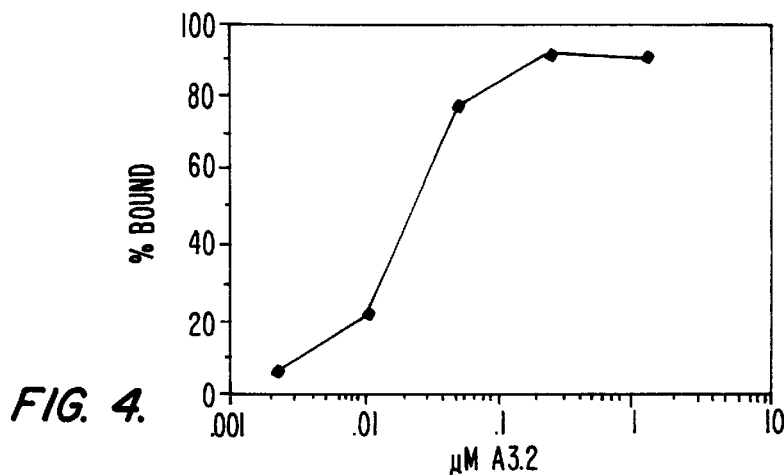
FIG. 4 shows binding of a radioactively labeled peptide of the invention to MHC molecules as measured by the % bound radioactivity.

A dose range of purified A3.2 was incubated with 10 nM of 941.12 at pH 7.0 and 23° C., in presence of a protease inhibitor cocktail (1 mM PMSF, 1.3 mM 1.10 phenanthroline, 73 µM pepstatin A, 8 mM EDTA, and 200 µM N $a_p$-tosyl-L-lysine chloromethyl ketone (TLCK)), in presence of 1 µM purified human β2 microglobulin. After two days, the % bound radioactivity was measured by gel filtration over TSK 2000 columns as previously described for class II peptide binding assays in Sette et al., in Seminars in Immunology, Vol. 3, Gefter, ed. (W. B. Saunders, Philadelphia, 1991), pp 195–202, which is incorporated herein by reference. (see, FIG. 4). Good binding (in the 60 to 100% range) was observed for A3.2 concentrations ranging between 35 and 300 nM. 30% binding was observed at 15 nM A3.2.

Figure 5:
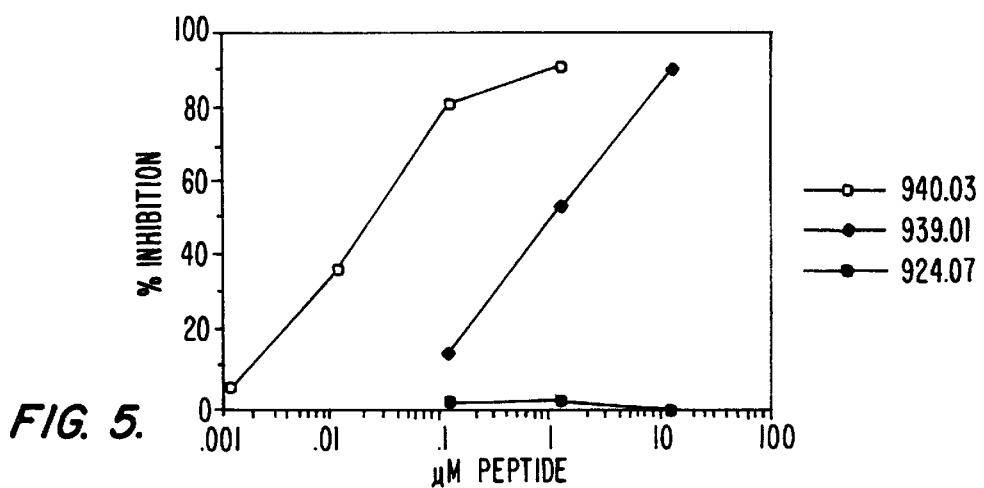
FIG. 5 shows inhibition of binding of a peptide of the invention to MHC molecules in the presence of three peptides [HBc 18–27 (924.07), a Prostate Specific Antigen peptide (939.01), and HIV nef 73–82 (940.03)].

To minimize A3.2 usage and to increase the sensitivity of the assay, a concentration of 5–10 nM A3.2 was selected for further assays. In the experiment shown in FIG. 5, 7nM A3.2 and an equivalent concentration of radiolabeled 941.12 were incubated using the conditions described above and in the presence of a dose range of three peptides (HBc 18–27

(924.07), a Prostate Specific Antigen peptide (939.01), and HIV nef 73–82 (940.03)). It was found that peptide 940.03 inhibited strongly, with a 50% inhibitory concentration (IC50%) of 22 nM, while a weaker inhibition was observed with peptide 939.01 (IC50% 940 nM). Finally, peptide 924.07 did not show any inhibition up to the 30 µM level. Thus, it is concluded that peptides 940.03 and 939.01 are high and intermediate affinity binders, respectively, while peptide 924.07 is classified as a low affinity or negative binder.

Throughout this disclosure, results have been expressed in terms of IC50's. Given the conditions in which the assays are run (i.e., limiting MHC and labeled peptide concentrations), these values approximate $K_D$ values. It should be noted that IC50 values can change, often dramatically, if the assay conditions are varied, and depending on the particular reagents used (e.g., Class I preparation, etc.). For example, excessive concentrations of MHC will increase the apparent measured IC50 of a given ligand.

An alternative way of expressing the binding data, to avoid these uncertainties, is as a relative value to a reference peptide. The reference peptide is included in every assay. As a particular assay becomes more, or less, sensitive, the IC50's of the peptides tested may change somewhat. However, the binding relative to the reference peptide will not change. For example, in an assay run under conditions such that the IC50 of the reference peptide increases 10-fold, all IC50 values will also shift approximately 10-fold. Therefore, to avoid ambiguities, the assessment of whether a peptide is a good, intermediate, weak, or negative binder should be based on it's IC50, relative to the IC50 of the standard peptide.

If the IC50 of the standard peptide measured in a particular assay is different from that reported in the table, then it should be understood that the threshold values used to determine good, intermediate, weak, and negative binders should be modified by a corresponding factor. For example, if in an A2.1 binding assay, the IC50 of the A2.1 standard (941.01) were to be measured as 8 nM instead of 5 nM, then a peptide ligand would be called a good binder only if it had an IC50 of less than 80 nM (i.e., 8nM×0.1), instead of the usual cut-off value of 50 nM.

The experimental system herein described can be used to test binding of large numbers of synthetic peptides to a variety of different class I specificities. Specific binding assays can be performed as follows.

HLA-A11-specific Assay

Figure 6:
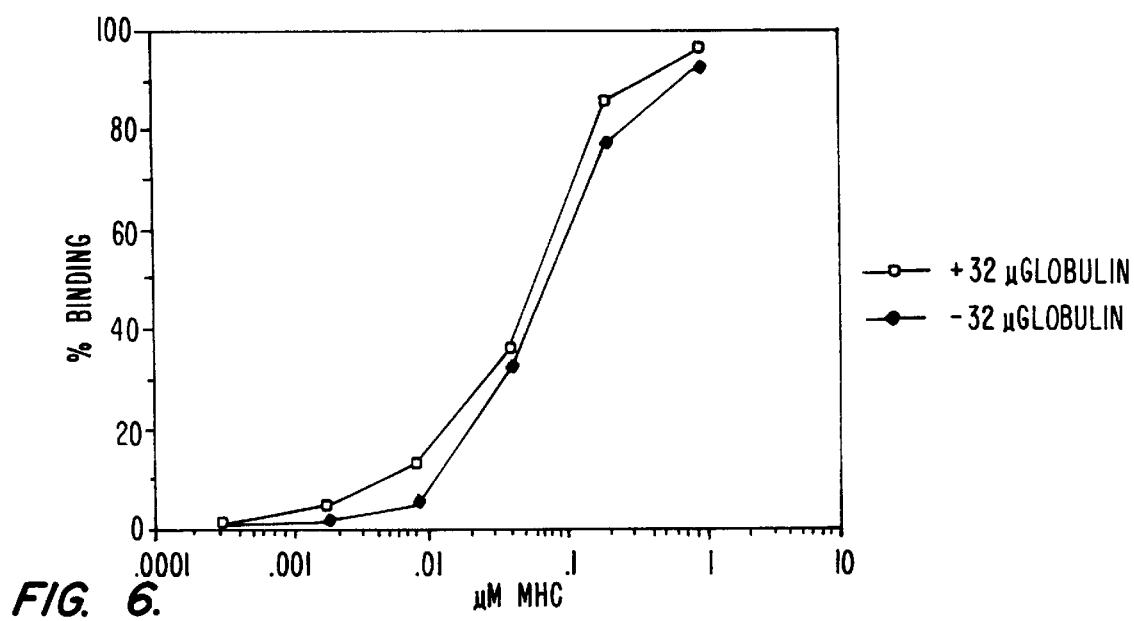
FIG. 6 shows the dependency of the binding on MHC concentration in the presence or absence of $\beta_2$ microglobulin.
Figure 7:
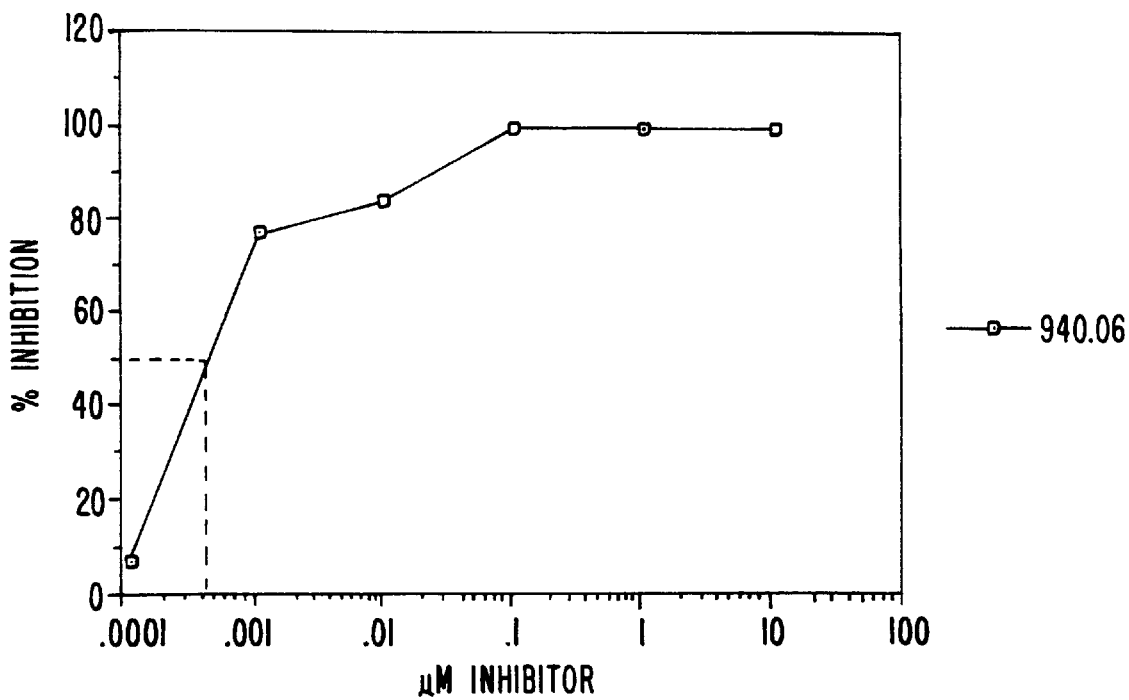
FIG. 7 shows close dependent inhibition of binding with the addition of unlabeled peptide.
Figure 8:
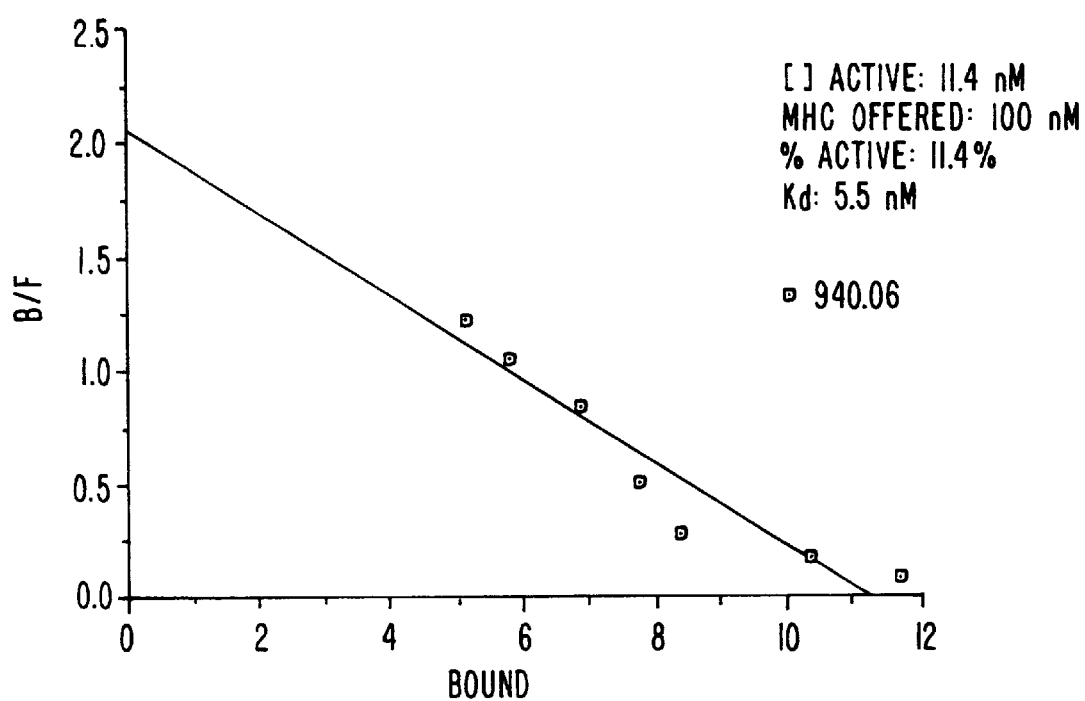
FIG. 8 Scatchard Analysis of binding to MHC All confirming an apparent $K_D$ of 6 nM.

The cell line BVR was used as a source of HLA. The dependency of the binding on MHC concentration in presence or absence of $\beta_2$M are shown in FIG. 6, while FIG. 7 depicts the dose dependency of the inhibition by excess unlabeled ligand. Finally, FIG. 8 shows a Scatchard analysis experiment. Values of apparent kD of ~6 nM and of 10% active receptor were obtained, and were remarkable for their similarity to the values obtained for A2.1 and A3.2. The sequence of the peptide used as a radiolabeled probe (940-06) is AVDLYHFLK (SEQ ID NO:125).

HLA-A1-specific Assay

Figure 9:
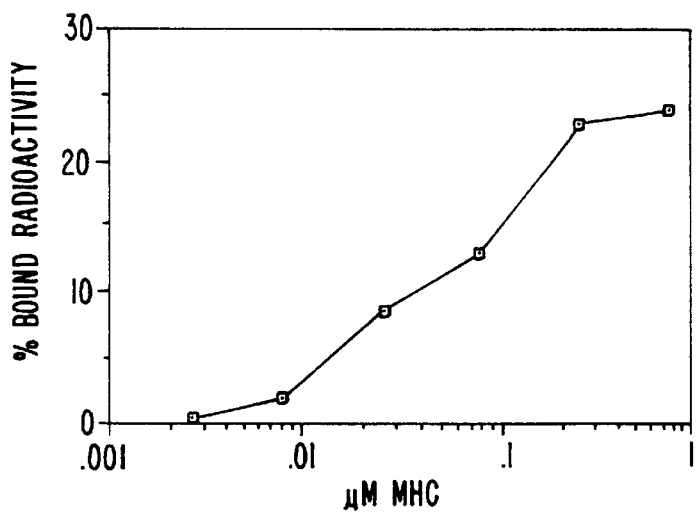
FIG. 9 shows the binding of a radioactively labeled peptide of the invention to MHC A1 as measured by % bound reactivity.
Figure 10:
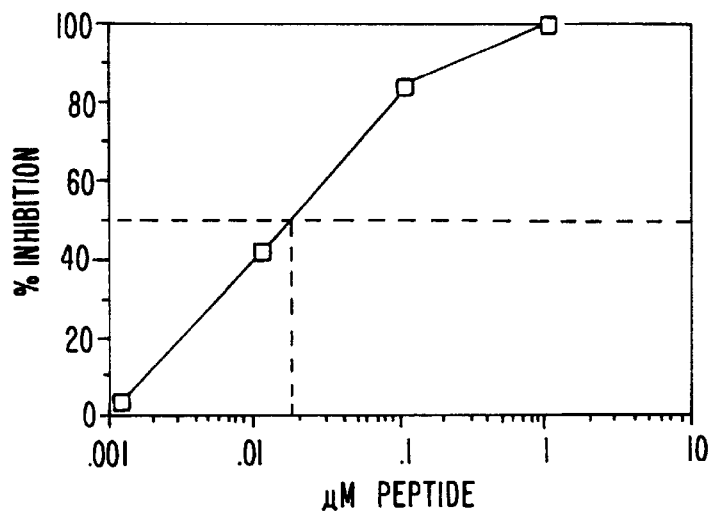
FIG. 10 shows dose dependent inhibition of binding with the addition of unlabeled peptide.
Figure 11:
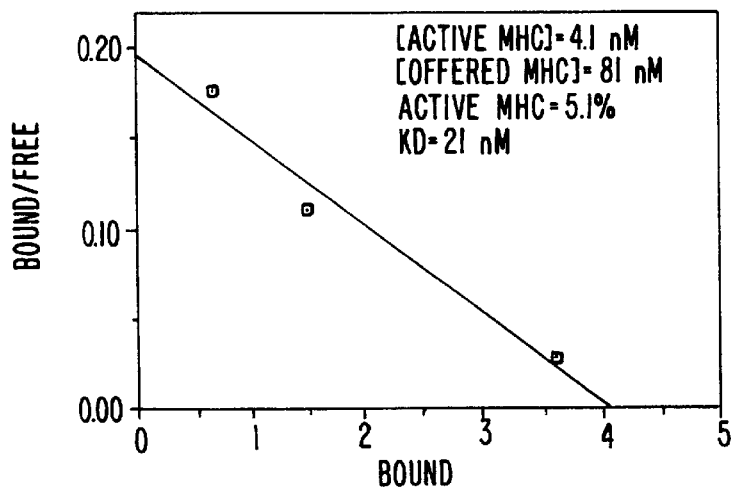
FIG. 11 Scatchard Analysis of binding to MHC A1 confirming an apparent $K_D$ of 21 nM.

In this case, the EBV cell line Steinlin was used as a source of purified HLA. The same protocol previously applied to purification of other HLA alleles (i.e., depletion of B, C molecules by a B1.23.2 mAb column, followed by purification of A molecules by means of a W632 mAb column) was utilized. On the basis of the pool sequencing data, consensus peptides were synthesized, directly radiolabeled, and tested for HLA binding using the standard protocol (1 mM $\beta_2$M, 2 days RT incubation in presence of protease inhibitors). A graph illustrating the relationship between % binding and µM input HLA A1 is shown in FIG. 9. From the data, it was concluded that in analogy with what was observed for HLA A2, 3, and 11, as little as 30 nM are sufficient to obtain ~10% binding. The sequence of the peptide used as a radiolabeled probe (944.02) is YLEPAIAKY (SEQ ID NO:126). In the next set of experiments, the specificity of the assay established was verified by its inhabitability by excess unlabeled peptide. The IC50% was measured (FIG. 10) as ≅20 nM. Further Scatchard analysis (FIG. 11) verified that the apparent $K_D$ of the interaction corresponded to 21 nM, with a % of active receptor corresponding to 5.1%.

HLA-A24 Specific Assay

Figure 12:
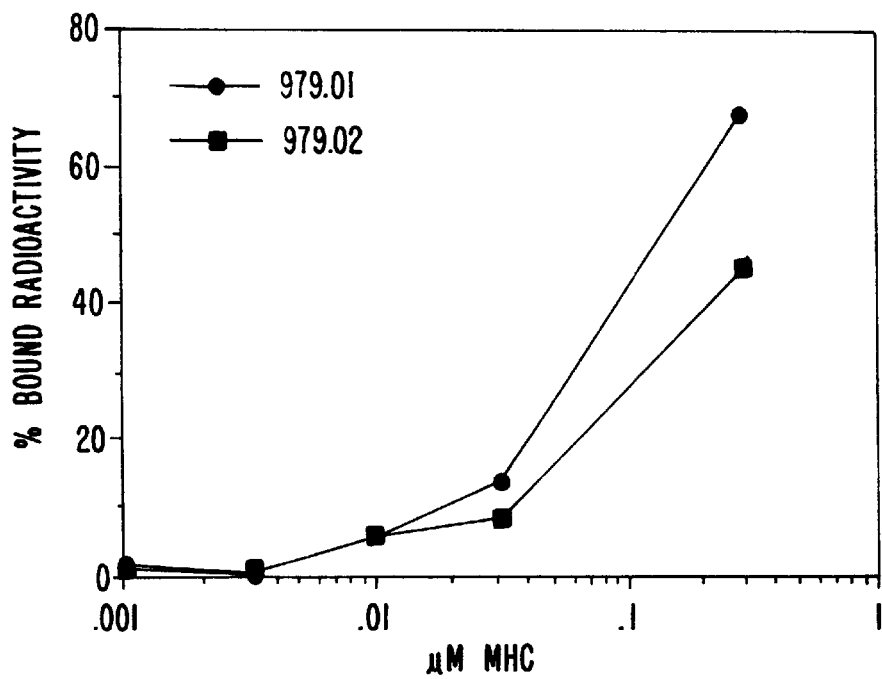
FIG. 12. shows the binding of two peptides of this invention as a function of MHC A24 concentration as measured by % bound reactivity.
Figure 13:
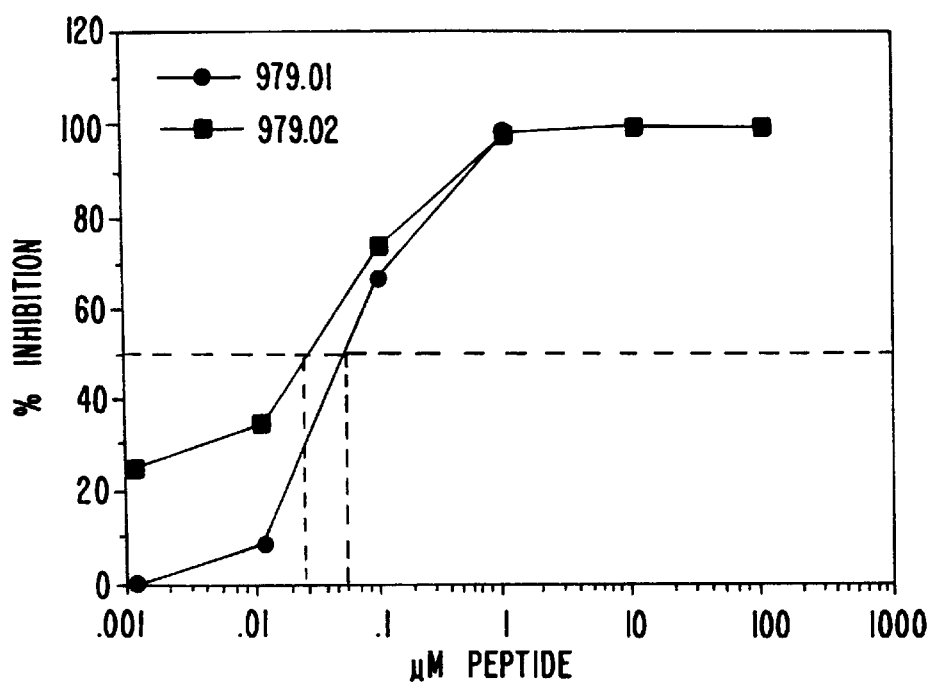
FIG. 13 shows the dose dependent inhibition of binding to MHC A24 with the addition of unlabeled peptides.
Figure 14A:
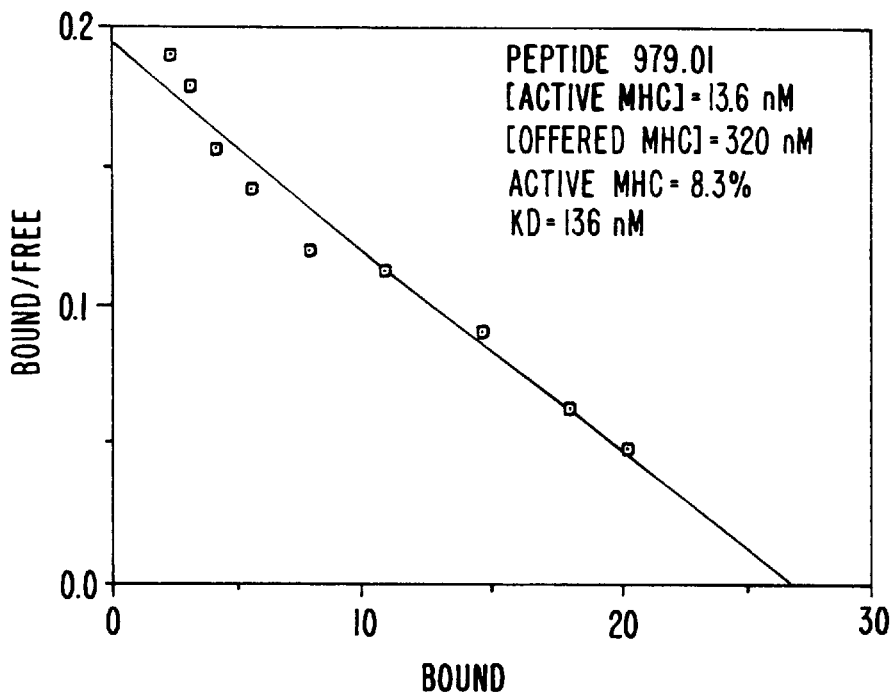
FIGS. 14(a) and 14(b) show the Scatchard Analysis of binding to MHC A24 of the two peptides confirming a $K_D$ of 30 and 60 nM, respectively.
Figure 14B:
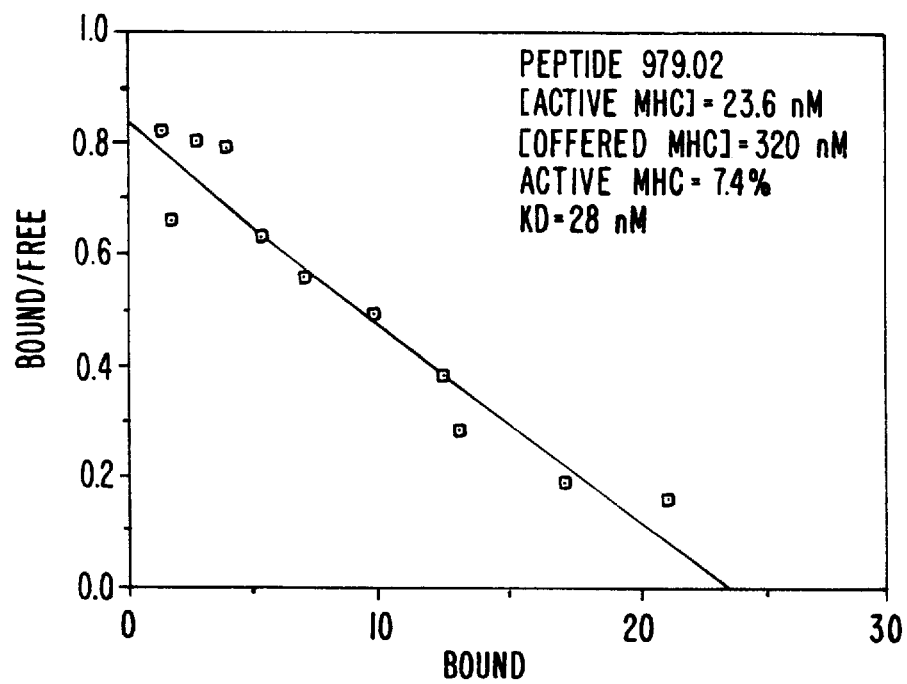
Figure 15A:
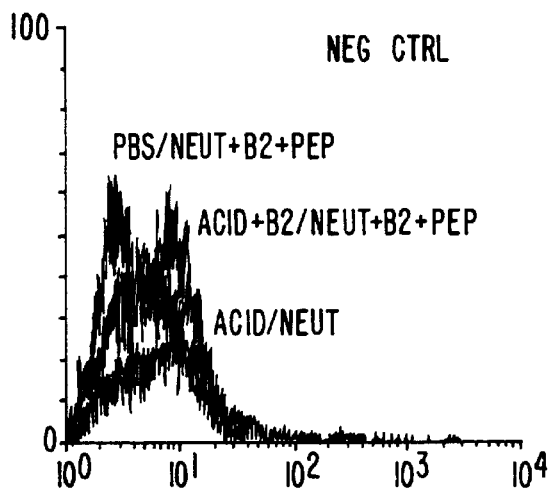
FIGS. 15A–15D show the effect on MHC class 1 molecules of $\beta_2$microglobulin and a peptide of choice on acid-stripped PHA blasts.
Figure 15B:
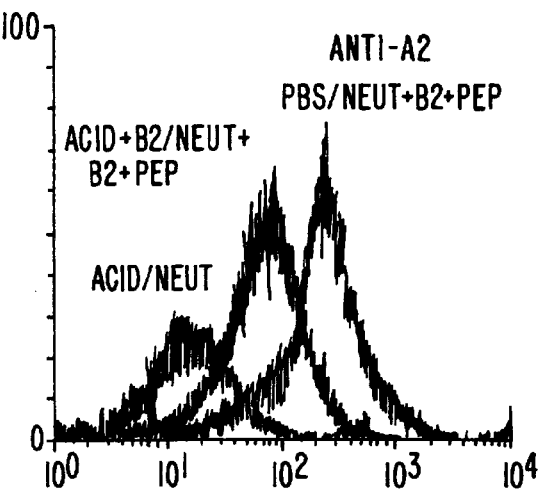
Figure 15C:
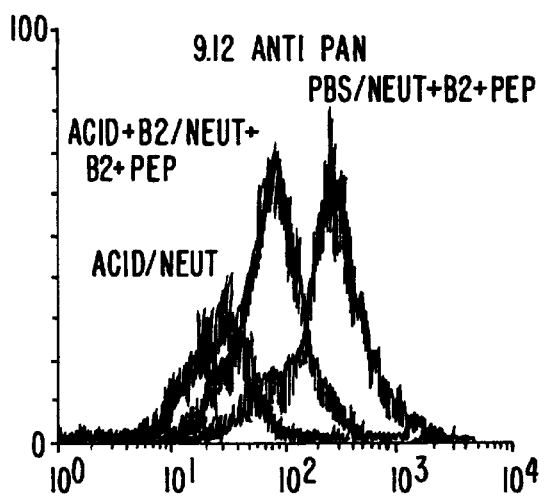
Figure 15D:
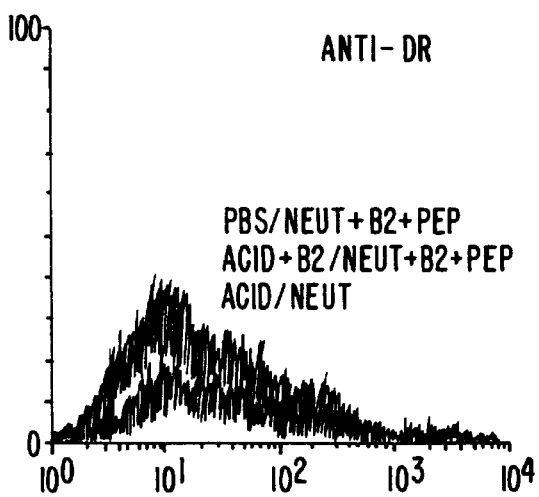

HLA A24 molecules were purified from the KT3 EBV cell line. In this case, two consensus peptides whose sequences were based on the pool sequencing data have been synthesized. Their sequences are: 979-01, AYIDNVYKF (SEQ ID NO:127) and 979.02, AYIDNYNKF (SEQ ID NO:128). The results of experiments in which the % bound of these two peptides as a function of input MHC was measured are shown in FIG. 12. In both cases, 10–15% binding was obtained with as little as 20–50 nM MHC. Cold inhibition experiments (FIG. 13), limiting MHC concentrations, revealed that the binding was readily inhibitable by excess unlabeled peptide, with an apparent $K_D$ of 30 and 60 nM, respectively. Further Scatchard experiments verified values of 136 nM and 28 nM, respectively. The apparent % of available receptor (active MHC) were 8.3% and 7.4%, respectively (FIG. 9a and b). On the basis of these data, peptide 979.02 was arbitrarily selected as standard label indicator for A24 assays. Furthermore, on the basis of the data herein described, we also conclude that the goal of establishing an A24-specific binding assay has been accomplished. In conclusion, specific assays for the five major HLA alleles have been described.

EXAMPLE 11

Expansion of HLA A Motifs

Establishing in vitro binding assays allows one to readily quantitate in vitro the binding capacity of various synthetic peptides to the various alleles of interest (HLA A1, A2, A3, A11, and A24). This allows verification of the correctness of the motifs by means of peptides carrying the various HLA A motifs for their capacity to bind purified HLA molecules. Typically, peptides were synthesized with specific HLA motifs embedded in a neutral backbone composed of only alanine residues. In some cases, a K residue was also introduced within the sequence, with the purpose of increasing solubility. The use of such "neutral" poly A backbones, as applied to the case of class II molecules, has been described in detail, for example, by Jardetzky et al. (Jardetzky et al., EMBO J. 9(6):1797,1990).

For example, in the case of A3.2, a motif has been defined with a hydrophobic residue in position 2 and a positive charge (K) in position 9. Thus, to verify that the presence of these two anchor residues would allow, in the context of a poly A backbone, for A3.2 binding, the poly A analog with the sequence AMAAAAAAK (SEQ ID NO:129) was synthesized (Table 13).

Similarly, other peptides carrying other HLA motifs were also synthesized and tested for HLA binding. It was found that in all cases, the presence of the specific HLA motifs was conducive to binding to the relevant HLA allele, with estimated $K_D$ comprised of between 125 and 2.8 nM. In most cases, the binding was also absolutely specific, in that no binding was detected to irrelevant alleles. Only two exceptions to this general rule were observed. Firstly, A3 and A11 peptides crossreacted extensively with each other, perhaps as could have been expected by the fact that the motifs for these two alleles are remarkably similar. Second, some A1 peptides crossreacted, albeit with much lower affinities, on A11 and A3.2.

To further define the structural requirements for the interaction between peptide epitopes and various class I alleles of interest, analogs of 10 residues in length of some of the 9 residue peptides shown in Table 13 were synthesized (Table 14). These analogs were generated by inserting an additional Ala residue within the poly A backbone, so that the anchor residues are not located in positions 2 and 10 (as opposed to 2 and 9 in the previous table). The results obtained illustrate that motifs of 10 residues are also capable of specifically binding to the relevant class I alleles, albeit with a slightly lower efficiency.

In summary, these data confirm that both 9-mer and 10-mer peptides which contain the appropriate motifs can bind HLA. On the basis of these data, 8-mer or 11-mer peptides should also be capable of binding, even if perhaps with lower affinities.

The data described above show that the presence of certain residues in the anchor positions does allow (at least in a "neutral" poly A backbone) for HLA binding. To investigate to what degree other amino acids (for example, chemically related amino acids) might be tolerated in these crucial anchor positions, analogs of some of the poly A peptides from Table 13 were synthesized, in which the residue present in position 2 (or 3) or 9 was varied. The results of this analysis are shown in Tables 15–19.

In the case of A3.2 (Table 15), in position 2, L, M, I, V, S, A, T, and F were found to be preferred (binding ≧0.1 relative to previously defined anchor residues), while C, G, and D were permitted (binding ≧0.01 to 0.1 relative to previously defined anchor residues). The substiution of E, because of its similarity to D, in this position should also be tolerated. In position 9, K, R, and Y were preferred. Because of a similarity in nature, that H and F should also be preferred (SEQ ID NO:1). No other residue was tolerated in position 9 for A3 binding.

In the case of A11 (Table 16), the preferred residues in position 2 were L, M, I, V, A, S, T, G, N (L and Q by similarity). Tolerated were C, F, D (and E by similarity). In position 9, K was preferred and R was tolerated. H should also be tolerated by similarity (SEQ ID NO:130).

In the case of A24 (Table 17), Y and F were preferred in position 2 (and W by similarity); no other residue was tolerated. In position 9, F, I, and L were preferred (and W and M by extension) (SEQ ID NO:131). No other residue was tolerated.

In the case of A1, three different anchor residues had previously been defined. The results shown in the preceding section show that they act independently of each other (i.e., that two out of three anchors would be sufficient for binding). This is indeed the case. For this reason, analogs containing two anchors were synthesized to define what residues might be preferred or tolerated in each position. The data shown in Table 18 show that in position 2, T, S, and M are preferred, and no other residue is tolerated. In position 3 (Table 19), D and E are preferred, and A,S (and T by similarity) are tolerated. Finally, in position 9, only Y is preferred, and no other residue appears to be tolerated (Table 19) (SEQ ID NO:132).

Thus, on the basis of the data, it is concluded that peptides carrying any combination of two preferred residues can bind. Peptides containing "imperfect" motifs, i.e., carrying a preferred residue at one position and a tolerated one at the other anchor position, should also be capable of binding, even if with somewhat lower affinity. Using the motifs of this invention for various MHC class I alleles amino acid sequences from various viral and tumor-related proteins were analyzed for the presence of motifs. The results of this motif analysis are shown in Table 23 a–k.

EXAMPLE 12

Validation of HLA Peptide Binding Motifs with an Unbiased Set of HPV 16 Peptides Human Papillomaviruses (HPVs) are implicated in the etiology of cervical cancer (Pfister, H. (1974) Biology and biochemistry of papillomaviruses, Rev. Physiol. Biochem. 99:111; zur Hausen, H. (1991). Human papillomaviruses in the pathogenesis of anogenital cancer. Virology. 184:9) and in up to 10% of total mortality due to cancer worldwide (zur Hausen, H. (1991). Viruses in Human Cancers. Science, 254:1167).

The HPV 16 E6 and E7 gene products are the most desirable target antigens for vaccination against HPV 16 induced tumors. Both are retained and highly expressed in HPV 16-transformed cancer cells in vivo (Baker, C. J., Phelps, W. C., Lindgren, V., Braun, M. J., Gonda, M. A., and Howley, P. M. [1987]. To determine the CTL epitopes and potential vaccine candidates of HPV 16 for humans, we screened peptides spanning the HPV 16 E6 and E7 protein sequences for their ability to bind to the most frequent human MHC molecules, namely HLA-A1, A3.2, A11.2 and A24. Combined these five alleles will cover about 90% of the world population (Dupont, B., ed. [1987]. Immunology of HLA Vol. I—Histocompatibility Testing. Springer-Verlag, New York).

A complete set of 240 overlapping synthetic peptides of 9 aa length and 8 aa overlap covering the entire HPV 16 E6 and E7 oncogene sequences were synthesized. The peptides were tested for their ability to bind the aforementioned HLA molecules in the binding assay described above. The results of this analysis show the relative affinity of all peptides for the respective HLA alleles and reveal the possible candidate CTL epitopes for use in peptide based vaccines for humans in tables 20(a)–(d).

The results confirm that peptide binding motifs described in this invention for the aforementioned HLA alleles predict which peptide of a protein is likely to bind into the groove of a specified HLA molecule. Since we used a large and unbiased set of peptides, the results of the peptide binding analyses were used to evaluate the value of these motifs both for their predictive capacities and the necessity to have particular anchor aa residues on positions 2, (3) and 9 in a peptide.

Peptides. Peptides were generated by solid phase strategies on a multiple peptide synthesizer (Abimed AMS 422) by repeated cycles in which addition of Fmoc protected amino acids to a resin of polystyrene was alternated with a Fmoc-deprotection procedure (Gausepohl, H., Kraft, M., Boulin, Ch., and Frank, R. W. [1990]. Automated multiple peptide synthesis with BOP activation in Proc. of the 11th American peptide symposium. J. E. Rivier and G. R.

Marshall, Ed. ESCOM, Leiden. 1003–1004). The peptides all carrying a COOH group at the C-terminal end, were cleaved from the resin and side chain protective groups were removed by treatment with aqueous TFA. Peptides were analyzed by reversed phase HPLC lyophilized and dissolved at a concentration of 1 mg/ml in phosphate-buffered saline with 3% DMSO (Sigma, St. Louis, Mo. 63175) before use. Once dissolved, the peptides were stored at −70° C. Since cysteine containing peptides are susceptible to (air) oxidation during synthesis and handling, these peptides were synthesized with an alanine instead of a cysteine.

Identification of peptides from HPV 16 E6 and E7 proteins that bind to different HLA-A alleles. A complete set of 240 peptides of 9 aa in length and overlapping by 8 aa, covering the sequences of the entire HPV 16 E6 and E7 proteins, was tested for binding to 5 different HLA-A molecules.

The results of this analysis are depicted in tables 20(a)–(d). Table 20(a) describes the peptides of HPV 16 that bound to HLA-A1 molecules. A11 peptides were tested. Listed are only peptides yielding ratio values of $\geq 0.001$. It can be seen that 2 peptides bound with high affinity to this molecule (>0.1), 6 with intermediate affinity (0.1–0.01) and 1 with low affinity (0.01–0.001). Peptides were ranked by ratio value to allow comparison of data obtained in different experiments. To calculate the concentration of a peptide necessary to yield a 50% inhibition dose ($IC_{50}$) one has to divide the value of the standard $IC_{50}$ by the ratio. For example, peptide E6-80 has an $IC_{50}$ of 23 nM (81/3.5).

Table 20(b) describes the peptides that bound to HLA-A3.2 molecules. Seven peptides were identified as high affinity binders, 6 as intermediate affinity binders and 13 as low affinity binders. Table 20(c) describes the peptides that bound to HLA-A11.2 molecules. Six high affinity peptides were identified, 4 intermediate affinity binders and 10 low affinity binders. Two high affinity binding peptides (E6-59 IVYRDGNPY (SEQ ID NO:133) and E6-80 ISEYRHYAY (SEQ ID NO:134)) and two weak affinity binding peptides with a Y at the 9th position (E6-42 QQLLRREVY (SEQ ID NO:135), E6-69 VADKALKFY (SEQ ID NO:136)) were identified for HLA-A11.2 Considering the high binding strength of the first two peptides and the similarity between the HLA-A11.2 motif and the HLA-A3.2 motif in which Y's are preferred at the 9th aa position, tyrosines should be included at the 9th position in the HLA-A11.2 motif. Comparing Tables 21(b) and (c) it is clear that there is a large overlap of peptides that bound to both A3.2 and A11.2 molecules. Eighteen out of 28 E6 and E7 peptides binding to these two HLA molecules overlapped and only 8 peptides were unique for HLA-A3.2 and 2 peptides unique for HLA-A11.2.

Finally, table 20(d) describes the peptides that bound to HLA-A24 molecules. Here 2 peptides were identified as high affinity binding peptides, 5 as intermediate affinity binding peptides and 5 as low binding peptides. One high affinity peptide (E6-72 KALKFYSKI (SEQ ID NO:137)) and one intermediate affinity peptide (E7-49 RAHYNIVTF (SEQ ID NO:138)) were identified, indicating that an A at the second position should be allowed in the HLA-A24 motif. All these inclusions are indicated in Table 20-e. In analyzing tables 1–5 it can be concluded that between 2 and 7 high affinity binding peptides were identified for all of the tested HLA-A molecules. Occasionally some peptides were binding to more alleles. Three peptides (E6-7, E6-37 and E6-79), bound to HLA-A2.1, A3.2 and A11.2. One peptide (E6-38) bound to HLA-A3.2, A11.2 and A24 and two peptides (E6-69 and E6-80) bound to HLA-A1, A3.2 and A11.2. But these crossreactive peptides bound only weakly to one or more of the different HLA molecules. In general, however, it can be concluded that, except for HLA-A3.2 and HLA-A11.2 molecules, almost all HLA molecules bind unique peptides.

Validation of HLA-A peptide binding motifs with an unbiased set of HPV 16 E6 and E7 peptides.

We analyzed how well the motifs for anchor positions described in this invention predicted the binding of a peptide, and also the reverse: how well binding peptides followed the identified motifs. For this, peptides were ranked as high binders, intermediate binders, weak binders, and negative binders and for each peptide the motif prediction based on the anchor motif rules of Tables 5–8 were analyzed. The overall efficiency of the 2; (3), and 9 anchor motifs was then calculated and this is summarized in Table 20(e). It can be concluded that the motifs described above for the different HLA-A molecules are quite accurate. One hundred percent of the HLA-A1, A3.2, and A24 high binders would be predicted as well as 67% of the HLA-11.2. Even for the intermediate binders between 40 and 100% would be predicted depending on the HLA-A molecule analyzed. Furthermore, the percent of weak binding peptides that would be predicted is low and the percent of those peptides that were predicted to bind but actually did not bind is very low for all these alleles.

Analyzed differently, of the 12 peptides predicted to bind to HLA-A1 actually 5 bound with high or intermediate affinity. This indicates that only a few peptides would have to be made to find these potential CTL epitopes. The figures for HLA-A3.2, A11.2, and A24 were 10/32, 7/26, and 4/7, respectively. This implies that the predictive value for all of these alleles is good.

EXAMPLE 13

Presence of a Motif is Necessary But Not Sufficient for High Affinity Class I Binding These data indicate that having the correct 2, (3) and 9 anchor residues is not always sufficient for binding and suggest that non-anchor residues can make negative contributions to the binding of a peptide.

To investigate further how the presence of different motifs might influence the capacity of different peptides to bind to the relevant HLA alleles, the sequences of various potential target molecules were scanned for the presence of motif-containing peptides. The peptides thus identified were synthesized and tested for binding. It was found (Table 20) that in the case of A3.2, only 39 (19%) of the 205 peptides bound with high affinity in the 1 to 50 nM range. 22.4% of them bound with intermediate affinities (in the 50 to 500 nM range), while 34.6% bound weakly (in the 500 nM to 50 $\mu$M range). Finally, 23.95 of them did not bind at all, at least up to the 50 $\mu$M level. In the case of A11, 33 (33%) of the 100 peptides bound with high affinity in the 1 to 50 nM range. 35% of them bound with intermediate affinities (in the 50 nM range), while 24% bound weakly (in the 500 nM to 50 $\mu$M range). Finally, 8% of them did not bind at all, at least up to the 50 $\mu$M level.

Similar results were also obtained (data not shown) in the case of A1 and A24.

The same type of analyses were also performed in the case of 10-mer peptides carrying either the A3.2, and A11 motifs (Tables 22(a) and (b)). It was found that in these cases, the frequency of good binders was even lower (17.5%, and 29.8%, respectively). These data confirm the fact that motif-containing 10-mer peptides can indeed bind, albeit with, in general, reduced affinity.

In summary, the data shown in this section clearly show that the presence of the correct anchor residues is not sufficient per se to allow for good HLA binding and that the nature of the residues contained in positions other than 2(3) and 9 (or 10) can influence binding. The most likely explanation of this observation is that the presence of certain residues (in positions other than 2 and 9) can negate or increase the binding potential of a peptide determinant.

The data shown in the preceding sections describe how specific binding assays can be used to identify, within motif-containing peptides, peptides that are immunogenic. We also wanted to devise an alternative strategy, namely to derive procedures that would be able to predict, within motif-containing peptides, which peptides might be good or intermediate binders and thereby might be immunogenic. In other experiments not shown intermediate or good binders have been shown to be immunogenic. In particular, to identify residues that have a negative impact on binding an analysis of all positions for A3.2, A11, and all motif-containing peptides, both 9-mers and 10-mers is carried out. In the case of A11, because of the small occurrence of nonbinding peptides, a different cutoff was used such that the analysis compares good and intermediate binders on the one hand to weak and nonbinders on the other.

EXAMPLE 14

Algorithms to Identify Immunogenic Peptides

In light of results presented in Example 13 above, algorithms were developed to provide a more exact predictor of binding based upon the effects of different residues at each position of a peptide sequence, in addition to the anchor or conserved residues. More specifically, we utilize the data bank obtained during the screening of our collection of A1, 3,11 or 24 motif-containing peptides to develop an algorithm for each particular allele which assigns a score for each amino acid at each position along a peptide. The score for each residue is taken as the ratio of the frequency of that residue in good and intermediate binders to the frequency of occurrence of that residue in nonbinders.

In the present algorithm residues have been grouped by similarity. This avoids the problem encountered with some rare residues, such as tryptophan, where there are too few occurrences to obtain a statistically significant ratio. A listing is made of scores obtained by grouping for each of the twenty amino acids by position for 9-mer peptides containing conserved residues that define their motif (2/9 motifs). A peptide is scored in the algorithm as a product of the scores of each of its residues.

The power of an algorithm to correlate with binding is further underlined by its ability to predict a population of peptides with the highest occurrence of good binders. If one were to rely, for example, solely on the 2/9 motif for predicting 9-mer peptides which bind to a specific MHC allele the large number of peptides containing the motif would be predicted to be good binders. In fact only a relatively small percentage of these peptides are good binders and a somewhat larger percentage are intermediate binders, while a still larger percentage of the peptides predicted by the motif are either weak or nonbinding peptides. In contrast, using the grouped algorithm of this invention a population of peptides are created with a greater percentage of good binders, a still greater percentage of intermediate binders, and a smaller percentage, relative to that predicted by motif-containing peptides, are weak and nonbinders.

The present example of an algorithm uses the ratio of the frequency of occurrence of an amino acid in binders and nonbinders to measure the impact of a particular residue at each position of a peptide. It is immediately apparent to one of ordinary skill in the art that there are alternative ways of creating a similar algorithm. For example, one could use average binding affinity values, or relative binding of single amino acid substitutions in a motif containing peptide with a poly-alanine backbone to generate an algorithm table.

An algorithm using average binding affinity has the advantage of including all of the peptides in the analysis, and not just good/intermediate binders and nonbinders. Moreover, it gives a more quantitative measure of affinity than the simpler group ratio algorithm. We have created such an algorithm by calculating for each amino acid, by position, the average log of binding when that particular residue occurs in our set of motif containing peptides. The algorithm score for a peptide is then taken as the sum of the scores by position for each of its residues.

The log of binding algorithms were further revised in two ways. First, poly-alanine (poly-A) data were incorporated into the algorithms at the anchor positions for residues included in the expanded motifs (see, Example 11) where data obtained by screening a large library of peptides were not available. Second, an "anchor requirement screening filter" was incorporated into the algorithm. The poly-A approach uses a panel of single amino acid substitutions of a 9- or 10-mer prototype poly-A binder that is tested for binding to the particular using the methods described above to examine the degree of degeneracy of the anchor-positions and the possible influence of non-anchor positions on binding. The "anchor requirement screening filter" refers to the way in which residues are scored at the anchor positions, thereby providing the ability to screen out peptides which do not have preferred or tolerated residues (see, Example 11) in the anchor positions. This is accomplished by assigning a score for unacceptable residues at the anchor positions which are so high as to preclude any peptide which contains them from achieving an overall score which would allow it to be considered as a potential binder.

The results for alleles A1, A3.2, and A11 are presented in Tables 31–36, below. In these tables, values are group values as follows: A; G; P; D,E; R,H,K; L,I,V,M; F,Y,W; S,T,C; and Q,N, except where noted in the tables.

EXAMPLE 15

Preparation of Effective HLA Allele-Specific Antigen Presenting Cells

This example demonstrates the use of cold temperature incubation or acid stripping/peptide loading method to prepare effective HLA-allele-specific antigen presenting cells (APC). The APC were used to sensitize precursor cytotoxic T lymphocytes which led to the development of antigen-specific cytotoxic cells. This was accomplished using either phytohemaglutinin (PHA) T-cell blasts or peripheral blood mononuclear cells (PBMC) or staphylococcus aureus Cowan I (SAC-I) activated PBMC as APC. The results are applicable to other APC and to the other MHC alleles.

The following describes sources for materials used in the following examples:

L-Ascorbic acid, Cat #B582, J. T. Baker, Phillipsburg, N.J.

Anti-HLA A2 (BB7.2), Cat #HB82, ATCC, Rockville, Md.

Anti-HLA DR (LB3.1), from J. Gorga, Children's Hospital, Pittsburgh, Pa.

Anti-HLA Alpha chain pan ABC (9.12.1), from R. DeMars, University of Wisconsin, Madison, Wis.

Anti-mouse IgG FITC conjugate, Cat #F2883, Sigma, St. Louis, Mo.

$\beta_2$microglobulin, Cat #M0114, Scripps Labs, San Diego, Calif.

BSA Fraction V, Cat #A9418, Sigma, St. Louis, Mo.

50 cc conical centrifuge tubes, Cat #2070, Falcon, Lincoln, Park, N.J.

Cryo 1° C. freezing container, Cat #5100-0001, Nalge, Rochester, N.Y.

Cryovial, Cat #5000-0012, Nalge, Rochester, N.Y.

Dimethyl sulfoxide (DMSO), Cat #D2650, Sigma, St. Louis, Mo.

DNAse, Cat #260912, Calbiochem, San Diego, Calif.

Dynabeads M-450 goat anti-mouse IgG, Cat #110.06, Dynal, Great Neck, N.Y.

EDTA tetrasodium salt, Cat #ED4SS, Sigma, St. Louis, Mo.

FACScan, Becton Dickinson, San Jose, Calif.

Fetal calf serum (FCS), Cat #3000, Irvine Scientific, Irvine, Calif.

Ficoll-Paque, Cat #17-0840-03, Pharmacia, Piscataway, N.J.

Gentamicin, Cat #600-5750AD, Gibco, Grand Island, N.Y.

L-Glutamine, Cat #9317, Irvine Scientific, Irvine, Calif.

GS-6KR centrifuge, Beckman Instruments, Palo Alto, Calif.

Human AB serum (HS), Cat #100-112, Gemini Bioproducts, Calabasas, Calif.

Human rIL-2, Sandoz, Basel, Switzerland.

Human rIL-7, Cat #F1-1587-1, Genzyme, Cambridge, Mass.

Isopropanol, Cat #A464-4, Fisher Scientific, Pittsburgh, Pa.

MicroCELLector T-150 culture flask for selection of CD4+ cells, Cat #8030, Applied Immune Sciences, Menlo Park, Calif.

Micromedic automatic gamma counter, ICN Micromedics Systems, Huntsville, Ala.

OKT4 hybridoma supernatant, Cat #CRL 8002, ATCC, Rockville, Md.

Paraformaldehyde, Cat #T-353, Fisher, Pittsburgh, Pa.

PBS calcium and magnesium free (CMF), Cat #17-516B, BioWhittaker, Walkersville, Md.

Peptides used in this study were synthesized at Cytel and described in Table 24 a.

Phytohemagglutinin (PHA), Cat #HA-16, Wellcome, Dartford, England.

RPMI 1640+Hepes+glutamine, Cat #12-115B, BioWhittaker, Walkersville, Md.

RPMI 1640+Hepes+glutamine, Cat #380-2400AJ, Gibco, Grand Island, N.Y.

Sodium chloride (NaCl), Cat #3624-05, J. T. Baker, Phillipsburg, N.J.

Sodium ($^{51}$Cr) chromate, Cat #NEZ 030, NEN, Wilmington, Del.

Sodium phosphate monobasic, Cat #S9638, Sigma, St. Louis, Mo.

Triton X-100, Cat #X-100, Sigma, St. Louis, Mo.

24 well tissue culture plate, Cat #3047, Falcon, Becton Dickinson, San Jose, Calif.

96 well U-bottomed cluster plate, Cat #3799, Costar, Cambridge, Mass.

Culture Medium. PHA blasts and CTL inductions were done in RPMI 1640+Hepes+glutamine (Gibco) supplemented with 2 mM L-glutamine (Irvine Scientific), 50 µg/ml gentamicin (Gibco), and 5% heat inactivated pooled human Type AB serum (Gemini Bioproducts) [RPMI/5% HS]. EBV transformed lymphoblastoid cell lines (LCL) were maintained in RPMI 1640+Hepes+glutamine (BioWhittaker) supplemented with L-glutamine and gentamicin as above and 10% heat inactivated fetal calf serum (Irvine Scientific) [RPMI/10% FCS]. Chromium release assays were performed in RPMI/10% FCS.

Cytokines. Recombinant human interleukin-2 (rIL-2) (Sandoz) was used at a final concentration of 10 U/ml. Recombinant human interleukin-7 (rIL-7) (Genzyme) was used at a final concentration of 10 ng/ml.

Isolation of Peripheral Blood Mononuclear Cells (PBMC). Whole blood was collected in heparin (10 U/ml) containing syringes and spun in 50 cc conical centrifuge tubes (Falcon) at 1600 rpm (Beckman GS-6KR) 15 min. The plasma layer was then removed and 10 ml of the buffy coat collected with a 10 ml pipette using a circular motion. The buffy coat was mixed thoroughly and diluted with an equal volume of serum free RPMI 1640. The diluted buffy coat was then layered over 20 ml Ficoll-Paque (Pharmacia) in a 50 cc conical tube and centrifuged 400×g for 20 min at room temperature with the brake off. The Ficoll-plasma interface containing the PBMCs was collected using a transfer pipet (two interfaces per 50 cc tube) and washed three times with 50 ml RPMI (1700, 1500, and 1300 rpm for 10 min.

Freezing and Thawing PBMC. PBMC were frozen at $30\times10^6$ cells/ml of 90% FCS +10% DMSO (Sigma), in 1 ml aliquots using cyrovials (Nalge). Cryovials were placed in Cryo 1° C. freezing containers (Nalge) containing isopropanol (Fisher) and placed at −70° C. from 4 hr (minimum) to overnight (maximum). Isopropanol was changed after every 5 uses. Cryovials were transferred to liquid nitrogen for long term storage. PBMC were thawed by continuous shaking in a 37° C. water bath until the last crystal was nearly thawed. Cells were immediately diluted into serum free RPMI medium containing DNAse 30 µg/ml (to avoid clumping) (Calbiochem), and washed twice.

Depletion of Lymphocyte Subpopulations. CD4 lymphocyte depletion was performed using antibody-coated flasks: MicroCELLector T-150 flasks for the selection of CD4+ cells (Applied Immune Sciences) were washed according to the manufacturer's instructions with 25 ml PBS CMF+1 mM EDTA (Sigma) by swirling flasks for 30 sec followed by incubation for 1 hr at room temperature on a flat surface. Buffer was aspirated and flasks were washed 2 additional times by shaking the flasks for 30 sec and maintaining coverage of the binding surface. To each washed flask, 25 ml culture medium+5% HS were added and incubated for 20 min at room temperature on a flat surface. Media was left in the flask until it was ready to receive the cells. PBMC were thawed in RPMI/5% HS containing 30 µg/ml DNAse, and washed twice. HS in the wash blocks Fc receptors on PBMCS. For one flask a maximum of $12\times10^7$ cells were resuspended in 25 ml culture medium. Culture medium was aspirated from the flask and then the cell suspension was gently added to the MicroCELLector. Flasks containing the cells were incubated for 1 hr at room temperature on a flat surface. At the end of the incubation, the flask was gently rocked from side to side for 10 sec to resuspend the nonadherent cells. Nonadherent CD4 depleted cells were harvested, and then flasks were washed twice with PBS CMF to collect the nonadherent cells. Harvested CD4-depleted cells were pelleted by centrifugation and resuspended in complete culture medium (RPMI/5%/HS).

Generation of PHA Blasts. PBMC were isolated using the standard Ficoll-Paque protocol. Frozen cells were washed twice before use. Cells were cultured at $2\times10^6$/ml in RPMI/5% HS containing 1 µg/ml PHA (Wellcome) and 10 U/ml rIL-2. PHA blasts were maintained in culture medium containing 10 U/ml rIL-2 with feeding and splitting as needed. PHA blasts were used as APC on day 6 of culture. Generation of empty class I molecules and peptide loading were only performed by the acid strip method when using these APC.

Acid Stripping/Peptide Loading of PBMC and PHA Blasts. PBMC were isolated using the Ficoll-Paque protocol. When using frozen cells, PBMC were washed twice before using. PHA blasts were prepared as previously described and washed twice before using. Once cells were prepared, they were washed once in cold sterile 0.9% NaCl (J. T. Baker) +1% BSA. In a 50 cc conical centrifuge tube, the cells were resuspended at $10^7$/ml in cold sterile citrate-phosphate buffer [0–13 M L-ascorbic acid (J. T. Baker), 0.06 M sodium phosphate monobasic (Sigma) pH 3, 1% BSA, 3 µg/ml $\beta_2$microglobulin (Scripps Labs)] and incubated for 2 min on ice. Immediately, 5 volumes of cold sterile neutralizing buffer #1 [0.15 M sodium phosphate monobasic pH 7.5, 1% BSA, 3 µg/ml $\beta_2$microglobulin, 10 µg/ml peptide] were added, and the cells were pelleted at 1500 rpm, 5 min at 4° C. Cells were resuspended in 1 volume cold sterile neutralizing buffer #2 [PBS CMF, 1% BSA, 30 lig/ml DNAse, 3 µg/ml $\beta_2$microglobulin, 40 µg/ml peptide] and incubated for 4 hrs at 20° C. Cells were diluted with culture medium to approximately $5\times10^6$/ml and irradiated with 6000 rads. Cells were then centrifuged at 1500 rpm for 5 min at room temperature and resuspended in culture medium. The acid stripped/peptide loaded cells were used immediately in the CTL induction cultures (below).

Induction of Primary CTL using Acid Stripped/Peptide Loaded Autologous PBMCs or PHA Blasts as Stimulators. Acid stripping/peptide loading of PBMC and PHA blasts are described above. During the last 4 hr incubation of stimulator cells with peptide, the responder cell population was prepared: Responders were PBMC that were depleted of CD4+ cells (described above). Responder cells were resuspended in culture medium at $3\times10^6$/ml. 1 ml of the responder cell suspension was dispensed into each well of a 24-well tissue culture plate (Falcon, Becton Dickinson). The plates were placed in the incubator at 37° C., 5% $CO_2$ until the stimulator population was ready. Once irradiated, stimulator APC were resuspended in culture medium containing 20 ng/ml rIL-7 at $10^6$/ml for the PBMC, or at $3\times10^5$/ml for the PHA blasts. 1 ml of stimulator cell suspension was added per well to the plates containing the responders. On day 7 after induction, a 100 µl culture medium containing 200 ng/ml rIL-7 was added to each well (20 ng/well rIL-7 final). On day 10 after induction, 100 µl of culture medium containing 200 U/ml rIL-2 was added to each well (20 U/well rIL-2 final).

Antigen Restimulation of CTL. On day 12–14 after the induction, the primary CTL were restimulated with peptide using adherent APC. Autologous PBMC were thawed and washed as described above. Cells were irradiated at 6000 rads. Cells were pelleted and resuspended in culture medium at $4\times10^6$/ml. 1 ml of cell suspension was added to each well of a 24-well tissue culture plate, and incubated for 2 hrs at 37° C., 5% $CO_2$. Non-adherent cells were removed by washing each well three times with serum free RPMI. After this step, a 0.5 ml culture medium containing 3 µg/ml $\beta_2$microglobulin and 20 µg/ml total peptide was added to each well. APC were incubated for 2 hrs at 37° C., under 5% $CO_2$ with the peptide and $\beta_2$microglobulin. Wells were aspirated and 1 ml of responder cells at $1.5\times10^6$/ml in culture medium was added to each well. After 2 days, 1 ml of culture medium containing 20 U/ml rIL-2 was added to each well.

Cytotoxicity Chromium Release Assay. Seven days following restimulation of primary induction, the cytotoxic activity of the cultures was assessed.

a. Effector Cell Preparation: the responders, which at this stage are renamed "effectors", were centrifuged and resuspended at $10^7$/ml in RPMI/10% FCS. Three-fold serial dilutions of effectors were performed to yield effector to target ratios of 100:1, 33:1, 11:1, and 3:1. Effector cells were aliquoted at 100 µl/well on 96 well U-bottomed cluster plates (Costar), in duplicate.

b. Target Cell Preparation: Approximately 16–20 hrs prior to the assay, target cells were resuspended at $3\times 10^5$/ml in RPMI/10% FCS in the presence or absence of 3 µg/ml $\beta_2$microglobulin and 10 µg/ml total peptide. After preincubation, target cells were centrifuged and pellets were resuspended in 200 µl (300 µCi) sodium ($^{51}$Cr) chromate (NEN). Cells were incubated at 37° C. for 1 hr with agitation. Labelled target cells were washed 3 times with RPMI/10% FCS.

c. Setting-Up the Assays: Target cell concentration was adjusted to $10^5$/ml in RPMI/10% FCS and 100 µl aliquots were added to each well containing responders. K562 cells (cold targets, to block NK, and LAK activity) were washed and resuspended in RPMI/10% FCS at $10^7$/ml. Aliquots of 20 µl were added per well, yielding a 20:1 of cold K562 target:labelled target. For the determination of the spontaneous $^{51}$Cr release, 100 µl/well of RPMI/10% FCS were added to 100 µl/well of labelled target cells, and 20 µl/well of K562. For maximum $^{51}$Cr release, 100 µl 1% Triton X-100 (Sigma) in PBS CMF, was added to the 100 µl/well labelled target cells, and 20 µl/well K562. Plates were centrifuged for 2 min at 1200 rpm to accelerate cell conjugate formation. Assays were incubated for 5 hr at 37° C., 5% $CO_2$. Assays were harvested by centrifuging plates for 5 min at 1200 rpm and collecting 100 µl/well of supernatant. Standard gamma counting techniques were used to determine percent specific lysis (Micromedic automatic gamma counter, 0.5 min per tube).

Cultured Cell Lines. JY, a HLA A2.1 expressing human EBV-transformed B-cell line, was grown in RPMI/10% FCS. K562, a NK cell sensitive erythroblastoma line was grown in RPMI/10% FCS. K562 was used to reduce background killing by NK and LAK cells in the chromium release assays.

Peptides. The peptides used in these studies were synthesized at Cytel and their sequences are described in Table 24 a. Peptides were routinely diluted in 100% DMSO at 20 mg/ml, aliquoted, and stored at −20° C.

FACS Analysis. Approximately $10^6$ cells were used for each antibody that was to be tested. Cells were washed twice with PBS CNU+0.1% BSA. To each sample, 100 µl PBS CMF+0.1% BSA+primary antibody at 2 µg/ml (BB7.2, ATCC) or (9.12.1, Inserm-CNRS, Marseille, France) or (LB3.1, Children's Hospital Pittsburgh) were added. A negative control was always included. Cells were incubated on ice for 20 min and washed twice with PBS CMF+0.1% BSA. Cells were resuspended in 100 µl anti-mouse IgG FITC conjugate (Sigma), diluted 1:50 in PBS CMF+0.1% BSA, and incubated 20 min on ice. Cells were washed twice with PBS CMF+0.1% BSA, and resuspended in PBS for FACS-can (Becton Dickinson) analysis. When it was necessary to postpone analysis to the subsequent days, the cells were fixed with PBS/1% paraformaldehyde (Fisher) and analyzed within one week.

Binding Assays Using Intact Cells and Radiolabelled Peptide. JY cells were treated with citrate-phosphate buffer and neutralizing buffer #1 as described above. JY control cells were left untreated in tissue culture media. After treatment both cell populations were washed twice with serum free RPMI and loaded with $^{125}$I-radiolabelled 941.01 (HBc15–27) peptide (standard chloramine T iodination). To determine binding specificity, $2\times10^6$ cells were resuspended in 200 μl neutralizing buffer #2 (described above) containing $^{125}$I-941.01 (105 cpms)+/−100 μg unlabelled 941.01. Cells were incubated for 4 hrs at 20° C. and washed twice with serum free RPMI to remove free peptide. Cells were resuspended in 200 μl of serum free RPMI. In a microfuge tube the cell suspension was layered over an 800 μl FCS and pelleted by centrifugation for 5 sec. Supernatants were aspirated and the radioactivity remaining in the pellet was measured (Micromedic automatic gamma counter, 1 min per tube).

EXAMPLE 16

Class I MHC Molecule Peptide Stripping/Loading by Mild Acid Treatment

Mild acid solutions of pH 3 such as glycine or citrate-phosphate buffers have been used by various groups to identify endogenous peptides and to identify tumor associated T cell epitopes. The treatment is unique in that only the MHC class I molecules are destabilized (and peptides released), while all other surface antigens remain intact including MHC class II molecules. Most importantly, treatment of cells with the mild acid solutions of this example do not affect the cell's viability or metabolic state. The mild acid treatment is rapid since the stripping of endogenous peptides occurs in two minutes at 4° C. and the APC is ready to perform its function after the appropriate peptides are loaded. In this example we utilized the technique to make peptide specific APCs for the generation of primary antigen-specific CTL. The resulting APC were efficient in inducing peptide-specific CD8+ CTL.

Measurements by FACS Analysis. PHA-induced T-cell blasts were acid stripped/peptide loaded according to the methods described in Example 15. The resulting cells were stained for FACS analysis using anti-HLA-A2 (BB7.2) and anti-HLA alpha chain-specific (9.12.1) monoclonal antibodies. Controls for this experiment included the same cell population which was not treated at pH 3 (but treated with PBS buffer at pH 7.2), and with cells treated with citrate-phosphate buffer (to strip the MHC) but neutralized in the absence of β$_2$microglobulin and peptide. The results presented in FIGS. 15A–15D, indicate that treatment of these cells with the citrate-phosphate (pH3) buffer significantly reduced (10-fold) the reactivity of the cells toward both anti-HLA class I antibodies alone (anti-HLA-A2 and the alpha chain specific), but not towards a monoclonal antibody specific for class II MHC molecules (anti-HLA-DR). Most importantly, neutralization of the acid-stripped cells in the presence of β$_2$microglobulin and peptide resulted in preservation of a significant amount of class I MHC antibody-reactive sites, with only a 2.5-fold decrease in fluorescence intensity. Importantly, the acid-treated cells remained viable, as measured by trypan blue exclusion and forward/lateral FACS scatter analysis. Similar results were obtained using EBV-transformed B cell lines, fresh (or frozen) PBMC and other peptides (which bind to either HLA-A2.1 or HLA-A1) (data not shown).

Binding of Radiolabeled Peptides to Empty MHC Molecules. To determine the efficiency of peptide loading using the cold temperature incubation or acid stripping/peptide loading protocol, JY cells (an HLA-A2.1 EBV-transformed B cell line) were preincubated at 26° C. overnight or acid-stripped to remove the endogenous MHC-associated peptides and the loading of exogenous peptide was determined using a $^{125}$I-radiolabelled HLA-A2.1 binding peptide. The specificity of this reaction was determined by measuring the inhibition of labelled peptide binding using a cold peptide of the same sequence. Results presented in Table 24 b demonstrate that acid-treatment of the cells increased significantly (approximately 10-fold) the amount of labelled peptide binding to the JY cells. Furthermore, the binding of labelled peptide was completely blocked by the addition of the cold peptide, demonstrating specific binding (data not shown).

In Vitro Induction of Primary Antigen-Specific CTL Using Acid Stripped/Peptide Loaded APCS. Additional critical parameters for the induction of primary CTL using both the cold temperature incubation and acid strip protocol are: 1) enrichment of CD8+ T-cells in the responder cell population (or depletion of CD4+ T-cells), 2) addition of rIL-7 to the CTL induction cultures from day 0, and 3) restimulation of the cultures with antigen on day 12–14 using autologous adherent cells pulsed with peptide.

Figure 16:
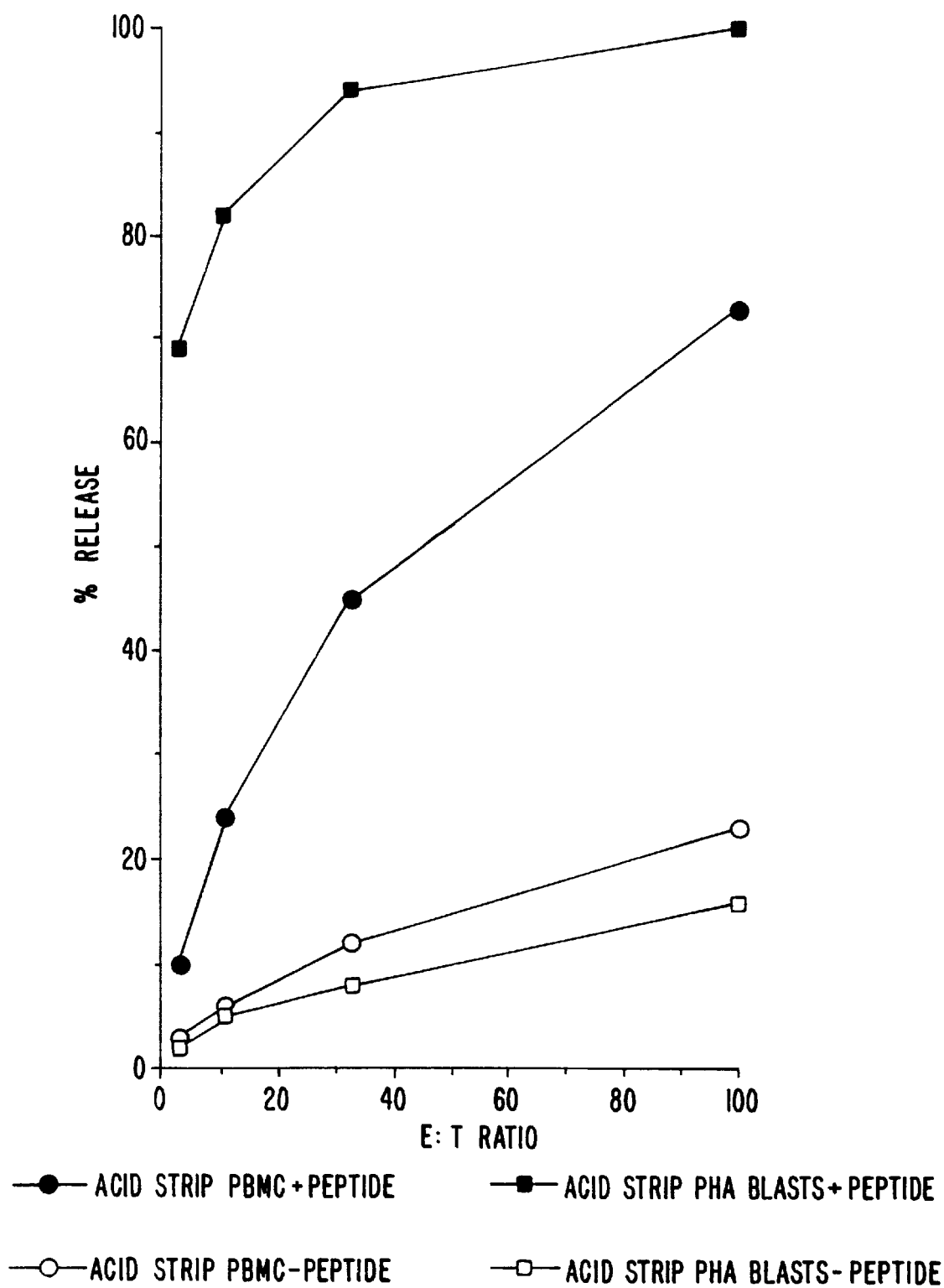
FIG. 16 shows CTL induction using GC43 A2.1 responders and autologous acid-stripped PBMCs or PHA blasts loaded with the 777.03-924.07-927.32 peptide pool.
Figure 17B:
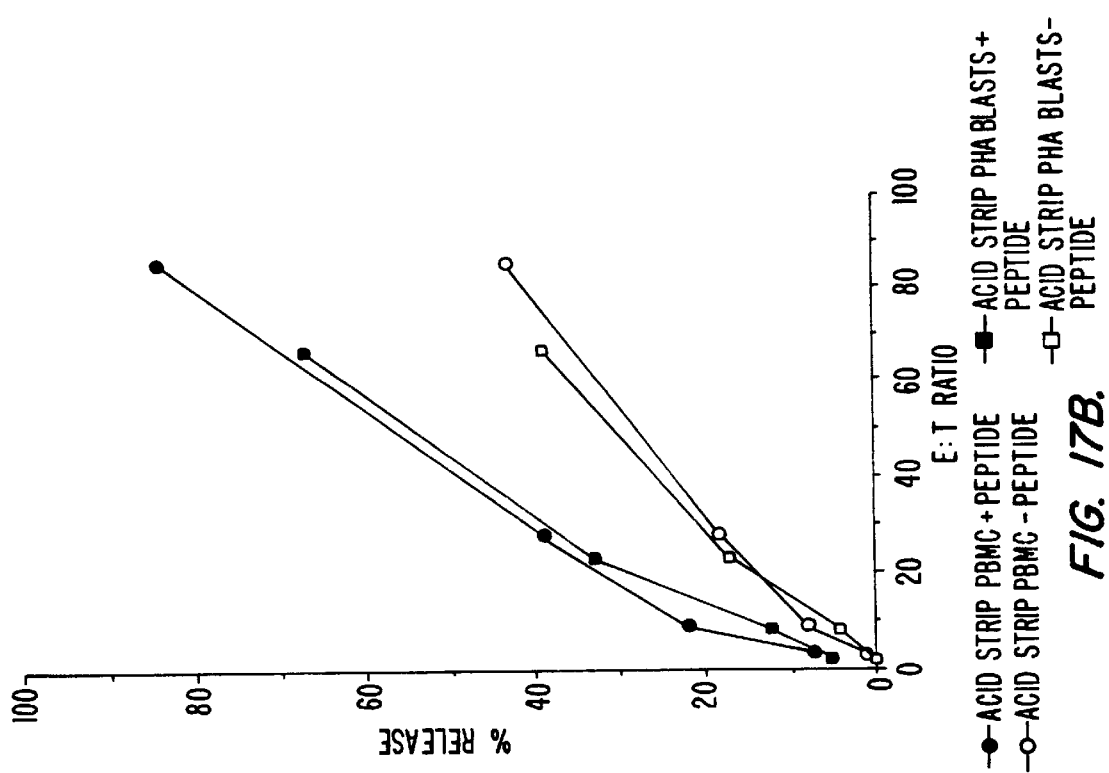
FIGS. 17A and 17B show CTL induction using X351 or X355 A2.1 responders and autologous acid stripped PBMCs or PHA blasts as stimulators after loading with the 1044.04-1044.05-1044.06 peptide pool.
Figure 17A:
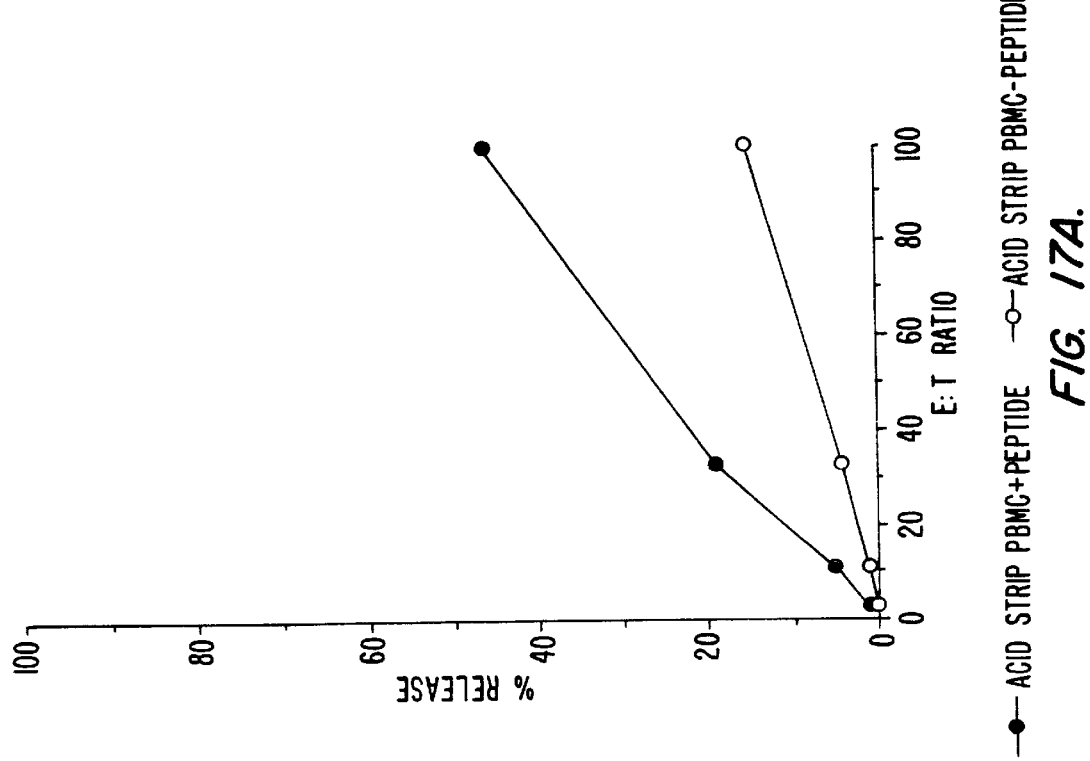
Figure 18:
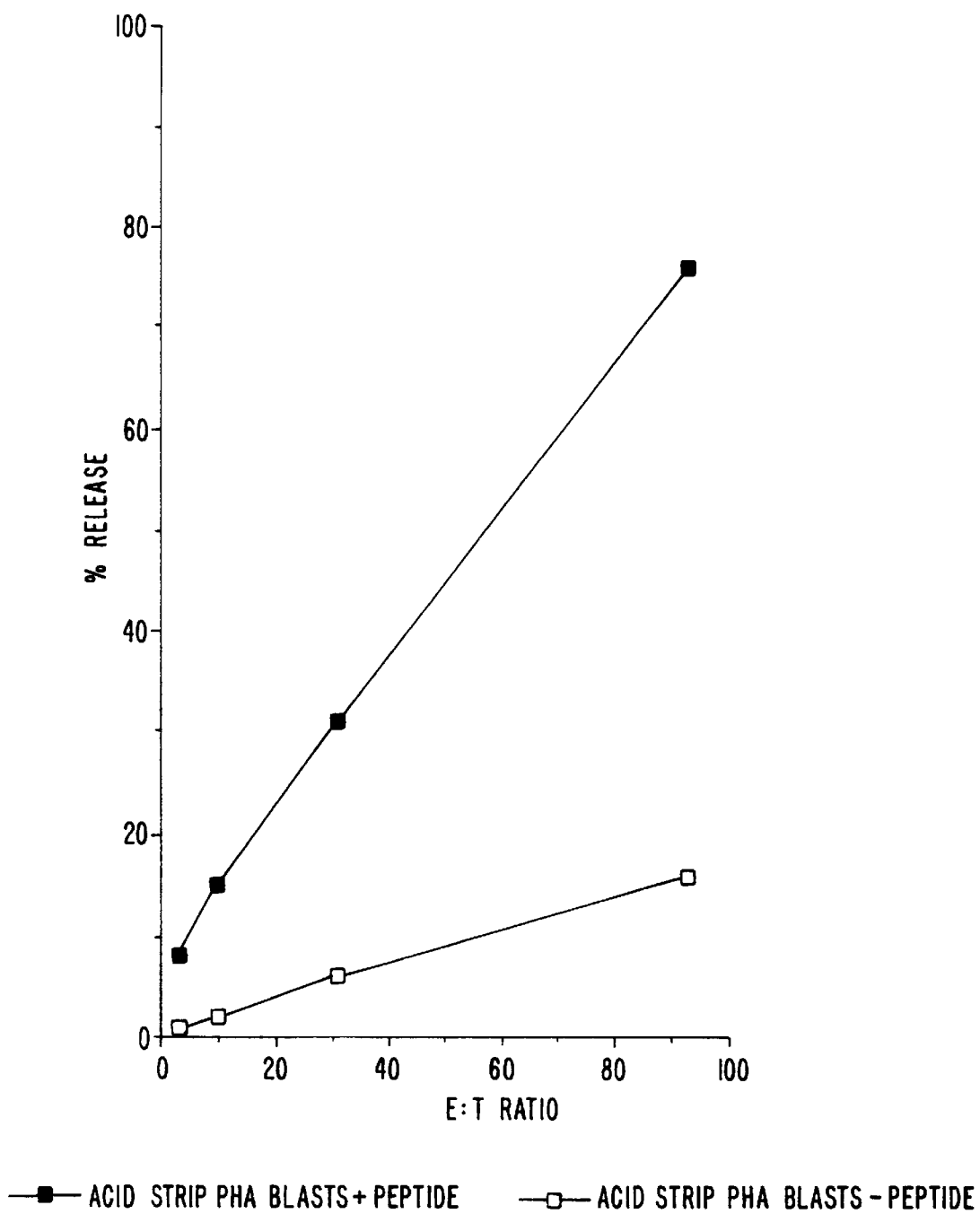
FIG. 18 shows CTL induction using GC49 A2.1 responders and Autologous Acid stripped PHA blasts as stimulators after loading with 939.03 peptide.
Figure 19A:
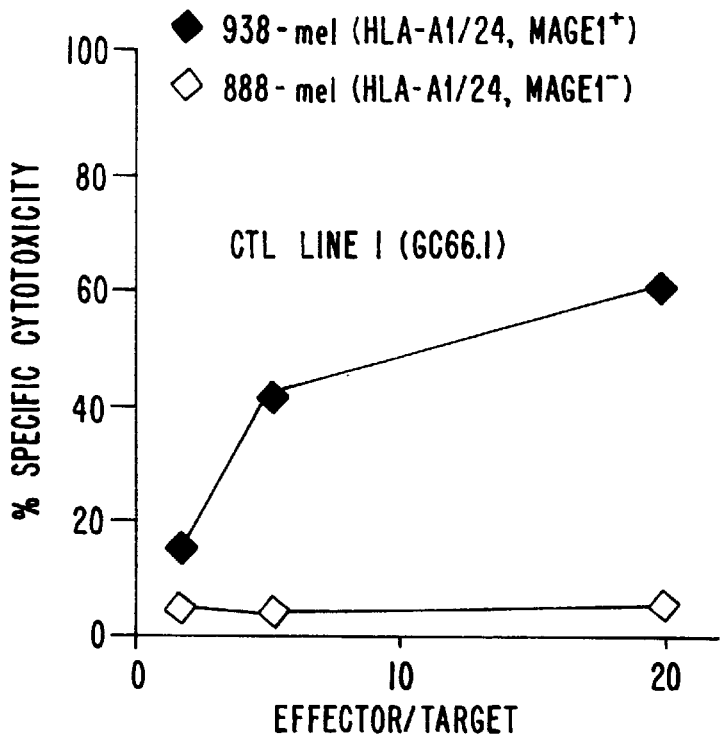
FIGS. 19A and 19B show CTL induction using GC66 A1 responders and autologous acid stripped PBMCs as stimulators after loading of peptide 938.01.
Figure 19B:
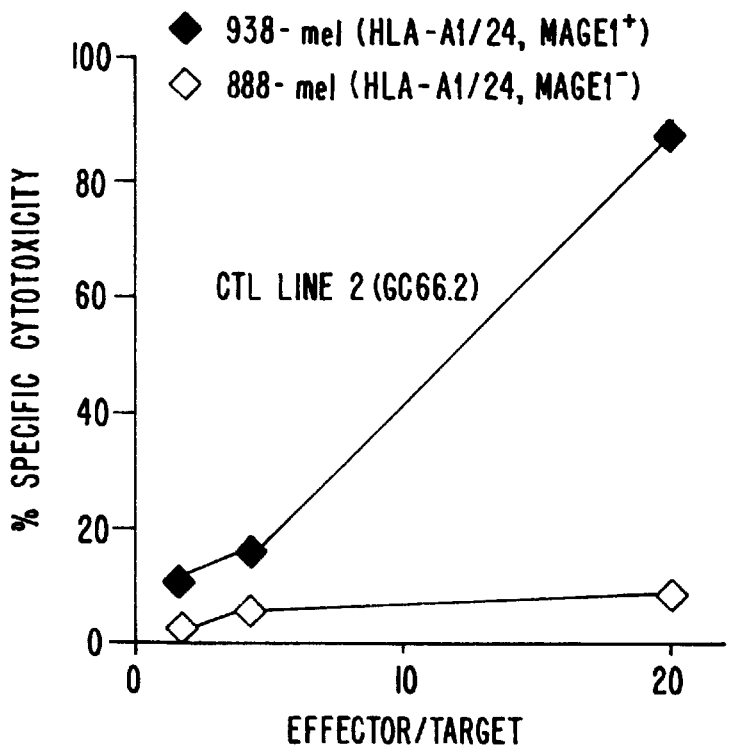

Results presented in FIGS. 16 and 17A and 17B show experiments performed using PBMC and PHA-induced T-cell blasts as APC. FIG. 18 shows experiments using PHA-induced T-cell blasts as APC while FIGS. 19A and 19B show the use of PBMC as APC.

EXAMPLE 17

Screening Peptides to Identify CTL Epitopes

In order to identify CTL epitopes, CTL was stimulated by SAC-I activated PBMCs as APC. Cold temperature expression of the MHC in which class 1 β-2-microglobulin complex is unstable was utilized in addition to acid stripping to generate PBMC APC.

Complete Culture Medium. The tissue culture medium used in this study consisted of RPMI 1640 with Hepes and L-glutamine (Gibco) supplemented with 2 mM L-glutamine (Irvine Scientific), 0.5 mM sodium pyruvate (Gibco), 100 U/100 ug/ml penicillin/streptomycin (Irvine), and 5% heat-inactivated Human Serum Type AB (RPMI/5% HS; Gemini Bioproducts). Culture media used in the growth of EBV-transformed lines contained 10% heat-inactivated fetal calf serum (RPMI/10% FCS, Irvine) instead of human serum.

Cytokines. Recombinant human Interleukin-2 (rIL-2) and Interleukin-4 (rIL-4) were obtained from Sandoz and used at a final concentration of 10 U/ml and 10 ng/ml, respectively. Human interferon-γ (IFN-γ) and recombinant human Interleukin-7 (rIL-7) were obtained from Genzyme and used at 20 U/ml and 10 ng/ml, respectively.

Peptides. Peptides were synthesized at Cytel and are described in Table 24 a. Peptides were routinely diluted in 100% DMSO at 20 mg/ml, aliquoted, and stored at −70° C. until use.

Cell Lines. JY, Steinlin, EHM, BVR, and KT3 are homozygous human EBV-transformed B cell lines expressing HLA $A_{2.1}$, $A_1$, $A_3$, $A_{11}$, and $A_{24}$, respectively. They are grown in RPMI/10% FCS. K562, an NK cell sensitive, erythoblastoma line grown in RPMI/10% FCS, was used for reduction of background killing in CTL assays. Melanoma cell lines either expressing the MAGE antigen, mel 397 and mel 938, or not expressing the MAGE antigen; mel 888, were also grown in RPMI/10% FCS.

Isolation of Peripheral Blood Mononuclear Cells (PBMCs). Whole blood was collected into heparin containing syringes and spun in 50 cc tubes at 1600 RPM (Beckman GS-6KR) for 15 minutes. The plasma layer was then removed and 10 ml of buffy coat was collected with a pipette using a circular motion. The buffy coat was mixed well and diluted with an equal volume of RPMI. The buffy coat (30 ml) was then layered on 20 ml of Ficoll-Paque (Pharmacia) and centrifuged at 1850 RPM (400×g) for 20 minutes, 25° C., with the brake off. The interface between the ficoll and the plasma containing the PBMCs was recovered with a transfer pipet (two interfaces per 50 ml tube) and washed three times with 50 ml of RPMI (1700, 1500, and 1300 RPM for 10 minutes). Cells were resuspended in 10–20 ml of culture medium, counted, and adjusted to the appropriate concentration.

Freezing PBMCS. 30 million cells/tube (90% FCS/10% DMSO; Sigma) were inserted into a Nalgene Cryo 1° C. Freezing Container containing isopropanol (Fisher) and placed at −70° C. from 4 hrs (minimum) to overnight (maximum). The isopropanol was changed every five times. Tubes were transferred to liquid nitrogen for long term storage. To thaw, PBMCs were continuously shaken in a 37° C. water bath until the last crystal was almost thawed (tubes were not allowed to sit in the water bath or at room temperature for any period of time). Cells were diluted into serum-free RPMI containing 30 μg/ml DNase to prevent clumping by dead cell DNA and washed twice.

Induction of Primary CTL Using SAC-I Activated PBMCs as APCs a. Preparation of APCs: PBMCs were purified using the standard Ficoll-Paque protocol and resuspended at 1×10⁶/ml in RPMI/5% FCS containing 0.005% Pansorbin cells (SAC-I cells expressing Protein A; Calbiochem), 20 μg/ml Immunobeads (Rabbit anti-Human IgM; Biorad), and 20 ng/ml of human rIL-4. Two ml of cells per well were plated in a 24-well plate (Falcon, Becton Dickinson) and cultured at 37° C. After 3 days, the medium was removed and the cells were washed three times followed by addition of RPMI/10% HS. The cells were used after culturing for an additional 2 days in RPMI/10% HS.

b. Expression of empty Class I molecules on the surface of APCs and peptide loading of APCs.

1. Cold temperature incubation:

a. Expression of empty MHC in APCs: The APCs were adjusted to a concentration of 2×10⁶/ml in complete culture medium containing 10 ng/ml rIL-4, 20 U/ml human IFN-γ, and 3 μg/ml β2-microglobulin ($β_2$m; Scripps Lab). The cells were then incubated overnight at 26° C. in the presence of 5% $CO_2$. It should be noted that these cells only express a fraction of Class I molecules in the empty state (~10%).

b. Peptide loading of APC stimulator cells: Empty Class I expressing APCs were washed 1–2 times with serum free RPMI (+L-glutamine and Hepes) and resuspended at 1×10⁷ in serum-free RPMI containing 50 μg/ml total of the peptide pool (i.e., 16.7 μg/ml of each peptide in a pool of three; 25 μg/ml of each peptide in a pool of two; 50 μg/ml of individual peptide), 30 μg/ml DNAse, and 3 μg/ml $β_2$m. Following a 4 hour incubation at 20° C., the cells were irradiated at 6100 rads (5×10⁶/ ml; 25 million cells/tube), washed and adjusted to the appropriate concentration for addition to the induction culture (see below).

2. Acid stripping: This was used as an alternative method for generating empty MHC on the surface of the APCs. The SAC-I activated PBMCs were washed once in cold 0.9% sodium chloride (J. T. Baker) containing 1% BSA. The cells were resuspended at 10⁷/ml in cold citrate-phosphate buffer (0.13M L-ascorbic acid [J. T. Baker], 0.06M sodium phosphate monobasic [Sigma], pH3) containing 1% BSA and 3 μg/ml $β_2$m and incubated on ice. After 2 minutes, 5 volumes of cold 0.15M sodium phosphate monobasic buffer, pH7.5, containing it BSA, 3 μg/ml $β_2$m, and 10 μg/ml peptide [neutralizing buffer #1] was added and the cells centrifuged at 1500 RPM for 5 minutes at 4° C. The cells were resuspended in 1 ml of cold PBS containing 1% BSA, 30 μg/ml DNase, 3 μg/ml $β_2$microglobulin, and 50 μg/ml peptide [neutralizing buffer #2] and incubated for 4 hours at 20° C. As above, subsequent to the four hour incubation at 20° C., the cells were irradiated at 6100 rads (5×10⁶/ ml; 25 million cells/tube), washed, then adjusted to the appropriate concentration for addition to the induction culture (see below).

c. Preparation of the CD4+ depleted PBMC responder cell population (depletion of lymphocyte sub-populations using AIS flasks). AIS MicroCellector T-150 flasks (specific for the depletion of CD4+ T cells; Menlo Park, Calif.) were primed by adding 25 ml of PBS/1 mM EDTA, swirling for 30 seconds so that all surfaces were moistened, and then incubating with the binding surface down at room temperature for 1 hour. Following this incubation, flasks were shaken vigorously for 30 seconds, washed 1 time with PBS/EDTA, 2 additional times with PBS and then incubated with 25 ml of culture medium for 15 minutes. PBMCs were thawed in serum-free RPMI (+L-glutamine+Hepes) containing 30 μg/ml DNAse, washed once, and incubated for 15 minutes in culture medium. Following aspiration of culture medium from the flasks, up to 180 million PBMCs were added in 25 ml of culture medium containing 30 μg/ml DNAse. After 1 hour at room temperature, the flasks were rocked gently for 10 seconds to resuspend the nonadherent cells. The nonadherent cell suspension containing the CD8+ T cells was collected and the flasks were washed 2 times with PBS. The CD4+ T cell depleted PBMCs were centrifuged and counted for addition to the induction culture. The CD4+ and CD8+ phenotype of the CD4+ depleted cell population was determined by FACS analysis (see below). In general, this technique resulted in a two-fold enrichment for CD8+ T cells with an average of approximately 40–50% CD8+ T cells and 15–20% remaining CD4+ T cells following depletion of CD4+ T cells. Depletion of CD4+ T cells can also be accomplished by antibody and complement or antibody coated magnetic beads (Dynabeads). Depletion of CD4+ T cells served the purpose of enriching CTLp and removing cells which would complete for cell nutrients and may interfere with CTLp expansion.

d. Induction of primary CTL. During the 4 hour peptide loading of the stimulator APCs, CD4+ depleted PBMC to be used as the responder population were prepared utilizing AIS flasks for selection of CD8+ T cells through the depletion of CD4+ T cells (above). The responder cells were plated at 3×10⁶/ml in a 1 ml volume (24 well plate) and placed at 37° C. until the peptide loaded stimulator APCs were prepared. The irradiated, peptide loaded APCs were washed 1 time in serum-free RPMI (+L-glutamine and Hepes), adjusted to 1×10⁶/ml in complete medium, and plated into a 24 well plate at 1 ml/plate: For PBMC, 1×10⁶ stimulator cells (1 ml volume) were plated into the wells containing the responder cells; For SAC-I activated PBMC and PHA blasts, 1 ml of 3×10⁵/ml stimulator cells were plated in each well. A final concentration of 10 μg/ml of additional peptide was added in addition to 10 ng/ml final concentration of rIL-7 (2 ml total volume). On day 7 an additional 10 μg/ml rIL-7 was added to the culture and 10 U/ml rIL-2 was added every 3 days thereafter. On day 12, the cultures were restimulated with peptide pulsed adherent cells and tested for cytolytic activity 7 days later (below).

Protocol for Restimulation of Primary CTL Using Adherent APC. PBMCs were thawed into serum-free RPMI (+L-glutamine and Hepes) containing 30g/ml DNAse, washed 2 times, and adjusted to 5×10⁶/ml in culture medium containing DNAse. PBMCs (25 million cells/tube in 5 ml) were irradiated at 6100R. After 1 wash, the PBMCs were resuspended in culture medium and adjusted to 4×10⁶/ml. 1 ml of irradiated PBMCs was added per well of a 24-well plate. The PBMC were incubated for 2 hours at 37° C., washed 3 times to remove non-adherent cells, and cultured in medium containing 20 μg/ml total peptide and 3 μg/ml β₂microglobulin added in a 0.5 ml volume and again incubated for 2 hours at 37° C. The peptide was aspirated and 1.5×10⁶ responder cells resuspended in culture medium were added in a 1 ml volume. After 2 days, 1 ml of culture medium containing 20 U/ml rIL-2 was added.

FACS Analysis. One million cells/tube were centrifuged, resuspended in 100 μl/tube PBS/0.1% BSA/0.02% sodium azide (Sigma) plus 10 μl/tube directly conjugated antibody (Becton Dickinson), and incubated on ice 15–20 minutes. Cells were then washed 2 times with PBS/0.1% BSA/0.02% sodium azide and resuspended in PBS to analyze on FACScan (Beckton Dickinson). When it was not possible to analyze samples within 1–2 days, cells were fixed with PBS containing 1% paraformaldehyde (Fisher) and analyzed within one week.

Figure 20:
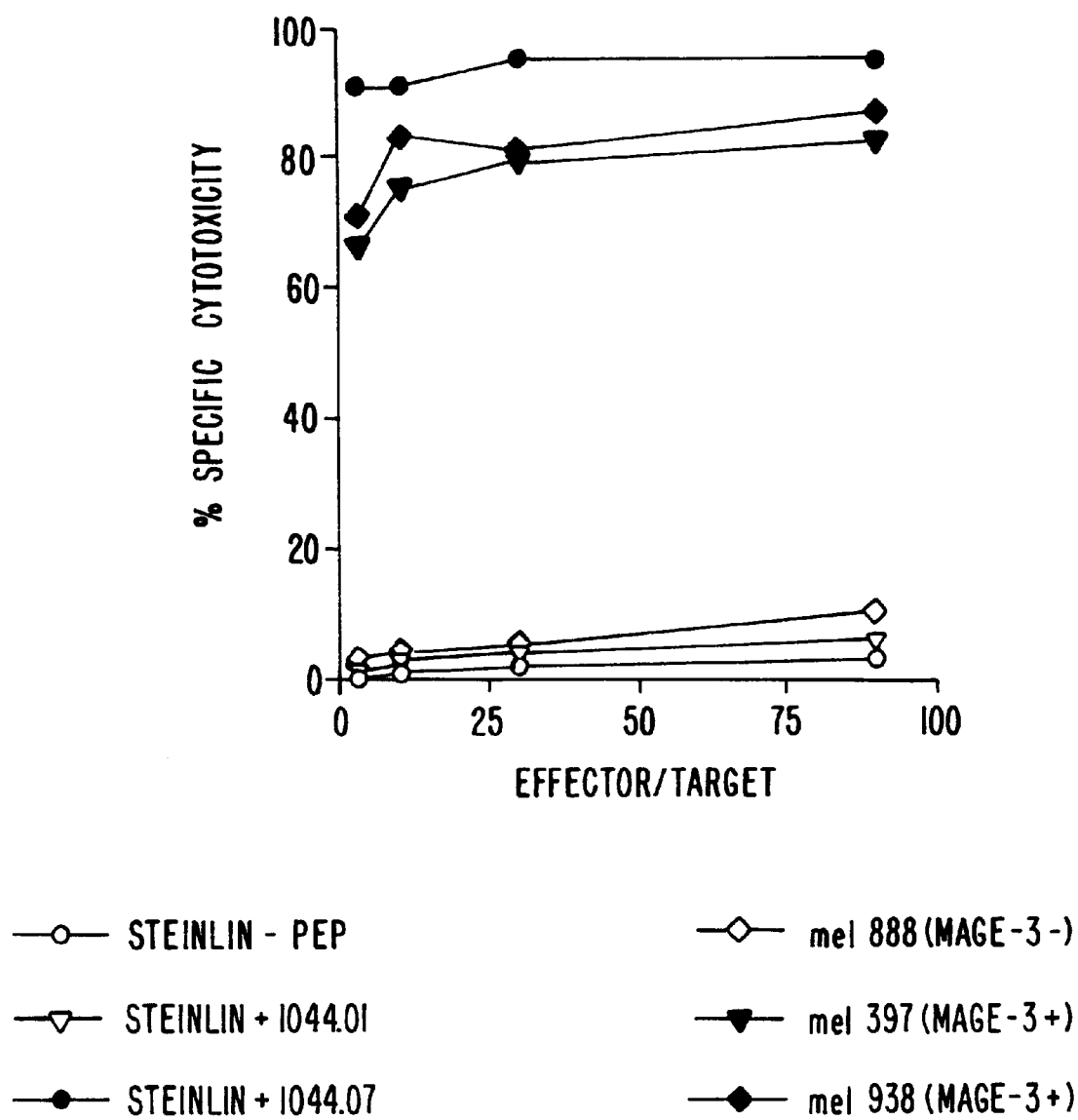
FIG. 20 illustrates the lysis of peptide sensitized targets and endogenous targets following stimulation with SAC-I activated PBMCs loaded with a MAGE 3 peptide.
Figure 21A:
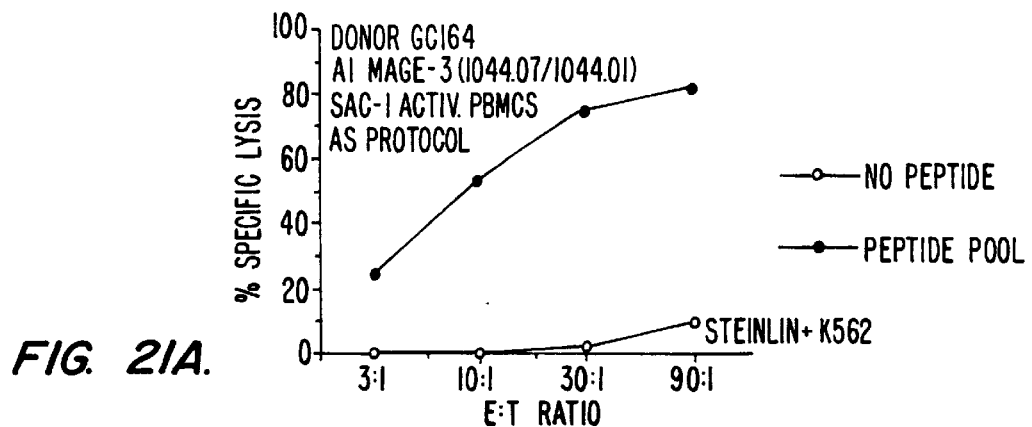
FIGS. 21A–21D show a comparison of the acid strip loading with the cold temperature incubation.
Figure 21B:
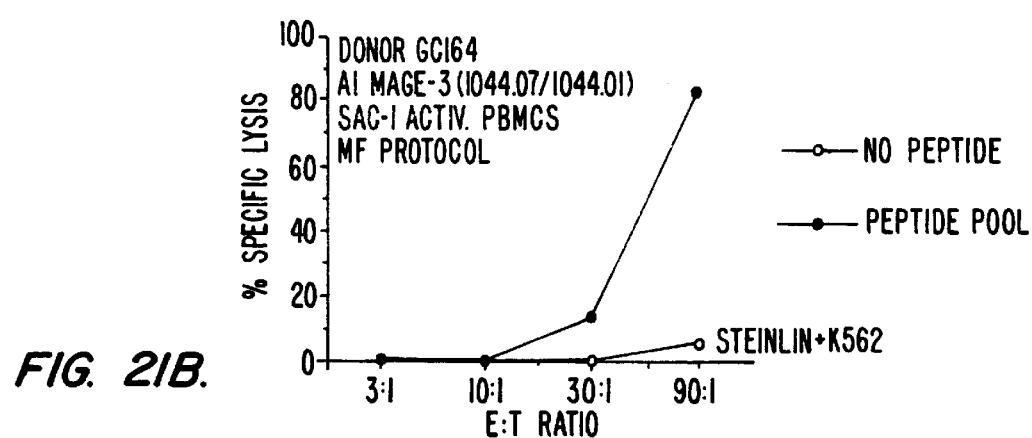
Figure 21C:
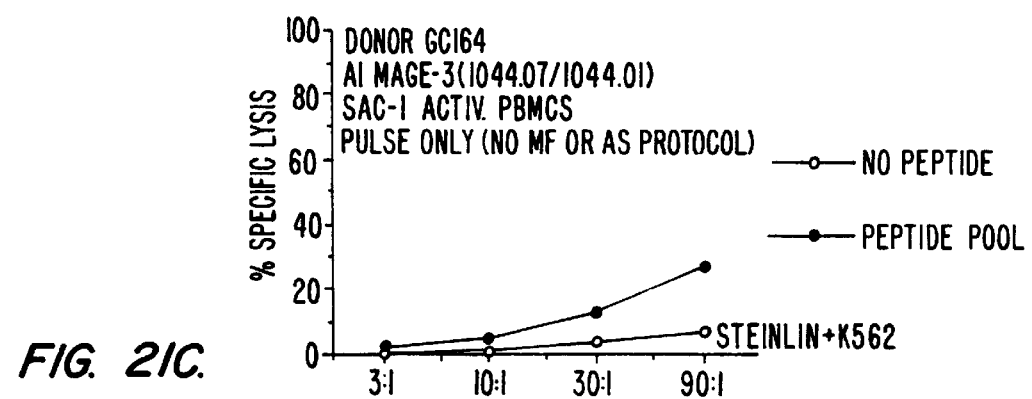
Figure 21D:
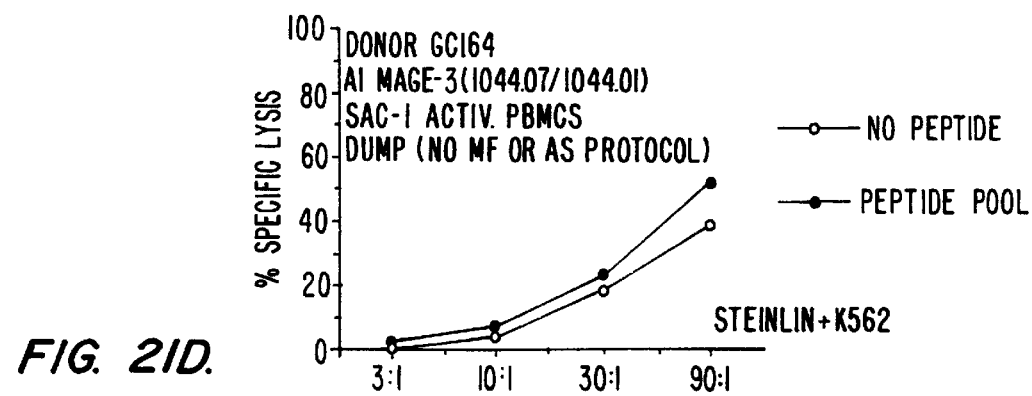
Figure 22A:
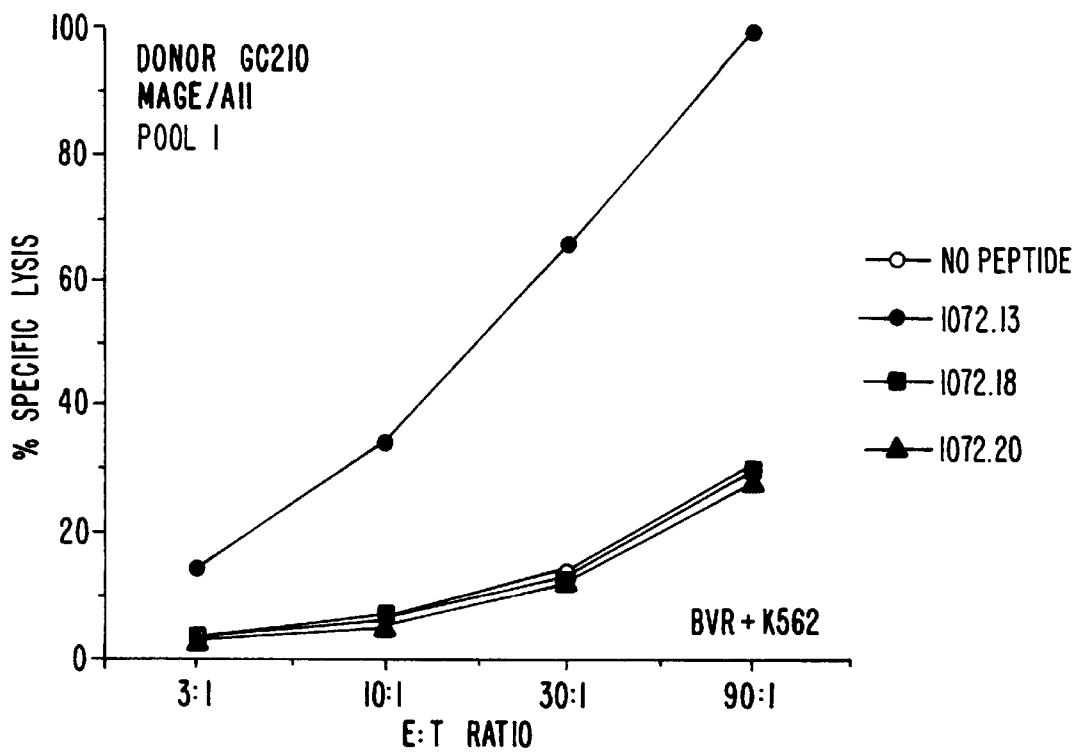
FIGS. 22A and 22B show a CTL response to an immunogenic peptide for MAGE/A11.
Figure 22B:
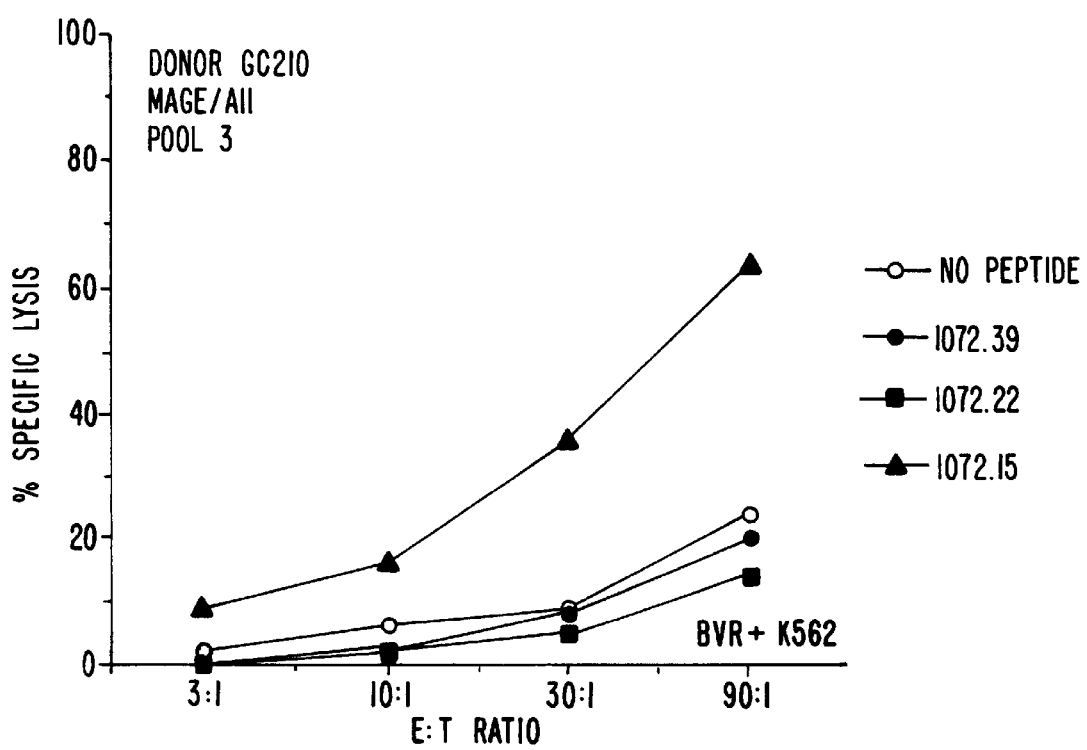
Figure 23A:
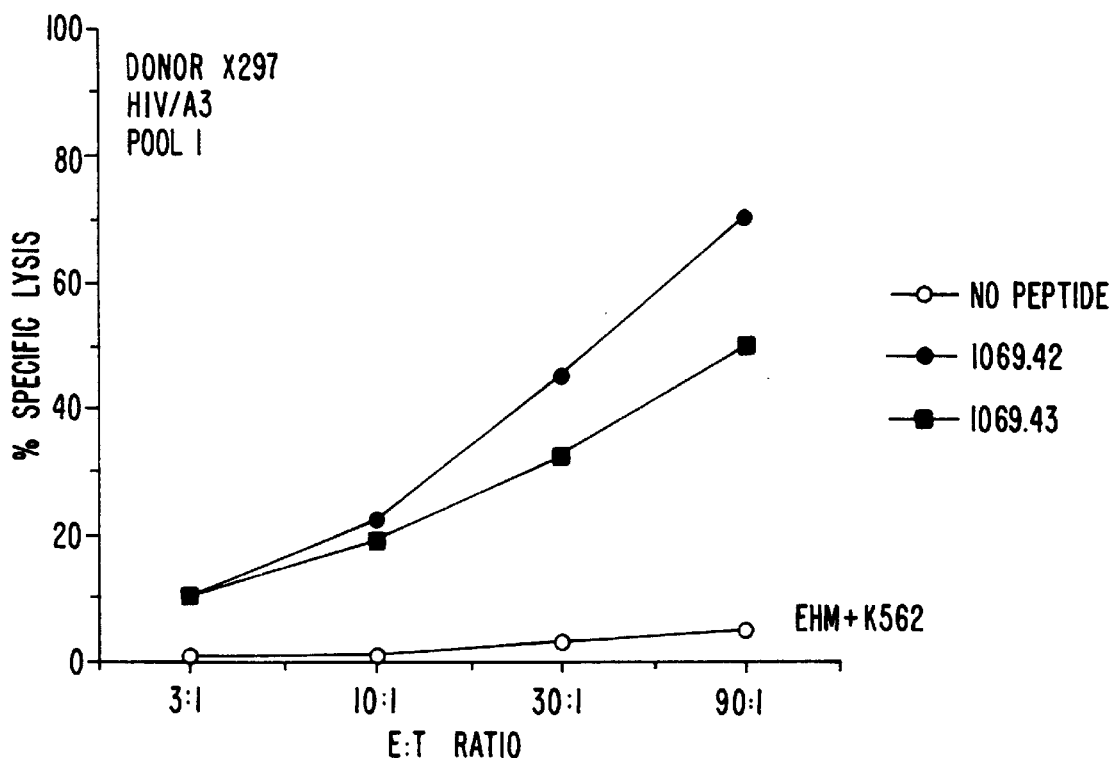
FIGS. 23A and 23B show a CTL response to an immunogenic peptide for HIV/A3.
Figure 23B:
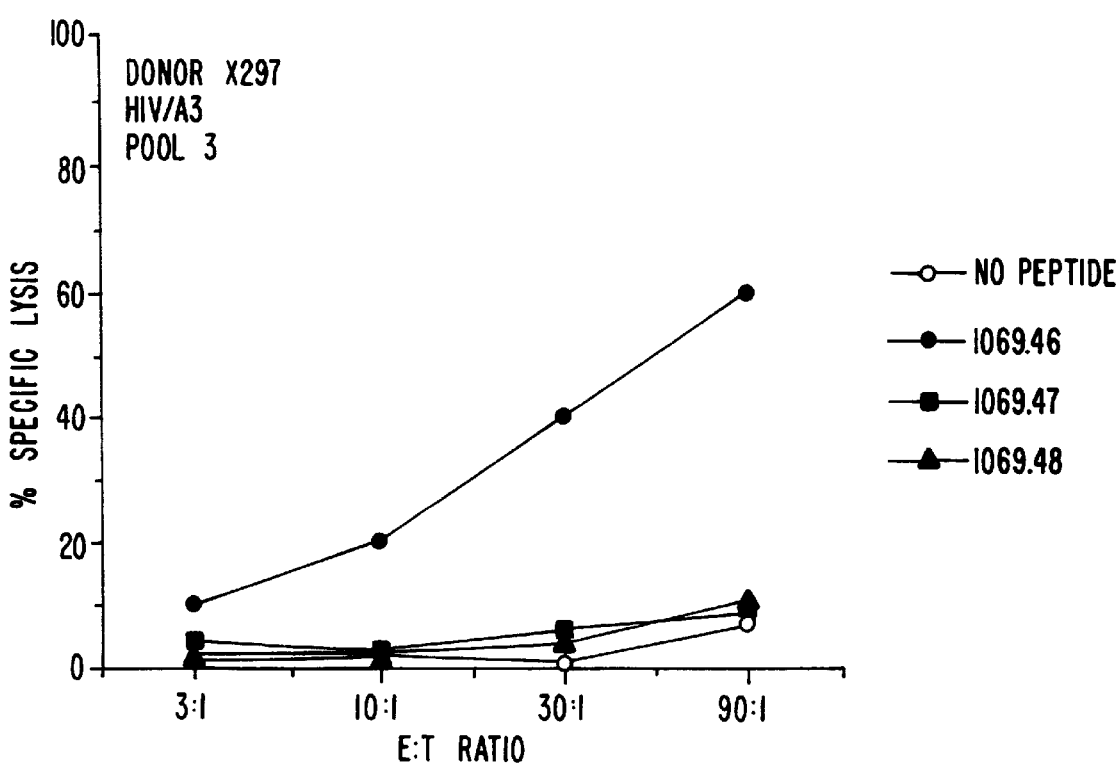
Figure 24:
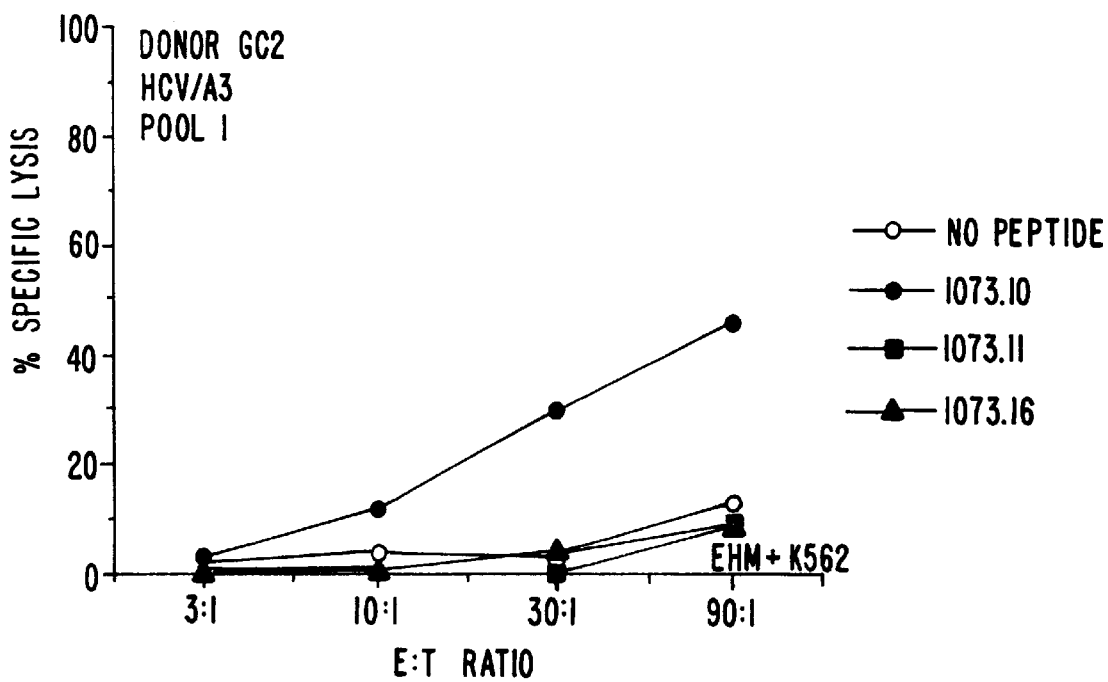
FIG. 24 shows a CTL response to an immunogenic peptide for HCV/A3.
Figure 25:
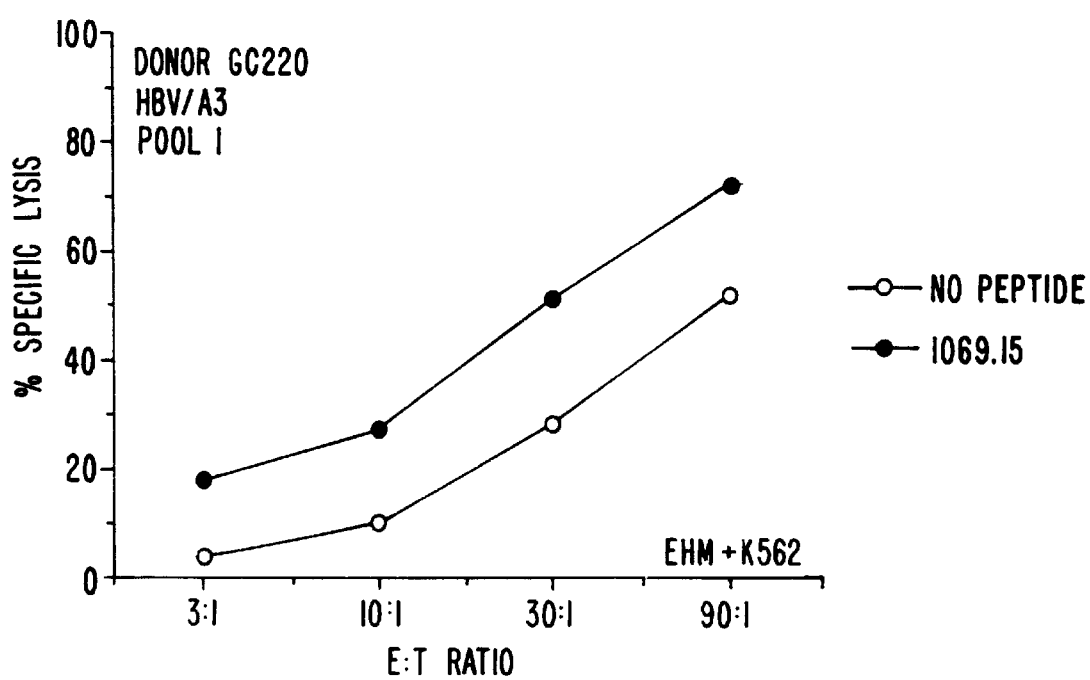
FIG. 25 shows a CTL response to an immunogenic peptide for HBV/A3.

Cytotoxicity Assay a. Target cell preparation. Approximately 16–20 hours prior to the CTL assay, target cells (Class I matched EBV-transformed lines) were washed once and resuspended in a 10 ml volume at 3×10⁵/ml in RPMI/5% FCS in the presence or absence of 10 μg/ml total peptide.

b. Labeling of target cells: Target cells were centrifuged and resuspended in 200 μl/tube sodium 51Cr chromate (NEN), then incubated at 37° C. for 1 hour on a shaker. Targets were washed 3 times (10 ml/wash) with RPMI/10% FCS and resuspended in 10 ml (to determine the efficiency of labelling, 50 μl/target was counted on the Micromedic automatic gamma counter).

c. CTL assay. Target cells were adjusted to 2×10⁵/ml and 50 μl of the cell culture was added to each well of a U-bottomed 96-well plate (Costar Corp.) for a final concentration of 1×10⁴/well. K562 cells were washed once, resuspended at 4×10⁶/ml, and 50 μl/well was added for a final concentration of 2×10⁵/ well (ratio of cold K562 to target was 20:1). Responder cells were washed once, resuspended at 9×10⁶/ml, and three fold serial dilutions were performed for effector to target ratios of 90:1, 30:1, 10:1, and 3:1. Responder cells were added in a volume of 100 μl in duplicate wells. For spontaneous release, 50 μl/well of labelled target cells, 50 μl/well K562, and 100 μl/well of medium was added. For maximum release, 50 μl/well target, 50 μl/well K562, and 100 μl/well of 0.1 Triton-X100 (Sigma) was added. Plates were centrifuged for 5 minutes at 1200 RPM. Following a 5 hour incubation at 37° C., plates were centrifuged again for 5 minutes at 1200 RPM, and 100 μl/well of supernatant was collected. Standard gamma counting techniques (Micromedic automatic gamma counter; 0.5 minutes/tube) were used to determine the percent specific lysis according to the formula: % specific lysis=cpm experimental−cpm spontaneous release/cpm maximum release−cpm spontaneous release×100. A cytotoxicity assay (CTL assay) was considered positive if the lysis by CTL of targets sensitized with a specific peptide at the two highest effector to target (E:T) ratios was 15% greater than lysis of control targets (i.e., target cells without peptide). A cytotoxicity assay (CTL assay) was considered borderline if the lysis by CTL of targets sensitized with a specific peptide at the two highest effector to target (E:T ratios was 6% greater than lysis of control targets (i.e., target cells without peptide).

d. Results. Of the peptides that bind to the indicated alleles, 9 of the 49 MAGE peptides, 10 of the 45 HIV peptides, 3 of the 25 HCV peptides, and 2 of the 20 HBV peptides tested to date induced primary CTL in vitro. Representative graphs illustrating CTL responses to various immunogenic peptides are shown for MAGE (FIGS. 22A and 22B), HIV (FIGS. 23A and 23B), HCV (FIG. 24), and HBV (FIG. 25). The CTL induction data are summarized in Table 24 which lists the immunogenic peptides which bind to the appropriate MHC and induce primary CTL in vitro. Indicated is the peptide's sequence, corresponding antigen and HLA allele to which it binds. Results shown in FIG. 20 illustrate lysis of peptide sensitized targets and endogenous targets following stimulation with SAC-I activated PBMCs loaded with a MAGE 3 peptide, 1044.07 by the cold temperature and incubation technique. FIGS. 21A–21D show a comparison of the acid strip loading technique (Panel a) with the cold temperature incubation technique (panel b).

EXAMPLE 18

Identification of Immunogenic Peptides in Autoantigens

As noted above, the motifs of the present invention can also be screened in antigens associated with autoimmune diseases. Using the motifs identified above amino acid sequences from myelin proteolipid (PLP), myelin basic protein (MBP), glutamic acid decarboxylase (GAD), and human collagen types II and IV were analyzed for the presence of these motifs. Sequences for the antigens were obtained from Trifilieff et al., *C.R. Sceances Acad. Sci.* 300:241 (1985); Eyler at al., *J. Biol. Chem.* 246:5770 (1971); Yamashita et al. *Biochiem. Biophys. Res. Comm.* 192:1347 (1993); Su et al., *Nucleic Acids Res.* 17:9473 (1989) and Pihlajaniemi et al. *Proc. Natl. Acad. Sci. USA* 84:940 (1987). In addition, these sequences were screened for the presence of a P in position 2 and VILMFW or Y in positions 8,9, or 10. Peptides carrying such motifs are predicted to be capable of binding to various class I types such as B7, Huzco et al. *J. Immunol.* 151:2572 (1993); B14, Koenig et al., *J. Immunol.* 151:3874 (1993); ZB35, Falk et al., *Immunogenetics* 38:161 (1993); B35 and B53, Hill et al., *Nature* 360:434 (1992); B51, Gotch et al., *J. Immunol.* 151:3361 (1993) and B54. The results are presented in Tables 26–30.

Using the assays described above, the peptides are next tested for the ability to bind MHC molecules. The ability of the peptides to suppress proliferative responses in autoreactive T cells is carried out using standard assays for T cell proliferation. For instance, methods as described by Miller et al. *Proc. Natl. Acad. Sci. USA,* 89:421 (1992) are suitable.

For further study, animal models of autoimmune disease can be used to demonstrate the efficacy of peptides of the invention. For instance, in HLA transgenic mice, autoimmune model diseases can be induced by injection of MBP, PLP or spinal cord homogenate (for MS), collagen (for arthritis). In addition, some mice become spontaneously affected by autoimmune disease (e.g., NOD mice in diabetes). Peptides of the invention are injected into the appropriate animals, to identify preferred peptides.

Although the present invention has been described in some detail by way of illustration and example for purposes of clarity and understanding, it will be apparent that certain changes and modifications may be practiced within the scope of the appended claims.

TABLE 13

VALIDATION OF CYTEL'S HLA MOTIFS
Binding Capacity (IC50 nM)

| SEQUENCE | MOTIF | A1 | A2.1 | A3.2 | A11 | A24 | SEQ ID NO: |
|---|---|---|---|---|---|---|---|
| AADKAAAAY | A1 | 50 | —* | — | — | — | 139 |
| ATAKAAAAY | A1 | 15 | — | 329 | 77 | — | 140 |
| ATDKAAAAY | A1 | 2.8 | — | 9250 | 840 | ND | 141 |
| ALAKAAAAV | A2.1 | — | 125 | — | — | — | 142 |
| AMAAAAAAK | A3.2 | — | — | 48 | 8.4 | — | 129 |
| ATAAAAAAK | A11 | — | — | 59 | 40 | — | 143 |
| AYAKAAAAF | A24 | — | — | — | — | 115 | 144 |

*A dash indicates an IC50 greater than 20,000 nM.

TABLE 14

VALIDATION OF CYTEL'S HLA MOTIFS
Binding Capacity (IC50 nM)

| SEQUENCE | MOTIF | A1 | A2.1 | A3.2 | A11 | SEQ ID NO: |
|---|---|---|---|---|---|---|
| AADKAAAAY | A1 | 45 | —* | — | — | 145 |
| ATAKAAAAY | A1 | 58 | — | 1100 | 1030 | 146 |
| ATDKAAAAY | A1 | 4.0 | — | 10000 | 4533 | 147 |
| ALAKAAAAV | A2.1 | ND | 1400 | — | — | 148 |
| AMAAAAAAK | A3.2 | ND | — | 85 | 24.0 | 149 |
| ATAAAAAAK | A11 | — | — | 216 | 88 | 150 |

*A dash indicates an IC50 greater than 20,000 nM.

TABLE 15

HLA-A3.2

| PEPTIDE | SEQUENCE | AVERAGE RATIO TO 952.25 | SUBSTITUTION | SEQ ID NO: |
|---|---|---|---|---|
| 952.25 | ALAAAAAAK | 1 | — | 151 |
| 952.26 | AMAAAAAAK | 1.2 | position 2 | 129 |
| 952.23 | AVAAAAAAK | 0.95 | | 152 |
| 981.04 | ASAAAAAAK | 0.89 | | 153 |
| 952.24 | AIAAAAAAK | 0.57 | | 154 |
| 952.27 | AAAAAAAAK | 0.57 | | 155 |
| 981.06 | ATAAAAAAK | 0.49 | | 143 |
| 981.08 | AFAAAAAAK | 0.13 | | 156 |
| 981.09 | AGAAAAAAK | 0.077 | | 157 |
| 981.13 | ACAAAAAAK | 0.031 | | 158 |
| 981.12 | ADAAAAAAK | 0.014 | | 159 |
| 981.11 | ANAAAAAAK | 0.0010 | | 160 |
| 981.05 | AKAAAAAAK | <0.0016 | | 161 |
| 981.07 | AYAAAAAAK | <0.0005 | | 162 |
| 981.10 | APAAAAAAK | <0.0006 | | 163 |
| 952.35 | ALAAAAAAR | 0.46 | position 9 | 164 |
| 981.36 | ALAAAAAAY | 0.15 | | 165 |
| 981.33 | ALAAAAAAA | 0.0034 | | 166 |

TABLE 15-continued

HLA-A3.2

| PEPTIDE | SEQUENCE | AVERAGE RATIO TO 952.25 | SUBSTITUTION | SEQ ID NO: |
|---|---|---|---|---|
| 981.35 | ALAAAAAAQ | <0.0006 | | 167 |
| 981.37 | ALAAAAAAS | <0.0005 | | 168 |
| 981.38 | ALAAAAAAT | <0.0005 | | 169 |
| 981.34 | ALAAAAAAN | <0.0005 | | 170 |

TABLE 15-continued

HLA-A3.2

| PEPTIDE | SEQUENCE | AVERAGE RATIO TO 952.25 | SUBSTITUTION | SEQ ID NO: |
|---|---|---|---|---|
| 981.39 | ALAAAAAAE | <0.0003 | | 171 |

TABLE 16

HLA-A11

| PEPTIDE | SEQUENCE | AVERAGE RATIO TO 952.25 | SUBSTITUTION | SEQ ID NO: |
|---|---|---|---|---|
| 952.25 | ALAAAAAAK | 1 | — | 151 |
| 952.26 | AMAAAAAAK | 2.5 | position 2 | 129 |
| 952.27 | AAAAAAAAK | 1.1 | | 155 |
| 952.24 | AIAAAAAAK | 0.72 | | 154 |
| 981.06 | ATAAAAAAK | 0.55 | | 143 |
| 981.04 | ASAAAAAAK | 0.46 | | 153 |
| 981.09 | AGAAAAAAK | 0.38 | | 157 |
| 952.23 | AVAAAAAAK | 0.23 | | 152 |
| 981.11 | ANAAAAAAK | 0.23 | | 160 |
| 981.13 | ACAAAAAAK | 0.019 | | 158 |
| 981.08 | AFAAAAAAK | 0.020 | | 156 |
| 981.12 | ADAAAAAAK | 0.012 | | 159 |
| 981.05 | AKAAAAAAK | 0.0065 | | 161 |
| 981.07 | AYAAAAAAK | <0.0065 | | 162 |
| 981.10 | APAAAAAAK | <0.0051 | | 163 |
| 952.35 | ALAAAAAAR | 0.015 | position 9 | 164 |
| 981.33 | ALAAAAAAA | <0.0059 | | 166 |
| 981.34 | ALAAAAAAN | <0.0071 | | 170 |
| 981.35 | ALAAAAAAQ | <0.0051 | | 167 |
| 981.36 | ALAAAAAAY | <0.0071 | | 165 |
| 981.37 | ALAAAAAAS | <0.0051 | | 168 |
| 981.38 | ALAAAAAAT | <0.0051 | | 169 |
| 981.39 | ALAAAAAAE | <0.0071 | | 171 |

TABLE 17

HLA-A24

| PEPTIDE | SEQUENCE | AVERAGE RATIO TO 938.01 | SUBSTI- TUTION | SEQ ID NO: |
|---|---|---|---|---|
| 983.01 | AYAKAAAAF | 1 | — | 144 |
| 983.08 | AFAKAAAAF | 0.24 | position 2 | 172 |
| 983.09 | APAKAAAAF | 0.0058 | | 173 |
| 983.10 | AAAKAAAAF | 0.0023 | | 174 |
| 983.11 | AKAKAAAAF | <0.0012 | | 175 |
| 983.05 | AYAKAAAAI | 0.20 | position 9 | 176 |
| 983.04 | AYAKAAAAL | 0.11 | | 177 |
| 983.06 | AYAKAAAAV | 0.0023 | | 178 |
| 983.02 | AYAKAAAAA | <0.0012 | | 179 |
| 983.03 | AYAKAAAAY | <0.0012 | | 180 |
| 983.07 | AYAKAAAAK | <0.0012 | | 181 |

TABLE 18

HLA-A1

| PEPTIDE | SEQUENCE | AVERAGE RATIO TO 982.07 | SUBSTI- TUTION | SEQ ID NO: |
|---|---|---|---|---|
| 982.011 | ATDKAAAAY | Motif | — | 141 |
| 982.07 | ATAKAAAAY | 1 | — | 140 |
| 982.09 | ASAKAAAAY | 0.17 | position 2 | 182 |
| 982.13 | AMAKAAAAY | 0.095 | no D in pos 3 | 183 |
| 982.08 | AAAKAAAAY | 0.0064 | | 184 |
| 954.09 | ALAKAAAAY | 0.0045 | | 185 |
| 954.11 | AIAKAAAAY | 0.0045 | | 186 |
| 954.13 | AVAKAAAAY | 0.0020 | | 187 |
| 982.10 | AKAKAAAAY | 0.0011 | | 188 |
| 982.11 | ANAKAAAAY | <0.0001 | | 189 |
| 982.12 | ADAKAAAAY | <0.0001 | | 190 |
| 982.14 | AGAKAAAAY | <0.0001 | | 191 |
| 982.15 | APAKAAAAY | <0.0001 | | 192 |
| 982.16 | AYAKAAAAY | <0.0001 | | 180 |
| 982.17 | AHAKAAAAY | <0.0001 | | 193 |
| 982.24 | ATAKAAAAA | 0.0040 | position 9 | 194 |
| 982.23 | ATAKAAAAF | 0.0019 | no D in pos 3 | 195 |
| 982.28 | ATAKAAAAH | 0.0010 | | 196 |
| 982.32 | ATAKAAAAV | 0.0005 | | 197 |
| 982.25 | ATAKAAAAN | <0.0001 | | 198 |
| 982.26 | ATAKAAAAD | <0.0001 | | 199 |
| 982.27 | ATAKAAAAW | <0.0001 | | 200 |
| 982.30 | ATAKAAAAK | <0.0001 | | 201 |
| 982.31 | ATAKAAAAI | <0.0001 | | 202 |
| 982.29 | ATAKAAAAP | <0.0001 | | 203 |

TABLE 19

HLA-A1

| PEPTIDE | SEQUENCE | AVERAGE RATIO TO 982.07 | SUBSTI- TUTION | SEQ ID NO: |
|---|---|---|---|---|
| 982.01 | ATDKAAAAY | Motif | — | 141 |
| 982.07 | ATAKAAAAY | 1 | — | 140 |
| 982.01 | AADKAAAAY | 0.14 | position 3 | 139 |
| 954.03 | AAEKAAAAY | 0.038 | no T in pos 2 | 204 |
| 982.02 | AAAKAAAAY | 0.0055 | | 205 |
| 982.06 | AASKAAAAY | 0.0024 | | 206 |
| 982.04 | AANKAAAAY | 0.0011 | | 207 |
| 982.03 | AAQKAAAAY | 0.0008 | | 208 |
| 982.05 | AAKKAAAAY | <0.0001 | | 209 |
| 982.20 | AADKAAAAA | 0.0016 | position 9 | 210 |
| 982.21 | AADKAAAAW | 0.0005 | no T in pos 2 | 211 |
| 982.19 | AADKAAAAF | <0.0001 | | 212 |
| 982.22 | AADKAAAAK | <0.0001 | | 213 |

TABLE 20(A)

HPV16 E6 AND E7 PEPTIDES BINDING TO HLA-A1

| Orgin | First aa Position | Sequence* | Binding Ratio to Standard[+] | Motif Pre- diction | SEQ ID NO: |
|---|---|---|---|---|---|
| E6 | 80 | ISEYRHYAY | 3.500 | + | 134 |
| E6 | 69 | VADKALKFY | 0.240 | + | 136 |
| E7 | 44 | QAEPDRAHY | 0.029 | + | 82 |
| E7 | 37 | EIDGPAGQA | 0.025 | − | 214 |
| E7 | 19 | TTDLYAYEQ | 0.023 | + | 215 |
| E6 | 144 | MSAARSSRT | 0.019 | +/− | 216 |
| E7 | 73 | HVDIRTLED | 0.014 | − | 217 |
| E6 | 139 | WTGRAMSAA | 0.010 | − | 218 |
| E6 | 61 | YRDGNPYAV | 0.008 | − | 219 |

*Bold A's indicate residues in which cysteine was replaced by alanine.
[++]The average $IC_{50}$ value ±SE of the standard in the course of the experiments considered in this table was 81 ± 30 nM. Listed in the table are peptides yielding ratio values of ≥0.001. All other peptides yielded ratio values of ≤0.001.

TABLE 20(B)

HPV16 E6 and E7 Peptides Binding to HLA-A3.2

| Orgin | First aa Position | Sequence* | Binding Ratio to Standard[+] | Motif Pre- diction | SEQ ID NO: |
|---|---|---|---|---|---|
| E6 | 107 | LIRAINAQK | 3.7000 | + | 220 |
| E6 | 59 | IVYRDGNPY | 3.0000 | + | 133 |
| E7 | 89 | IVAPIASQK | 2.2000 | + | 221 |
| E6 | 33 | IILEAVYAK | 1.5000 | + | 222 |
| E6 | 125 | HLDKKQRFH | 0.4400 | + | 223 |
| E6 | 143 | AMSAARSSR | 0.1800 | + | 224 |
| E6 | 7 | AMFQDPQER | 0.1000 | + | 225 |
| E6 | 93 | TTLEQQYNK | 0.0780 | + | 78 |
| E6 | 37 | AVYAKQQLL | 0.0320 | − | 226 |
| E7 | 51 | HYNIVTFAA | 0.0210 | − | 227 |
| E6 | 145 | SAARSSRTR | 0.0200 | + | 228 |
| E6 | 75 | KFYSKISEY | 0.0100 | + | 229 |
| E6 | 89 | SLYGTTLEQ | 0.0080 | + | 230 |
| E7 | 52 | YNIVTFAAK | 0.0067 | − | 231 |
| E6 | 80 | ISEYRHYAY | 0.0064 | + | 134 |
| E6 | 42 | QQLLRREVY | 0.0058 | − | 135 |
| E6 | 68 | AVADKALKF | 0.0056 | + | 232 |
| E6 | 97 | QQYNKPLAD | 0.0045 | − | 233 |
| E6 | 79 | KISEYRHYA | 0.0044 | − | 234 |
| E6 | 84 | RHYAYSLYG | 0.0036 | − | 235 |
| E6 | 69 | VADKALKFY | 0.0025 | + | 136 |
| E6 | 146 | AARSSRTRR | 0.0020 | + | 236 |
| E7 | 58 | AAKADSTLR | 0.0016 | + | 237 |
| E6 | 38 | VYAKQQLLR | 0.0012 | − | 238 |

TABLE 20(B)-continued

HPV16 E6 and E7 Peptides Binding to HLA-A3.2

| Orgin | First aa Position | Sequence* | Binding Ratio to Standard+ | Motif Prediction | SEQ ID NO: |
|---|---|---|---|---|---|
| E6 | 67 | YAVADKALK | 0.0012 | + | 239 |
| E7 | 60 | KADSTLRLA | 0.0012 | – | 240 |

*Bold A's indicate residues in which cysteine was replaced by alanine.

++The average IC$_{50}$ value ±SE of the standard in the course of the experiments considered in this table was 30 ± 3 nM. Listed in the table are peptides yielding ratio value of ≧0.001. All other peptides yielded ratio values of ≦0.001.

TABLE 20(C)

HPV16 E6 and E7 Peptides Binding to HLA-A11.2

| Orgin | First aa Position | Sequence* | Binding Ratio to Standard+ | Motif Prediction | SEQ ID NO: |
|---|---|---|---|---|---|
| E6 | 33 | IILEAVYAK | 6.7000 | + | 222 |
| E6 | 93 | TTLEQQYNK | 1.8000 | + | 78 |
| E7 | 89 | IVAPIASQK | 1.3000 | + | 241 |
| E6 | 7 | AMFQDPQER | 0.8400 | +/– | 225 |
| E6 | 59 | IVYRDGNPY | 0.4700 | – (+)§ | 133 |
| E6 | 80 | ISEYRHYAY | 0.4300 | – (+)§ | 134 |
| E6 | 37 | AVYAKQQLL | 0.0450 | – | 226 |
| E6 | 145 | SAARSSRTR | 0.0330 | +/– | 228 |
| E6 | 107 | LIRAINAQK | 0.0120 | + | 220 |
| E7 | 58 | AAKADSTLR | 0.0110 | +/– | 237 |
| E6 | 42 | QQLLRREVY | 0.0084 | +/– (+)§ | 135 |
| E6 | 143 | AMSAARSSR | 0.0084 | – | 224 |
| E6 | 79 | KISEYRHYA | 0.0076 | – | 234 |
| E6 | 67 | YAVADKALK | 0.0074 | + | 239 |
| E7 | 52 | YNIVTFAAK | 0.0060 | + | 231 |
| E6 | 68 | AVADKALKF | 0.0037 | – | 232 |
| E6 | 69 | VADKALKFY | 0.0030 | – (+)§ | 136 |
| E6 | 38 | VYAKQQLLR | 0.0022 | +/– | 238 |
| E6 | 140 | TGRAMSAAR | 0.0012 | +/– | 242 |

TABLE 20(C)-continued

HPV16 E6 and E7 Peptides Binding to HLA-A11.2

| Orgin | First aa Position | Sequence* | Binding Ratio to Standard+ | Motif Prediction | SEQ ID NO: |
|---|---|---|---|---|---|
| E7 | 90 | VAPIASQKP | 0.0012 | – | 243 |
| E7 | 51 | HYNIVTFAA | 0.0010 | – | 227 |

*Bold A's indicate residues in which cysteine was replaced by alanine.

++The average IC$_{50}$ value ±SE of the standard in the course of the experiments considered in this table was 10 ± 3 nM. Listed in the table are peptides yielding ratio value of ≧0.001. All other peptides yielded ratio values of ≦0.001.

§Brackets indicate score according to adjusted motif.

TABLE 20(D)

HPV16 E6 and E7 Peptides Binding to HLA-A24

| Orgin | First aa Position | Sequence* | Binding Ratio to Standard+ | Motif Prediction | SEQ ID NO: |
|---|---|---|---|---|---|
| E6 | 87 | AYSLYGTTL | 0.1200 | + | 244 |
| E6 | 72 | KALKFYSKI | 0.1100 | – (+)§ | 137 |
| E6 | 131 | RFHNIRGRW | 0.1000 | + | 245 |
| E7 | 49 | RAHYNIVTF | 0.0670 | – (+)§ | 138 |
| E6 | 49 | VYDFAFRDL | 0.0610 | + | 246 |
| E6 | 82 | EYRHYAYSL | 0.0460 | + | 247 |
| E6 | 26 | LQTTIHDII | 0.0200 | – | 248 |
| E6 | 66 | PYAVADKAL | 0.0055 | – | 249 |
| E6 | 1 | MHQKRTAMF | 0.0049 | – | 250 |
| E6 | 85 | HYAYSLYGT | 0.0037 | – | 251 |
| E6 | 44 | LLRREVYDF | 0.0023 | + | 252 |
| E6 | 38 | VYAKQQLLR | 0.0011 | – | 253 |

*Bold A's indicate residues in which cysteine was replaced by alanine.

++The average IC$_{50}$ value ±SE of the standard in the course of the experiments considered in this table was 22 ± 6 nM. Listed in the table are peptides yielding ratio value of ≧0.001. All other peptides yielded ratio values of ≦0.001.

Brackets indicate score according to adjusted motif.

TABLE 20(E)

SUMMARY OF EFFICACY OF 2, (3), 9 ANCHOR MOTIFS

| Percentage Binders with Motifs | HLA Allele | | | |
|---|---|---|---|---|
| | A1 Predicted/Found | A3.2 Predicted/Found | A11.2 Predicted/Found | A24 Predicted/Found |
| High (≧0.1) | 2 2(100%) | 7 7(100%) | 6 6(100%) | 2 3(67%) |
| Intermediate (0.1–0.01) | 3 6(50%) | 3 5(60%) | 3 4(75%) | 2 4(50%) |
| Weak (0.01–0.001) | 0 1(0%) | 6 14(43%) | 6 11(55%) | 1 5(20%) |
| Negative (≦0.001) | 7 231(3%) | 16 214(7%) | 14 219(6%) | 2 228(1%) |
| Totals | 12 240 | 32 240 | 26 240 | 7 240 |

TABLE 21(A)

A3.2 9-MER OPTIMAL MOTIFS

| 9-mers | GOOD BINDERS | INTERMEDIATE BINDERS | WEAK BINDERS | NON-BINDERS | TOTAL |
|---|---|---|---|---|---|
| IK | 3(15%) | 4(26%) | 7(35%) | 6(30%) | 20(100%) |
| IR | 3(15.8%) | 4(21.1%) | 7(36.8%) | 5(26.3%) | 19(100%) |
| LK | 13(48.1%) | 6(22.2%) | 5(18.5%) | 3(11.1%) | 27(100%) |
| LR | 4(8.5%) | 9(19.1%) | 20(42.6%) | 14(29.8%) | 47(100%) |
| SK | 0 | 0 | 0 | 0 | 0 |
| SR | 0 | 0 | 0 | 1(100%) | 1(100%) |
| TK | 3(15%) | 6(30%) | 7(35%) | 4(20%) | 20(100%) |
| TR | 2(16.7%) | 1(6.0%) | 2(16.7%) | 7(58.3%) | 12(100%) |
| VK | 9(28.1%) | 13(40.6%) | 9(28.1%) | 1(3.1%) | 32(100%) |
| VR | 2(7.4%) | 3(11.1%) | 14(51.9%) | 8(29.6%) | 27(100%) |
| Total | 39(19%) | 46(22.4%) | 71(34.6%) | 49(23.9%) | 205(100%) |

TABLE 21(B)

A11 9-MER OPTIMAL MOTIFS

| 9-mers | GOOD BINDERS | INTERMEDIATE BINDERS | WEAK BINDERS | NON-BINDERS | TOTAL |
|---|---|---|---|---|---|
| GK | 0 | 1(100%) | 0 | 0 | 1(100%) |
| IK | 5(25%) | 5(25%) | 7(35%) | 3(15%) | 20(100%) |
| LK | 6(22.2%) | 10(37%) | 9(33.3%) | 2(7.4%) | 27(100%) |
| TK | 10(50%) | 4(20%) | 4(20%) | 2(10%) | 20(100%) |
| VK | 12(37.5%) | 15(46.9%) | 4(12.5%) | 1(3.1%) | 32(100%) |
| Total | 33(33%) | 35(35%) | 24(24%) | 8(8%) | 100(100%) |

TABLE 22(A)

A3.2 10-MER OPTIMAL MOTIFS

| 10-mers | GOOD BINDERS | INTERMEDIATE BINDERS | WEAK BINDERS | NON-BINDERS | TOTAL |
|---|---|---|---|---|---|
| AK | 1(33.3%) | 1(33.3%) | 1(33.3%) | 0 | 3(100%) |
| AR | 0 | 0 | 1(100%) | 0 | 1(100%) |
| FK | 0 | 0 | 0 | 0 | 0 |
| FR | 0 | 0 | 1(25%) | 3(75%) | 4(100%) |
| IK | 0 | 6(27.3%) | 10(45.5%) | 6(27.3%) | 22(100%) |
| IR | 1(7.1%) | 1(7.1%) | 2(14.2%) | 10(71.4%) | 14(100%) |
| LK | 16(53.3%) | 7(23.3%) | 5(16.7%) | 2(6.7%) | 30(100%) |
| LR | 4(12.5%) | 9(28.1%) | 11(34.3%) | 8(25%) | 32(100%) |
| MK | 1(100%) | 0 | 0 | 0 | 1(100%) |
| MR | 1(100%) | 0 | 0 | 0 | 1(100%) |
| TK | 2(11.8%) | 5(29.4%) | 8(47.1%) | 2(11.8%) | 17(100%) |
| TR | 1(4.8%) | 1(4.8%) | 9(42.9%) | 10(47.6%) | 21(100%) |
| VK | 7(35%) | 4(20%) | 5(25%) | 4(20%) | 20(100%) |
| VR | 0 | 6(21.4%) | 15(53.6%) | 7(25%) | 28(100%) |
| Total | 34(17.5%) | 40(20.6%) | 68(35.1%) | 52(26.8%) | 194(100%) |

TABLE 22(B)

A11 10-MER OPTIMAL MOTIFS

| 10-mers | GOOD BINDERS | INTERMEDIATE BINDERS | WEAK BINDERS | NON-BINDERS | TOTAL |
|---|---|---|---|---|---|
| AK | 1(33.3%) | 1(33.3%) | 1(33.3%) | 0 | 3(100%) |
| CK | 0 | 0 | 1(100%) | 0 | 1(100%) |
| GK | 0 | 0 | 0 | 0 | 0 |

TABLE 22(B)-continued

A11 10-MER OPTIMAL MOTIFS

| 10-mers | GOOD BINDERS | INTERMEDIATE BINDERS | WEAK BINDERS | NON-BINDERS | TOTAL |
|---|---|---|---|---|---|
| IK | 4(18.2%) | 5(22.7%) | 12(54.5%) | 1(4.5%) | 22(100%) |
| LK | 9(30%) | 12(40%) | 8(26.7%) | 1(3.3%) | 30(100%) |
| MK | 1(100%) | 0 | 0 | 0 | 1(100%) |
| TK | 6(35.3%) | 5(29.4%) | 5(29.4%) | 1(5.9%) | 17(100%) |
| VK | 7(35%) | 8(40%) | 4(20%) | 1(5%) | 20(100%) |
| Total | 28(29.8%) | 31(33%) | 31(33%) | 4(4.3%) | 94(100%) |

TABLE 23 (a)

| Peptide | Sequence | AA | Virus | Strain | Molecule | Pos. | Motif | A1 | A2.1 | A3.2 | A11 | A24 | SEQ. ID NO: |
|---|---|---|---|---|---|---|---|---|---|---|---|---|---|
| 1.0300 | HLDMLRHLY | 9 | c-ERB2 | | | 42 | 1 | 9.1 | | 0.037 | 0.0002 | | 254 |
| 1.0346 | LLDIDETEY | 9 | c-ERB2 | | | 869 | 1 | 7.6 | | 0.0003 | 0 | | 255 |
| 1.0305 | GTQLFEDNY | 9 | c-ERB2 | | | 104 | 1 | 0.18 | | 0 | 0.028 | | 256 |
| 1.0355 | LTCSPQPEY | 9 | c-ERB2 | | | 1131 | 1 | 0.13 | | 0 | 0.0061 | | 257 |
| 1.0317 | ETLEEITGY | 9 | c-ERB2 | | | 401 | 1 | 0.043 | | | <0.0002 | | 258 |
| 1.0338 | QLVTQLMPY | 9 | c-ERB2 | | | 795 | 1 | 0.0024 | | 0.011 | 0.0039 | | 259 |
| 1.0749 | FTHQSDVWSY | 10 | c-ERB2 | | | 899 | 1 | 2.7 | | 0.0003 | 0.0005 | | 260 |
| 1.0747 | RLLDIDETEY | 10 | c-ERB2 | | | 868 | 1 | 1.3 | | 0.0017 | 0 | | 261 |
| 1.0715 | TLEEITGYLY | 10 | c-ERB2 | | | 402 | 1 | 1.1 | | 0 | 0 | | 262 |
| 1.0737 | YVMAGVGSPY | 10 | c-ERB2 | | | 772 | 1 | 1.1 | 0 | 0.010 | 0.012 | 0 | 263 |
| 1.0764 | GTPTAENPEY | 10 | c-ERB2 | | | 1239 | 1 | 0.063 | | <0.0002 | 0.0022 | | 264 |
| 1.0724 | RVLQGLPREY | 10 | c-ERB2 | | | 545 | 1 | <0.0015 | | 0.035 | 0.0050 | | 265 |
| 1.0705 | LIQRNPQLCY | 10 | c-ERB2 | | | 154 | 1 | 0.030 | | 0.0012 | <0.0002 | | 266 |
| 1.0693 | VVQGNLELTY | 10 | c-ERB2 | | | 55 | 1 | 0.018 | | 0.0024 | 0.011 | | 267 |
| 1.0756 | MGDLVDAEEY | 10 | c-ERB2 | | | 1014 | 1 | 0.012 | | <0.0002 | <0.0002 | | 268 |
| 1.1028 | KIRKYTMRR | 9 | c-ERB2 | | | 681 | 3,11 | | | 0.76 | 0.0018 | | 269 |
| 1.1027 | VVFGILIKR | 9 | c-ERB2 | | | 669 | 3,11 | | | 0.11 | 0.72 | | 270 |
| 1.0344 | LVKSPNHVK | 9 | c-ERB2 | | | 852 | 3,11 | | | 0.48 | 0.070 | | 271 |
| 1.0335 | VLRENTSPK | 9 | c-ERB2 | | | 754 | 3,11 | | | 0.40 | 0.013 | | 272 |
| 1.0329 | ILIKRRQQK | 9 | c-ERB2 | | | 673 | 3,11 | | | 0.38 | 0.0097 | | 273 |
| 1.0311 | ILWKDIFHK | 9 | c-ERB2 | | | 167 | 3,11 | | | 0.28 | 0.31 | | 274 |
| 1.1033 | KITDFGLAR | 9 | c-ERB2 | | | 860 | 3,11 | | | 0.17 | 0.24 | | 275 |
| 1.0869 | GVVFGILIK | 9 | c-ERB2 | | | 668 | 3,11 | | | 0.0047 | 0.089 | | 276 |
| 1.0299 | QVCTGTDMK | 9 | c-ERB2 | | | 24 | 3,11 | | | 0.0007 | 0.052 | | 277 |
| 1.1031 | LLDHVRENR | 9 | c-ERB2 | | | 806 | 3,11 | | | 0.037 | <0.0006 | | 278 |
| 1.1026 | CVNCSQFLR | 9 | c-ERB2 | | | 528 | 3,11 | | | 0.0015 | 0.031 | | 279 |
| 1.1023 | TVCAGGCAR | 9 | c-ERB2 | | | 218 | 3,11 | | | 0.0004 | 0.023 | | 280 |
| 1.0331 | ILKETELRK | 9 | c-ERB2 | | | 714 | 3,11 | | | 0.019 | 0.0023 | | 281 |
| 1.1024 | VTAEDGTQR | 9 | c-ERB2 | | | 322 | 3,11 | | | <0.0002 | 0.014 | | 282 |
| 1.0326 | DLSYMPIWK | 9 | c-ERB2 | | | 607 | 3,11 | | | 0.0005 | 0.010 | | 283 |
| 1.0707 | TILWKDIFHK | 10 | c-ERB2 | | | 166 | 3,11 | | | 0.043 | 3.6 | | 284 |
| 1.0712 | GTQRCEKCSK | 10 | c-ERB2 | | | 327 | 3,11 | | | 0.021 | 0.61 | | 285 |
| 1.0736 | KVLRENTSPK | 10 | c-ERB2 | | | 753 | 3,11 | | | 0.38 | 0.22 | | 286 |
| 1.0702 | QLRSLTEILK | 10 | c-ERB2 | | | 141 | 3,11 | | | 0.20 | 0.013 | | 287 |
| 1.1142 | RLVHRDLAAR | 10 | c-ERB2 | | | 840 | 3,11 | | | 0.18 | 0 | | 288 |
| 1.0741 | LLNWCMQIAK | 10 | c-ERB2 | | | 822 | 3,11 | | | 0.14 | 0.14 | | 289 |
| 1.0752 | TIDVYMIMVK | 10 | c-ERB2 | | | 948 | 3,11 | | | 0.013 | 0.12 | | 290 |
| 1.0731 | RILKETELRK | 10 | c-ERB2 | | | 713 | 3,11 | | | 0.057 | 0.11 | | 291 |
| 1.0745 | VLVKSPNHVK | 10 | c-ERB2 | | | 851 | 3,11 | | | 0.082 | 0.0072 | | 292 |
| 1.1131 | SVFQNLQVIR | 10 | c-ERB2 | | | 423 | 3,11 | | | 0.017 | 0.075 | | 293 |
| 1.1133 | HTVPWDQLFR | 10 | c-ERB2 | | | 478 | 3,11 | | | 0.0035 | 0.072 | | 294 |
| 1.1127 | ILKGGVLIQR | 10 | c-ERB2 | | | 148 | 3,11 | | | 0.040 | 0.0005 | | 295 |
| 1.1143 | LVSEFSRMAR | 10 | c-ERB2 | | | 972 | 3,11 | | | 0.0072 | 0.033 | | 296 |
| 1.1136 | GVVFGILIKR | 10 | c-ERB2 | | | 668 | 3,11 | | | 0.018 | 0.033 | | 297 |
| 1.0726 | CVARCPSGVK | 10 | c-ERB2 | | | 596 | 3,11 | | | 0.022 | 0.0042 | | 298 |
| 1.1137 | VVFGILIKRR | 10 | c-ERB2 | | | 669 | 3,11 | | | 0.0030 | 0.016 | | 299 |
| 1.0728 | GILIKRRQQK | 10 | c-ERB2 | | | 672 | 3,11 | | | 0.015 | 0.0014 | | 300 |
| 1.1129 | RTVCAGGCAR | 10 | c-ERB2 | | | 217 | 3,11 | | | 0.0068 | 0.013 | | 301 |
| 1.1134 | GLACHQLCAR | 10 | c-ERB2 | | | 508 | 3,11 | | | 0.011 | 0 | | 302 |
| 1.1139 | KIPVAIKVLR | 10 | c-ERB2 | | | 747 | 3,11 | | | 0.0009 | 0.0099 | | 303 |

TABLE 23 (b)

| Peptide | Sequence | AA | Virus | Strain | Molecule | Pos. | Motif | A1 | A2.1 | A3.2 | A11 | A24 | SEQ. ID NO: |
|---|---|---|---|---|---|---|---|---|---|---|---|---|---|
| 1.0291 | VGEADYFEY | 9 | EBNA1 | | | 409 | 1 | 0.016 | | | | | 304 |
| 1.0295 | PLRESIVCY | 9 | EBNA1 | | | 553 | 1 | 0.010 | | | | | 305 |

TABLE 23 (b)-continued

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0681 | PVGEADYFEY | 10 | EBNA1 | | | 408 | 1 | 0.015 | | | | | 306 |
| 1.0683 | GTWVAGVFVY | 10 | EBNA1 | | | 501 | 1 | 0.014 | | | | | 307 |
| 1.0293 | GVFVYGGSK | 9 | EBNA1 | | | 506 | 3,11 | | | 0.30 | 0.61 | | 308 |
| 1.1016 | KTSLYNLRR | 9 | EBNA1 | | | 514 | 3,11 | | | 0.31 | 0.12 | | 309 |
| 1.0297 | AIKDLVMTK | 9 | EBNA1 | | | 578 | 3,11 | | | 0.048 | 0.034 | | 310 |
| 1.0687 | QTHIFAEVLK | 10 | EBNA1 | | | 567 | 3,11 | | | 0.010 | 0.21 | | 311 |
| 1.1124 | GTALAIPQCR | 10 | EBNA1 | | | 523 | 3,11 | | | 0.0028 | 0.056 | | 312 |

TABLE 23 (c)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 5.0005 | CTELKLSDY | 9 | FLU | A | NP | 44 | 1 | 3.6 | | | | | 313 |
| 5.0006 | STLELRSRY | 9 | FLU | A | NP | 377 | 1 | 0.020 | | | | | 314 |
| 5.0044 | ILRGSVAHK | 9 | FLU | A | NP | 265 | 3 | | | 1.5 | 0.0037 | | 315 |
| 5.0051 | RMCNILKGK | 9 | FLU | A | NP | 221 | 3 | | | 0.27 | 0.062 | | 316 |
| 5.0046 | LMQGSTLPR | 9 | FLU | A | NP | 166 | 3 | | | 0.031 | 0.10 | | 317 |
| 5.0048 | MIDGIRFY | 9 | FLU | A | NP | 32 | 3 | | | 0.059 | 0.0010 | | 318 |
| 5.0049 | MVLSAFDER | 9 | FLU | A | NP | 66 | 3 | | | 0.0016 | 0.041 | | 319 |
| 5.0054 | YIQMCTELK | 9 | FLU | A | NP | 40 | 3 | | | 0.0031 | 0.030 | | 320 |
| 5.0042 | GINDRNFWR | 9 | FLU | A | NP | 200 | 3 | | | 0.0028 | 0.024 | | 321 |
| 5.0104 | SLMQGSTLPR | 10 | FLU | A | NP | 165 | 3 | | | 0.12 | 0.84 | | 322 |
| 5.0095 | KMIDGIGRFY | 10 | FLU | A | NP | 31 | 3 | | | 0.50 | 0.0079 | | 323 |
| 5.0096 | LILRGSVAHK | 10 | FLU | A | NP | 264 | 3 | | | 0.36 | 0.037 | | 324 |
| 5.0102 | RSGAAGAAVK | 10 | FLU | A | NP | 175 | 3 | | | 0.019 | 0.0046 | | 325 |
| 5.0105 | SSTLELRSRY | 10 | FLU | A | NP | 376 | 3 | | | 0.0018 | 0.016 | | 326 |
| 5.0103 | RSRYWAIRTR | 10 | FLU | A | NP | 382 | 3 | | | 0.012 | 0 | | 327 |
| 5.0101 | RMVLSAFDER | 10 | FLU | A | NP | 65 | 3 | | | 0.0014 | 0.010 | | 328 |
| 5.0061 | FYIQMCTEL | 9 | FLU | A | NP | 39 | 24 | | | | | 2.9 | 329 |
| 5.0060 | AYERMCNIL | 9 | FLU | A | NP | 218 | 24 | | | | | 0.031 | 330 |
| 5.0112 | RFYIQMCTEL | 10 | FLU | A | NP | 38 | 24 | | | | | 0.15 | 331 |

TABLE 23 (d)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0155 | LLDTASALY | 9 | HBV | adr | CORE | 420 | 1 | 25 | | 0.0007 | 0 | | 332 |
| 1.0186 | SLDVSAAFY | 9 | HBV | adr | POL | 1001 | 1 | 17.2 | | 0.0037 | 0.0006 | | 333 |
| 2.0125 | PTTGRTSLY | 9 | HBV | ALL | | 1,382 | 1 | 1.3 | | 0.0008 | 0 | | 334 |
| 2.0126 | MSTTDLEAY | 9 | HBV | adr | | 1,521 | 1 | 0.85 | | <0.0008 | 0 | | 335 |
| 1.0208 | PTTGRTSLY | 9 | HBV | adr | POL | 1382 | 1 | 0.77 | | 0 | 0 | | 334 |
| 1.0387 | LTKQYLNLY | 9 | HBV | adw | POL | 1280 | 1 | 0.50 | | 0.0003 | 0.0075 | | 336 |
| 1.0166 | KVGNFTGLY | 9 | HBV | adr | POL | 629 | 1 | 0.068 | | 0.30 | 0.014 | | 337 |
| 2.0127 | MSPTDLEAY | 9 | HBV | adw | | 1,550 | 1 | 0.067 | | | | | 338 |
| 2.0120 | FSQFSRGNY | 9 | HBV | ayw | | 984 | 1 | 0.057 | | | | | 339 |
| 2.0112 | PSSWAFAKY | 9 | HBV | adw | | 316 | 1 | 0.054 | | | | | 340 |
| 2.0119 | QSAYRKEAY | 9 | HBV | adw | | 881 | 1 | 0.025 | | | | | 341 |
| 1.0174 | PLDKGIKPY | 9 | HBV | adr | POL | 698 | 1 | 0.019 | | <0.0002 | <0.0002 | | 342 |
| 1.0378 | SLMLLYKTY | 9 | HBV | adw | POL | 1092 | 1 | 0.017 | | | | | 343 |
| 2.0115 | ASRDLVVSY | 9 | HBV | ayw | | 499 | 1 | 0.013 | | | | | 344 |
| 2.0124 | PSRGRLGLY | 9 | HBV | adr/adw | | 1,364 | 1 | 0.011 | | | | | 345 |
| 2.0121 | SSTSRNINY | 9 | HBV | adr | | 1,036 | 1 | 0.0097 | | | | | 346 |
| 1.0519 | DLLDTASALY | 10 | HBV | adr | CORE | 419 | 1 | 11.1 | | 0 | 0 | | 347 |
| 1.0513 | LLDPRVRGLY | 10 | HBV | adr | ENV | 120 | 1 | 6.3 | | 0.17 | 0 | | 348 |
| 2.0239 | LSLDVSAAFY | 10 | HBV | ALL | | 1,000 | 1 | 4.2 | | <0.0009 | 0.0037 | | 349 |
| 1.0911 | FLCQQYLHLY | 10 | HBV | adr | POL | 1250 | 1 | 1.1 | 0.0025 | 0.014 | 0.0048 | 0.0017 | 350 |
| 2.0216 | QTFGRKLHLY | 10 | HBV | ayw | POL | 1087 | 1 | 1.1 | | 0.0056 | 0.012 | | 351 |
| 2.0244 | KTYGRKLHLY | 10 | HBV | adw | | 1,098 | 1 | 0.69 | 0.0003 | 0.59 | 0.22 | 0 | 352 |
| 1.0791 | KTYGRKLHLY | 10 | HBV | adw | POL | 1098 | 1 | 0.57 | 0.0020 | 0.53 | 0.35 | 0.0001 | 352 |
| 2.0242 | QTFGRKLHLY | 10 | HBV | ayw | | 1,087 | 1 | 0.37 | | 0.0037 | 0.011 | | 351 |
| 1.0556 | KTFGRKLHLY | 10 | HBV | adr | POL | 1069 | 1 | 0.34 | 0.0023 | 0.094 | 0.090 | 0 | 353 |
| 2.0241 | KTFGRKLHLY | 10 | HBV | adr | | 1,069 | 1 | 0.30 | 0.0002 | 0.15 | 0.095 | 0 | 353 |
| 1.0766 | LQDPRVRALY | 10 | HBV | adw | ENV | 120 | 1 | 0.21 | | 0.014 | 0 | | 354 |
| 1.0806 | TTPAQGTSMY | 10 | HBV | adw | ENV | 288 | 1 | 0.20 | | 0 | 0 | | 355 |
| 2.0240 | LSSTSRNINY | 10 | HBV | adr | | 1,035 | 1 | 0.20 | | <0.0009 | 0 | | 356 |
| 1.0541 | PLDKGIKPYY | 10 | HBV | adr | POL | 698 | 1 | 0.16 | | 0 | 0 | | 357 |
| 2.0238 | HSASFCGSPY | 10 | HBV | ayw | | 767 | 1 | 0.15 | 0 | 0.019 | 0.017 | 0 | 358 |
| 1.0795 | FLTKQYLNLY | 10 | HBV | adw | POL | 1279 | 1 | 0.12 | | 0 | 0 | | 359 |

TABLE 23 (d)-continued

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 2.0237 | RSASFCGSPY | 10 | HBV | adr/adw |  | 738 | 1 | 0.11 | 0 | 0.033 | 0.020 | 0 | 360 |
| 1.0774 | WLWGMDIDPY | 10 | HBV | adw | CORE | 416 | 1 | 0.081 |  | <0.0002 | <0.0002 |  | 361 |
| 2.0233 | TTPAQGTSMY | 10 | HBV | ayw |  | 288 | 1 | 0.066 |  |  |  |  | 355 |
| 1.0542 | HTLWKAGILY | 10 | HBV | adr | POL | 723 | 1 | 0.030 |  |  |  |  | 362 |
| 2.0231 | TSCPPICPGY | 10 | HBV | adr |  | 226 | 1 | 0.018 |  |  |  |  | 363 |
| 2.0246 | KSVQHLESLY | 10 | HBV | adw |  | 1,161 | 1 | 0.016 |  |  |  |  | 364 |
| 1.0910 | NLYVSLLLLY | 10 | HBV | adr | POL | 1059 | 1 | 0.015 |  |  |  |  | 365 |
| 2.0089 | LLYQTFGRK | 9 | HBV | ayw | POL | 1084 | 3 |  |  | 1.8 | 0.64 |  | 366 |
| 2.0116 | IMPARFYPK | 9 | HBV | ayw |  | 713 | 3 |  |  | 0.99 | 1.5 |  | 367 |
| 2.0082 | CLHQSPVRK | 9 | HBV | ayw | POL | 867 | 3 |  |  | 0.14 | 0.025 |  | 368 |
| 5.0056 | SAICSVVRR | 9 | HBV |  | POL | 531 | 3 |  |  | <0.0003 | 0.067 |  | 369 |
| 2.0077 | HLHQDIIKK | 9 | HBV | ayw | POL | 686 | 3 |  |  | 0.041 | 0.0075 |  | 370 |
| 2.0219 | SLPQEHIIQK | 10 | HBV | ayw | POL | 1197 | 3 |  |  | 0.36 | 4.2 |  | 371 |
| 2.0234 | SMFPSCCCTK | 10 | HBV | adr/adw |  | 295 | 3 |  |  | 0.43 | 1.9 |  | 372 |
| 2.0235 | SMYPSCCCTK | 10 | HBV | ayw |  | 295 | 3 |  |  | 1.1 | 1.79 |  | 373 |
| 5.0107 | QAFTFSPTYK | 10 | HBV |  | POL | 665 | 3 |  |  | 0.15 | 1.3 |  | 374 |
| 2.0214 | LLLYQTFGRK | 10 | HBV | ayw | POL | 1083 | 3 |  |  | 0.89 | 0.021 |  | 375 |
| 2.0245 | YMDDVVLGAK | 10 | HBV | ALL |  | 1,123 | 3 |  |  | 0.16 | 0.0076 |  | 376 |
| 5.0108 | TSAICSVVRR | 10 | HBV |  | POL | 530 | 3 |  |  | 0.0006 | 0.013 |  | 377 |
| 2.0094 | PTYKAFLCK | 9 | HBV | ayw | POL | 1263 | 11 |  |  | 0.030 | 0.085 |  | 378 |
| 2.0068 | PTDLEAYFK | 9 | HBV | adw | "χ" | 1552 | 11 |  |  | 0.0002 | 0.016 |  | 379 |
| 2.0061 | KYTSFPWLL | 9 | HBV | ALL |  | 1,330 | 24 |  |  |  |  | 3.6 | 380 |
| 2.0059 | LYAAVTNFL | 9 | HBV | adw |  | 1,169 | 24 |  |  |  |  | 3.2 | 381 |
| 2.0046 | FYPNLTKYL | 9 | HBV | adr |  | 689 | 24 |  |  |  |  | 2.1 | 382 |
| 2.0045 | LYSSTVPSF | 9 | HBV | adw/ayw |  | 665 | 24 |  |  |  |  | 1.9 | 383 |
| 2.0048 | FYPKVTKYL | 9 | HBV | ayw |  | 718 | 24 |  |  |  |  | 1.7 | 384 |
| 2.0049 | FYPNVTKYL | 9 | HBV | adw |  | 718 | 24 |  |  |  |  | 1.6 | 385 |
| 2.0039 | LYSILSPFL | 9 | HBV | ayw |  | 368 | 24 |  |  |  |  | 0.50 | 386 |
| 2.0044 | LYSSTVPVL | 9 | HBV | adr |  | 636 | 24 |  |  |  |  | 0.37 | 387 |
| 2.0038 | LYNILSPFL | 9 | HBV | adr |  | 368 | 24 |  |  |  |  | 0.34 | 388 |
| 2.0051 | NYRVSWPKF | 9 | HBV | ayw |  | 991 | 24 |  |  |  |  | 0.18 | 389 |
| 2.0050 | HYFQTRHYL | 9 | HBV | adw/ayw |  | 743 | 24 |  |  |  |  | 0.15 | 390 |
| 2.0047 | HYFKTRHYL | 9 | HBV | adr |  | 714 | 24 |  |  |  |  | 0.057 | 391 |
| 2.0060 | GYPALMPLY | 9 | HBV | ALL |  | 1,224 | 24 |  |  |  |  | 0.049 | 392 |
| 5.0062 | AYRPPNAPI | 9 | HBV | NUC; χNUCFUS |  | 131 | 24 |  |  |  |  | 0.026 | 393 |
| 2.0054 | LYQTFGRKL | 9 | HBV | ayw |  | 1,085 | 24 |  |  |  |  | 0.014 | 394 |
| 2.0043 | SYQHFRRLL | 9 | HBV | ayw |  | 607 | 24 |  |  |  |  | 0.011 | 395 |
| 2.0181 | LYSHPIILGF | 10 | HBV | ALL |  | 1,077 | 24 |  |  |  |  | 1.1 | 396 |
| 2.0182 | LYAAVTNFLL | 10 | HBV | adw |  | 1,169 | 24 |  |  |  |  | 0.32 | 397 |
| 2.0188 | LYRPLLSLPF | 10 | HBV | adr |  | 1,371 | 24 |  |  |  |  | 0.25 | 398 |
| 2.0174 | SYQHFRRLLL | 10 | HBV | ayw |  | 607 | 24 |  |  |  |  | 0.16 | 399 |
| 2.0173 | SYQHFRKLLL | 10 | HBV | adr/adw |  | 578 | 24 |  |  |  |  | 0.066 | 400 |
| 2.0176 | YYPEHLVNHY | 10 | HBV | ayw |  | 735 | 24 |  |  |  |  | 0.040 | 401 |
| 2.0172 | AYRPPNAPIL | 10 | HBV | ALL |  | 521 | 24 |  |  |  |  | 0.022 | 402 |
| 2.0171 | GYRWMCLRRF | 10 | HBV | ALL |  | 234 | 24 |  |  |  |  | 0.011 | 403 |
| 5.0115 | NFLLSLGIHL | 10 | HBV |  | POL | 572 | 24 |  |  |  |  | 0.0099 | 404 |
| 1.0377 | YVSLMLLYK | 9 | HBV | adw | POL | 1090 | 3,11 |  |  | 0.31 | 7.4 |  | 405 |
| 1.0189 | LLYKTFGRK | 9 | HBV | adr | POL | 1066 | 3,11 |  |  | 5.0 | 0.30 |  | 406 |
| 1.0379 | LLYKTYGRK | 9 | HBV | adw | POL | 1095 | 3,11 |  |  | 2.5 | 0.40 |  | 407 |
| 1.0370 | VTKYLPLDK | 9 | HBV | adw | POL | 722 | 3,11 |  |  | 0.014 | 1.3 |  | 408 |
| 1.0176 | RHYLHTLWK | 9 | HBV | adr | POL | 719 | 3,11 |  |  | 1.2 | 0.010 |  | 409 |
| 1.0367 | STVPSFNPK | 9 | HBV | adw | POL | 668 | 3,11 |  |  | 0.021 | 0.93 |  | 410 |
| 1.0215 | TTDLEAYFK | 9 | HBV | adr | "χ" | 1523 | 3,11 |  |  | 0.0006 | 0.92 |  | 411 |
| 1.0848 | YVSLLLLYK | 9 | HBV | adr | POL | 1061 | 3,11 |  |  | 0.39 | 0.92 |  | 412 |
| 1.0383 | PTYKAFLTK | 9 | HBV | adw | POL | 1274 | 3,11 |  |  | 0.17 | 0.71 |  | 413 |
| 1.0987 | HLYPVARQR | 9 | HBV | adr | POL | 1257 | 3,11 |  |  | 0.54 | 0.0020 |  | 414 |
| 1.0358 | STNRQLGRK | 9 | HBV | adw | ENV | 85 | 3,11 |  |  | 0.51 | 0.34 |  | 415 |
| 1.0991 | ALRFTSARR | 9 | HBV | adr | "χ" | 1488 | 3,11 |  |  | 0.44 | <0.0005 |  | 416 |
| 1.0197 | PVNRPIDWK | 9 | HBV | adr | POL | 1197 | 3,11 |  |  | 0.080 | 0.41 |  | 417 |
| 1.0369 | TVNENRRLK | 9 | HBV | adw | POL | 703 | 3,11 |  |  | 0.016 | 0.40 |  | 418 |
| 1.1041 | VVNHYFQTR | 9 | HBV | adw | POL | 740 | 3,11 |  |  | 0.030 | 0.33 |  | 419 |
| 1.0152 | STTSTGPCK | 9 | HBV | adr | ENV | 277 | 3,11 |  |  | 0.011 | 0.29 |  | 420 |
| 1.0213 | QVLPKLLHK | 9 | HBV | adr | "χ" | 1505 | 3,11 |  |  | 0.10 | 0.28 |  | 421 |
| 1.0172 | LTKYLPLDK | 9 | HBV | adr | POL | 693 | 3,11 |  |  | 0.0039 | 0.23 |  | 422 |
| 1.0374 | CLHQSAVRK | 9 | HBV | adw | POL | 878 | 3,11 |  |  | 0.22 | 0.017 |  | 423 |
| 1.0980 | VVDFSQFSR | 9 | HBV | adr | POL | 963 | 3,11 |  |  | 0.011 | 0.20 |  | 424 |
| 1.0382 | PLYACIQAK | 9 | HBV | adw | POL | 1259 | 3,11 |  |  | 0.18 | 0.034 |  | 425 |
| 2.0074 | YVNTNMGLK | 9 | HBV | ayw | CORE | 507 | 3,11 |  |  | 0.16 | 0.048 |  | 426 |
| 1.0199 | PLYACIQSK | 9 | HBV | adr | POL | 1230 | 3,11 |  |  | 0.11 | 0.018 |  | 427 |
| 1.0972 | RLADEGLNR | 9 | HBV | adr | POL | 601 | 3,11 |  |  | 0.10 | 0.025 |  | 428 |
| 1.0976 | AVNHYFKTR | 9 | HBV | adr | POL | 711 | 3,11 |  |  | 0.0071 | 0.098 |  | 429 |
| 1.0975 | RLKLIMPAR | 9 | HBV | adr | POL | 680 | 3,11 |  |  | 0.095 | 0.0002 |  | 430 |
| 1.0977 | ILYKRETTR | 9 | HBV | adr | POL | 730 | 3,11 |  |  | 0.095 | <0.0005 |  | 431 |
| 1.0993 | KVFVLGGCR | 9 | HBV | adr | "χ" | 1548 | 3,11 |  |  | 0.042 | 0.082 |  | 432 |
| 1.0165 | NVSIPWTHK | 9 | HBV | adr | POL | 621 | 3,11 |  |  | 0.072 | 0.076 |  | 433 |
| 1.0982 | LLLYKTFGR | 9 | HBV | adr | POL | 1065 | 3,11 |  |  | 0.072 | 0.0045 |  | 434 |

TABLE 23 (d)-continued

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0978 | RLVFQTSTR | 9 | HBV | adr | POL | 757 | 3,11 | | | 0.068 | 0.0032 | | 435 |
| 1.0219 | FVLGGCRHK | 9 | HBV | adr | "χ" | 1550 | 3,11 | | | 0.065 | 0.019 | | 436 |
| 1.1042 | RLVLQTSTR | 9 | HBV | adw | POL | 786 | 3,11 | | | 0.064 | 0.0002 | | 437 |
| 1.1043 | MLLYKTYGR | 9 | HBV | adw | POL | 1094 | 3,11 | | | 0.061 | 0.0032 | | 438 |
| 1.0170 | TVNEKRRLK | 9 | HBV | adr | POL | 674 | 3,11 | | | 0.048 | 0.037 | | 439 |
| 1.1045 | NLYPVARQR | 9 | HBV | adw | POL | 1286 | 3,11 | | | 0.042 | 0.0011 | | 440 |
| 1.1046 | LPYRPTTGR | 9 | HBV | adw | POL | 1407 | 3,11 | | | 0.021 | 0 | | 441 |
| 1.0845 | LVSFGVWIR | 9 | HBV | adr | CORE | 509 | 3,11 | | | 0.0033 | 0.020 | | 442 |
| 1.0981 | LVGSSGLPR | 9 | HBV | adr | POL | 1022 | 3,11 | | | 0.0008 | 0.015 | | 443 |
| 1.0967 | HISCLTFGR | 9 | HBV | adr | CORE | 494 | 3,11 | | | 0.013 | 0.011 | | 444 |
| 1.1047 | SVPSRLPDR | 9 | HBV | adw | POL | 1424 | 3,11 | | | 0.0007 | 0.010 | | 445 |
| 1.0989 | SVPSHLPDR | 9 | HBV | adr | POL | 1395 | 3,11 | | | 0.0004 | 0.010 | | 446 |
| 1.0564 | TLPQEHIVLK | 10 | HBV | adr | POL | 1179 | 3,11 | | | 0.092 | 5.6 | | 447 |
| 2.0205 | TVPVFNPHWK | 10 | HBV | ayw | POL | 669 | 3,11 | | | 0.0067 | 4.2 | | 448 |
| 1.0543 | TLWKAGILYK | 10 | HBV | adr | POL | 724 | 3,11 | | | 3.5 | 1.0 | | 449 |
| 1.0807 | SMYPSCCCTK | 10 | HBV | ayw | ENV | 295 | 3,11 | | | 1.5 | 3.4 | | 373 |
| 1.1153 | RLPYRPTTGR | 10 | HBV | adw | POL | 1406 | 3,11 | | | 2.8 | 0.030 | | 450 |
| 1.0584 | STTDLEAYFK | 10 | HBV | adr | "χ" | 1522 | 3,11 | | | 0.0066 | 2.7 | | 451 |
| 1.0554 | LLLYKTFGRK | 10 | HBV | adr | POL | 1065 | 3,11 | | | 2.5 | 0.012 | | 452 |
| 1.0799 | TVNAHRNLPK | 10 | HBV | adw | "χ" | 1529 | 3,11 | | | 0.82 | 0.65 | | 453 |
| 1.0586 | EAYFKDCLFK | 10 | HBV | adr | "χ" | 1527 | 3,11 | | | 0.037 | 0.74 | | 454 |
| 1.1081 | LVVDFSQFSR | 10 | HBV | adr | POL | 962 | 3,11 | | | 0.0009 | 0.63 | | 455 |
| 1.0789 | MLLYKTYGRK | 10 | HBV | adw | POL | 1094 | 3,11 | | | 0.61 | 0.020 | | 456 |
| 1.0546 | TAYSHLSTSK | 10 | HBV | adr | POL | 858 | 3,11 | | | 0.26 | 0.092 | | 457 |
| 1.0562 | SLGIHLNPNK | 10 | HBV | adr | POL | 1150 | 3,11 | | | 0.20 | 0.078 | | 458 |
| 1.1152 | RLGLYRPLLR | 10 | HBV | adw | POL | 1397 | 3,11 | | | 0.19 | 0.0049 | | 459 |
| 1.0547 | VTGGVFLVDK | 10 | HBV | adr | POL | 943 | 3,11 | | | 0.035 | 0.17 | | 460 |
| 1.1150 | RIRTPRTPAR | 10 | HBV | adw | POL | 962 | 3,11 | | | 0.17 | 0.0002 | | 461 |
| 1.0581 | TVNGHQVLPK | 10 | HBV | adr | "χ" | 1500 | 3,11 | | | 0.073 | 0.092 | | 462 |
| 1.1091 | SLPFQPTTGR | 10 | HBV | adr | POL | 1377 | 3,11 | | | 0.077 | 0.043 | | 463 |
| 1.1072 | TLPETTVVRR | 10 | HBV | adr | CORE | 532 | 3,11 | | | <0.0003 | 0.075 | | 464 |
| 1.1089 | GTDNSVVLSR | 10 | HBV | adr | POL | 1320 | 3,11 | | | 0.025 | 0.072 | | 465 |
| 1.1071 | STLPETTVVR | 10 | HBV | adr | CORE | 531 | 3,11 | | | 0.0005 | 0.068 | | 466 |
| 2.0210 | KVTKYLPLDK | 10 | HBV | ayw | POL | 721 | 3,11 | | | 0.027 | 0.053 | | 467 |
| 1.1148 | STRHGDKSFR | 10 | HBV | adw | POL | 792 | 3,11 | | | 0.0057 | 0.038 | | 468 |
| 1.0935 | VLSCWWLQFR | 10 | HBV | adw | POL | 923 | 3,11 | | | 0.029 | 0.0087 | | 469 |
| 1.0781 | NVTKYLPLDK | 10 | HBV | adw | POL | 721 | 3,11 | | | <0.0004 | 0.023 | | 470 |
| 1.1092 | RVCCQLDPAR | 10 | HBV | adr | "χ" | 1422 | 3,11 | | | 0.0019 | 0.023 | | 471 |
| 1.0793 | SLGIHLNPQK | 10 | HBV | adw | POL | 1179 | 3,11 | | | 0.017 | 0.014 | | 472 |
| 1.0909 | YLVSFGVWIR | 10 | HBV | adr | CORE | 508 | 3,11 | | | 0.015 | 0.0027 | | 473 |
| 2.0207 | FVGPLTVNEK | 10 | HBV | ayw | POL | 698 | 3,11 | | | 0.0057 | 0.015 | | 474 |
| 1.0535 | YVGPLTVNEK | 10 | HBV | adr | POL | 669 | 3,11 | | | 0.0069 | 0.014 | | 475 |
| 1.1075 | RLADEGLNRR | 10 | HBV | adr | POL | 601 | 3,11 | | | 0.013 | 0.0004 | | 476 |
| 1.1086 | IVLKLKQCFR | 10 | HBV | adr | POL | 1185 | 3,11 | | | 0.013 | 0.0024 | | 477 |
| 1.0773 | PIPSSWAFAK | 10 | HBV | adw | ENV | 314 | 3,11 | | | <0.0003 | 0.010 | | 478 |
| 1.0778 | LTVNENRRLK | 10 | HBV | adw | POL | 702 | 3,11 | | | 0.0025 | 0.0095 | | 479 |

TABLE 23 (e)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0118 | CTCGSSDLY | 9 | HCV | | LORF | 1123 | 1 | 3.0 | | 0 | 0.010 | | 480 |
| 1.0112 | NIVDVQYLY | 9 | HCV | | NS1/ENV2 | 697 | 1 | 0.60 | | 0 | 0.010 | | 481 |
| 2.0034 | VQDCNCSIY | 9 | HCV | | | 302 | 1 | 0.54 | | 0.0005 | 0.0003 | | 120 |
| 2.0035 | LTPRCMVDY | 9 | HCV | | | 605 | 1 | 0.078 | | | | | 122 |
| 1.0145 | RVCEKMALY | 9 | HCV | | LORF | 2588 | 1 | 0.053 | | | | | 482 |
| 1.0140 | DVVCCSMSY | 9 | HCV | | LORF | 2416 | 1 | 0.039 | | | | | 483 |
| 2.0036 | FTIFKIRMY | 9 | HCV | | | 626 | 1 | 0.012 | | | | | 123 |
| 1.0509 | GLSAFSLHSY | 10 | HCV | | LORF | 2888 | 1 | 0.41 | 0.0002 | 0.013 | 0.0034 | 0.0002 | 484 |
| 1.0489 | TLHGPTPLLY | 10 | HCV | | LORF | 1617 | 1 | 0.30 | | 0.11 | 0.0024 | | 485 |
| 2.0037 | EYVLLLFLL | 9 | HCV | | | 719 | 24 | | | | | 1.4 | 486 |
| 2.0169 | MYVGGVEHRL | 10 | HCV | | | 633 | 24 | | | | | 0.026 | 487 |
| 2.0170 | EYVLLLFLLL | 10 | HCV | | | 719 | 24 | | | | | 0.010 | 488 |
| 1.0139 | SVPAEILRK | 9 | HCV | | LORF | 2269 | 3,11 | | | 0.016 | 0.87 | | 489 |
| 1.0955 | QLFTFSPRR | 9 | HCV | | ENV1 | 290 | 3,11 | | | 0.75 | 0.033 | | 490 |
| 1.0090 | RLGVRATRK | 9 | HCV | | CORE | 43 | 3,11 | | | 0.74 | 0.16 | | 119 |
| 1.0123 | LIFCHSKKK | 9 | HCV | | LORF | 1391 | 3,11 | | | 0.54 | 0.19 | | 491 |
| 1.0122 | HLIFCHSKK | 9 | HCV | | LORF | 1390 | 3,11 | | | 0.25 | 0.010 | | 492 |
| 1.0952 | KTSERSQPR | 9 | HCV | | CORE | 51 | 3,11 | | | 0.16 | 0.064 | | 493 |
| 1.0120 | AVCTRGVAK | 9 | HCV | | LORF | 1183 | 3,11 | | | 0.016 | 0.038 | | 494 |
| 1.0143 | EVFCVQPEK | 9 | HCV | | LORF | 2563 | 3,11 | | | 0.0019 | 0.033 | | 495 |
| 1.0137 | ITRVESENK | 9 | HCV | | LORF | 2241 | 3,11 | | | 0.015 | 0.0079 | | 496 |

TABLE 23 (e)-continued

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0957 | CIITSLTGR | 9 | HCV | | LORF | 1042 | 3,11 | | | 0.0095 | 0.011 | | 497 |
| 1.0496 | GVAGALVAFK | 10 | HCV | | LORF | 1858 | 3,11 | | | 0.87 | 1.1 | | 498 |
| 1.0480 | HLHAPTGSGK | 10 | HCV | | LORF | 1227 | 3,11 | | | 0.57 | 0.0051 | | 499 |
| 1.1062 | RMYVGGVEHR | 10 | HCV | | NS1/ENV2 | 632 | 3,11 | | | 0.27 | 0.012 | | 500 |
| 1.0485 | HLIFCHSKKK | 10 | HCV | | LORF | 1390 | 3,11 | | | 0.27 | 0.025 | | 501 |
| 1.0484 | TLGFGAYMSK | 10 | HCV | | LORF | 1261 | 3,11 | | | 0.17 | 0.13 | | 502 |
| 1.1067 | GVGIYLLPNR | 10 | HCV | | LORF | 3002 | 3,11 | | | 0.0029 | 0.032 | | 503 |
| 1.1063 | LLFLLLADAR | 10 | HCV | | NS1/ENV2 | 723 | 3,11 | | | 0.015 | 0 | | 504 |

TABLE 23(f)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0014 | FRDYVDRFY | 9 | HIV | | GAG | 298 | 1 | 0.090 | | | | | 505 |
| 2.0129 | IYQYMDDLY | 9 | HIV | | | 875 | 1 | 0.064 | | | | | 506 |
| 1.0028 | TVLDVGDAY | 9 | HIV | | POL | 802 | 1 | 0.018 | | <0.0002 | 0.0056 | | 507 |
| 1.0412 | VTVLDVGDAY | 10 | HIV | | POL | 801 | 1 | 0.28 | | 0 | 0.0004 | | 508 |
| 1.0415 | VIYQYMDDLY | 10 | HIV | | POL | 874 | 1 | 0.25 | | 0.0007 | 0.0090 | | 509 |
| 2.0252 | VTVLDVGDAY | 10 | HIV | | | 801 | 1 | 0.088 | | | | | 508 |
| 1.0431 | EVNIVTDSQY | 10 | HIV | | POL | 1187 | 1 | 0.053 | | | | | 510 |
| 1.0441 | LVAVHVASGY | 10 | HIV | | POL | 1329 | 1 | 0.039 | | | | | 511 |
| 1.0442 | PAETGQETAY | 10 | HIV | | POL | 1345 | 1 | 0.013 | | | | | 512 |
| 2.0251 | ISKIGPENPY | 10 | HIV | | | 742 | 1 | 0.013 | | | | | 513 |
| 2.0255 | QMAVFIHNFK | 10 | HIV | | | 1,432 | 3 | | | 0.61 | 0.64 | | 514 |
| 2.0064 | RYLKDQQLL | 9 | HIV | | | 2,778 | 24 | | | | | 0.76 | 515 |
| 2.0134 | RYLKDQQLL | 9 | HIV | | | 2,778 | 24 | | | | | 0.32 | 515 |
| 2.0065 | TYQIYQEPF | 9 | HIV | | | 1,033 | 24 | | | | | 0.30 | 516 |
| 2.0131 | TYQIYQEPF | 9 | HIV | | | 1,033 | 24 | | | | | 0.20 | 516 |
| 2.0063 | IYQEPFKNL | 9 | HIV | | | 1,036 | 24 | | | | | 0.052 | 517 |
| 2.0132 | IYQEPFKNL | 9 | HIV | | | 1,036 | 24 | | | | | 0.033 | 517 |
| 2.0066 | IYQYMDDLY | 9 | HIV | | | 875 | 24 | | | | | 0.013 | 518 |
| 2.0247 | IYKRWIILGL | 10 | HIV | | | 266 | 24 | | | | | 0.017 | 519 |
| 2.0190 | IYKRWIILGL | 10 | HIV | | | 266 | 24 | | | | | 0.014 | 519 |
| 2.0249 | LYPLASLRSL | 10 | HIV | | | 506 | 24 | | | | | 0.014 | 520 |
| 1.0069 | KLAGRWPVK | 9 | HIV | | POL | 1358 | 3,11 | | | 2.7 | 0.069 | | 521 |
| 1.0944 | AVFIHNFKR | 9 | HIV | | POL | 1434 | 3,11 | | | 0.17 | 1.8 | | 522 |
| 1.0032 | AIFQSSMTK | 9 | HIV | | POL | 853 | 3,11 | | | 1.1 | 0.96 | | 523 |
| 1.0046 | IVIWGKTPK | 9 | HIV | | POL | 1075 | 3,11 | | | 0.085 | 0.37 | | 524 |
| 1.0079 | KLTEDRWNK | 9 | HIV | | VIF | 1712 | 3,11 | | | 0.013 | 0.27 | | 525 |
| 1.0027 | GIPHPAGLK | 9 | HIV | | POL | 788 | 3,11 | | | 0.23 | 0.065 | | 526 |
| 1.0059 | QIIEQLIKK | 9 | HIV | | POL | 1215 | 3,11 | | | 0.0091 | 0.16 | | 527 |
| 1.0939 | KIWPSYKGR | 9 | HIV | | GAG | 443 | 3,11 | | | 0.12 | 0.0005 | | 528 |
| 1.0072 | IIATDIQTK | 9 | HIV | | POL | 1458 | 3,11 | | | 0.025 | 0.098 | | 529 |
| 1.0036 | MGYELHPDK | 9 | HIV | | POL | 925 | 3,11 | | | 0.064 | 0.096 | | 530 |
| 1.0062 | YLAWVPAHK | 9 | HIV | | POL | 1227 | 3,11 | | | 0.077 | 0.057 | | 531 |
| 1.0938 | KIWPSHKGR | 9 | HIV | | GAG | 443 | 3,11 | | | 0.077 | <0.0005 | | 532 |
| 1.0047 | FVNTPPLVK | 9 | HIV | | POL | 1111 | 3,11 | | | 0.012 | 0.066 | | 533 |
| 1.0024 | NTPVFAIKK | 9 | HIV | | POL | 752 | 3,11 | | | 0.033 | 0.060 | | 534 |
| 1.0080 | TVQCTHGIK | 9 | HIV | | ENV | 2420 | 3,11 | | | 0.0021 | 0.046 | | 535 |
| 1.0013 | ILDIRQGPK | 9 | HIV | | GAG | 287 | 3,11 | | | 0.042 | 0.0048 | | 536 |
| 1.0015 | RDYVDRFYK | 9 | HIV | | GAG | 299 | 3,11 | | | 0.0007 | 0.040 | | 537 |
| 1.0058 | GIIQAQPDK | 9 | HIV | | POL | 1199 | 3,11 | | | <0.0009 | 0.040 | | 538 |
| 1.0064 | VLFLDGIDK | 9 | HIV | | POL | 1254 | 3,11 | | | 0.038 | 0.032 | | 539 |
| 1.0026 | LVDFRELNK | 9 | HIV | | POL | 769 | 3,11 | | | 0.011 | 0.030 | | 540 |
| 1.0078 | KVVPRRKAK | 9 | HIV | | POL | 1513 | 3,11 | | | 0.029 | 0.0039 | | 541 |
| 1.0942 | MTKILEPFR | 9 | HIV | | POL | 859 | 3,11 | | | <0.0008 | 0.016 | | 542 |
| 1.0463 | TVYYGVPVWK | 10 | HIV | | ENV | 2185 | 3,11 | | | 3.8 | 7.8 | | 543 |
| 1.0418 | TVQPIVLPEK | 10 | HIV | | POL | 935 | 3,11 | | | 0.16 | 5.6 | | 544 |
| 1.0447 | AVFIHNFKRK | 10 | HIV | | POL | 1434 | 3,11 | | | 0.66 | 0.85 | | 545 |
| 1.0437 | KVLFLDGIDK | 10 | HIV | | POL | 1253 | 3,11 | | | 0.36 | 0.78 | | 546 |
| 1.0408 | KLVDFRELNK | 10 | HIV | | POL | 768 | 3,11 | | | 0.51 | 0.090 | | 547 |
| 1.0403 | KLKPGMDGPK | 10 | HIV | | POL | 706 | 3,11 | | | 0.39 | 0.076 | | 548 |
| 1.0395 | FLGKIWPSYK | 10 | HIV | | GAG | 440 | 3,11 | | | 0.32 | 0.024 | | 549 |
| 1.1056 | KIQNFRVYYR | 10 | HIV | | POL | 1474 | 3,11 | | | 0.032 | 0.21 | | 550 |
| 1.0410 | GIPHPAGLKK | 10 | HIV | | POL | 788 | 3,11 | | | 0.011 | 0.17 | | 551 |
| 1.0426 | LVKLWYQLEK | 10 | HIV | | POL | 1117 | 3,11 | | | 0.056 | 0.082 | | 552 |
| 1.0398 | MIGGIGGFIK | 10 | HIV | | POL | 642 | 3,11 | | | 0.0099 | 0.055 | | 553 |
| 1.0413 | MTKILEPFRK | 10 | HIV | | POL | 859 | 3,11 | | | 0.015 | 0.038 | | 554 |
| 1.0453 | VVIQDNSDIK | 10 | HIV | | POL | 1504 | 3,11 | | | <0.0005 | 0.021 | | 555 |
| 1.0394 | FLGKIWPSHK | 10 | HIV | | GAG | 440 | 3,11 | | | 0.020 | 0.0013 | | 556 |
| 1.1059 | IVQQQNNLLR | 10 | HIV | | ENV | 2741 | 3,11 | | | 0.0024 | 0.019 | | 557 |
| 1.0417 | FTTPDKKHQK | 10 | HIV | | PCL | 909 | 3,11 | | | <0.0002 | 0.015 | | 558 |

TABLE 23(f)-continued

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0405 | LVEICTEMEK | 10 | HIV | | POL | 729 | 3,11 | | | 0.0002 | 0.012 | | 559 |
| 1.0392 | LVQNANPDCK | 10 | HIV | | GAG | 327 | 3,11 | | | <0.0002 | 0.011 | | 560 |

TABLE 23(g)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0225 | ISEYRHYCY | 9 | HPV | 16 | E6 | 80 | 1 | 7.8 | | 0.0011 | 0.036 | | 76 |
| 1.0230 | QAEPDRAHY | 9 | HPV | 16 | E7 | 44 | 1 | 0.021 | | <0.0002 | <0.0002 | | 82 |
| 1.0610 | LQDIEITCVY | 10 | HPV | 18 | E6 | 25 | 1 | 0.25 | | 0.0056 | 0.012 | | 86 |
| 2.0159 | YSKISEYRHY | 10 | HPV | 16 | E6 | 77 | 1 | 0.17 | | <0.0009 | 0 | | 75 |
| 2.0162 | YSKISEYRHY | 10 | HPV | 16 | E6 | 77 | 1 | 0.11 | | <0.0009 | 0 | | 75 |
| 1.0599 | HGDTPTLHEY | 10 | HPV | 16 | E7 | 2 | 1 | 0.087 | | <0.0002 | <0.0002 | | 80 |
| 1.0601 | QPETTDLYCY | 10 | HPV | 16 | E7 | 16 | 1 | 0.033 | | | | | 81 |
| 1.0913 | IHDIILECVY | 10 | HPV | 16 | E6 | 30 | 1 | 0.032 | | | | | 73 |
| 1.0594 | AVCDKCLKFY | 10 | HPV | 16 | E6 | 68 | 1 | 0.0095 | | 0.0052 | 0.019 | | 561 |
| 2.0160 | YSRIRELRHY | 10 | HPV | 18 | E6 | 72 | 1 | 0.018 | | <0.0002 | <0.0002 | | 88 |
| 2.0164 | YSRIRELRHY | 10 | HPV | 18 | E6 | 72 | 1 | 0.012 | | | | | 88 |
| 2.0161 | LLIRCLRCQK | 10 | HPV | 18 | E6 | 101 | 3 | | | 0.081 | 0.078 | | 90 |
| 2.0032 | HTMLCMCCK | 9 | HPV | 18 | E7 | 59 | 11 | | | 0.020 | 0.079 | | 91 |
| 2.0029 | VYCKTVLEL | 9 | HPV | 18 | E6 | 33 | 24 | | | | | 0.33 | 562 |
| 2.0027 | CYSLYGTTL | 9 | HPV | 16 | E6 | 87 | 24 | | | | | 0.057 | 563 |
| 2.0024 | VYDFAFRDL | 9 | HPV | 16 | E6 | 49 | 24 | | | | | 0.032 | 564 |
| 2.0031 | LYNLLIRCL | 9 | HPV | 18 | E6 | 98 | 24 | | | | | 0.019 | 565 |
| 2.0030 | VYGDTLEKL | 9 | HPV | 18 | E6 | 85 | 24 | | | | | 0.010 | 566 |
| 1.0239 | SVYGDTLEK | 9 | HPV | 18 | E6 | 84 | 3,11 | | | 0.39 | 2.3 | | 89 |
| 1.0243 | SVYGDTLEK | 9 | HPV | 18 | E6 | 84 | 3,11 | | | 0.55 | 1.1 | | 89 |
| 1.0244 | SVYGDTLEK | 9 | HPV | 18 | E6 | 84 | 3,11 | | | 0.70 | 0.95 | | 89 |
| 1.0226 | TTLEQQYNK | 9 | HPV | 16 | E6 | 93 | 3,11 | | | 0.010 | 0.67 | | 78 |
| 1.0241 | SIPHAACHK | 9 | HPV | 18 | E6 | 59 | 3,11 | | | 0.0094 | 0.25 | | 567 |
| 1.0237 | SIPHAACHK | 9 | HPV | 18 | E6 | 59 | 3,11 | | | 0.017 | 0.12 | | 567 |
| 1.0233 | IVCPICSQK | 9 | HPV | 16 | E7 | 89 | 3,11 | | | 0.035 | 0.023 | | 83 |
| 1.0997 | KLRHLNEKR | 9 | HPV | 18 | E6 | 117 | 3,11 | | | 0.025 | <0.0005 | | 568 |
| 1.0234 | LIRCLRCQK | 9 | HPV | 18 | E6 | 102 | 3,11 | | | 0.019 | 0.0012 | | 569 |
| 1.0853 | IILECVYCK | 9 | HPV | 16 | E6 | 33 | 3,11 | | | 0.0016 | 0.019 | | 570 |
| 1.0999 | CIDFYSRIR | 9 | HPV | 18 | E6 | 68 | 3,11 | | | 0.017 | 0.0018 | | 571 |
| 1.0998 | CIDFYSRIR | 9 | HPV | 18 | E6 | 68 | 3,11 | | | 0.010 | 0.0009 | | 571 |
| 1.0596 | GTTLEQQYNK | 10 | HPV | 16 | E6 | 92 | 3,11 | | | 0.010 | 0.98 | | 77 |
| 1.0606 | LLIRCLRCQK | 10 | HPV | 18 | E6 | 101 | 3,11 | | | 0.076 | 0.29 | | 90 |
| 1.0598 | LLIRCINCQK | 10 | HPV | 16 | E6 | 106 | 3,11 | | | 0.12 | 0.24 | | 79 |
| 1.0629 | LLIRCLRCQK | 10 | HPV | 18 | E6 | 101 | 3,11 | | | 0.16 | 0.11 | | 90 |
| 1.0614 | LTEVFEFAFK | 10 | HPV | 18 | E6 | 41 | 3,11 | | | 0.0009 | 0.11 | | 87 |
| 1.0605 | GIVCPICSQK | 10 | RPV | 16 | E7 | 88 | 3,11 | | | 0.0017 | 0.060 | | 572 |
| 1.0625 | LTEVFEFAFK | 10 | HPV | 18 | E6 | 41 | 3,11 | | | 0.0012 | 0.041 | | 87 |
| 1.0591 | DIILECVYCK | 10 | HPV | 16 | E6 | 32 | 3,11 | | | 0.0065 | 0.021 | | 573 |
| 1.1101 | KLRHLNEKRR | 10 | HPV | 18 | E6 | 117 | 3,11 | | | 0.013 | 0 | | 574 |
| 1.1095 | CVYCKQQLLR | 10 | HPV | 16 | E6 | 37 | 3,11 | | | 0.011 | 0.0059 | | 575 |

TABLE 23(h)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 2.0020 | EVDPIGHLY | 9 | MAGE | 3 | | 161 | 1 | 18 | | 0.0002 | 0.0009 | | 576 |
| 3.0172 | EADPTSNTY | 9 | MAGE | 5/51 | | 161 | 1 | 9.9 | | 0.0006 | 0.0006 | 0 | 577 |
| 1.0258 | TQDLVQEKY | 9 | MAGE | 1 | | 240 | 1 | 2.1 | | 0 | 0.0002 | | 106 |
| 3.0173 | EVDPIGHVY | 9 | MAGE | 6 | | 161 | 1 | 1.9 | | <0.0002 | <0.0002 | 0 | 578 |
| 1.0254 | EADPTGHSY | 9 | MAGE | 1 | | 161 | 1 | 1.1 | | 0 | 0 | | 99 |
| 1.0259 | LVQEKYLEY | 9 | MAGE | 1 | | 243 | 1 | 0.42 | | 0.0013 | 0.053 | | 579 |
| 6.0053 | TSYVKVLEY | 9 | MAGE | 1 | new | 275 | 1 | 0.099 | | | | | 580 |
| 2.0009 | SSLPTTMNY | 9 | MAGE | 3 | | 9 | 1 | 0.055 | | | | | 581 |
| 2.0011 | GSVVGNWQY | 9 | MAGE | 3 | | 77 | 1 | 0.050 | | | | | 582 |
| 2.0008 | SSFSTTINY | 9 | MAGE | 2 | | 9 | 1 | 0.043 | | | | | 583 |
| 1.0252 | MLESVIKNY | 9 | MAGE | 1 | | 128 | 1 | 0.011 | | | | | 97 |
| 2.0147 | ASSLPTTMNY | 10 | MAGE | 3 | | 8 | 1 | 2.6 | | <0.0009 | 0.033 | | 584 |
| 2.0167 | LTQDLVQEKY | 10 | MAGE | 1 | | 239 | 1 | 1.2 | | <0.0009 | 0.0073 | | 105 |
| 6.0114 | ETSYVKVLEY | 10 | MAGE | 1 | new | 274 | 1 | 0.56 | | | | | 585 |
| 2.0141 | ASSFSTTINY | 10 | MAGE | 2 | | 8 | 1 | 0.17 | | <0.0009 | 0.026 | | 586 |
| 1.0648 | DLVQEKYLEY | 10 | MAGE | 1 | | 242 | 1 | 0.044 | | | | | 587 |
| 6.0065 | TSYVKVLEY | 9 | MAGE | 1 | new | 275 | 3 | | | 0.71 | 0.010 | | 580 |
| 4.0119 | TTINFTRQR | 9 | MAGE | 1 | | 66 | 3 | | | 0.043 | 0.37 | | 588 |
| 6.0064 | ALAETSYVK | 9 | MAGE | 1 | new | 271 | 3 | | | 0.31 | 0.36 | | 589 |
| 4.0132 | LTQDLVQEK | 9 | MAGE | 1 | | 239 | 3 | | | <0.0003 | 0.14 | | 104 |
| 6.0062 | LVQEKYLEY | 9 | MAGE | 1 | new | 243 | 3 | | | 0.0026 | 0.034 | | 579 |

TABLE 23(h)-continued

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 4.0131 | HSAYGEPRK | 9 | MAGE | 1 | | 229 | 3 | | | 0.014 | 0.0009 | | 590 |
| 4.0122 | LFRAVITKK | 9 | MAGE | 1 | | 97 | 3 | | | 0.011 | 0.0005 | | 591 |
| 6.0124 | RVRFFFPSLR | 10 | MAGE | 1 | new | 290 | 3 | | | 0.43 | 0.0089 | | 592 |
| 4.0161 | ADLVGFLLLK | 10 | MAGE | 1 | | 107 | 3 | | | 0.35 | 0.29 | | 593 |
| 4.0160 | ESLFRAVITK | 10 | MAGE | 1 | | 95 | 3 | | | 0.14 | 0.088 | | 594 |
| 6.0119 | DLVQEKYLEY | 10 | MAGE | 1 | new | 242 | 3 | | | 0.032 | 0.0051 | | 587 |
| 6.0123 | YVIKVSARVR | 10 | MAGE | 1 | new | 283 | 3 | | | 0.019 | 0.0009 | | 595 |
| 4.0168 | LSVMEVYDGR | 10 | MAGE | 1 | | 218 | 3 | | | <0.0003 | 0.012 | | 596 |
| 4.0163 | KAEMLESVIK | 10 | MAGE | 1 | | 125 | 3 | | | <0.0003 | 0.0097 | | 597 |
| 6.0125 | RALAETSYVK | 10 | MAGE | 1 | new | 270 | 11 | | | 0.18 | 0.24 | | 598 |
| 2.0010 | NYPLWSQSY | 9 | MAGE | 3 | | 16 | 24 | | | | | 0.027 | 599 |
| 2.0165 | NYKHCFPEIF | 10 | MAGE | 1 | | 135 | 24 | | | | | 0.25 | 600 |
| 2.0151 | LYIFATCLGL | 10 | MAGE | 3 | | 115 | 24 | | | | | 0.048 | 601 |
| 6.0126 | SYVKVLEYVI | 10 | MAGE | 1 | new | 276 | 24 | | | | | 0.036 | 602 |
| 1.0248 | SLFRAVITK | 9 | MAGE | 1 | | 96 | 3,11 | | | 4.1 | 2.7 | | 93 |
| 1.1006 | SVMEVYDGR | 9 | MAGE | 1 | | 219 | 3,11 | | | 0.0093 | 1.3 | | 603 |
| 1.1004 | TTINFTRQR | 9 | MAGE | 1 | | 66 | 3,11 | | | 0.016 | 1.0 | | 588 |
| 1.0257 | LTQDLVQEK | 9 | MAGE | 1 | | 239 | 3,11 | | | 0.0002 | 0.38 | | 104 |
| 1.0634 | SLFRAVITKK | 10 | MAGE | 1 | | 96 | 3,11 | | | 1.2 | 0.98 | | 94 |
| 1.0647 | LLTQDLVQEK | 10 | MAGE | 1 | | 238 | 3,11 | | | 0.0004 | 0.16 | | 103 |
| 1.0640 | MLESVIKNYK | 10 | MAGE | 1 | | 128 | 3,11 | | | 0.14 | 0.027 | | 96 |
| 1.0644 | LLGDNQIMPK | 10 | MAGE | 1/3 | | 182 | 3,11 | | | 0.020 | 0.011 | | 100 |
| 1.0630 | SLEQRSLHCK | 10 | MAGE | 1 | | 2 | 3,11 | | | 0.015 | 0.015 | | 92 |

TABLE 23(i)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 1.0281 | GSDCTTIHY | 9 | p53 | | | 226 | 1 | 29.5 | | 0.0010 | 0.029 | | 604 |
| 1.0667 | GTAKSVTCTY | 10 | p53 | | | 117 | 1 | 0.33 | 0 | 0.023 | 0.049 | 0 | 605 |
| 1.0672 | RVEGNLRVEY | 10 | p53 | | | 196 | 1 | 0.022 | | 0.0014 | 0.0020 | | 606 |
| 1.0278 | RVPAMAIYK | 9 | p53 | | | 156 | 3,11 | | | 1.5 | 0.73 | | 607 |
| 1.0276 | CTYSPALNK | 9 | p53 | | | 124 | 3,11 | | | 0.46 | 1.1 | | 608 |
| 1.0285 | NTSSSPQPK | 9 | p53 | | | 311 | 3,11 | | | 0.0009 | 0.095 | | 609 |
| 1.0284 | RTEEENLRK | 9 | p53 | | | 283 | 3,11 | | | 0.0015 | 0.091 | | 610 |
| 1.0287 | ELNEALELK | 9 | p53 | | | 343 | 3,11 | | | 0.020 | 0.0052 | | 611 |
| 1.0678 | RTEEENLRKK | 10 | p53 | | | 283 | 3,11 | | | 3.3 | 0.0080 | | 612 |
| 1.1113 | KTYQGSYGFR | 10 | p53 | | | 101 | 3,11 | | | 2.6 | 0.88 | | 613 |
| 1.1115 | VVRRCPHHER | 10 | p53 | | | 172 | 3,11 | | | 0.099 | 0.0017 | | 614 |
| 1.0679 | NTSSSPQPKK | 10 | p53 | | | 311 | 3,11 | | | 0.0035 | 0.054 | | 615 |
| 1.1121 | RVCACPGRDR | 10 | p53 | | | 273 | 3,11 | | | 0.014 | 0.011 | | 616 |
| 1.1116 | GLAPPQHLIR | 10 | p53 | | | 187 | 3,11 | | | 0.013 | 0.0006 | | 617 |

TABLE 23(j)

| Peptide | Sequence | AA | Virus | Strain | Molecule | Pos. | Motif | A1 | A2.1 | A3.2 | A11 | A24 | SEQ ID NO: |
|---|---|---|---|---|---|---|---|---|---|---|---|---|---|
| 3.0175 | KGEYFVEMY | 9 | PAP | | | 322 | 1 | 3.4 | | <0.0002 | 0.0002 | 0 | 618 |
| 3.0174 | LGEYIRKRY | 9 | PAP | | | 81 | 1 | 0.78 | | <0.0002 | 0.0002 | 0 | 619 |
| 3.0166 | ASCHLTELY | 9 | PAP | | | 311 | 1 | 0.77 | <0.0002 | <0.0002 | 0.055 | 0 | 620 |
| 3.0163 | ESYKHEQVY | 9 | PAP | | | 95 | 1 | 0.098 | | <0.0002 | 0.0002 | 0 | 621 |
| 3.0237 | LSELSLLSLY | 10 | PAP | | | 238 | 1 | 14 | | 0.0026 | 0.0004 | 0 | 622 |
| 3.0235 | LSELSLLSLY | 10 | PAP | | | 238 | 1 | 12 | | 0.0005 | 0.0004 | 0 | 622 |
| 3.0236 | LTQLGMEQHY | 10 | PAP | | | 70 | 1 | 0.62 | 0.0005 | 0.015 | 0.0024 | 0.0022 | 623 |
| 3.0238 | KGEYFVEMYY | 10 | PAP | | | 322 | 1 | 0.018 | | 0.0057 | 0.089 | | 624 |
| 3.0230 | LVNEILNHMK | 10 | PAP | | | 263 | 3 | | | 0.056 | 0.12 | | 625 |
| 3.0158 | ATQIPSYKK | 9 | PAP | | | 274 | 11 | | | 0.10 | 1.2 | | 626 |
| 3.0231 | ETLKSEEFQK | 10 | PAP | | | 170 | 11 | | | <0.0004 | 0.014 | | 627 |
| 3.0161 | LYFEKGEYF | 9 | PAP | | | 318 | 24 | | | | | 2.5 | 628 |
| 3.0160 | LYCESVHNF | 9 | PAP | | | 213 | 24 | | | | | 0.44 | 629 |
| 3.0159 | PYKDFIATL | 9 | PAP | | | 183 | 24 | | | | | 0.11 | 630 |
| 3.0162 | VYNGLLPPY | 9 | PAP | | | 302 | 24 | | | | | 0.032 | 631 |
| 3.0232 | PYASCHLTEL | 10 | PAP | | | 309 | 24 | | | | | 0.024 | 632 |

TABLE 23(k)

| Peptide | Sequence | AA | Virus Strain | Molecule | Pos. | Motif | A1 | A3.2 | A11 | A24 | SEQ ID No: |
|---|---|---|---|---|---|---|---|---|---|---|---|
| 1.0270 | ALPERPSLY | 9 | | PSA | 231 | 1 | 0.011 | | | | 633 |
| 2.0157 | VSHSFPHPLY | 10 | | PSA | 88 | 1 | 0.15 | <0.0003 | 0.0015 | | 109 |
| 1.0265 | PLYDMSLLK | 9 | | PSA | 95 | 3,11 | | 0.24 | 0.037 | | 110 |
| 1.0273 | VVHYRKWIK | 9 | | PSA | 242 | 3,11 | | 0.0072 | 0.093 | | 116 |
| 1.0272 | YTKVVHYRK | 9 | | PSA | 239 | 3,11 | | 0.0006 | 0.058 | | 114 |
| 1.1009 | SLLFNRFLR | 9 | | PSA | 100 | 3,11 | | 0.0024 | 0.047 | | 634 |
| 1.0260 | IVGGWECEK | 9 | | PSA | 21 | 3,11 | | 0.041 | 0.019 | | 107 |
| 1.0269 | QVHPQKVTK | 9 | | PSA | 182 | 3,11 | | 0.0060 | 0.014 | | 112 |
| 1.1112 | SLYTKVVHYR | 10 | | PSA | 237 | 3,11 | | 0.28 | 0.23 | | 635 |
| 1.0653 | LTAAHCIRNK | 10 | | PSA | 57 | 3,11 | | 0.14 | 0.083 | | 108 |
| 1.0651 | RIVGGWECEK | 10 | | PSA | 20 | 3,11 | | 0.046 | 0.067 | | 636 |
| 1.0662 | KVVHYRKWIK | 10 | | PSA | 241 | 3,11 | | 0.045 | 0.045 | | 115 |
| 1.1111 | VTKFMLCAGR | 10 | | PSA | 188 | 3,11 | | 0.0003 | 0.012 | | 637 |
| 3.0108 | MLLRLSEPA | 9 | | PSA | 118 | Random | | | | | 638 |

TABLE 24

CTL EPITOPES IDENTIFIED IN PEPTIDE SCREENING.

| Sequence | Antigen | Motif | Id | SEQ ID NO: |
|---|---|---|---|---|
| EVDPIGHLY | MAGE3 | A01 | 1044.07 | 576 |
| ASSLPTTMNY | MAGE3 | A01 | 1044.01 | 584 |
| EADPTGHSY | MAGE1 | A01 | 958.01 | 99 |
| SSLPTTMNY* | MAGE3 | A01 | 1072.02* | 581 |
| GSVVGNWQY* | MAGE3 | A01 | 1072.03* | 582 |
| ALAETSYVK* | MAGE1N | A03 | 1072.38* | 589 |
| SLFRAVITK | MAGE1 | A11 | 1072.13 | 93 |
| RALAETSYVK | MAGE1N | A11 | 1072.39 | 598 |
| ESLFRAVITK | MAGE1 | A11 | 1072.15 | 594 |
| KVYLAWVPAHK | HIV | A3/11* | 1069.42 | 639 |
| TVYYGVPVWK | HIV | A03 | 1069.43 | 543 |
| KLAGRWPVK | HIV | A03 | 1069.44 | 521 |
| KMIGGIGGFIK | HIV | A03 | 1069.45 | 640 |
| AIFQSSMTK | HIV | A03 | 966.01 | 523 |
| WTYQIYQEPFK | HIV | A03 | 1069.46 | 641 |
| FLGKIWPSHK* | HIV | A03 | 1069.56* | 556 |
| TVYYGVPVWK | HIV | A11 | 1052.03 | 543 |
| VTVYYGVPVWK | HIV | A11 | 1069.47 | 642 |
| GVAGALVAFK | HCV | A03 | 1073.10 | 498 |
| CTCGSSDLY | HCV | A11 | 1069.62 | 480 |
| GVAGALVAFK | HCV | A11 | 1052.05 | 498 |
| LLDTASALY* | HBV | A01 | 1069.01* | 332 |
| TLWKAGILYK | HBV | A03 | 1069.15 | 449 |

*borderline positive

TABLE 25

Peptides Synthesized by Cytel For Loading Onto Acid Stripped Autologous PBMCs and PHA Blasts

| Peptide ID# | Antigen | Sequence | SEQ ID NO: |
|---|---|---|---|
| 777.03 | HBs | FLLTRILTI | 643 |
| 924.07 | HBc | FLPSDFFPSV | 644 |
| 927.32 | HBp | GLYSSTVPV | 645 |
| 938.01 | MAGE 1 | EADPTGHSY | 99 |
| 939.03 | PSA | VLVHPQWVL | 646 |
| 941.01 | HBc | FLPSDYFPSV | 647 |
| 1044.04 | PAP | ILLWDPIPV | 648 |
| 1044.05 | PSA | KLQCVDLVHI | 649 |
| 1044.06 | PSA | MLLRLSEPAEL | 650 |

TABLE 25 b

| Cell Population | $^{125}$I-Labeled Peptide +/− Cold Peptide | CPMS +/− std. dev. | |
|---|---|---|---|
| JY acid stripped | − cold peptide | 3553 ± 157 | n = 3 |
| JY acid stripped | + cold peptide | 13 | n = 1 |
| JY control | − cold peptide | 370 ± 37 | n = 3 |
| JY control | + cold peptide | 50 | n = 1 |

TABLE 26

Human PLP peptides

| Pos | AA | P1 | P2 | P3 | P4 | P5 | P6 | P7 | P8 | P9 | P10 | Allele | Motif | SEQ ID NO. |
|---|---|---|---|---|---|---|---|---|---|---|---|---|---|---|
| 42 | 9 | G | T | E | K | L | I | E | T | Y | | A1 | (TSM) 2; (DE) 3; Yc | 651 |
| 74 | 9 | G | T | A | S | F | F | F | L | Y | | | | 652 |
| 169 | 9 | C | S | A | V | P | V | Y | I | Y | | | | 653 |
| 255 | 9 | L | T | F | M | I | A | A | T | Y | | | | 654 |
| 42 | 10 | G | T | E | K | L | I | E | T | Y | F | | | 655 |
| 46 | 10 | L | I | E | T | Y | F | S | K | N | Y | | | 656 |
| 51 | 10 | F | S | K | N | Y | Q | D | Y | E | Y | | | 657 |
| 148 | 10 | H | P | D | K | F | V | G | I | T | Y | | | 658 |
| 198 | 10 | G | S | L | C | A | D | A | R | M | Y | | | 659 |

TABLE 26-continued

Human PLP peptides

| Pos | AA | P1 | P2 | P3 | P4 | P5 | P6 | P7 | P8 | P9 | P10 | Allele | Motif | SEQ ID NO. |
|---|---|---|---|---|---|---|---|---|---|---|---|---|---|---|
| 166 | 10 | V | F | A | C | S | A | V | P | V | Y | | Algorithm | 660 |
| 168 | 10 | A | C | S | A | V | P | V | Y | I | Y | | | 661 |
| 45 | 9 | K | L | I | E | T | Y | F | S | K | | A3/11 | (LMIVT) 2; (KR) c | 662 |
| 116 | 9 | T | V | T | G | G | Q | K | G | R | | | | 663 |
| 261 | 9 | A | T | Y | N | F | A | V | L | K | | A3/11 | (LMIVT) 2; (KR) c | 664 |
| 96 | 10 | A | V | R | Q | I | F | G | D | Y | K | | | 665 |
| 115 | 10 | A | T | V | T | G | G | Q | K | G | R | | | 666 |
| 196 | 10 | S | I | G | S | L | C | A | D | A | R | | | 667 |
| 209 | 10 | V | L | P | W | I | A | F | P | G | K | | | 668 |
| 267 | 10 | V | L | K | L | M | G | R | G | T | K | | | 669 |
| 71 | 9 | V | I | Y | G | T | A | S | F | F | | | Algorithm | 670 |
| 114 | 9 | S | A | T | V | T | G | G | Q | K | | | | 671 |
| 184 | 9 | C | D | S | I | A | F | P | S | K | | | | 672 |
| 197 | 9 | I | G | S | L | C | A | D | A | R | | | | 673 |
| 221 | 9 | G | S | N | L | L | S | I | C | K | | | | 674 |
| 229 | 9 | K | T | A | E | F | Q | M | T | F | | | | 675 |
| 235 | 9 | M | T | F | H | L | F | I | A | A | | | | 676 |
| 255 | 9 | L | T | F | M | I | A | A | T | Y | | | | 654 |
| 18 | 10 | S | L | V | A | T | G | L | C | F | F | | | 677 |
| 30 | 10 | A | L | F | C | G | C | G | H | E | A | | | 678 |
| 64 | 10 | V | I | H | A | F | Q | Y | V | I | Y | | | 679 |
| 102 | 10 | G | D | Y | K | T | T | I | C | G | K | | | 680 |
| 118 | 10 | T | G | G | Q | K | G | R | G | S | R | | | 681 |
| 142 | 10 | L | G | K | W | L | G | H | P | D | K | | | 682 |
| 183 | 10 | T | C | D | S | I | A | F | P | S | K | | | 683 |
| 220 | 10 | C | G | S | N | L | L | S | I | C | K | | | 684 |
| 229 | 10 | K | T | A | E | F | Q | M | T | F | H | | | 685 |
| 235 | 10 | M | T | F | H | L | F | I | A | A | F | | | 686 |
| 257 | 10 | F | M | I | A | A | T | Y | N | F | A | | | 687 |
| 260 | 10 | A | A | T | Y | N | F | A | V | L | K | | | 688 |
| 16 | 9 | F | A | S | L | V | A | T | G | L | | A24 | (YFWA) 2; (FILMW) c | 689 |
| 38 | 9 | E | A | L | T | G | T | E | K | L | | | | 690 |
| 54 | 9 | N | Y | Q | D | Y | E | Y | L | I | | | | 691 |
| 57 | 9 | D | Y | E | Y | L | I | N | V | I | | | | 692 |
| 72 | 9 | I | Y | G | T | A | S | F | F | F | | | | 693 |
| 77 | 9 | S | F | F | F | L | Y | G | A | L | | | | 694 |
| 78 | 9 | F | F | F | L | Y | G | A | L | L | | | | 695 |
| 79 | 9 | F | F | L | Y | G | A | L | L | L | | | | 696 |
| 83 | 9 | G | A | L | L | A | E | G | F | | | | | 697 |
| 100 | 9 | I | F | G | D | Y | K | T | T | I | | | | 698 |
| 144 | 9 | K | W | L | G | H | P | D | K | F | | | | 699 |
| 151 | 9 | K | F | V | G | I | T | Y | A | L | | | | 700 |
| 156 | 9 | T | Y | A | L | T | V | V | W | L | | | | 701 |
| 157 | 9 | Y | A | L | T | V | V | W | L | L | | | | 702 |
| 170 | 9 | S | A | V | P | V | Y | I | Y | F | | | | 703 |
| 232 | 9 | E | F | Q | M | T | F | H | L | F | | | | 704 |
| 236 | 9 | T | F | H | L | F | I | A | A | F | | | | 705 |
| 243 | 9 | A | F | V | G | A | A | A | T | L | | | | 706 |
| 246 | 9 | G | A | A | A | T | L | V | S | L | | A24 | (YFWA) 2; (FILMW) c | 707 |
| 247 | 9 | A | A | A | T | L | V | S | L | L | | | | 708 |
| 260 | 9 | A | A | T | Y | N | F | A | V | L | | | | 709 |
| 262 | 9 | T | Y | N | F | A | V | L | K | L | | | | 710 |
| 7 | 10 | C | A | R | C | L | V | G | A | P | F | | | 711 |
| 15 | 10 | P | F | A | S | L | V | A | T | G | L | | | 712 |
| 31 | 10 | L | F | C | G | C | G | H | E | A | L | | | 713 |
| 38 | 10 | E | A | L | T | G | T | E | K | L | I | | | 714 |
| 59 | 10 | E | Y | L | I | N | V | I | H | A | F | | | 715 |
| 69 | 10 | Q | Y | V | I | Y | G | T | A | S | F | | | 716 |
| 72 | 10 | I | Y | G | T | A | S | F | F | F | L | | | 717 |
| 77 | 10 | S | F | F | F | L | Y | G | A | L | L | | | 718 |
| 78 | 10 | F | F | F | L | Y | G | A | L | L | L | | | 719 |
| 91 | 10 | F | Y | T | T | G | A | V | R | Q | I | | | 720 |
| 156 | 10 | T | Y | A | L | T | V | V | W | L | L | | | 721 |
| 167 | 10 | F | A | C | S | A | V | P | V | Y | I | | | 722 |
| 180 | 10 | T | W | T | T | C | D | S | I | A | F | | | 723 |
| 188 | 10 | A | F | P | S | K | T | S | A | S | I | | | 724 |
| 201 | 10 | C | A | D | A | R | M | Y | G | V | L | | | 725 |
| 203 | 10 | D | A | R | M | Y | G | V | L | P | W | | | 726 |
| 206 | 10 | M | Y | G | V | L | P | W | I | A | F | | | 727 |
| 230 | 10 | T | A | E | F | Q | M | T | F | H | L | | | 728 |
| 232 | 10 | E | F | Q | M | T | F | H | L | F | I | | | 729 |

TABLE 26-continued

Human PLP peptides

| Pos | AA | P1 | P2 | P3 | P4 | P5 | P6 | P7 | P8 | P9 | P10 | Allele | Motif | SEQ ID NO. |
|---|---|---|---|---|---|---|---|---|---|---|---|---|---|---|
| 242 | 10 | A | A | F | V | G | A | A | A | T | L | | | 730 |
| 246 | 10 | G | A | A | A | T | L | V | S | L | L | | | 731 |
| 248 | 10 | A | A | T | L | V | S | L | L | T | F | | | 732 |
| 256 | 10 | T | F | M | I | A | A | T | Y | N | F | | | 733 |
| 259 | 10 | I | A | A | T | Y | N | F | A | V | L | | | 734 |
| 262 | 10 | T | Y | N | F | A | V | L | K | L | M | | | 735 |
| 148 | 8 | H | P | D | K | F | V | G | I | | | B | P2; (VILMFWY) c | 736 |
| 189 | 9 | F | P | S | K | T | S | A | S | I | | | | 737 |
| 148 | 10 | H | P | D | K | F | V | G | I | T | Y | | | 658 |
| 172 | 10 | V | P | V | Y | I | Y | F | N | T | W | | | 738 |
| 210 | 10 | L | P | W | I | A | F | P | G | K | V | | | 739 |
| 215 | 10 | F | P | G | K | V | C | G | S | N | L | | | 740 |

TABLE 27

Human Collagen TypeIV peptides

| Pos | AA | P1 | P2 | P3 | P4 | P5 | P6 | P7 | P8 | P9 | P10 | Allele | Motif | SEQ ID NO. |
|---|---|---|---|---|---|---|---|---|---|---|---|---|---|---|
| 108 | 9 | G | L | Q | G | V | P | G | P | K | | A3/11 | (LMIVT) 2; (KR) c | 741 |
| 120 | 9 | G | L | D | G | A | K | G | E | K | | | | 742 |
| 162 | 9 | G | V | P | G | P | A | G | P | K | | | | 743 |
| 192 | 9 | G | L | H | G | P | P | G | D | K | | | | 744 |
| 33 | 10 | L | L | G | P | L | G | H | D | G | K | | | 745 |
| 36 | 10 | P | L | G | H | D | G | K | G | P | R | | | 746 |
| 53 | 10 | P | L | G | P | Q | G | P | L | G | K | | | 747 |
| 236 | 10 | G | L | P | V | Q | G | C | W | N | K | | | 748 |
| 20 | 9 | G | A | L | G | M | L | G | Q | K | | | Algorithm | 749 |
| 34 | 9 | L | G | P | L | G | H | D | G | K | | | | 750 |
| 54 | 9 | L | G | P | Q | G | P | L | G | K | | | | 751 |
| 76 | 9 | G | S | P | G | E | K | G | E | K | | | | 752 |
| 210 | 9 | G | S | R | G | P | K | G | D | K | | | | 753 |
| 19 | 10 | L | G | A | L | G | M | L | G | Q | K | | | 754 |
| 60 | 10 | L | G | K | D | G | P | P | G | V | K | | | 755 |
| 72 | 10 | N | G | H | P | G | S | P | G | E | K | | | 756 |
| 75 | 10 | P | G | S | P | G | E | K | G | E | K | | | 757 |
| 107 | 10 | P | G | L | Q | G | V | P | G | P | K | | | 758 |
| 116 | 10 | K | G | E | A | G | L | D | G | A | K | | | 759 |
| 119 | 10 | A | G | L | D | G | A | K | G | E | K | | | 760 |
| 125 | 10 | K | G | E | K | G | F | Q | G | E | K | | | 761 |
| 128 | 10 | K | G | F | Q | G | E | K | G | D | R | | | 762 |
| 161 | 10 | I | G | V | P | G | P | A | G | P | K | | | 763 |
| 167 | 10 | A | G | P | K | G | E | R | G | S | K | | | 764 |
| 194 | 10 | H | G | P | P | G | D | K | G | N | R | | | 765 |
| 200 | 10 | K | G | N | R | G | E | R | G | K | K | | | 766 |
| 206 | 10 | R | G | K | K | G | S | R | G | P | K | | | 767 |
| 209 | 10 | K | G | S | R | G | P | K | G | D | K | | | 768 |
| 4 | 9 | L | A | L | M | G | P | L | G | L | | A24 | (YFWA) 2; (FILMW) c | 769 |
| 89 | 9 | Q | A | G | S | P | V | P | G | L | | | | 770 |
| 4 | 10 | L | A | L | M | G | P | L | G | L | L | | | 771 |
| 89 | 10 | Q | A | G | S | P | V | P | G | L | L | | | 772 |
| 17 | 8 | G | P | L | G | A | L | G | M | | | B | P2; (VILMFWY) c | 773 |
| 102 | 8 | G | P | P | G | P | P | G | L | | | | | 774 |
| 105 | 8 | G | P | P | G | L | Q | G | V | | | | | 775 |
| 114 | 8 | G | P | K | G | E | A | G | L | | | | | 776 |
| 154 | 8 | P | P | G | T | P | G | P | I | | | | | 777 |
| 183 | 8 | G | P | T | G | A | A | G | L | | | | | 778 |
| 230 | 8 | C | P | L | G | Q | D | G | L | | | | | 779 |
| 8 | 9 | G | P | L | G | L | L | G | Q | I | | | | 780 |
| 17 | 9 | G | P | L | G | A | L | G | M | L | | | | 781 |
| 43 | 9 | G | P | R | G | K | L | G | D | M | | | | 782 |
| 52 | 9 | G | P | L | G | P | Q | G | P | L | | | | 783 |
| 153 | 9 | G | P | P | G | T | P | G | P | I | | | | 784 |
| 103 | 10 | P | P | G | P | P | G | L | Q | G | V | | | 785 |
| 112 | 10 | V | P | G | P | K | G | E | A | G | L | | | 786 |
| 154 | 10 | P | P | G | T | P | G | P | I | G | V | | | 787 |
| 223 | 10 | A | P | G | L | D | A | P | C | P | L | | | 788 |
| 228 | 10 | A | P | C | P | L | G | Q | D | G | L | | | 789 |

TABLE 27-continued

Human Collagen TypeIV peptides

| Pos | AA | P1 | P2 | P3 | P4 | P5 | P6 | P7 | P8 | P9 | P10 | Allele | Motif | SEQ ID NO. |
|---|---|---|---|---|---|---|---|---|---|---|---|---|---|---|
| 230 | 10 | C | P | L | G | Q | D | G | L | P | V | | | 790 |

TABLE 28

Human Collagen TypeII peptides

| Pos | AA | P1 | P2 | P3 | P4 | P5 | P6 | P7 | P8 | P9 | P10 | Allele | Motif | SEQ ID NO. |
|---|---|---|---|---|---|---|---|---|---|---|---|---|---|---|
| 230 | 9 | G | T | D | G | I | P | G | A | K | | A1 | (TSM) 2; (DE) 3; Yc | 791 |
| 545 | 9 | G | T | D | G | P | K | G | A | S | | | | 792 |
| 230 | 10 | G | T | D | G | I | P | G | A | K | G | | | 793 |
| 545 | 10 | G | T | D | G | P | K | G | A | S | G | | | 794 |
| 1 | 9 | Q | M | A | G | G | F | D | E | K | | A3/11 | (LMIVT) 2; (KR) c | 795 |
| 53 | 9 | G | V | S | G | P | M | G | P | R | | | | 796 |
| 98 | 9 | G | T | P | G | L | P | G | V | K | | | | 797 |
| 101 | 9 | G | L | P | G | V | K | G | H | R | | | | 798 |
| 230 | 9 | G | T | D | G | I | P | G | A | K | | | | 791 |
| 419 | 9 | G | V | M | G | F | P | G | P | K | | | | 799 |
| 440 | 9 | G | L | P | G | A | P | G | L | R | | | | 800 |
| 512 | 9 | G | L | V | G | P | R | G | E | R | | | | 801 |
| 542 | 9 | G | T | P | G | T | D | G | P | K | | | | 802 |
| 566 | 9 | G | L | Q | G | M | P | G | E | R | | | | 803 |
| 578 | 9 | G | I | A | G | P | K | G | D | R | | | | 804 |
| 698 | 9 | G | V | T | G | P | K | G | A | R | | | | 805 |
| 800 | 9 | G | I | V | G | L | P | G | Q | R | | | | 806 |
| 803 | 9 | G | L | P | G | Q | R | G | E | R | | | | 807 |
| 926 | 9 | G | I | Q | G | P | Q | G | P | R | | | | 808 |
| 267 | 10 | P | L | G | P | K | G | Q | T | G | K | | | 809 |
| 714 | 10 | A | T | G | F | P | G | A | A | G | R | | | 810 |
| 846 | 10 | L | T | G | P | A | G | E | P | G | R | | | 811 |
| 1002 | 10 | P | I | G | P | P | G | P | R | G | R | | | 812 |
| 248 | 9 | G | A | P | G | F | P | G | P | R | | | Algorithm | 813 |
| 263 | 9 | G | A | T | G | P | L | G | P | K | | | | 814 |
| 268 | 9 | L | G | P | K | G | Q | T | G | K | | | | 815 |
| 281 | 9 | G | F | K | G | E | Q | G | P | K | | | | 816 |
| 427 | 9 | K | G | A | N | G | E | P | G | K | | | | 817 |
| 509 | 9 | G | A | P | G | L | V | G | P | R | | | | 818 |
| 530 | 9 | G | A | Q | G | L | Q | G | P | R | | | | 819 |
| 575 | 9 | G | A | A | G | I | A | G | P | K | | | | 820 |
| 592 | 9 | K | G | P | E | G | A | P | G | K | | | | 821 |
| 659 | 9 | G | A | D | G | Q | P | G | A | K | | | | 822 |
| 827 | 9 | G | A | P | G | A | S | G | D | R | | | | 823 |
| 1040 | 9 | S | A | F | A | G | L | G | P | R | | | | 824 |
| 97 | 10 | P | G | T | P | G | L | P | G | V | K | | | 825 |
| 109 | 10 | R | G | Y | P | G | L | D | G | A | K | | Algorithm | 826 |
| 118 | 10 | K | G | E | A | G | A | P | G | V | K | | | 827 |
| 142 | 10 | M | G | P | R | G | L | P | G | E | R | | | 828 |
| 184 | 10 | P | G | F | P | G | A | P | G | A | K | | | 829 |
| 202 | 10 | R | G | P | E | G | A | Q | G | P | R | | | 830 |
| 262 | 10 | Q | G | A | T | G | P | L | G | P | K | | | 831 |
| 274 | 10 | T | G | K | P | G | I | A | G | F | K | | | 832 |
| 280 | 10 | A | G | F | K | G | E | Q | G | P | K | | | 833 |
| 337 | 10 | P | G | Q | D | G | L | A | G | P | K | | | 834 |
| 343 | 10 | A | G | P | K | G | A | P | G | E | R | | | 835 |
| 352 | 10 | R | G | P | S | G | L | A | G | P | K | | | 836 |
| 418 | 10 | P | G | V | M | G | F | P | G | P | K | | | 837 |
| 508 | 10 | A | G | A | P | G | L | V | G | P | R | | | 838 |
| 541 | 10 | P | G | T | P | G | T | D | G | P | K | | | 839 |
| 565 | 10 | P | G | L | Q | G | M | P | G | E | R | | | 840 |
| 574 | 10 | R | G | A | A | G | I | A | G | P | K | | | 841 |
| 583 | 10 | K | G | D | R | G | D | V | G | E | K | | | 842 |
| 613 | 10 | P | G | P | A | G | A | N | G | E | K | | | 843 |
| 667 | 10 | K | G | E | Q | G | E | A | G | Q | K | | | 844 |
| 694 | 10 | Q | G | P | T | G | V | T | G | P | K | | | 845 |
| 742 | 10 | S | G | K | D | G | P | K | G | A | R | | | 846 |
| 766 | 10 | Q | G | P | A | G | P | P | G | E | K | | | 847 |
| 799 | 10 | R | G | I | V | G | L | P | G | Q | R | | | 848 |
| 925 | 10 | R | G | I | Q | G | P | Q | G | P | R | | | 849 |
| 928 | 10 | Q | G | P | Q | G | P | R | G | D | K | | | 850 |
| 937 | 10 | K | G | E | A | G | E | P | G | E | R | | | 851 |

TABLE 28-continued

Human Collagen TypeII peptides

| Pos | AA | P1 | P2 | P3 | P4 | P5 | P6 | P7 | P8 | P9 | P10 | Allele | Motif | SEQ ID NO. |
|---|---|---|---|---|---|---|---|---|---|---|---|---|---|---|
| 940 | 10 | A | G | E | P | G | E | R | G | L | K | | | 852 |
| 973 | 10 | S | G | P | A | G | P | S | G | P | R | | | 853 |
| 1039 | 10 | M | S | A | F | A | G | L | G | P | R | | | 854 |
| 413 | 9 | G | A | R | G | Q | P | G | V | M | | A24 | (YFWA) 2; (FILMW) c | 855 |
| 995 | 9 | G | A | N | G | I | P | G | P | I | | | | 856 |
| 9 | 10 | K | A | G | G | A | Q | L | G | V | M | | | 857 |
| 33 | 10 | P | A | G | A | P | G | P | Q | G | F | | | 858 |
| 795 | 10 | L | A | G | Q | R | G | I | V | G | L | | | 859 |
| 939 | 10 | E | A | G | E | P | G | E | R | G | L | | | 860 |
| 51 | 8 | E | P | G | V | S | G | P | M | | | B | P2; (VILMFWY) c | 861 |
| 89 | 8 | G | P | Q | G | A | R | G | F | | | | | 862 |
| 140 | 8 | G | P | M | G | P | R | G | L | | | | | 863 |
| 179 | 8 | G | P | A | G | G | P | G | F | | | | | 864 |
| 315 | 8 | E | P | G | G | V | G | P | I | | | | | 865 |
| 479 | 8 | G | P | S | G | F | Q | G | L | | | B | P2; (VILMFWY) c | 866 |
| 515 | 8 | G | P | R | G | E | R | G | F | | | | | 867 |
| 563 | 8 | G | P | P | G | L | Q | G | M | | | | | 868 |
| 647 | 8 | G | P | P | G | T | S | G | I | | | | | 869 |
| 692 | 8 | G | P | Q | G | P | T | G | V | | | | | 870 |
| 710 | 8 | G | P | P | G | A | T | G | F | | | | | 871 |
| 717 | 8 | F | P | G | A | A | G | R | V | | | | | 872 |
| 788 | 8 | G | P | P | G | P | Q | G | L | | | | | 873 |
| 839 | 8 | G | P | V | G | P | P | G | L | | | | | 874 |
| 920 | 8 | G | P | A | G | A | R | G | I | | | | | 875 |
| 1032 | 8 | P | P | G | P | G | I | D | M | | | | | 876 |
| 1051 | 8 | G | P | D | P | L | Q | Y | M | | | | | 877 |
| 170 | 9 | G | P | A | G | P | P | G | P | V | | | | 878 |
| 260 | 9 | D | P | Q | G | A | T | G | P | L | | | | 879 |
| 581 | 9 | G | P | K | G | D | R | G | D | V | | | | 880 |
| 980 | 9 | G | P | R | G | P | P | G | P | V | | | | 881 |
| 1029 | 9 | P | P | G | P | P | G | P | G | I | | | | 882 |
| 1031 | 9 | G | P | P | G | P | G | I | D | M | | | | 883 |
| 1034 | 9 | G | P | G | I | D | M | S | A | F | | | | 884 |
| 45 | 10 | N | P | G | E | P | G | E | P | G | V | | | 885 |
| 87 | 10 | P | P | G | P | Q | G | A | R | G | F | | | 886 |
| 96 | 10 | F | P | G | T | P | G | L | P | G | V | | | 887 |
| 102 | 10 | L | P | G | V | K | G | H | R | G | Y | | | 888 |
| 138 | 10 | S | P | G | P | M | G | P | R | G | L | | | 889 |
| 243 | 10 | A | P | G | I | A | G | A | P | G | F | | | 890 |
| 348 | 10 | A | P | G | E | R | G | P | S | G | L | | | 891 |
| 366 | 10 | D | P | G | R | P | G | E | P | G | L | | | 892 |
| 372 | 10 | E | P | G | L | P | G | A | R | G | L | | | 893 |
| 432 | 10 | E | P | G | K | A | G | E | K | G | L | | | 894 |
| 441 | 10 | L | P | G | A | P | G | L | R | G | L | | | 895 |
| 477 | 10 | A | P | G | P | S | G | F | Q | G | L | | | 896 |
| 504 | 10 | V | P | G | E | A | G | A | P | G | L | | | 897 |
| 558 | 10 | P | P | G | A | Q | G | P | P | G | L | | | 898 |
| 570 | 10 | M | P | G | E | R | G | A | A | G | I | | | 899 |
| 597 | 10 | A | P | G | K | D | G | G | R | G | L | | | 900 |
| 690 | 10 | A | P | G | P | Q | G | P | T | G | V | | | 901 |
| 756 | 10 | P | P | G | R | A | G | E | P | G | L | | | 902 |
| 804 | 10 | L | P | G | Q | R | G | E | R | G | F | | | 903 |
| 837 | 10 | P | P | G | P | V | G | P | P | G | L | | | 904 |
| 864 | 10 | P | P | G | R | D | G | A | A | G | V | | | 905 |
| 1028 | 10 | G | P | P | G | P | P | G | P | G | I | | | 906 |
| 1046 | 10 | G | P | R | E | K | G | P | D | P | L | | | 907 |

TABLE 29

Human GAD peptides

| Pos | AA | P1 | P2 | P3 | P4 | P5 | P6 | P7 | P8 | P9 | P10 | Allele | Motif | SEQ ID NO: |
|---|---|---|---|---|---|---|---|---|---|---|---|---|---|---|
| 21 | 9 | T | T | N | L | R | P | T | T | Y | | A1 | (TSM)2; (DE)3; Yc | 908 |
| 81 | 9 | N | S | D | R | D | A | R | F | R | | | | 909 |
| 90 | 9 | R | T | E | T | D | F | S | N | L | | | | 910 |
| 92 | 9 | E | T | D | F | S | N | L | F | A | | | | 911 |

TABLE 29-continued

Human GAD peptides

| Pos | AA | P1 | P2 | P3 | P4 | P5 | P6 | P7 | P8 | P9 | P10 | Allele | Motif | SEQ ID NO: |
|---|---|---|---|---|---|---|---|---|---|---|---|---|---|---|
| 150 | 9 | G | M | E | G | F | N | L | E | L | | | | 912 |
| 158 | 9 | L | S | D | H | P | E | S | L | E | | | | 913 |
| 224 | 9 | L | M | E | Q | I | T | L | K | K | | | | 914 |
| 286 | 9 | T | S | E | Q | S | H | Y | S | I | | | | 915 |
| 304 | 9 | G | T | D | N | V | I | L | I | K | | | | 916 |
| 328 | 9 | I | L | E | A | K | Q | K | G | Y | | | | 917 |
| 483 | 9 | C | L | E | L | A | E | Y | L | Y | | | | 918 |
| 546 | 9 | M | M | E | S | G | T | T | M | V | | | | 919 |
| 548 | 9 | E | S | G | T | T | M | V | G | Y | | | | 920 |
| 577 | 9 | Q | S | D | I | D | F | L | I | E | | | | 921 |
| 20 | 10 | N | T | T | N | L | R | P | T | T | Y | | | 922 |
| 81 | 10 | N | S | D | R | D | A | R | F | R | R | | | 923 |
| 90 | 10 | R | T | E | T | D | F | S | N | L | F | | | 924 |
| 92 | 10 | E | T | D | F | S | N | L | F | A | R | | | 925 |
| 150 | 10 | G | M | E | G | F | N | L | E | L | S | | | 926 |
| 158 | 10 | L | S | D | H | P | E | S | L | E | Q | | | 927 |
| 169 | 10 | L | V | D | C | R | D | T | L | K | Y | | | 928 |
| 207 | 10 | S | T | A | N | T | N | M | F | T | Y | | | 929 |
| 224 | 10 | L | M | E | Q | I | T | L | K | K | M | | | 930 |
| 256 | 10 | N | M | Y | S | I | M | A | A | R | Y | | | 931 |
| 258 | 10 | Y | S | I | M | A | A | R | Y | K | Y | | | 932 |
| 286 | 10 | T | S | E | Q | S | H | Y | S | I | K | | | 933 |
| 304 | 10 | G | T | D | N | V | I | L | I | K | C | | | 934 |
| 437 | 10 | Q | P | D | K | Q | Y | D | V | S | Y | | | 935 |
| 546 | 10 | M | M | E | S | G | T | T | M | V | G | | | 936 |
| 577 | 10 | Q | S | D | I | D | F | L | I | E | E | | | 937 |
| 437 | 10 | Q | P | D | K | Q | Y | D | V | S | Y | | | 935 |
| 257 | 9 | M | Y | S | I | M | A | A | R | Y | | | Algorithm | 938 |
| 358 | 9 | E | I | A | D | I | C | E | K | Y | | | | 939 |
| 341 | 10 | V | N | A | T | A | G | T | T | V | Y | | | 940 |
| 547 | 10 | M | E | S | G | T | T | M | V | G | Y | | | 941 |
| 76 | 9 | L | L | S | C | E | N | S | D | R | | A3/11 | (LMIVT)2; (KR)c | 942 |
| 122 | 9 | D | I | L | L | N | Y | V | R | K | | | | 943 |
| 169 | 9 | L | V | D | C | R | D | T | L | K | | | | 944 |
| 223 | 9 | V | L | M | E | Q | I | T | L | K | | | | 945 |
| 224 | 9 | L | M | E | Q | I | T | L | K | K | | | | 914 |
| 256 | 9 | N | M | Y | S | I | M | A | A | R | | | | 946 |
| 304 | 9 | G | T | D | N | V | I | L | I | K | | | | 916 |
| 308 | 9 | V | I | L | I | K | C | N | E | R | | | | 947 |
| 310 | 9 | L | I | K | C | N | E | R | G | K | | | | 948 |
| 319 | 9 | I | I | P | A | D | F | E | A | K | | | | 949 |
| 379 | 9 | G | L | L | M | S | R | K | H | R | | | | 950 |
| 381 | 9 | L | M | S | R | K | H | R | H | K | | | | 951 |
| 443 | 9 | D | V | S | Y | D | T | G | D | K | | | | 952 |
| 485 | 9 | E | L | A | E | Y | L | Y | A | K | | | | 953 |
| 489 | 9 | Y | L | Y | A | K | I | K | N | R | | | | 954 |
| 524 | 9 | G | V | P | D | S | P | Q | R | R | | | | 955 |
| 75 | 10 | N | L | L | S | C | E | N | S | D | R | A3/11 | (LMIVT)2; (KR)c | 956 |
| 92 | 10 | E | T | D | F | S | N | L | F | A | R | | | 925 |
| 120 | 10 | V | V | D | I | L | L | N | Y | V | R | | | 957 |
| 164 | 10 | S | L | E | Q | I | L | V | D | C | R | | | 958 |
| 168 | 10 | I | L | V | D | C | R | D | T | L | K | | | 959 |
| 222 | 10 | F | V | L | M | E | Q | I | T | L | K | | | 960 |
| 223 | 10 | V | L | M | E | Q | I | T | L | K | K | | | 961 |
| 272 | 10 | K | T | K | G | M | A | A | V | P | K | | | 962 |
| 307 | 10 | N | V | I | L | I | K | C | N | E | R | | | 963 |
| 309 | 10 | I | L | I | K | C | N | E | R | G | K | | | 964 |
| 318 | 10 | K | I | I | P | A | D | F | E | A | K | | | 965 |
| 380 | 10 | L | L | M | S | R | K | H | R | H | K | | | 966 |
| 410 | 10 | L | L | Q | c | g | A | I | L | V | K | | | 967 |
| 460 | 10 | D | I | F | K | F | W | L | M | W | K | | | 968 |
| 473 | 10 | T | V | G | F | E | N | Q | I | N | K | | | 969 |
| 534 | 10 | K | L | H | K | V | A | P | K | I | K | | | 970 |
| 553 | 10 | M | V | G | Y | Q | P | Q | G | D | K | | | 971 |
| 33 | 9 | C | G | V | A | H | G | C | T | R | | | Algorithm | 972 |
| 60 | 9 | K | S | R | L | V | S | A | F | K | | | | 973 |
| 99 | 9 | F | A | R | D | L | L | P | A | K | | | | 974 |
| 135 | 9 | S | T | K | V | L | D | F | H | H | | | | 975 |
| 214 | 9 | F | T | Y | E | I | A | P | V | F | | | | 976 |
| 258 | 9 | Y | S | I | M | A | A | R | Y | K | | | | 977 |
| 283 | 9 | V | L | F | T | S | E | Q | S | H | | | | 978 |
| 377 | 9 | G | G | G | L | L | M | S | R | K | | | | 979 |

TABLE 29-continued

Human GAD peptides

| Pos | AA | P1 | P2 | P3 | P4 | P5 | P6 | P7 | P8 | P9 | P10 | Allele | Motif | SEQ ID NO: |
|---|---|---|---|---|---|---|---|---|---|---|---|---|---|---|
| 397 | 9 | N | S | V | T | W | N | P | H | K | | | | 980 |
| 413 | 9 | C | S | A | I | L | V | K | E | K | | | | 981 |
| 432 | 9 | A | G | Y | L | L | Q | P | D | K | | | | 982 |
| 455 | 9 | C | G | R | H | V | D | I | F | K | | | | 983 |
| 461 | 9 | I | F | K | F | W | L | M | W | K | | | | 984 |
| 463 | 9 | K | F | W | L | M | W | K | A | K | | | | 985 |
| 474 | 9 | V | G | F | E | N | Q | I | N | K | | | | 986 |
| 559 | 9 | Q | G | D | K | A | N | F | F | R | | | | 987 |
| 33 | 10 | C | G | V | A | H | G | C | T | R | K | | | 988 |
| 65 | 10 | S | A | F | K | E | R | Q | S | S | K | | | 989 |
| 121 | 10 | V | D | I | L | L | N | Y | V | R | K | | | 990 |
| 175 | 10 | T | L | K | Y | G | V | R | T | G | H | | | 991 |
| 259 | 10 | S | I | M | A | A | R | Y | K | Y | F | | | 992 |
| 286 | 10 | T | S | E | Q | S | H | Y | S | I | K | | | 933 |
| 203 | 10 | F | G | T | D | N | V | I | L | I | K | | | 993 |
| 376 | 10 | W | G | G | G | L | L | M | S | R | K | | | 994 |
| 431 | 10 | C | A | G | Y | L. | L | Q | P | D | K | | | 995 |
| 448 | 10 | T | G | D | K | A | I | Q | C | G | R | | | 996 |
| 454 | 10 | Q | C | G | R | H | V | D | I | F | K | | | 997 |
| 514 | 10 | C | F | W | Y | I | P | Q | S | L | R | | | 998 |
| 16 | 9 | G | A | D | P | N | T | T | N | L | | A24 | (YFWA)2; (FILMW)c | 999 |
| 35 | 9 | V | A | H | G | C | T | R | K | L | | | | 1000 |
| 49 | 9 | G | F | L | Q | R | T | N | S | L | | | | 1001 |
| 87 | 9 | R | F | R | R | T | E | T | D | F | | | | 1002 |
| 115 | 9 | Q | F | L | L | E | V | V | D | I | | | | 1003 |
| 131 | 9 | T | F | D | R | S | T | K | V | L | | | | 1004 |
| 140 | 9 | D | F | H | H | P | H | Q | L | L | | | | 1005 |
| 187 | 9 | F | F | N | Q | L | S | T | G | L | | | | 1006 |
| 252 | 9 | G | A | I | S | N | M | Y | S | I | | | | 1007 |
| 276 | 9 | M | A | A | V | P | K | L | V | L | | | | 1008 |
| 277 | 9 | A | A | V | P | K | L | V | L | F | | | | 1009 |
| 302 | 9 | G | F | G | T | D | N | V | I | L | | | | 1010 |
| 321 | 9 | P | A | D | F | E | A | K | I | L | | | | 1011 |
| 351 | 9 | G | A | F | D | P | I | Q | E | I | | | | 1012 |
| 368 | 9 | L | W | L | H | V | D | A | A | W | | | | 1013 |
| 373 | 9 | D | A | A | W | G | G | G | L | L | | | | 1014 |
| 374 | 9 | A | A | W | G | G | G | L | L | M | | | | 1015 |
| 445 | 9 | S | Y | D | T | G | D | K | A | I | | | | 1016 |
| 486 | 9 | L | A | E | Y | L | Y | A | K | I | | | | 1017 |
| 514 | 9 | C | F | W | Y | I | P | Q | S | L | | | | 1018 |
| 538 | 9 | V | A | P | K | I | K | A | L | M | | | | 1019 |
| 562 | 9 | K | A | N | F | F | R | M | V | I | | | | 1020 |
| 574 | 9 | A | A | T | Q | S | D | I | D | F | | | | 1021 |
| 94 | 10 | D | F | S | N | L | F | A | R | D | L | | | 1022 |
| 115 | 10 | Q | F | L | L | E | V | V | D | I | L | | | 1023 |
| 186 | 10 | R | F | F | N | Q | L | S | T | G | L | | | 1024 |
| 213 | 10 | M | F | T | Y | E | I | A | P | V | F | | | 1025 |
| 215 | 10 | T | Y | E | I | A | P | V | F | V | L | | | 1026 |
| 221 | 10 | V | F | V | L | M | E | Q | I | T | L | | | 1027 |
| 238 | 10 | G | W | S | S | K | D | G | D | G | I | | | 1028 |
| 252 | 10 | G | A | I | S | N | M | Y | S | I | M | | | 1029 |
| 267 | 10 | Y | F | P | E | V | K | T | K | G | M | | | 1030 |
| 276 | 10 | M | A | A | V | P | K | L | V | L | F | | | 1031 |
| 302 | 10 | G | F | G | T | D | N | V | I | L | I | | | 1032 |
| 330 | 10 | E | A | K | Q | K | G | Y | V | P | F | | | 1033 |
| 344 | 10 | T | A | G | T | T | V | Y | G | A | F | | | 1034 |
| 359 | 10 | I | A | D | I | C | E | K | Y | N | L | | | 1035 |
| 373 | 10 | D | A | A | W | G | G | G | L | L | M | | | 1036 |
| 414 | 10 | S | A | I | L | V | K | E | K | G | I | | | 1037 |
| 467 | 10 | M | W | K | A | K | G | T | V | G | F | | | 1038 |
| 475 | 10 | G | F | E | N | Q | I | N | K | C | L | | | 1039 |
| 491 | 10 | Y | A | K | I | K | N | R | E | E | F | | | 1040 |
| 538 | 10 | V | A | P | K | I | K | A | L | M | M | | | 1041 |
| 573 | 10 | P | A | A | T | Q | S | D | I | D | F | | | 1042 |
| 574 | 10 | A | A | T | Q | S | D | I | D | F | L | | | 1043 |
| 581 | 10 | D | F | L | I | E | E | I | E | R | L | | | 1044 |
| 25 | 8 | R | P | T | T | Y | D | T | W | | | B | P2; (VILMFWY)c | 1045 |
| 161 | 8 | H | P | E | S | L | E | Q | I | | | | | 1046 |
| 184 | 8 | H | P | R | F | F | N | Q | L | | | | | 1047 |
| 402 | 8 | N | P | H | K | M | M | G | V | | | | | 1048 |
| 437 | 8 | Q | P | D | K | Q | Y | D | V | | | | | 1049 |
| 518 | 8 | I | P | Q | S | L | R | G | V | | | | | 1050 |

TABLE 29-continued

Human GAD peptides

| Pos | AA | P1 | P2 | P3 | P4 | P5 | P6 | P7 | P8 | P9 | P10 | Allele | Motif | SEQ ID NO: |
|---|---|---|---|---|---|---|---|---|---|---|---|---|---|---|
| 528 | 8 | S | P | Q | R | R | E | K | L | | | | | 1051 |
| 539 | 8 | A | P | K | I | K | A | L | M | | | | | 1052 |
| 143 | 9 | H | P | H | Q | L | L | E | G | M | | | | 1053 |
| 161 | 9 | H | P | E | S | L | E | Q | I | L | | | | 1054 |
| 249 | 9 | S | P | G | G | A | I | S | N | M | | | | 1055 |
| 268 | 9 | F | P | E | V | K | T | K | G | M | | | | 1056 |
| 320 | 9 | I | P | A | D | F | E | A | K | I | | | | 1057 |
| 354 | 9 | D | P | I | Q | E | I | A | D | I | | | | 1058 |
| 402 | 9 | N | P | H | K | M | M | G | V | L | | | | 1059 |
| 507 | 9 | E | P | E | H | T | S | V | C | F | | | | 1060 |
| 539 | 9 | A | P | K | I | K | A | L | M | M | | | | 1061 |
| 557 | 9 | Q | P | Q | G | D | K | A | N | F | | | | 1062 |
| 572 | 9 | N | P | A | A | T | Q | S | D | I | | | | 1063 |
| 161 | 10 | H | P | E | S | L | E | Q | I | L | V | | | 1064 |
| 219 | 10 | A | P | V | F | V | L | M | E | Q | I | | | 1065 |
| 249 | 10 | S | P | G | G | A | I | S | N | M | Y | | | 1066 |
| 320 | 10 | I | P | A | D | F | E | A | K | I | L | | | 1067 |
| 402 | 10 | N | P | H | K | M | M | G | V | L | L | | | 1068 |
| 437 | 10 | Q | P | D | K | Q | Y | D | V | S | Y | | | 935 |
| 507 | 10 | E | P | E | H | T | S | V | C | F | W | | | 1069 |
| 557 | 10 | Q | P | Q | G | D | K | A | N | F | F | | | 1070 |

TABLE 30

Human MBP peptides

| Pos | AA | P1 | P2 | P3 | P4 | P5 | P6 | P7 | P8 | P9 | P10 | Allele | Motif | SEQ ID NO: |
|---|---|---|---|---|---|---|---|---|---|---|---|---|---|---|
| 6 | 9 | P | S | Q | R | H | G | S | K | Y | | A1 | (TSM)2; (DE)3; Yc | 1071 |
| 20 | 9 | T | M | D | H | A | R | H | G | F | | | | 1072 |
| 131 | 9 | A | S | D | Y | K | S | A | H | K | | | | 1073 |
| 20 | 10 | T | M | D | H | A | R | H | G | F | L | | | 1074 |
| 131 | 10 | A | S | D | Y | K | S | A | H | K | G | | | 1075 |
| 5 | 10 | R | P | S | Q | R | H | G | S | K | Y | | Algorithm | 1076 |
| 20 | 10 | T | M | D | H | A | R | H | G | F | L | A2.1 | (LM)2; (LVI)c | 1074 |
| 28 | 10 | F | L | P | R | H | R | D | T | G | I | | | 1077 |
| 110 | 9 | S | L | S | R | F | S | W | G | A | | | Algorithm | 1078 |
| 71 | 9 | S | L | P | Q | K | S | H | G | R | | A3/11 | (LMIVT)2; (KR)c | 1079 |
| 97 | 9 | R | T | P | P | P | S | Q | G | K | | | | 1080 |
| 16 | 10 | A | T | A | S | T | M | D | H | A | R | | | 1081 |
| 34 | 10 | D | T | G | I | L | D | S | I | G | R | | | 1082 |
| 40 | 10 | S | I | G | R | F | F | G | G | D | R | | | 1083 |
| 143 | 10 | G | V | D | A | Q | G | T | L | S | K | | | 1084 |
| 17 | 9 | T | A | S | T | M | D | H | A | R | | | Algorithm | 1085 |
| 23 | 9 | H | A | R | H | G | F | L | P | R | | | | 1086 |
| 35 | 9 | T | G | I | L | D | S | I | G | R | | | | 1087 |
| 41 | 9 | I | G | R | F | F | G | G | D | R | | | | 1088 |
| 46 | 9 | G | G | D | R | G | A | P | K | R | | | | 1089 |
| 50 | 9 | G | A | P | K | R | G | S | G | K | | | | 1090 |
| 105 | 9 | K | G | R | G | L | S | L | S | R | | | | 1091 |
| 127 | 9 | Y | G | G | R | A | S | D | Y | K | | | | 1092 |
| 131 | 9 | A | S | D | Y | K | S | A | H | K | | | | 1073 |
| 144 | 9 | V | D | A | Q | G | T | L | S | K | | | | 1093 |
| 147 | 9 | Q | G | T | L | S | K | I | F | K | | | | 1094 |
| 49 | 10 | R | G | A | P | K | R | G | S | G | K | | | 1095 |
| 66 | 10 | T | A | H | Y | G | S | L | P | Q | K | | | 1096 |
| 88 | 10 | H | F | F | K | N | I | V | T | P | R | | | 1097 |
| 113 | 10 | R | F | S | W | G | A | E | G | Q | R | | | 1098 |
| 130 | 10 | R | A | S | D | Y | K | S | A | H | K | | | 1099 |
| 13 | 9 | K | Y | L | A | T | A | S | T | M | | A24 | (YFWA)2; (FILMW)c | 1100 |
| 117 | 9 | G | A | E | G | Q | R | P | G | F | | | | 1101 |
| 133 | 9 | D | Y | K | S | A | H | K | G | F | | | | 1102 |
| 145 | 9 | D | A | Q | G | T | L | S | K | I | | | | 1103 |
| 63 | 10 | P | A | R | T | A | H | Y | G | S | L | | | 1104 |
| 145 | 10 | D | A | Q | G | T | L | S | K | I | F | | | 1105 |
| 62 | 8 | H | P | A | R | T | A | H | Y | | | B | P2; | 1106 |

TABLE 30-continued

Human MBP peptides

| Pos | AA | P1 | P2 | P3 | P4 | P5 | P6 | P7 | P8 | P9 | P10 | Allele | Motif | SEQ ID NO: |
|---|---|---|---|---|---|---|---|---|---|---|---|---|---|---|
| | | | | | | | | | | | | | (VILMFWY)c | |
| 29 | 9 | L | P | R | H | R | D | T | G | I | | | | 1107 |
| 5 | 10 | R | P | S | Q | R | H | G | S | K | Y | | | 1076 |
| 29 | 10 | L | P | R | H | R | D | T | G | I | L | | | 1108 |
| 84 | 10 | N | P | V | V | H | F | F | K | N | I | | | 1109 |
| 100 | 10 | P | P | S | Q | G | K | G | R | G | L | | | 1110 |

TABLE 31

A11 9-mer Algorithm

| | 1 | 2 | 3 | 4 | 5 | 6 | 7 | 8 | 9 |
|---|---|---|---|---|---|---|---|---|---|
| A | -1.97 | -0.46 | -2.36 | -2.33 | -2.37 | -1.70 | -3.14 | -2.54 | -15.00 |
| C | -2.49 | -2.34 | -2.00 | -1.99 | -1.73 | -2.66 | -2.97 | -1.45 | -15.00 |
| D | -3.27 | -2.68 | -2.68 | -2.52 | -2.13 | -3.05 | -2.00 | -1.75 | -15.00 |
| E | -3.13 | -15.00 | -3.26 | -1.94 | -2.76 | -3.21 | -3.13 | -2.16 | -15.00 |
| F | -2.98 | -2.43 | -0.76 | -2.05 | -1.80 | -0.44 | -1.54 | -2.39 | -15.00 |
| G | -2.00 | -0.32 | -3.02 | -2.18 | -2.81 | -2.21 | -2.19 | -3.08 | -15.00 |
| H | -3.23 | -15.00 | -2.12 | -1.93 | -1.39 | -2.60 | -2.88 | -1.01 | -3.30 |
| I | -2.12 | -0.64 | -1.74 | -2.29 | -2.66 | -2.07 | -2.02 | -2.56 | -15.00 |
| K | -1.99 | -15.00 | -2.37 | -2.03 | -2.72 | -3.21 | -3.28 | -2.51 | -0.74 |
| L | -2.12 | -0.74 | -2.42 | -2.43 | -1.82 | -2.07 | -1.44 | -2.61 | -15.00 |
| M | -2.32 | -0.10 | 0.12 | -4.00 | -0.67 | -3.63 | -1.59 | -2.19 | -15.00 |
| N | -2.74 | -1.24 | -2.01 | -2.01 | -2.98 | -2.49 | -2.88 | -2.19 | -15.00 |
| P | -3.13 | -15.00 | -2.79 | -2.98 | -2.02 | -2.34 | -1.85 | -1.86 | -15.00 |
| Q | -2.11 | -15.00 | -2.94 | -2.22 | -1.98 | -1.98 | -1.65 | -2.82 | -15.00 |
| R | -2.17 | -15.00 | -3.13 | -2.58 | -2.78 | -2.87 | -3.04 | -2.13 | -2.32 |
| S | -0.99 | -0.60 | -1.59 | -2.36 | -2.01 | -2.21 | -2.84 | -2.61 | -15.00 |
| T | -2.01 | -0.80 | -2.67 | -2.45 | -2.22 | -2.20 | -2.94 | -1.71 | -15.00 |
| V | -1.90 | -1.07 | -2.51 | -2.75 | -2.60 | -1.94 | -2.55 | -3.05 | -15.00 |
| W | -4.00 | -15.00 | -3.14 | -1.96 | -3.43 | -2.09 | -1.10 | -2.13 | -15.00 |
| Y | -2.56 | -15.00 | -1.73 | -1.86 | -1.59 | -1.94 | -1.61 | -1.24 | -15.00 |

Poly A values are used at positions 2 and 9, and are ratios to the T2 poly-A peptide.

TABLE 32

A11 10-mer Algorithm

| | 1 | 2 | 3 | 4 | 5 | 6 | 7 | 8 | 9 | 10 |
|---|---|---|---|---|---|---|---|---|---|---|
| A | -2.46 | -0.46 | -2.77 | -2.61 | -1.99 | -2.33 | -3.20 | -2.18 | -3.01 | -15.00 |
| C | -3.45 | -2.34 | -2.17 | -2.34 | -1.97 | -1.86 | -1.64 | -1.86 | -2.41 | -15.00 |
| D | -3.15 | -2.68 | -2.69 | -2.24 | -2.11 | -2.22 | -2.89 | -3.03 | -2.32 | -15.00 |
| E | -3.22 | -15.00 | -2.65 | -2.39 | -2.13 | -2.10 | -2.43 | -3.50 | -2.13 | -15.00 |
| F | -2.65 | -2.43 | -1.40 | -1.57 | -1.52 | -2.18 | -1.79 | -2.04 | -0.93 | -15.00 |
| G | -2.54 | -0.32 | -2.46 | -2.37 | -2.17 | -2.76 | -2.57 | -2.65 | -2.94 | -15.00 |
| H | -2.31 | -15.00 | -2.63 | -2.79 | -1.89 | -2.69 | -3.45 | -2.04 | -2.06 | -3.30 |
| I | -2.73 | -0.64 | -1.52 | -2.43 | -1.96 | -2.31 | -1.08 | -2.02 | -2.70 | -15.00 |
| K | -1.69 | -15.00 | -2.27 | -1.82 | -2.05 | -2.78 | -2.37 | -3.00 | -1.89 | -0.74 |
| L | -2.19 | -0.74 | -2.45 | -2.55 | -2.46 | -1.97 | -2.67 | -1.90 | -2.53 | -15.00 |
| M | -1.93 | -0.10 | -2.18 | -2.51 | -1.92 | -1.48 | -2.09 | -1.61 | -3.90 | -15.00 |
| N | -2.62 | -1.24 | -1.78 | -1.76 | -2.85 | -2.31 | -1.85 | -2.94 | -1.75 | -15.00 |
| P | -3.49 | -15.00 | -2.31 | -2.28 | -2.94 | -2.58 | -2.29 | -2.42 | -2.14 | -15.00 |
| Q | -2.21 | -15.00 | -1.78 | -1.58 | -2.72 | -2.44 | -2.02 | -2.42 | -2.34 | -15.00 |
| R | -2.19 | -15.00 | -3.44 | -2.30 | -3.32 | -2.77 | -2.87 | -2.98 | -2.35 | -2.32 |
| S | -1.06 | -0.60 | -2.70 | -2.92 | -2.65 | -2.68 | -2.42 | -2.45 | -2.40 | -15.00 |
| T | -0.44 | -0.80 | -2.00 | -3.14 | -2.75 | -1.98 | -2.43 | -2.27 | -2.41 | -15.00 |
| V | -2.35 | -1.07 | -2.16 | -2.59 | -3.03 | -1.93 | -1.97 | -1.64 | -2.77 | -15.00 |
| W | -3.52 | -15.00 | 0.00 | -1.33 | -1.43 | -2.54 | -1.49 | -1.95 | -1.55 | -15.00 |
| Y | -3.08 | -15.00 | -1.85 | -2.32 | -2.40 | -2.90 | -0.88 | -1.64 | -1.77 | -15.00 |

M at 3, 4, and 7, and W at 7 are group values.
Poly A values are used at positions 2 and 9, and are ratios to the T2 poly-A peptide.

TABLE 33

A3.2 10-mer Algorithm

|   | 1 | 2 | 3 | 4 | 5 | 6 | 7 | 8 | 9 | 10 |
|---|---|---|---|---|---|---|---|---|---|---|
| A | −1.92 | −2.20 | −2.31 | −2.28 | −2.14 | −2.80 | −3.22 | −2.58 | −2.69 | −4.32 |
| C | −3.12 | −3.47 | −2.54 | −2.29 | −2.05 | −1.87 | −2.27 | −2.07 | −2.62 | −15.00 |
| D | −3.04 | −3.94 | −2.79 | −2.57 | −3.86 | −2.41 | −2.54 | −3.21 | −2.70 | −15.00 |
| E | −3.36 | −15.00 | −2.80 | −2.94 | −2.28 | −3.00 | −2.43 | −3.10 | −2.50 | −15.00 |
| F | −2.67 | −2.92 | −1.25 | −1.77 | −2.52 | −2.50 | −2.06 | −2.77 | −1.73 | −3.42 |
| G | −2.69 | −2.84 | −2.52 | −2.59 | −1.91 | −2.40 | −2.63 | −2.08 | −2.58 | −15.00 |
| H | −2.14 | −15.00 | −2.39 | −2.10 | −1.64 | −2.36 | −2.78 | −1.96 | −1.91 | −3.67 |
| I | −2.68 | −2.20 | −1.87 | −2.60 | −2.10 | −2.53 | −1.59 | −1.88 | −2.87 | −15.00 |
| K | −1.23 | −15.00 | −2.08 | −1.74 | −1.69 | −2.84 | −2.95 | −2.74 | −2.05 | −1.94 |
| L | −2.49 | −2.19 | −2.26 | −2.42 | −2.20 | −2.44 | −2.36 | −2.18 | −2.75 | −15.00 |
| M | −1.42 | −2.19 | −2.17 | −2.69 | −3.40 | −1.64 | −2.14 | −2.34 | −3.17 | −15.00 |
| N | −3.61 | −15.00 | −1.73 | −2.55 | −3.15 | −2.49 | −1.79 | −2.74 | −2.17 | −15.00 |
| P | −3.85 | −15.00 | −3.01 | −2.62 | −2.70 | −2.28 | −2.51 | −2.52 | −1.93 | −15.00 |
| Q | −2.18 | −15.00 | −2.65 | −2.38 | −2.86 | −2.11 | −2.57 | −2.79 | −2.49 | −15.00 |
| R | −1.08 | −15.00 | −2.67 | −2.34 | −2.62 | −2.41 | −2.86 | −2.73 | −1.93 | −2.74 |
| S | −1.60 | −1.84 | −2.80 | −2.75 | −2.84 | −2.74 | −2.45 | −1.90 | −2.65 | −15.00 |
| T | −1.21 | −2.20 | −3.36 | −2.19 | −2.72 | −2.20 | −2.18 | −2.04 | −2.46 | −15.00 |
| V | −2.46 | −2.22 | −2.18 | −3.14 | −3.01 | −1.75 | −2.19 | −2.51 | −3.03 | −15.00 |
| W | −3.25 | −15.00 | 0.54 | −1.47 | −1.74 | −2.44 | −1.44 | −1.58 | −1.71 | −15.00 |
| Y | −3.06 | −15.00 | −1.67 | −1.54 | −2.90 | −3.17 | −0.19 | −2.31 | −1.22 | −3.42 |

M at pos. 3, 4 and 7 used group values.
W at pos. 7 used group value.

Values obtained with a large collection of unrelated peptides (peptide library values) match acceptably with the poly-A values, so the values at 2 are directly from the poly-A data. The value used is derived by taking the poly-A ratio of the peptide library score for L2.

At position 9, the poly-A ratios and the values obtained with a large collection of unrelated peptides (peptide library values) are different by about a six-fold factor.

Therefore, except for K and R, which are values obtained with a large collection of unrelated peptides (peptide library values), the position 9 score is taken from the poly-A data, and −0.80 (i.e., the log of 1/6) is added to the log value.

TABLE 34

A3.2 9-mer Algorithm

|   | 1 | 2 | 3 | 4 | 5 | 6 | 7 | 8 | 9 |
|---|---|---|---|---|---|---|---|---|---|
| A | −1.70 | −2.20 | −1.80 | −2.64 | −2.55 | −1.40 | −2.22 | −2.42 | −4.32 |
| C | −2.45 | −3.47 | −2.73 | −2.32 | −1.27 | −2.35 | −2.87 | −2.41 | −15.00 |
| D | −3.52 | −3.94 | −2.69 | −2.59 | −2.59 | −3.35 | −2.82 | −3.05 | −15.00 |
| E | −3.27 | −15.00 | −3.42 | −2.41 | −3.06 | −3.09 | −2.28 | −2.57 | −15.00 |
| F | −2.19 | −2.92 | −0.90 | −1.70 | −2.01 | −1.09 | −2.07 | −3.20 | −3.42 |
| G | −2.63 | −2.84 | −3.29 | −1.89 | −3.12 | −2.53 | −2.13 | −2.66 | −15.00 |
| H | −2.01 | −15.00 | −1.96 | −1.52 | −1.70 | −2.71 | −3.08 | −1.13 | −3.67 |
| I | −2.10 | −2.20 | −1.97 | −2.39 | −2.12 | −2.43 | −2.32 | −3.05 | −15.00 |
| K | −0.93 | −15.00 | −2.51 | −1.61 | −2.56 | −3.27 | −2.92 | −2.21 | −1.94 |
| L | −1.88 | −2.19 | −2.50 | −2.29 | −2.30 | −2.30 | −1.79 | −2.59 | −15.00 |
| M | −2.65 | −2.19 | −2.03 | −4.00 | −1.04 | −2.64 | −1.35 | −3.55 | −15.00 |
| N | −2.72 | −15.00 | −2.18 | −2.89 | −3.07 | −1.98 | −2.92 | −2.00 | −15.00 |
| P | −3.14 | −15.00 | −3.15 | −2.29 | −1.90 | −2.84 | −2.35 | −1.82 | −15.00 |
| Q | −2.40 | −15.00 | −3.67 | −2.53 | −1.78 | −2.70 | −1.73 | −2.60 | −15.00 |
| R | −1.39 | −15.00 | −1.93 | −1.95 | −2.43 | −2.45 | −2.92 | −1.71 | −2.74 |
| S | −1.88 | −1.84 | −2.17 | −2.60 | −1.96 | −1.88 | −1.84 | −2.71 | −15.00 |
| T | −3.00 | −2.20 | −2.84 | −2.83 | −2.26 | −1.80 | −2.44 | −1.53 | −15.00 |
| V | −2.45 | −2.22 | −2.33 | −2.87 | −2.42 | −2.46 | −2.38 | −2.68 | −15.00 |
| W | −3.84 | −15.00 | −1.93 | −2.33 | −2.12 | −1.19 | −2.17 | −2.77 | −15.00 |
| Y | −2.43 | −15.00 | −0.77 | −2.36 | −1.28 | −1.73 | −2.71 | −1.75 | −3.42 |

Values obtained with a large collection of unrelated peptides (peptide library values) match acceptably with the poly-A values, so the values at 2 are directly from the poly-A data. The value used is derived by taking the poly-A ratio of the peptide library score for L2.

At position 9, the poly-A ratios and the values obtained with a large collection of unrelated peptides (peptide library values) are different by about a six-fold factor.

Therefore, except for K and R, which are values obtained with a large collection of unrelated peptides (peptide library values), the position 9 score is taken from the poly-A data, and −0.80 (i.e., the log of 1/6) is added to the log value.

TABLE 35

A1 9-mer Algorithm

|   | 1 | 2 | 3 | 4 | 5 | 6 | 7 | 8 | 9 |
|---|---|---|---|---|---|---|---|---|---|
| A | −1.36 | −0.20 | −1.98 | −1.96 | −1.47 | 1.24 | −1.16 | −1.87 | −15.00 |
| C | −0.67 | −3.00 | −0.18 | −0.98 | −0.74 | −0.52 | −0.52 | −0.84 | −15.00 |
| D | −1.17 | −2.59 | −0.60 | −1.77 | −0.86 | −1.20 | −0.84 | −1.18 | −15.00 |
| E | −1.17 | −2.59 | −1.94 | −1.77 | −0.86 | −1.20 | −0.84 | −1.18 | −15.00 |
| F | −2.30 | −2.14 | −1.36 | −0.59 | −1.03 | −1.52 | −1.45 | −1.47 | −15.00 |
| G | −0.19 | −1.09 | −1.77 | −0.96 | −1.96 | −1.10 | −2.05 | −2.03 | −15.00 |
| H | −0.50 | −2.35 | −1.74 | −2.03 | −1.38 | −1.73 | −1.24 | −1.62 | −15.00 |
| I | −0.94 | −0.36 | −1.89 | −1.41 | −1.48 | −1.72 | −1.60 | −0.72 | −15.00 |
| K | −0.50 | −3.00 | −1.57 | −2.03 | −1.38 | −1.73 | −1.24 | −1.62 | −15.00 |
| L | −0.94 | 0.14 | −1.30 | −1.41 | −1.48 | −1.72 | −1.60 | −0.72 | −15.00 |
| M | −0.94 | −0.36 | −1.87 | −1.41 | −1.48 | −1.72 | −1.60 | −0.72 | −15.00 |
| N | −2.52 | −3.00 | −0.99 | −0.66 | −1.63 | −1.37 | −1.67 | −1.57 | −15.00 |
| P | −1.46 | −3.00 | −1.92 | −1.39 | −2.30 | −2.36 | −2.05 | −2.57 | −15.00 |
| Q | −2.52 | 0.03 | −0.99 | −0.66 | −1.63 | −1.37 | −1.67 | −1.57 | −15.00 |
| R | −0.50 | −1.04 | −1.96 | −2.03 | −1.38 | −1.73 | −1.24 | −1.62 | −15.00 |
| S | −0.67 | −1.42 | −1.26 | −0.98 | −0.74 | −0.52 | −0.52 | −0.84 | −15.00 |
| T | −0.67 | −1.07 | −0.51 | −0.98 | −0.74 | −0.52 | −0.52 | −0.84 | −15.00 |
| V | −0.94 | −1.12 | −2.23 | −1.41 | −1.48 | −1.72 | −1.60 | −0.72 | −15.00 |
| W | −2.30 | −2.14 | −1.58 | −0.59 | −1.03 | −1.52 | −1.45 | −1.47 | −15.00 |
| Y | −2.30 | −2.14 | −1.70 | −0.59 | −1.03 | −1.52 | −1.45 | −1.47 | −1.30 |

Values are group values.
Positions 2 and 3 uses single aa values.
DFHIMW at pos 2 are group values.
HMNW at pos 3 are group values.
G at pos 3 is from full log alg.
P at pos 6 is from full log alg.

Positions 2 and 3 are additionally scored collectively such that if a preferred or tolerated residue does not occur in the correct position at either position 2 or 3 an additional −15 is added to the algorithm score.

TABLE 36

A1 10-mer Algorithm

|   | 1 | 2 | 3 | 4 | 5 | 6 | 7 | 8 | 9 | 10 |
|---|---|---|---|---|---|---|---|---|---|---|
| A | -0.78 | -1.85 | -0.92 | -0.56 | -1.61 | -1.58 | -1.44 | -0.79 | -1.89 | -15.00 |
| C | -1.56 | -1.06 | -1.51 | -1.73 | -1.29 | -1.47 | -1.03 | -0.91 | -1.46 | -15.00 |
| D | -1.70 | -3.00 | -1.61 | -0.99 | -1.51 | -1.52 | -1.34 | -1.33 | -1.59 | -15.00 |
| E | -1.70 | -3.00 | -1.16 | -0.99 | -1.51 | -1.52 | -1.34 | -1.33 | -1.59 | -15.00 |
| F | -1.37 | -3.00 | -0.68 | -2.07 | -1.48 | -1.72 | -1.87 | -1.30 | -1.77 | -15.00 |
| G | -1.76 | -1.55 | -2.40 | -0.99 | -1.46 | -1.75 | -1.37 | -1.10 | -2.12 | -15.00 |
| H | -1.30 | -2.49 | -0.98 | -1.43 | -1.34 | -0.89 | -1.83 | -1.34 | -1.66 | -15.00 |
| I | -1.34 | -2.09 | -1.53 | -1.55 | -1.30 | -1.28 | -1.38 | -1.82 | -1.13 | -15.00 |
| K | -1.30 | -2.49 | -2.23 | -1.43 | -1.34 | -0.89 | -1.83 | -1.34 | -1.66 | -15.00 |
| L | -1.34 | -1.38 | -1.39 | -1.55 | -1.30 | -1.28 | -1.38 | -1.82 | -1.13 | -15.00 |
| M | -1.34 | -1.63 | -1.01 | -1.55 | -1.30 | -1.28 | -1.38 | -1.82 | -1.13 | -15.00 |
| N | -1.49 | -1.43 | -1.27 | -1.32 | -1.66 | -2.62 | -1.08 | -2.14 | -0.58 | -15.00 |
| P | -1.91 | -1.46 | -1.57 | -1.79 | -1.78 | -1.86 | -2.17 | -1.88 | -1.75 | -15.00 |
| Q | -1.49 | -1.43 | -1.18 | -1.32 | -1.66 | -2.62 | -1.08 | -2.14 | -0.58 | -15.00 |
| R | -1.30 | -2.49 | -2.10 | -1.43 | -1.34 | -0.89 | -1.83 | -1.34 | -1.66 | -15.00 |
| S | -1.56 | -1.01 | -1.07 | -1.73 | -1.29 | -1.47 | -1.03 | -0.91 | -1.46 | -15.00 |
| T | -1.56 | -1.10 | -1.51 | -1.73 | -1.29 | -1.47 | -1.03 | -0.91 | -1.46 | -15.00 |
| V | -1.34 | -1.88 | -1.82 | -1.55 | -1.30 | -1.28 | -1.38 | -1.82 | -1.13 | -15.00 |
| W | -1.37 | -3.00 | -1.97 | -2.07 | -1.48 | -1.72 | -1.87 | -1.30 | -1.77 | -15.00 |
| Y | -1.37 | -3.00 | -0.96 | -2.07 | -1.48 | -1.72 | -1.87 | -1.30 | -1.77 | -1.44 |

Values are group values.
Positions 2 and 3 uses single aa values.
CDKMNRW at pos 2 are group values.
I at pos 3 is group value.

TABLE 37

| Sequence | Antigen | Molecule | A1 Bind. | A3 Bind. | A11 Bind. | A24 Bind. | SEQ ID NO: |
|---|---|---|---|---|---|---|---|
| FTFSPTYKAFLSK | HBV | POL | | 1.5000 | 0.6900 | | 1111 |
| GTLPQEHIVLKLK | HBV | POL | | 0.2400 | 0.1300 | | 1112 |
| FTFSPTYKAFLCK | HBV | POL | | 0.1900 | 0.1900 | | 1113 |
| GTLPQEHIVLKIK | HBV | POL | | 0.0420 | 0.0250 | | 1114 |
| LVVSYVNTNMGLK | HBV | POL | | 0.0410 | 0.0170 | | 1115 |
| STTDLEAYFKDCLFK | HBV | X | | 0.0220 | 0.2100 | | 1116 |
| LVVSYVNVNMGLK | HBV | NUC | | 0.0140 | 0.0210 | | 1117 |
| GTLPQDHIVQKIK | HBV | POL | | 0.0120 | 0.0220 | | 1118 |
| STSSCLHQSAVRK | HBV | POL | | 0.0041 | 0.0110 | | 1119 |
| TTVNAHQILPKVLHK | HBV | X | | 0.0025 | 0.0140 | | 1120 |
| RTPARVTGGVFLVDK | HBV | POL | | 0.0020 | 0.0170 | | 1121 |
| HTTNFASK | HBV ayw | | | 0.0360 | 0.0065 | | 1122 |
| FTFSPTYK | HBV ayw | | | 0.0310 | 0.0580 | | 1123 |
| PTYKAFLCKQY | HBVayw | | 0.0020 | 0.0052 | 0.0160 | 0.0007 | 1124 |
| CTTPAQGTSMY | HBVayw | | 0.1500 | 0.0003 | 0.0002 | 0.0001 | 1125 |
| PTSCPPTCPGY | HBVayw | | 0.0540 | 0.0003 | 0.0002 | 0.0001 | 1126 |
| FSQFSRGNY | HBVayw | | 0.0570 | | | | 339 |
| LMPLYACIQSK | HBVayw | | | 0.0440 | 0.0750 | | 1127 |
| RVTGGVFLVDK | HBVayw | POL | | 0.0420 | 0.0940 | | 1128 |
| HTLWKAGILYK | HBVayw | | | 3.9000 | 1.5000 | | 1129 |
| QTRHYLHTLWK | HBVayw | | | 1.7000 | 0.0930 | | 1130 |
| GTDNSVVLSRK | HBVayw | | | 0.1500 | 0.4300 | | 1131 |
| SYVNTNMGLKF | HBVayw | | | | | 0.2000 | 1132 |
| LYSILSPF | HBVayw | | | | | 0.0930 | 1133 |
| WYWGPSLYSIL | HBVayw | | | | | 0.0307 | 1134 |
| LYSILSPFLPL | HBVayw | | | | | 0.0210 | 1135 |
| PYKEFGATVEL | HBVayw | | | | | 0.0150 | 1136 |
| CTWMNSTGFTK | HCV | | | 0.7600 | 0.7500 | | 1137 |
| MYVGDLCGSVF | HCV | | | | | 0.2600 | 1138 |
| VYLLPRRGPRL | HCV | | | | | 0.0200 | 1139 |
| ITKIQNFRVYY | HIV | | 0.0110 | | | | 1140 |
| KVYLAWVPAHK | HIV | | | 8.6000 | 2.3000 | | 639 |
| KMIGGIGGFIK | HIV | | | 2.3000 | 0.7000 | | 640 |
| IVASCDKCQLK | HIV | | | 0.0970 | 0.1000 | | 1141 |
| KVKQWPLTEEK | HIV | | | 0.0750 | 0.0330 | | 1142 |
| TVNDIQKLVGK | HIV | | | 0.0400 | 0.1700 | | 1143 |
| DVKQLTEAVQK | HIV | | | 0.0048 | 0.0240 | | 1144 |
| AVVIQDNSDIK | HIV | | | 0.0004 | 0.0150 | | 1145 |
| WTYQIYQEPFK | HIV | | | 0.9200 | 0.0540 | | 641 |
| VTVYYGVPVWK | HIV | | | 0.8600 | 4.1000 | | 642 |
| LTEDRWNKPQK | HIV | | | 0.0390 | 0.0130 | | 1146 |
| ATDIQTKELQK | HIV | | | 0.0051 | 0.1800 | | 1147 |

TABLE 37-continued

| Sequence | Antigen | Molecule | A1 Bind. | A3 Bind. | A11 Bind. | A24 Bind. | SEQ ID NO: |
|---|---|---|---|---|---|---|---|
| QTKELQKQITK | HIV | | | 0.0050 | 0.0100 | | 1148 |
| WTVQPIVLPEK | HIV | | | 0.0011 | 0.0510 | | 1149 |
| QVPLRPMTYK | HIV nef 73–82 | | 0.0002 | 0.9900 | 0.3820 | | 1150 |
| QVPLYPMTFK | HIV nef 73–82 | | | 0.4800 | 0.7330 | | 1151 |
| VPLRPMTYK | HIV nef 74–82 | | 0.0001 | 0.0420 | 0.0057 | | 1152 |
| AVDLYHFLK | HIV nef 84–94 | | | 0.2500 | 1.0000 | | 125 |
| AVDLSHFLK | HIV nef 84–94 | | 0.0039 | 0.0740 | 1.1000 | | 1153 |
| ATLYCVHQR | HIV, p17, 82–90 | | | 0.0150 | 0.7100 | | 1154 |
| RLRDLLLIV | HIV-1 NL43 768–776 | | 0.0001 | 0.0210 | 0.0004 | | 1155 |
| RLRDLLLIVTR | HIV-1 NL43 768–778 | | 0.0022 | 1.1000 | 0.0009 | | 1156 |
| RLRDYLLIVTR | HIV-1 NL43 768–778 | | | 0.2700 | 0.0008 | | 1157 |
| LRDLLLIVTR | HIV-1 NL43 769–778 | | 0.0016 | 0.0130 | 0.0035 | | 1158 |
| QIYQEPFKNLK | HIV-1 RT 507–517 | | 0.0001 | 0.2800 | 0.2900 | | 1159 |
| AVFIHNFK | HIVcon | | | 0.0280 | 0.0380 | | 1160 |
| RTLNAWVK | HIVcon | | | 0.0410 | 0.0560 | | 1161 |
| ETAYFLLK | HIVcon | | | 0.0037 | 0.0430 | | 1162 |
| RLRPGGKKK | HIVgag p17/2 | | | 0.3100 | 0.0002 | | 1163 |
| KIRLRPGGKK | HIVgag p17/2 | | | 0.3000 | 0.0005 | | 1164 |
| KIRLRPGGK | HIVgag p17/2 | | | 0.1400 | 0.0002 | | 1165 |
| ETTDLYCY | HPV16 | E7 | 0.0780 | 0.0002 | 0.0001 | 0.0001 | 1166 |
| GTLGIVCPICSQK | HPV16 | E7 | | 0.4400 | 0.9100 | | 1167 |
| LMGTLGIVCPICSQK | HPV16 | E7 | | 0.0180 | 0.0240 | | 1168 |
| AVCDKCLK | HPV16 | E6 | | 0.0053 | 0.0110 | | 1169 |
| PYAVCDKCLKF | HPV16 | E6 | | | | 0.1100 | 1170 |
| HYCYSLYGTTL | HPV16 | E6 | | | | 0.0650 | 1171 |
| FYSRIREL | HPV16 | E6 | | | | 0.0260 | 1172 |
| TLEKLTNTGLY | HPV18 | E6 | 5.9000 | 0.0003 | 0.0002 | 0.0001 | 1173 |
| KTVLELTEVFEFAFK | HPV18 | E6 | | 0.2100 | 0.2300 | | 1174 |
| TMLCMCCK | HPV18 | E7 | | 0.0240 | 0.0240 | | 1175 |
| NTSLQDIEITCVYCK | HPV18 | E6 | | 0.0110 | 0.0580 | | 1176 |
| EVFEFAFK | HPV18 | E6 | | 0.0025 | 0.0180 | | 1177 |
| KQSSKALQR | Leukemia | β3A2 CMI | | 0.1400 | 0.0220 | | 1178 |
| ATGFKQSSK | Leukemia | β3A2 CMI | | 0.0200 | 0.0620 | | 1179 |
| HSATGFKQSSK | Leukemia | β3A2 CMI | | 0.0150 | 0.0480 | | 1180 |
| FKQSSKALQR | Leukemia | β3A2 CMI | | 0.0110 | 0.0012 | | 1181 |
| VTCLGLSY | MAGE1 | | 0.2300 | 0.0002 | 0.0045 | 0.0001 | 1182 |
| ITKKVADLVGFLLLK | MAGE1 | | | 0.4000 | 1.0000 | | 1183 |
| LVGFLLLK | MAGE1 | | | 0.0640 | 0.0860 | | 1184 |
| VTKAEMLESVIKNYK | MAGE1 | | | 0.0240 | 0.0530 | | 1185 |
| TSCILESLFR | MAGE1 | | | 0.0002 | 0.0150 | | 1186 |
| NYKHCFPEI | MAGE1 | | | | | 4.8000 | 1187 |
| SYVLVTCL | MAGE1 | | | | | 0.0120 | 1188 |
| ETDPISHTY | MAGE1(a) | | 12.0000 | | | | 1189 |
| ETDPTSHLY | MAGE1(a) | | 11.0000 | | | | 1190 |
| ETDPTSNTY | MAGE1(a) | | 11.0000 | | | | 1191 |
| ETDPTSHVY | MAGE1(a) | | 8.3000 | | | | 1192 |
| ETDPTSHSY | MAGE1(a) | | 6.4000 | | | | 1193 |
| ETDPASHTY | MAGE1(a) | | 5.0000 | | | | 1194 |
| EVDPTSHTY | MAGE1(a) | | 3.9000 | | | | 1195 |
| ETDPTGHTY | MAGE1(a) | | 3.6000 | | | | 1196 |
| ETDRTSHTY | MAGE1(a) | | 3.1000 | | | | 1197 |
| EADPTSHTY | MAGE1(a) | | 0.6800 | | | | 1198 |
| ETVPTSHTY | MAGE1(a) | | 0.1300 | | | | 1199 |
| ETDPTSHTY | MAGE1 consensus | | 5.9000 | | | | 1200 |
| ETDPTGHSY | MAGE1 T(a) | | 11.0000 | | | | 1201 |
| MFPDLESEF | MAGE2 | | | 0.0002 | 0.0001 | 0.0140 | 1202 |
| TTINYTLWR | MAGE2 | | | 0.0890 | 1.1000 | | 1203 |
| VIFSKASEY | MAGE2 | | | 0.0810 | 0.0330 | | 1204 |
| LVHFLLLKY | MAGE2 | | | 0.0660 | 0.0120 | | 1205 |
| LVHFLLLKY | MAGE2 | | | 0.0660 | 0.0120 | | 1205 |
| LVHFLLLKYR | MAGE2 | | | 0.0400 | 0.0014 | | 1206 |

TABLE 37-continued

| Sequence | Antigen | Molecule | A1 Bind. | A3 Bind. | A11 Bind. | A24 Bind. | SEQ ID NO: |
|---|---|---|---|---|---|---|---|
| PVIFSKASEY | MAGE2 | | | 0.0160 | 0.0033 | | 1207 |
| STTINYTLWR | MAGE2 | | | 0.0014 | 0.0910 | | 1208 |
| VVEVVPISH | MAGE2 | | | 0.0007 | 0.0100 | | 1209 |
| EYLQLVFGI | MAGE2 | | | | | 3.5000 | 1210 |
| IFSKASEYL | MAGE2 | | | | | 0.0230 | 1211 |
| SFSTTINYTL | MAGE2 | | | | | 0.0150 | 1212 |
| LYILVTCLGL | MAGE2 | | | | | 0.0140 | 1213 |
| FATCLGLSY | MAGE3 | | 0.0380 | 0.0003 | 0.0004 | | 1214 |
| VVGNWQYFFPVIFSK | MAGE3 | | | 1.6000 | 0.3400 | | 1215 |
| LIIVLAIIAR | MAGE3 | | | 0.0280 | 0.0021 | | 1216 |
| YFFPVIFSK | MAGE3 | | | 0.0020 | 0.0270 | | 1217 |
| NWQYFFPVI | MAGE3 | | | | | 0.5300 | 1218 |
| NWQYFFPVIF | MAGE3 | | | | | 0.0170 | 1219 |
| IFSKASSSL | MAGE3 | | | | | 0.0160 | 1220 |
| EVDPTSNTY | MAGE41 | | 1.9000 | | | | 1221 |
| RYPLTFGWCY | nef/182 | | | | | 0.0150 | 1222 |
| RYPLTFGWC | nef/182 | | | | | 0.0130 | 1223 |
| ATQIPSYK | PAP | | | 0.0180 | 0.0700 | | 1224 |
| LTELYFEK | PAP | | | 0.0014 | 0.0100 | | 1225 |
| HSFPHPLY | PSA | | 0.0260 | 0.0890 | 0.0006 | 0.0001 | 1226 |
| TQEPALGTTCY | PSA | | 0.0190 | 0.0003 | 0.0002 | 0.0001 | 1227 |
| VTKFMLCAGRWTGGK | PSA | | | 0.0470 | 0.2500 | | 1228 |
| HVISNDVCAQVHPQK | PSA | | | 0.0220 | 0.0550 | | 1229 |
| LYDMSLLKNRF | PSA | | | | | 0.1200 | 1230 |
| ETDPTGHSY | T2 analog of MAGE-3 | | 11.0000 | | | | 1201 |

What is claimed is:

1. A method for making an immunogenic peptide comprising an HLA-A24.1-restricted T cell epitope consisting of about 8–11 amino acid residues that binds to an HLA-A4.1 molecule and induces an HLA-A24.1-restricted cytotoxic T cell response, said method comprising steps of:

(a) providing an amino acid sequence of an antigen of interest;

(b) identifying within said sequence a putative T cell epitope, wherein said putative epitope consists of about 8–11 amino acid residues and is identified by the presence of a structural motif associated with peptide binding to HLA-A24.1, said structural motif comprising a first amino acid anchor residue at position two from the epitope's N-terminal residue, said first anchor residue selected from the group consisting of Y, F, and W, and a second anchor residue selected from the group consisting of F, I, L, and W as the epitope's carboxyl-terminal amino acid residue (SEQ ID NOS:1231–1234);

(c) preparing one or more peptide fragments of said antigen of interest that comprise a structural motif of step (b);

(d) testing complexes of said one or more peptide fragments and an HLA-A24.1 molecule for an ability to be recognized by HLA-A24.1 cytotoxic T cells, and to thereby induce a cytotoxic T cell response to the epitope; and (e) selecting said one or more peptide fragments comprising an HLA-A24.1 structural motif of step (b) that induce an HLA-A24.1 cytotoxic T cell response to the epitope.

2. The method of claim 1, wherein one of the peptide fragments has 8, 9, 10 or 11 residues.

3. The method of claim 1, wherein at least two peptide fragments are prepared.

4. The method of claim 1, further comprising a step of determining binding affinity of said one or more peptide fragments for an HLA-A24.1 molecule.

5. The method of claim 4, further comprising a step of identifying said one or more peptide fragments which has a dissociation constant for the HLA-A24.1 molecule of less than 500 nM.

6. The method of claim 1, further comprising a step of:

(f) determining binding affinity of said one or more peptide fragments for an HLA molecule that is not HLA-A24.1.

7. The method of claim 1, wherein the preparing step comprises isolation of the one or more peptide fragments from a natural source.

8. The method of claim 1, wherein the preparing step comprises synthesis of the one or more of the peptide fragments.

9. The method of claim 8, wherein the synthesis comprises chemical synthesis.

10. The method of claim 1, wherein the preparing step comprises expressing in a cell a recombinant nucleic acid molecule that encodes said one or more of the peptide fragments.

11. The method of claim 10, wherein the recombinant nucleic acid molecule encodes more than one peptide fragment.

12. The method of claim 1, wherein the testing step occurs in vitro.

13. The method of claim 1, wherein the testing step occurs in vivo.

14. A method of making a peptide that binds to an HLA-A24.1 molecule at a dissociation constant less than 500 nM, the method comprising steps of:

(a) providing an amino acid sequence of an antigen of interest;

(b) identifying within said sequence a putative T cell epitope from the provided amino acid sequence, wherein said putative epitope consists of about 8–11 amino acid residues and is identified by the presence of a structural motif associated with peptide binding to HLA-A24.1, said structural motif comprising a first amino acid anchor residue at position two from the epitope's N-terminal residue, said first anchor residue selected from the group consisting of Y, F, and W, and a second amino acid anchor residue selected from the group consisting of F, I, L, and W as the epitope's carboxyl-terminal amino acid residue (SEQ ID NOS:1231–1234);

(c) preparing one or more peptide fragments of said antigen of interest that comprise a structural motif of step (b);

(d) contacting said one or more peptide fragments of step (c) with an HLA-A24.1 molecule; and, (e) selecting said one or more peptide fragments comprising an HLA-A24.1 structural motif of step (b) that bind to an HLA-A24.1 molecule at a dissociation constant of less than 500 nM.

15. The method of claim 14, further comprising a step of:

(f) contacting an HLA-A24.1 cytotoxic T lymphocyte with a complex of the peptide of step (e) and an HLA-A24.1 molecule.

16. The method of claim 14, wherein the contacting step occurs in vitro.

17. The method of claim 14, wherein the contacting step occurs in vivo.

18. A method for making an immunogenic peptide comprising an HLA-A1-restricted T cell epitope consisting of about 8–11 amino acid residues that binds to an HLA-A1 molecule and induces an HLA-A1-restricted cytotoxic T cell response, said method comprising steps of:

(a) providing an amino acid sequence of an antigen of interest;

(b) identifying within said sequence a putative T cell epitope, wherein said putative epitope consists of about 8–11 amino acid residues and is identified by the presence of a structural motif associated with peptide binding to HLA-A1, said structural motif is selected from the group consisting of:

(i) a first structural motif having a first amino acid anchor residue at position two from the epitope's N-terminal amino acid residue, said first anchor residue selected from the group consisting of T, S, and M, and a second amino acid anchor residue of Y as the epitope's carboxyl-terminal amino acid residue (SEQ ID NOS:1235–1238); and (ii) a second structural motif having a first amino acid anchor residue at position three from the epitope's N-terminal amino acid residue, said first anchor residue selected from the group consisting of D, E, A, and S, and a second amino acid anchor residue of Y as the epitope's carboxyl-terminal amino acid (SEQ ID NOS:1239–1242);

(c) preparing one or more peptide fragments of said antigen of interest that comprise a structural motif of step (b);

(d) testing complexes of said one or more peptide fragments and an HLA-A1 molecule for an ability to be recognized by HLA-A1 cytotoxic T cells, and to thereby induce a cytotoxic T cell response to the epitope; and (e) selecting said one or more peptide fragments comprising an HLA-A1 structural motif of step (b) that induce an HLA-A1 cytotoxic T cell response to the epitope.

19. The method of claim 18, wherein one of the peptide fragments has 8, 9, 10 or 11 residues.

20. The method of claim 18, wherein at least two peptide fragments are prepared.

21. The method of claim 18, further comprising a step of deter binding affinity of said one or more peptide fragments for an HLA-A1 molecule.

22. The method of claim 21, further comprising a step of identifying said one or more peptide fragments which has a dissociation constant for the HLA-A1 molecule of less than 500 nM.

23. The method of claim 21, further comprising a step of:

(f) determining binding affinity of said one or more peptide fragments for an HLA molecule that is not HLA-A1.

24. The method of claim 18, wherein the preparing step comprises isolation of the one or more peptide fragments from a natural source.

25. The method of claim 18, wherein the preparing step comprises synthesis of the one or more of the peptide fragments.

26. The method of claim 25, wherein the synthesis comprises chemical synthesis.

27. The method of claim 18, wherein the preparing step comprises expressing in a cell a recombinant nucleic acid molecule that encodes said one or more of the peptide fragments.

28. The method of claim 27, wherein the recombinant nucleic acid molecule encodes more than one peptide fragment.

29. The method of claim 18, wherein the testing step occurs in vitro.

30. The method of claim 18, wherein the testing step occurs in vivo.

31. A method of making a peptide that binds to an HLA-A1 molecule at a dissociation constant less than 500 nM, the method comprising steps of:

(a) providing an amino acid sequence of an antigen of interest;

(b) identifying within said sequence a putative T cell epitope from the provided amino acid sequence, wherein said putative epitope consists of about 8–11 amino acid residues and is identified by the presence of a structural motif associated with peptide binding to HLA-A1, said structural motif wherein the motif is selected from the group consisting of:

(i) a first structural motif having a first amino acid anchor residue at position two from the epitope's N-terminal amino acid residue, said first anchor residue selected from the group consisting of T, S, and M, and a second amino acid anchor residue of Y as the epitope's carboxyl-terminal amino acid residue (SEQ ID NOS:1235–1238); and (ii) a second structural motif having a first amino acid anchor residue at position three from the epitope's N-terminal amino acid residue, said first anchor residue selected from the group consisting of D, E, A, and S, and a second amino acid anchor residue of Y as the epitope's carboxyl-terminal amino acid (SEQ ID NOS:1239–1242);

(c) preparing one or more peptide fragments of said antigen of interest that comprise a structural motif of step (b);

(d) contacting said one or more peptide fragments of step (c) with an HLA-A1 molecule; and, (e) selecting said one or more peptide fragments comprising an HLA-A1 structural motif of step (b) that bind to an HLA-A1 molecule at a dissociation constant of less than 500 nM.

32. The method of claim 31, further comprising a step of:

(f) contacting an HLA-A1 cytotoxic T lymphocyte with a complex of the peptide of step (e) and an HLA-A1 molecule.

33. The method of claim 31, wherein the contacting step occurs in vitro.

34. The method of claim 31, wherein tie contacting step occurs in vivo.

35. A method for making an immunogenic peptide comprising an HLA-A11-restricted T cell epitope consisting of about 8–11 amino acid residues that binds to an HLA-A11 molecule and induces an HLA-A11-restricted cytotoxic T cell response, said method comprising steps of:

(a) providing the amino acid sequence of an antigen of interest;

(b) identifying within said sequence a putative T cell epitope, wherein said putative epitope consists of about 8–11 amino acid residues and is identified by the presence of a structural motif associated with peptide binding to HLA-A11, said structural motif comprising a first amino acid anchor residue at position two from the epitope's N-terminal amino acid residue, said first anchor residue selected from the group consisting of L, M, I, V, A, S, T. G, N, C, F, and D, and a second amino acid anchor residue selected from the group consisting of K, R, and H at the epitope's carboxyl-terminal amino acid residue (SEQ ID NOS:1243–1246);

(c) preparing one or more peptide fragments of said antigen of interest that comp se a structural motif of step (b);

(d) testing complexes of said one or more peptide fragments and an HLA-A11 molecule for an ability to be recognized by HLA-A11 cytotoxic T cells, and to thereby induce a cytotoxic T cell response to the epitope; and (e) selecting said one or more peptide fragments comprising an HLA-A11 structural motif of step (b) that induce an HLA-A11 cytotoxic T cell response to the epitope.

36. The method of claim 35, wherein one of the peptide fragments has 8, 9, 10 or 11 residues.

37. The method of claim 35, wherein at least two peptide fragments are prepared.

38. The method of claim 35, further comprising a step of determining binding affinity of said one or more peptide fragments for an HLA-A11 molecule.

39. The method of claim 38, further comprising a step of identifying said one or more peptide fragments which has a dissociation constant for the HLA-A11 molecule of less than 500 nM.

40. The method of claim 35, further comprising a step of:
(f) determining binding affinity of said one or more peptide fragments for an HLA molecule that is not HLA-A11.

41. The method of claim 35, wherein the preparing step comprises isolation of the one or more peptide fragments from a natural source.

42. The method of claim 35, wherein the preparing step comprises synthesis of the one or more of the peptide fragments.

43. The method of claim 42, wherein the synthesis comprises chemical synthesis.

44. The method of claim 35, wherein the preparing step comprises expressing in a cell a recombinant nucleic acid molecule that encodes said one or more of the peptide fragments.

45. The method of claim 44, wherein the recombinant nucleic acid molecule encodes more than one peptide fragment.

46. The method of claim 35, wherein the testing step occurs in vitro.

47. The method of claim 35, wherein the testing step occurs in vivo.

48. A method of making a peptide that binds to an HLA-A11 molecule at a dissociation constant less than 500 nM, the method comprising steps of:
(a) providing an amino acid sequence of an antigen of interest;
(b) identifying within said sequence a putative T cell epitope from the provided amino acid sequence, wherein said putative epitope consists of about 8–11 amino acid residues and is identified by the presence of a structural motif associated with peptide binding to HLA-A11, said structural motif comprising a first amino acid anchor residue at position two from the epitope's N-terminal amino acid residue, said first anchor residue selected from the group consisting of L, M, I, V, A, S, T, G, N, C, F, and D, and a second amino acid anchor residue selected from the group consisting of K, R, and H at the epitope's carboxyl-terminal amino acid residue (SEQ ID NOS:1247–1250);

(c) preparing one or more peptide fragments of said antigen of interest that comprise a structural motif of step (b);

(d) contacting said one or more peptide fragments of step (c) with an HLA-A11 molecule; and, (e) selecting said one or more peptide fragments comprising an HLA-A11 structural motif of step (b) that bind to an HLA-A11 molecule at a dissociation constant of less than 500 nM.

49. The method of claim 48, further comprising a step of:
(f) contacting an HLA-A11 cytotoxic T lymphocyte with a complex of the peptide of step (e) and an HLA-A11 molecule.

50. The method of claim 48, wherein the contacting step occurs in vitro.

51. The method of claim 48, wherein the contacting step occurs in vivo.

52. A method for making an immunogenic peptide comprising an HLA-A3.2-restricted T cell epitope consisting of about 8–11 amino acid residues that binds to an HLA-A3.2 molecule and induces an HLA-A3.2-restricted cytotoxic T cell response, said method comprising steps of:

(a) providing the amino acid sequence of an antigen of interest;

(b) identifying within said sequence a putative T cell epitope, wherein said putative epitope consists of about 8–11 amino acid residues and is identified by the presence of a structural motif associated with peptide binding to HLA-A3.2, said structural motif comprising a first amino acid anchor residue at position two from the epitope's N-terminal amino acid residue, said first anchor residue selected from the group consisting of L, M, I, V, S, A, T, F, C, G, and D, and a second amino acid anchor residue selected from the group consisting of K, R, Y, H, and F at the epitope's carboxyl-terminal amino acid residue (SEQ ID NOS:1251–1254);

(c) preparing one or more peptide fragments of said antigen of interest that comprise a structural motif of step (b);

(d) testing complexes of said one or more peptide fragments and an HLA-A3.2 molecule for an ability to be recognized by HLA-A3.2 cytotoxic T cells, and to thereby induce a cytotoxic T cell response to the epitope; and (e) selecting said one or more peptide fragments comprising an HLA-A3.2 structural motif of step (b) that induce an HLA-A3.2 cytotoxic T cell response to the epitope.

53. The method of claim 52, wherein one of the peptide fragments has 8, 9, 10 or 11 residues.

54. The method of claim 52, wherein at least two peptide fragments are prepared.

55. The method of claim 52, further comprising a step of determining binding affinity of said one or more peptide fragments for an HLA-A3.2 molecule.

56. The method of claim 55, further comprising a step of identifying said one or more peptide fragments which has a dissociation constant for the HLA-A3.2 molecule of less than 500 nM.

57. The method of claim 52, further comprising a step of:
(f) determining binding affinity of said one or more peptide fragments for an HLA molecule that is not HLA-A3.2.

58. The method of claim 52, wherein the preparing step comprises isolation of the one or more peptide fragments from a natural source.

59. The method of claim 52, wherein the preparing step comprises synthesis of the one or more of the peptide fragments.

60. The method of claim 59, wherein the synthesis comprises chemical synthesis.

61. The method of claim 52, wherein the preparing step comprises expressing in a cell a recombinant nucleic acid molecule that encodes said one or more of the peptide fragments.

62. The method of claim 61, wherein the recombinant nucleic acid molecule encodes more than one peptide fragment.

63. The method of claim 52, wherein the testing step occurs in vitro.

64. The method of claim 52, wherein the testing step occurs in vivo.

65. A method of making a peptide that binds to an HLA-A3.2 molecule at a dissociation constant less than 500 nM, the method comprising steps of:
(a) providing an amino acid sequence of an antigen of interest;
(b) identifying within said sequence a putative T cell epitope from the provided amino acid sequence, wherein said putative epitope consists of about 8–11 amino acid residues and is identified by the presence of a structural motif associated with peptide binding to HLA-A3.2, wherein the motif has a first amino acid anchor residue at position two from the epitope's N-terminal amino acid residue, said first anchor residue selected from the group consisting of L, M, I, V, S, A, T, F, C, G, and D, and a second amino acid residue selected from the group consisting of K, R, Y, H, and F at the epitope's carboxyl-terminal amino acid residue (SEQ ID NOS:1251–1254);
(c) preparing one or more peptide fragments of said antigen of interest that comprise a structural motif of step (b);
(d) contacting said one or more peptide fragments of step (c) with an HLA-A3.2 molecule; and,
(e) selecting said one or more peptide fragments comprising an HLA-A3.2 structural motif of step (b) that bind to an HLA-A3.2 molecule at a dissociation constant of less than 500 nM.

66. The method of claim 65, further comprising a step of:
(f) contacting an HLA-A3.2 cytotoxic T lymphocyte with a complex of the peptide of step (e) and an HLA-A3.2 molecule.

67. The method of claim 65, wherein the contacting step occurs in vitro.

68. The method of claim 65, wherein the contacting step occurs in vivo.

* * * * *

UNITED STATES PATENT AND TRADEMARK OFFICE
CERTIFICATE OF CORRECTION

PATENT NO. : 6,037,135
DATED : March 14, 2000
INVENTOR(S) : Ralph T. Kubo, et. al.

It is certified that error appears in the above-indentified patent and that said Letters Patent is hereby corrected as shown below:

At column 611, line 27, delete "HLA-A4.1" and substitute therefor --HLA-A24.1--.

At column 613, line 58, delete "deter" and substitute therefor --determining--.

At column 614, line 61, delete "tie" and substitute therefor --the--.

At column 615, line 11, delete "T." and substitute therefor --T,--. Same column, line 16, delete "comp se" and substitute therefor --comprise--.

Signed and Sealed this

Twentieth Day of March, 2001

Attest:

NICHOLAS P. GODICI

*Attesting Officer*    *Acting Director of the United States Patent and Trademark Office*